US010920208B2

(12) United States Patent
Liu et al.

(10) Patent No.: US 10,920,208 B2
(45) Date of Patent: Feb. 16, 2021

(54) EVOLUTION OF PROTEASES

(71) Applicant: President and Fellows of Harvard College, Cambridge, MA (US)

(72) Inventors: David R. Liu, Lexington, MA (US); Bryan Dickinson, Chicago, IL (US); Michael S. Packer, Cambridge, MA (US); Ahmed Hussein Badran, Dorchester, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 7 days.

(21) Appl. No.: 15/518,639

(22) PCT Filed: Oct. 22, 2015

(86) PCT No.: PCT/US2015/057012
§ 371 (c)(1),
(2) Date: Apr. 12, 2017

(87) PCT Pub. No.: WO2016/077052
PCT Pub. Date: May 19, 2016

(65) Prior Publication Data

US 2017/0233708 A1 Aug. 17, 2017

Related U.S. Application Data

(60) Provisional application No. 62/067,194, filed on Oct. 22, 2014.

(51) Int. Cl.

| | |
|---|---|
| ***C12N 9/50*** | (2006.01) |
| ***C12N 9/12*** | (2006.01) |
| ***C12N 15/10*** | (2006.01) |
| ***C12N 7/00*** | (2006.01) |
| ***C12N 15/52*** | (2006.01) |
| ***C12N 15/62*** | (2006.01) |
| ***C12N 15/86*** | (2006.01) |

(52) U.S. Cl.
CPC ................ *C12N 9/50* (2013.01); *C12N 7/00* (2013.01); *C12N 9/1247* (2013.01); *C12N 15/1037* (2013.01); *C12N 15/1058* (2013.01); *C12N 15/52* (2013.01); *C12N 15/62* (2013.01); *C12N 15/86* (2013.01); *C12Y 207/07006* (2013.01); *C12Y 304/00* (2013.01); *C07K 2319/50* (2013.01); *C12N 2795/00022* (2013.01)

(58) Field of Classification Search
CPC combination set(s) only.
See application file for complete search history.

(56) References Cited

U.S. PATENT DOCUMENTS

| | | | |
|---|---|---|---|
| 5,057,432 | A | 10/1991 | Wangersky et al. |
| 5,223,409 | A | 6/1993 | Ladner et al. |
| 5,658,727 | A | 8/1997 | Barbas et al. |
| 5,712,089 | A | 1/1998 | Borrebaeck et al. |
| 5,821,047 | A | 10/1998 | Garrard et al. |
| 5,880,275 | A | 3/1999 | Fischhoff et al. |
| 5,965,124 | A | 10/1999 | Feinberg et al. |
| 6,033,874 | A | 3/2000 | Baum et al. |
| 6,156,509 | A | 12/2000 | Schellenberger |
| 6,429,298 | B1 | 8/2002 | Ellington et al. |
| 6,713,063 | B1 | 3/2004 | Malvar et al. |
| 6,962,705 | B2 | 11/2005 | Malvar et al. |
| 6,969,731 | B1 | 11/2005 | Tang et al. |
| 7,064,249 | B2 | 6/2006 | Corbin et al. |
| 7,070,982 | B2 | 7/2006 | Malvar et al. |
| 9,023,594 | B2 | 5/2015 | Liu et al. |
| 9,267,127 | B2 | 2/2016 | Liu et al. |
| 9,359,599 | B2 | 6/2016 | Liu et al. |
| 9,394,537 | B2 | 7/2016 | Liu et al. |
| 9,567,589 | B2 | 2/2017 | Jin et al. |
| 9,766,216 | B2 | 9/2017 | Wada et al. |
| 9,771,574 | B2 | 9/2017 | Liu et al. |
| 10,179,911 | B2 | 1/2019 | Liu et al. |
| 10,227,581 | B2 | 3/2019 | Liu et al. |

(Continued)

FOREIGN PATENT DOCUMENTS

| | | | |
|---|---|---|---|
| EP | 0289479 | A2 | 11/1988 |
| EP | 3115457 | A1 | 1/2017 |

(Continued)

OTHER PUBLICATIONS

Yang et al., Molecular Microbiology, vol. 53(1), pp. 283-295, 2004.*

Guzman et al. J. Bacteriol. vol. 177, 4121-4130, 1995.*

International Preliminary Report on Patentability for PCT/US/2016/043559, dated Feb. 1, 2018.

International Preliminary Report on Patentability for PCT/US/2016/044546, dated Feb. 8, 2018.

International Preliminary Report on Patentability for PCT/US2016/043513, dated Feb. 1, 2018.

Invitation to Pay Additional Fees for PCT/US2018/14867, dated Apr. 5, 2018.

(Continued)

*Primary Examiner* — Richard G Hutson

(74) *Attorney, Agent, or Firm* — Wolf, Greenfield & Sacks, P.C.

(57) ABSTRACT

Some aspects of this disclosure provide methods for phage-assisted continuous evolution (PACE) of proteases. Some aspects of this invention provide methods for evaluating and selecting protease inhibitors based on the likelihood of the emergence of resistant proteases as determined by the protease PACE methods provided herein. Some aspects of this disclosure provide strategies, methods, and reagents for protease PACE, including fusion proteins for translating a desired protease activity into a selective advantage for phage particles encoding a protease exhibiting such an activity and improved mutagenesis-promoting expression constructs. Evolved proteases that recognize target cleavage sites which differ from their canonical cleavage site are also provided herein.

12 Claims, 26 Drawing Sheets

Specification includes a Sequence Listing.

(56) References Cited

U.S. PATENT DOCUMENTS

| | | | |
|---|---|---|---|
| 10,336,997 | B2 | 7/2019 | Liu et al. |
| 10,392,674 | B2 | 8/2019 | Liu et al. |
| 10,612,011 | B2 | 4/2020 | Liu et al. |
| 2002/0132327 | A1 | 9/2002 | Hay et al. |
| 2003/0119764 | A1 | 6/2003 | Loeb et al. |
| 2003/0167533 | A1 | 9/2003 | Yadav et al. |
| 2003/0203480 | A1 | 10/2003 | Kovesdi et al. |
| 2005/0019753 | A1 | 1/2005 | Kukolj et al. |
| 2005/0100973 | A1 | 5/2005 | Steward et al. |
| 2006/0112447 | A1 | 5/2006 | Bogdanova et al. |
| 2006/0166319 | A1 | 7/2006 | Chan et al. |
| 2008/0220502 | A1 | 9/2008 | Schellenberger et al. |
| 2009/0215110 | A1 | 8/2009 | Gibson et al. |
| 2009/0227463 | A1 | 9/2009 | Reif et al. |
| 2009/0300777 | A1 | 12/2009 | Nakayama |
| 2010/0297180 | A1 | 11/2010 | Shone |
| 2011/0177495 | A1 | 7/2011 | Liu et al. |
| 2012/0128649 | A1 | 5/2012 | Chaddock et al. |
| 2012/0231498 | A1 | 9/2012 | Shaw et al. |
| 2013/0059931 | A1 | 3/2013 | Petersen-Mahrt et al. |
| 2013/0117869 | A1 | 5/2013 | Duchateau et al. |
| 2013/0345064 | A1 | 12/2013 | Liu et al. |
| 2013/0345065 | A1 | 12/2013 | Hassibi et al. |
| 2014/0057317 | A1 | 2/2014 | Liu et al. |
| 2014/0201858 | A1 | 7/2014 | Ostertag et al. |
| 2015/0056177 | A1 | 2/2015 | Liu et al. |
| 2015/0165054 | A1 | 6/2015 | Liu et al. |
| 2015/0259721 | A1 | 9/2015 | Van Brunt et al. |
| 2015/0275202 | A1 | 10/2015 | Liu et al. |
| 2016/0002301 | A1 | 1/2016 | Je et al. |
| 2016/0201040 | A1 | 7/2016 | Liu et al. |
| 2016/0348096 | A1 | 12/2016 | Liu et al. |
| 2017/0009224 | A1 | 1/2017 | Liu et al. |
| 2017/0029473 | A1 | 2/2017 | Liu et al. |
| 2017/0044520 | A1 | 2/2017 | Liu et al. |
| 2018/0057545 | A9 | 3/2018 | Liu et al. |
| 2018/0087046 | A1 | 3/2018 | Liu et al. |
| 2018/0237758 | A1 | 8/2018 | Liu et al. |
| 2019/0256842 | A1 | 8/2019 | Liu et al. |
| 2019/0276816 | A1 | 9/2019 | Liu et al. |
| 2020/0071722 | A1 | 3/2020 | Liu et al. |

FOREIGN PATENT DOCUMENTS

| | | | | |
|---|---|---|---|---|
| JP | H0937764 | A | 2/1997 | |
| JP | 2011-081011 | | 4/2011 | |
| WO | WO-90/02809 | A1 | 3/1990 | |
| WO | WO-91/17271 | A1 | 11/1991 | |
| WO | WO-92/01047 | A1 | 1/1992 | |
| WO | WO-92/09690 | A2 | 6/1992 | |
| WO | WO-92/15679 | A1 | 9/1992 | |
| WO | WO-92/18619 | A1 | 10/1992 | |
| WO | WO-92/20791 | A1 | 11/1992 | |
| WO | WO-93/01288 | A1 | 1/1993 | |
| WO | WO 94/18316 | A2 | 8/1994 | |
| WO | WO-96/04403 | A1 | 2/1996 | |
| WO | WO-98/32845 | A1 | 7/1998 | |
| WO | WO-00/71694 | A1 | 11/2000 | |
| WO | WO-01/05950 | A2 | 1/2001 | |
| WO | WO-01/61049 | A1 | 8/2001 | |
| WO | WO-2005/081632 | A2 | 9/2005 | |
| WO | WO-2007/066923 | A1 | 6/2007 | |
| WO | WO-2008/005529 | A2 | 1/2008 | |
| WO | WO-2009/082488 | A2 | 7/2009 | |
| WO | WO-2009/108180 | A2 | 9/2009 | |
| WO | WO-2010/028347 | A2 | 3/2010 | |
| WO | WO 2011/039518 | A2 | 4/2011 | |
| WO | WO-2011/066747 | A1 | 6/2011 | |
| WO | WO-2011/147590 | A2 | 12/2011 | |
| WO | WO-2012/088381 | A2 | 6/2012 | |
| WO | WO-2012088381 | A2 * | 6/2012 | ......... C12N 15/1058 |
| WO | WO 2012/138927 | A2 | 10/2012 | |
| WO | WO 2013/047844 | | 4/2013 | |
| WO | WO-2014/039585 | A2 | 3/2014 | |
| WO | WO-2014/157820 | A1 | 10/2014 | |
| WO | WO-2014/158593 | A1 | 10/2014 | |
| WO | WO 2015/134121 | A2 | 9/2015 | |
| WO | WO 2015/193897 | A1 | 12/2015 | |
| WO | WO 2016/077052 | A9 | 5/2016 | |
| WO | WO 2016/168631 | A1 | 10/2016 | |
| WO | WO 2017/015559 | A2 | 1/2017 | |
| WO | WO 2017/070632 | A2 | 4/2017 | |
| WO | WO 2018/039438 | A1 | 3/2018 | |

OTHER PUBLICATIONS

International Search Report and Written Opinion for PCT/US2018/14867, dated May 23, 2018.

Badran et al., In vivo continuous directed evolution. Curr Opin Chem Biol. 2014;1-10.

Dickinson et al., A system for the continuous directed evolution of proteases rapidly reveals drug-resistance mutations. Nat Commun. Oct. 30, 2014;5:5352. doi: 10.1038/ncomms6352.

Leconte et al., A population-based experimental model for protein evolution: effects of mutation rate and selection stringency on evolutionary outcomes. Biochemistry. Feb. 26, 2013; 52(8): 1490-1499.

Lei et al., Efficient targeted gene disruption in Xenopus embryos using engineered transcription activator-like effector nucleases (TALENs). PNAS Oct. 23, 2012;109(43):17484-17489; https://doi.org/10.1073/pnas.1215421109.

Maeder et al., Robust, synergistic regulation of human gene expression using TALE activators. Nat Methods. Mar. 2013;10(3):243-5. doi: 10.1038/nmeth.2366. Epub Feb. 10, 2013.

Ahluwalia et al., Hypermutability and error catastrophe due to defects in ribonucleotide reductase. Proc Natl Acad Sci U S A. Nov. 12, 2013;110(46):18596-601. doi: 10.1073/pnas.1310849110. Epub Oct. 28, 2013.

Akopian et al., Chimeric recombinases with designed DNA sequence recognition. Proc Natl Acad Sci U S A. Jul. 22, 2003;100(15):8688-91. Epub Jul. 1, 2003.

Armstrong et al., Chapter 3. Vectors for Phage Display. In: Phage Display of Peptides and Proteins. Kay et al., eds. Academic Press. San Diego, CA. 1996:35-53.

Badran et al., Continuous evolution of Bacillus thuringiensis toxins overcomes insect resistance. Nature. May 5, 2016;533(7601):58-63. doi: 10.1038/nature17938. Epub Apr. 27, 2016.

Badran et al., Development of potent in vivo mutagenesis plasmids with broad mutational spectra. Nat Commun. Oct. 7, 2015;6:8425. doi: 10.1038/ncomms9425.

Baker et al., Chemical complementation: a reaction-independent genetic assay for enzyme catalysis. Proc Natl Acad Sci U S A. Dec. 24, 2002;99(26):16537-42. Epub Dec. 13, 2002.

Barbas et al., Assembly of combinatorial antibody libraries on phage surfaces: the gene III site. Proc Natl Acad Sci U S A. Sep. 15, 1991;88(18):7978-82.

Bennet et al., Unlocking of the filamentous bacteriophage virion during infection is mediated by the C domain of pIII. J Mol Biol. Feb. 17, 2006;356(2):266-73. Epub Dec. 9, 2005.

Birling et al., Site-specific recombinases for manipulation of the mouse genome. Methods Mol Biol. 2009;561:245-63. doi: 10.1007/978-1-60327-019-9_16.

Bloom et al., Evolving strategies for enzyme engineering. Curr Opin Struct Biol. Aug. 2005;15(4):447-52.

Boch et al., Breaking the code of DNA binding specificity of TAL-type III effectors. Science. Dec. 11, 2009;326(5959):1509-12. Doi: 10.1126/science.1178811.

Boeke et al., Effects of bacteriophage f1 gene III protein on the host cell membrane. Mol Gen Genet. 1982;186(2):185-92.

Boersma et al., Selection strategies for improved biocatalysts. FEBS J. May 2007;274(9):2181-95.

Bolusani et al., Evolution of variants of yeast site-specific recombinase Flp that utilize native genomic sequences as recombination target sites. Nucleic Acids Res. 2006;34(18):5259-69. Epub Sep. 26, 2006.

Braun et al., Immunogenic duplex nucleic acids are nuclease resistant. J Immunol. Sep. 15, 1988;141(6):2084-9.

Breaker et al., Emergence of a replicating species from an in vitro RNA evolution reaction. Proc Natl Acad Sci U S A. Jun. 21, 1994;91(13):6093-7.

(56) References Cited

OTHER PUBLICATIONS

Brieba et al., Role of T7 RNA polymerase His784 in start site selection and initial transcription. Biochemistry. Apr. 23, 2002;41(16):5144-9.
Buchholz et al., Alteration of Cre recombinase site specificity by substrate-linked protein evolution. Nat Biotechnol. Nov. 2001;19(11):1047-52.
Caldwell et al., Randomization of Genes by PCR Mutagenesis. PCR Methods Applic. 1992;2:28-33.
Camps et al., Targeted gene evolution in *Escherichia coli* using a highly error-prone DNA polymerase I. Proc Natl Acad Sci U S A. Aug. 19, 2003;100(17):9727-32. Epub Aug. 8, 2003.
Carlson et al., Negative selection and stringency modulation in phage-assisted continuous evolution. Nat Chem Biol. Mar. 2014;10(3):216-22. doi: 10.1038/nchembio.1453. Epub Feb. 2, 2014. With Supplementary Results.
Chasteen et al., Eliminating helper phage from phage display. Nucleic Acids Res. 2006;34(21):e145. Epub Nov. 6, 2006.
Chaturvedi et al., Stabilization of triple-stranded oligonucleotide complexes: use of probes containing alternating phosphodiester and stereo-uniform cationic phosphoramidate linkages. Nucleic Acids Res. Jun. 15, 1996;24(12):2318-23.
Cheetham et al., Structural basis for initiation of transcription from an RNA polymerase-promoter complex. Nature. May 6, 1999;399(6731):80-3.
Chen et al., Information theory based T7-like promoter models: classification of bacteriophages and differential evolution of promoters and their polymerases. Nucleic Acids Res. Oct. 31, 2005;33(19):6172-87. Print 2005.
Clackson et al., Making antibody fragments using phage display libraries. Nature. Aug. 15, 1991;352(6336):624-8.
Click et al., Filamentous phage infection: required interactions with the TolA protein. J Bacteriol. Oct. 1997;179(20):6464-71.
Cobb et al., Directed evolution: an evolving and enabling synthetic biology tool. Curr Opin Chem Biol. Aug. 2012;16(3-4):285-91. doi: 10.1016/j.cbpa.2012.05.186. Epub Jun. 4, 2012.
Corey et al., Trypsin display on the surface of bacteriophage. Gene. Jun. 15, 1993;128(1):129-34.
Crameri et al., Display of biologically active proteins on the surface of filamentous phages: a cDNA cloning system for selection of functional gene products linked to the genetic information responsible for their production. Gene. Dec. 27, 1993;137(1):69-75.
Cwirla et al., Peptides on phage: a vast library of peptides for identifying ligands. Proc Natl Acad Sci U S A. Aug. 1990;87(16):6378-82.
Das et al., Viral evolution as a tool to improve the tetracycline-regulated gene expression system. J Biol Chem. Apr. 30, 2004;279(18):18776-82. Epub Feb. 2, 2004.
Datsenko et al., One-step inactivation of chromosomal genes in *Escherichia coli* K-12 using PCR products. Proc Natl Acad Sci U S A. Jun. 6, 2000;97(12):6640-5.
Davis et al., Viral mutagenesis as a means for generating novel proteins. J Virol. Feb. 2010;84(3):1625-30. Epub Nov. 11, 2009.
De Haard et al., A large non-immunized human Fab fragment phage library that permits rapid isolation and kinetic analysis of high affinity antibodies. J Biol Chem. Jun. 25, 1999;274(26):18218-30.
Deussing, Targeted mutagenesis tools for modelling psychiatric disorders. Cell Tissue Res. Oct. 2013;354(1):9-25. doi: 10.1007/s00441-013-1708-5. Epub Sep. 10, 2013.
Dickinson et al., Experimental interrogation of the path dependence and stochasticity of protein evolution using phage-assisted continuous evolution. Proc Natl Acad Sci USA. May 2013;110(22):9007-12.
Dove et al., Conversion of the omega subunit of *Escherichia coli* RNA polymerase into a transcriptional activator or an activation target. Genes Dev. Mar. 1, 1998;12(5):745-54.
Doyon et al., Directed evolution and substrate specificity profile of homing endonuclease I-SceI. J Am Chem Soc. Feb. 22, 2006;128(7):2477-84.
Drake, A constant rate of spontaneous mutation in DNA-based microbes. Proc Natl Acad Sci U S A. Aug. 15, 1991;88(16):7160-4.
Durai et al., A bacterial one-hybrid selection system for interrogating zinc finger-DNA interactions. Comb Chem High Throughput Screen. May 2006;9(4):301-11.
Durniak et al., The structure of a transcribing T7 RNA polymerase in transition from initiation to elongation. Science. Oct. 24, 2008;322(5901):553-7.
Esvelt et al., A system for the continuous directed evolution of biomolecules. Nature. Apr. 28, 2011;472(7344):499-503. Epub Apr. 10, 2011.
Extended European Search Report for EP 09812363, dated Mar. 30, 2012.
Extended European Search Report for EP 16 20 3684, dated May 26, 2017.
Extended European Search Report for EP 17 16 0955, dated May 16, 2017.
Fijalkowska et al., Mutants in the Exo I motif of *Escherichia coli* dnaQ: defective proofreading and inviability due to error catastrophe. Proc Natl Acad Sci U S A. Apr. 2, 1996;93(7):2856-61.
Fowlkes et al., Multipurpose vectors for peptide expression on the M13 viral surface. Biotechniques. Sep. 1992;13(3):422-8.
Friedberg et al., Error-prone DNA polymerases: novel structures and the benefits of infidelity. Cell. Oct. 5, 2001;107(1):9-12.
Fuchs et al., Targeting Recombinant Antibodies to the Surface of *Escherichia coli*: Fusion to a Peptidoglycan Associated Lipoprotein. Bio/Technology. 1991;9:1370-72.
Gaj et al., Expanding the scope of site-specific recombinases for genetic and metabolic engineering. Biotechnol Bioeng. Jan. 2014;111(1):1-15. doi: 10.1002/bit.25096. Epub Sep. 13, 2013.
Garrard et al., Fab assembly and enrichment in a monovalent phage display system. Biotechnology (N Y). Dec. 1991;9(12):1373-7.
Gibson et al., Enzymatic assembly of DNA molecules up to several hundred kilobases. Nat Methods. May 2009;6(5):343-5. Epub Apr. 12, 2009.
Gordley et al., Evolution of programmable zinc finger-recombinases with activity in human cells. J Mol Biol. Mar. 30, 2007;367(3):802-13. Epub Jan. 12, 2007.
Gram et al., In vitro selection and affinity maturation of antibodies from a naive combinatorial immunoglobulin library. Proc Natl Acad Sci U S A. Apr. 15, 1992;89(8):3576-80.
Griffiths et al., Human anti-self antibodies with high specificity from phage display libraries. EMBO J. Feb. 1993;12(2):725-34.
Hart et al., Directed Evolution to Investigate Steric Control of Enzymatic Oxidosqualene Cyclization. An Isoleucine-to-Valine Mutation in Cycloartenol Synthase Allows Lanosterol and Parkeol Biosynthesis. J Am Chem Soc. 1999;121:9887-88.
Hawkins et al., Selection of phage antibodies by binding affinity. Mimicking affinity maturation. J Mol Biol. Aug. 5, 1992;226(3):889-96.
Hay et al., Bacteriophage cloning and *Escherichia coli* expression of a human IgM Fab. Hum Antibodies Hybridomas. Apr. 1992;3(2):81-5.
Hoogenboom et al., Antibody phage display technology and its applications. Immunotechnology. Jun. 1998;4(1):1-20.
Hoogenboom et al., Multi-subunit proteins on the surface of filamentous phage: methodologies for displaying antibody (Fab) heavy and light chains. Nucleic Acids Res. Aug. 11, 1991;19(15):4133-7.
Hoogenboom et al., Natural and designer binding sites made by phage display technology. Immunol Today. Aug. 2000;21(8):371-8.
Houshmand et al., Use of Bateriophage T7 Displayed Peptides for Determination of Monoclonal Anitbody Specificity and Biosensor Analysis of the Binding Reaction. Anal Biochem. 1999;268:363-70.
Hu et al., *Escherichia coli* one- and two-hybrid systems for the analysis and identification of protein-protein interactions. Methods. Jan. 2000;20(1):80-94.
Hubbard et al., Continuous directed evolution of DNA-binding proteins to improve TALEN specificity. Nat Methods. Oct. 2015;12(10):939-42. doi: 10.1038/nmeth.3515. Epub Aug. 10, 2015. With Supplementary Information.
Huse et al., Generation of a large combinatorial library of the immunoglobulin repertoire in phage lambda. Science. Dec. 8, 1989;246(4935):1275-81.

(56) References Cited

OTHER PUBLICATIONS

Husimi et al., Cellstat-a continuous culture system of a bacteriophage for the study of the mutation rate and the selection process of the DNA level. Rev Sci Instrum. Apr. 1982;53(4):517-22.
Husimi, Selection and evolution of bacteriophages in cellstat. Adv Biophys. 1989;25:1-43.
Ichetovkin et al., Substrate recognition by the leucyl/phenylalanyl-tRNA-protein transferase. Conservation within the enzyme family and localization to the trypsin-resistant domain. J Biol Chem. Dec. 26, 1997;272(52):33009-14.
Ikeda et al., In vivo and in vitro activities of point mutants of the bacteriophage T7 RNA polymerase promoter. Biochemistry. Sep. 22, 1992;31(37):9073-80.
Ikeda et al., Selection and characterization of a mutant T7 RNA polymerase that recognizes an expanded range of T7 promoter-like sequences. Biochemistry. Sep. 7, 1993;32(35):9115-24.
Imburgio et al., Studies of promoter recognition and start site selection by T7 RNA polymerase using a comprehensive collection of promoter variants. Biochemistry. Aug. 29, 2000;39(34):10419-30.
International Preliminary Report on Patentability for PCT/US2009/056194 dated Mar. 17, 2011.
International Preliminary Report on Patentability for PCT/US2011/066747, dated Jul. 4, 2013.
International Preliminary Report on Patentability for PCT/US2015/012022, dated Aug. 4, 2016.
International Preliminary Report on Patentability for PCT/US2015/057012, dated May 4, 2017.
International Search Report and Written Opinion for PCT/US/2016/043559, dated Mar. 10, 2017.
International Search Report and Written Opinion for PCT/US2009/056194 dated Jun. 21, 2010.
International Search Report and Written Opinion for PCT/US2011/066747, dated Oct. 30, 2012.
International Search Report and Written Opinion for PCT/US2015/012022, dated Sep. 25, 2015.
International Search Report and Written Opinion for PCT/US2015/057012, dated Jun. 10, 2016.
International Search Report and Written Opinion for PCT/US2016/027795, dated Aug. 11, 2016.
International Search Report and Written Opinion for PCT/US2016/043513, dated Nov. 30, 2016.
International Search Report and Written Opinion for PCT/US2016/044546, dated Dec. 28, 2016.
Invitation to Pay Additional Fees for PCT/US/2016/043559, dated Jan. 12, 2017.
Invitation to Pay Additional Fees for PCT/US2011/066747, dated Aug. 30, 2012.
Invitation to Pay Additional Fees for PCT/US2016/044546, dated Oct. 12, 2016.
International Preliminary Report on Patentability for PCT/US2016/027795, dated Oct. 26, 2017.
Irion et al., Identification and targeting of the ROSA26 locus in human embryonic stem cells. Nat Biotechnol. Dec. 2007;25(12):1477-82. Epub Nov. 25, 2007.
Johns et al., The promise and peril of continuous in vitro evolution. J Mol Evol. Aug. 2005;61(2):253-63. Epub Jun. 27, 2005.
Joho et al., Identification of a region of the bacteriophage T3 and T7 RNA polymerases that determines promoter specificity. J Mol Biol. Sep. 5, 1990;215(1):31-9.
Joung et al., A bacterial two-hybrid selection system for studying protein-DNA and protein-protein interactions. Proc Natl Acad Sci U S A. Jun. 20, 2000;97(13):7382-7.
Karpinsky et al., Directed evolution of a recombinase that excises the provirus of most HIV-1 primary isolates with high specificity. Nat Biotechnol. Apr. 2016;34(4):401-9. doi: 10.1038/nbt.3467. Epub Feb. 22, 2016.
Kawarasaki et al., Enhanced crossover SCRATCHY: construction and high-throughput screening of a combinatorial library containing multiple non-homologous crossovers. Nucleic Acids Res. Nov. 1, 2003;31(21):e126.
Khlebnikov et al., Modulation of gene expression from the arabinose-inducible araBAD promoter. J Ind Microbiol Biotechnol. Jul. 2002;29(1):34-7.
Klement et al., Discrimination between bacteriophage T3 and T7 promoters by the T3 and T7 RNA polymerases depends primarily upon a three base-pair region located 10 to 12 base-pairs upstream from the start site. J Mol Biol. Sep. 5, 1990;215(1):21-9.
Kozak et al., Structural features in eukaryotic mRNAs that modulate the initiation of translation. J Biol Chem. Oct. 25, 1991;266(30):19867-70.
Kuzmine et al., Binding of the priming nucleotide in the initiation of transcription by T7 RNA polymerase. J Biol Chem. Jan. 31, 2003;278(5):2819-23. Epub Nov. 9, 2002.
Latimer et al., Specificity of monoclonal antibodies produced against phosphorothioate and ribo modified DNAs. Mol Immunol. Oct. 1995;32(14-15):1057-64.
Lincoln et al., Self-sustained replication of an RNA enzyme. Science. Feb. 27, 2009;323(5918):1229-32. Epub Jan. 8, 2009.
Lindemann et al., Evolution of bacteriophage in continuous culture: a model system to test antiviral gene therapies for the emergence of phage escape mutants. J Virol. Jun. 2002;76(11):5784-92.
Lutz et al., Creating multiple-crossover DNA libraries independent of sequence identity. Proc Natl Acad Sci U S A. Sep. 25, 2001;98(20):11248-53. Epub Sep. 18, 2001.
Makeyev et al., Evolutionary potential of an RNA virus. J Virol. Feb. 2004;78(4):2114-20.
Malmborg et al., Selective phage infection mediated by epitope expression on F pilus. J Mol Biol. Oct. 31, 1997;273(3):544-51.
Martin et al., Kinetic analysis of T7 RNA polymerase-promoter interactions with small synthetic promoters. Biochemistry. May 19, 1987;26(10):2690-6.
McCafferty et al., Phage antibodies: filamentous phage displaying antibody variable domains. Nature. Dec. 6, 1990;348(6301):552-4.
McConnell et al., Constrained peptide libraries as a tool for finding mimotopes. Gene. Dec. 30, 1994;151(1-2):115-8.
Milligan et al., Oligoribonucleotide synthesis using T7 RNA polymerase and synthetic DNA templates. Nucleic Acids Res. Nov. 11, 1987;15(21):8783-98.
Mills et al., An extracellular Darwinian experiment with a self-duplicating nucleic acid molecule. Proc Natl Acad Sci U S A. Jul. 1967;58(1):217-24.
Nelson et al., Filamentous phage DNA cloning vectors: a noninfective mutant with a nonpolar deletion in gene III. Virology. Jan. 30, 1981;108(2):338-50.
Nern et al., Multiple new site-specific recombinases for use in manipulating animal genomes. Proc Natl Acad Sci U S A. Aug. 23, 2011;108(34):14198-203. doi: 10.1073/pnas.1111704108. Epub Aug. 9, 2011.
O'Maille et al., Structure-based combinatorial protein engineering (SCOPE). J Mol Biol. Aug. 23, 2002;321(4):677-91.
Opperman et al., A model for a umuDC-dependent prokaryotic DNA damage checkpoint. Proc Natl Acad Sci U S A. Aug. 3, 1999;96(16):9218-23.
Ostendorf et al., Characterization of a dam mutant of Serratia marcescens and nucleotide sequence of the dam region. J Bacteriol. Jul. 1999;181(13):3880-5.
Ostermeier e al., A combinatorial approach to hybrid enzymes independent of DNA homology. Nat Biotechnol. Dec. 1999;17(12):1205-9.
Peyrottes et al., Oligodeoxynucleoside phosphoramidates (P-NH2): synthesis and thermal stability of duplexes with DNA and RNA targets. Nucleic Acids Res. May 15, 1996;24(10):1841-8.
Pu et al., Evolution of a split RNA polymerase as a versatile biosensor platform. Nat Chem Biol. Apr. 2017;13(4):432-438. doi: 10.1038/nchembio.2299. Epub Feb. 13, 2017.
Rakonjac et al., Filamentous phage are released from the bacterial membrane by a two-step mechanism involving a short C-terminal fragment of pIII. J Mol Biol. Jun. 25, 1999;289(5):1253-65.

(56) References Cited

OTHER PUBLICATIONS

Rakonjac et al., Filamentous phage infection-mediated gene expression: construction and propagation of the gIII deletion mutant helper phage R408d3. Gene. Oct. 1, 1997;198(1-2):99-103.
Rakonjac et al., Roles of pIII in filamentous phage assembly. J Mol Biol. Sep. 11, 1998;282(1):25-41.
Raskin et al., Substitution of a single bacteriophage T3 residue in bacteriophage T7 RNA polymerase at position 748 results in a switch in promoter specificity. J Mol Biol. Nov. 20, 1992;228(2):506-15.
Raskin et al., T7 RNA polymerase mutants with altered promoter specificities. Proc Natl Acad Sci U S A. Apr. 15, 1993;90(8):3147-51.
Rebar et al., Phage display methods for selecting zinc finger proteins with novel DNA-binding specificities. Methods Enzymol. 1996;267:129-49.
Reidhaar-Olson et al., Random mutagenesis of protein sequences using oligonucleotide cassettes. Methods Enzymol. 1991;208:564-86.
Reuven et al., Lesion bypass by the *Escherichia coli* DNA polymerase V requires assembly of a RecA nucleoprotein filament. J Biol Chem. Feb. 23, 2001;276(8):5511-7. Epub Nov. 17, 2000.
Riechmann et al., The C-terminal domain of TolA is the coreceptor for filamentous phage infection of *E. coli*. Cell. Jul. 25, 1997;90(2):351-60.
Ringquist et al., Translation initiation in *Escherichia coli*: sequences within the ribosome-binding site. Mol Microbiol. May 1992;6(9):1219-29.
Rosenberg et al.,T7 Select® Phage Display System: A Powerful new protein display system based on bacteriophage T7. Innovations. 1996;6:1-6.
Santini et al., Efficient display of an HCV cDNA expression library as C-terminal fusion to the capsid protein D of bacteriophage lambda. J Mol Biol. Sep. 11, 1998;282(1):125-35.
Santoro et al., Directed evolution of the site specificity of Cre recombinase. Proc Natl Acad Sci U S A. Apr. 2, 2002;99(7):4185-90. Epub Mar. 19, 2002.
Schultz et al., Oligo-2'-fluoro-2'-deoxynucleotide N3'-->P5' phosphoramidates: synthesis and properties. Nucleic Acids Res. Aug. 1, 1996;24(15):2966-73.
Scott et al., Searching for peptide ligands with an epitope library. Science. Jul. 27, 1990;249(4967):386-90.
Sices et al., A genetic screen for the isolation and characterization of site-specific proteases. Proc Natl Acad Sci U S A. Mar. 17, 1998;95(6):2828-33.
Sices et al., Rapid genetic selection of inhibitor-resistant protease mutants: clinically relevant and novel mutants of the HIV protease. AIDS Res Hum Retroviruses. Sep. 1, 2001;17(13):1249-55.
Sieber et al., Libraries of hybrid proteins from distantly related sequences. Nat Biotechnol. May 2001;19(5):456-60.
Silva et al., Selective disruption of the DNA polymerase III α-β complex by the umuD gene products. Nucleic Acids Res. Jul. 2012;40(12):5511-22. doi: 10.1093/nar/gks229. Epub Mar. 9, 2012.
Smith, Filamentous fusion phage: novel expression vectors that display cloned antigens on the virion surface. Science. Jun. 14, 1985;228(4705):1315-7.
Stemmer, Rapid evolution of a protein in vitro by DNA shuffling. Nature. Aug. 4, 1994;370(6488):389-91.
Sutter et al., Non-replicating vaccinia vector efficiently expresses bacteriophage T7 RNA polymerase. FEBS Lett. Aug. 28, 1995;371(1):9-12.
Torres et al., Non-integrative lentivirus drives high-frequency cre-mediated cassette exchange in human cells. PLoS One. 2011;6(5):e19794. doi: 10.1371/journal.pone.0019794. Epub May 23, 2011.
Tracewell et al., Directed enzyme evolution: climbing fitness peaks one amino acid at a time. Curr Opin Chem Biol. Feb. 2009;13(1):3-9. doi: 10.1016/j.cbpa.2009.01.017. Epub Feb. 25, 2009.
Tsuji et al., Random multi-recombinant PCR for the construction of combinatorial protein libraries. Nucleic Acids Res. Oct. 15, 2001;29(20):E97.
Tzagoloff et al., The Initial Steps in Infection With Coliphage M13. Virology. Nov. 1964;24:372-80.
Vidal et al., Yeast forward and reverse 'n'-hybrid systems. Nucleic Acids Res. Feb. 15, 1999;27(4):919-29.
Vidal-Aroca et al., One-step high-throughput assay for quantitative detection of beta-galactosidase activity in intact gram-negative bacteria, yeast, and mammalian cells. Biotechniques. Apr. 2006;40(4):433-4, 436, 438 passim.
Voigt et al., Rational evolutionary design: the theory of in vitro protein evolution. Adv Protein Chem. 2000;55:79-160.
Voytek et al., Emergence of a fast-reacting ribozyme that is capable of undergoing continuous evolution. Proc Natl Acad Sci U S A. Sep. 25, 2007;104(39):15288-93. Epub Sep. 18, 2007.
Wang et al., Evolution of new nonantibody proteins via iterative somatic hypermutation. Proc Natl Acad Sci U S A. Nov. 30, 2004;101(48):16745-9. Epub Nov. 19, 2004.
Wang et al., Programming cells by multiplex genome engineering and accelerated evolution. Nature. Aug. 13, 2009;460(7257):894-8. Epub Jul. 26, 2009.
Wharton et al., A new-specificity mutant of 434 repressor that defines an amino acid-base pair contact. Nature. Apr. 30-May 6, 1987;326(6116):888-91.
Wharton et al., Changing the binding specificity of a repressor by redesigning an alpha-helix. Nature. Aug. 15-21, 1985;316(6029):601-5.
Wright et al., Continuous in vitro evolution of catalytic function. Science. Apr. 25, 1997;276(5312):614-7.
Yuan et al., Laboratory-directed protein evolution. Microbiol Mol Biol Rev. Sep. 2005;69(3):373-92.
Zhou et al., Optimization of the Tet-On system for regulated gene expression through viral evolution. Gene Ther. Oct. 2006;13(19):1382-90. Epub May 25, 2006.
EP 09812363.1, Mar. 30, 2012, Extended European Search Report.
EP 16 20 3684, May 26, 2017, Extended European Search Report.
EP 17 16 0955, May 16, 2017, Extended European Search Report.
Cao et al., Characterization of the transgenic rice event TT51-1 and construction of a reference plasmid. J Agric Food Chem. Aug. 24, 2011;59(16):8550-9. doi: 10.1021/jf201699s. Epub Jul. 21, 2011.
Invitation to Pay Additional Fees for PCT/US2018/040692 dated Sep. 12, 2018.
International Search Report and Written Opinion for PCT/US2018/040692 dated Nov. 15, 2018.
International Preliminary Report on Patentability for PCT/US2018/040692 dated Jan. 16, 2020.
Invitation to Pay Additional Fees for PCT/US2018/051557, dated Jan. 4, 2019.
International Preliminary Report on Patentability for PCT/US2018/051557, dated Apr. 2, 2020.
International Search Report and Written Opinion for Application No. PCT/US2019/037216 dated Sep. 4, 2019.
Invitation to Pay Additional Fees for Application No. PCT/US18/48134 dated Nov. 19, 2018.
International Search Report and Written Opinion for Application No. PCT/US18/48134 dated Jan. 22, 2019.
International Preliminary Report on Patentability for Application No. PCT/US18/48134 dated Mar. 5, 2020.
[No Author Listed] NCBI Accession No. XP_015843220.1. C ->U editing enzyme APOBEC-1 [Peromyscus maniculatus bairdii], XP002793540.
[No Author Listed] NCBI Accession No. XP_021505673.1. C ->U editing enzyme APOBEC-1 [Meriones unguiculatus], XP002793541.
Cattaneo et al., SEL1L affects human pancreatic cancer cell cycle and invasiveness through modulation of PTEN and genes related to cell-matrix interactions. Neoplasia. 2005;7(11):1030-1038.
Chen, Clinical uses of botulinum neurotoxins: current indications, limitations and future developments. Toxins (Basel). 2012;4(10):913-939.
Deribe, Mechanistic insights into the role of truncating PREX2 mutations in melanoma. Mol Cell Oncol. 2016;3(3):e1160174.

(56) References Cited

OTHER PUBLICATIONS

Harris et al., Measurement of enzyme activity. Methods Enzymol. 2009;463:57-71.
Kim et al., DJ-1, a novel regulator of the tumor suppressor PTEN. Cancer Cell. 2005;7(3):263-273.
Kim et al., Increasing the genome-targeting scope and precision of base editing with engineered Cas9-cytidine deaminase fusions. Nature Biotechnology; Feb. 13, 2007; 35(4): 371-376.
Laskowska et al., IbpA and IbpB, the new heat-shock proteins, bind to endogenous *Escherichia coli* proteins aggregated intracellularly by heat shock. Biochimie. 1996;78(2):117-22.
Lu, The destructive effect of botulinum neurotoxins on the SNARE protein: SNAP-25 and synaptic membrane fusion. PeerJ. 2015;3:e1065. Published Jun. 30, 2015.
Masuyer et al., Engineered botulinum neurotoxins as new therapeutics. Annu Rev Pharmacol Toxicol. 2014;54:27-51.
Mihai et al., PTEN inhibition improves wound healing in lung epithelia through changes in cellular mechanics that enhance migration. Am J Physiol Lung Cell Mol Physiol. 2012;302(3):L287-L299.
Oeemig et al., Solution structure of DnaE intein from Nostoc punctiforme: structural basis for the design of a new split intein suitable for site-specific chemical modification. FEBS Lett. May 6, 2009;583(9):1451-6.
Rawlings et al., MEROPS: the database of proteolytic enzymes, their substrates and inhibitors. Nucleic Acids Res. Jan. 2014;42(Database issue):D503-9.
Wang et al., Continuous directed evolutions of proteins with improved soluble expression. Nature Chemical Biology. Nat Publishing Group. Aug. 20, 2018; 14(10):972-980.
Webb et al., Production of catalytically inactive BoNT/A1 holoprotein and comparison with BoNT/A1 subunit vaccines against toxin subtypes A1, A2, and A3. Vaccine. 2009;27(33):4490-4497.
U.S. Appl. No. 13/062,098, filed Apr. 4, 2011, Liu et al.
U.S. Appl. No. 14/704,226, filed May 5, 2015, Liu et al.
U.S. Appl. No. 15/713,403, filed Sep. 22, 2017, Liu et al.
U.S. Appl. No. 13/996,208, filed Jun. 20, 2013, Liu et al.
U.S. Appl. No. 15/188,627, filed Jun. 21, 2016, Liu et al.
U.S. Appl. No. 16/410,767, filed May 13, 2019, Liu et al.
U.S. Appl. No. 14/320,519, filed Jun. 30, 2014, Liu et al.
U.S. Appl. No. 14/913,458, filed Feb. 22, 2016, Liu et al.
U.S. Appl. No. 16/266,937, filed Feb. 4, 2019, Liu et al.
U.S. Appl. No. 15/112,759, filed Jul. 20, 2016, Liu et al.
U.S. Appl. No. 16/238,386, filed Jan. 2, 2019, Liu et al.
U.S. Appl. No. 15/217,839, filed Jul. 22, 2016, Liu et al.
U.S. Appl. No. 15/567,312, filed Oct. 17, 2017, Liu et al.
U.S. Appl. No. 15/748,053, filed Jan. 26, 2018, Liu et al.
U.S. Appl. No. 15/216,844, filed Jul. 22, 2016, Liu et al.
U.S. Appl. No. 16/521,371, filed Jul. 24, 2019, Liu et al.
International Search Report and Written Opinion for PCT/US2014/052231, dated Jan. 30, 2015.
Preliminary Report on Patentability for PCT/US2014/052231, dated Mar. 3, 2016.
International Preliminary Report on Patentability for PCT/US2018/14867 dated Aug. 1, 2019.
International Search Report and Written Opinion for PCT/US2018/051557, dated Feb. 25, 2019.
Guilinger et al., Broad specificity profiling of TALENs results in engineered nucleases with improved DNA-cleavage specificity. Nat Methods. Apr. 2014;11(4):429-35. doi: 10.1038/nmeth.2845. Epub Feb. 16, 2014.
McNaughton et al., Mammalian cell penetration, siRNA transfection, and DNA transfection by supercharged proteins. Proc Natl Acad Sci U S A. Apr. 14, 2009;106(15):6111-6. doi: 10.1073/pnas.0807883106. Epub Mar. 23, 2009.
Miller et al., A TALE nuclease architecture for efficient genome editing. Nat Biotechnol. Feb. 2011;29(2):143-8. doi:10.1038/nbt.1755. Epub Dec. 22, 2010.
Mussolino et al., TALE nucleases: tailored genome engineering made easy. Curr Opin Biotechnol. Oct. 2012;23(5):644-50. doi: 10.1016/j.copbio.2012.01.013. Epub Feb. 17, 2012.
Yamamoto et al., Virological and immunological bases for HIV-1 vaccine design. Uirusu 2007;57(2):133-139. https://doi.org/10.2222/jsv.57.133.
U.S. Appl. No. 16/804,228, filed Feb. 28, 2020, Liu et al.
U.S. Appl. No. 16/628,456, filed Jan. 3, 2020, Liu et al.
U.S. Appl. No. 16/648,162, filed Mar. 17, 2020, Liu et al.
U.S. Appl. No. 16/641,630, filed Feb. 24, 2020, Liu et al.
International Search Report and Written Opinion for PCT/US2018/044242, dated Nov. 21, 2018.
Komor et al., Programmable editing of a target base in genomic DNA without double-stranded DNA cleavage. Nature. May 19, 2016;533(7603):420-4. doi: 10.1038/nature17946. Epub Apr. 20, 2016.

* cited by examiner

| T7 lysozyme | Target protease substrate | T7 RNAP | |
|---|---|---|---|
| ...**NELVTSDR**GSGGGASGGAG | **ENLYFQS**–AGGSAGSGAGG | **NTINIAKN**... | TEV |
| ...**NELVTSDR**GSGGGASGG | **TEDVVCCSMSY**GGSAGSGAGG | **NTINIAKN**... | HCV |
| ...**NELVTSDR**GSGGGASGGA– | **LEVLFQGP**–GGSAGSGAGG | **NTINIAKN**... | HRV |

Library 36

HNLYFQSA

| Substrate _NLYFQ/S | E | **H** | E' | **H** | E | **H** |
|---|---|---|---|---|---|---|
| Protease | NA | NA | WT | WT | I138T, N171D, N176T | I138T, N171D, N176T |

TEV_L2A:
D127A, S135F, T146S, D148P, F162S, N171D, N176T, N177M, V209M, W211I, M218F, K229E

TEV_L1:
D127A, S135F, T146A, D148P, N176I, N177R, V209M, W211I, M218F, K229E

| Substrate | TEDVVC CSMSY | TEDVaC CSMSY | TEDVgS CCMSY | QEREVP CHRPS | QEREaP CHRPS | QEREgP CHRPS | LADDER | TEDVVC CSMSY | TEDVaC CSMSY | TEDVgS CCMSY | QEREVP CHRPS | QEREaP CHRPS | QEREgP CHRPS |
|---|---|---|---|---|---|---|---|---|---|---|---|---|---|
| Protease | WT | WT | WT | WT | WT | WT | | I132L, K136L, S159H | I132L, K136L, S159H | I132L, K136L, S159H | I132L, K136L, S159H | I132L, K136L, S159H | I132L, K136L, S159H |

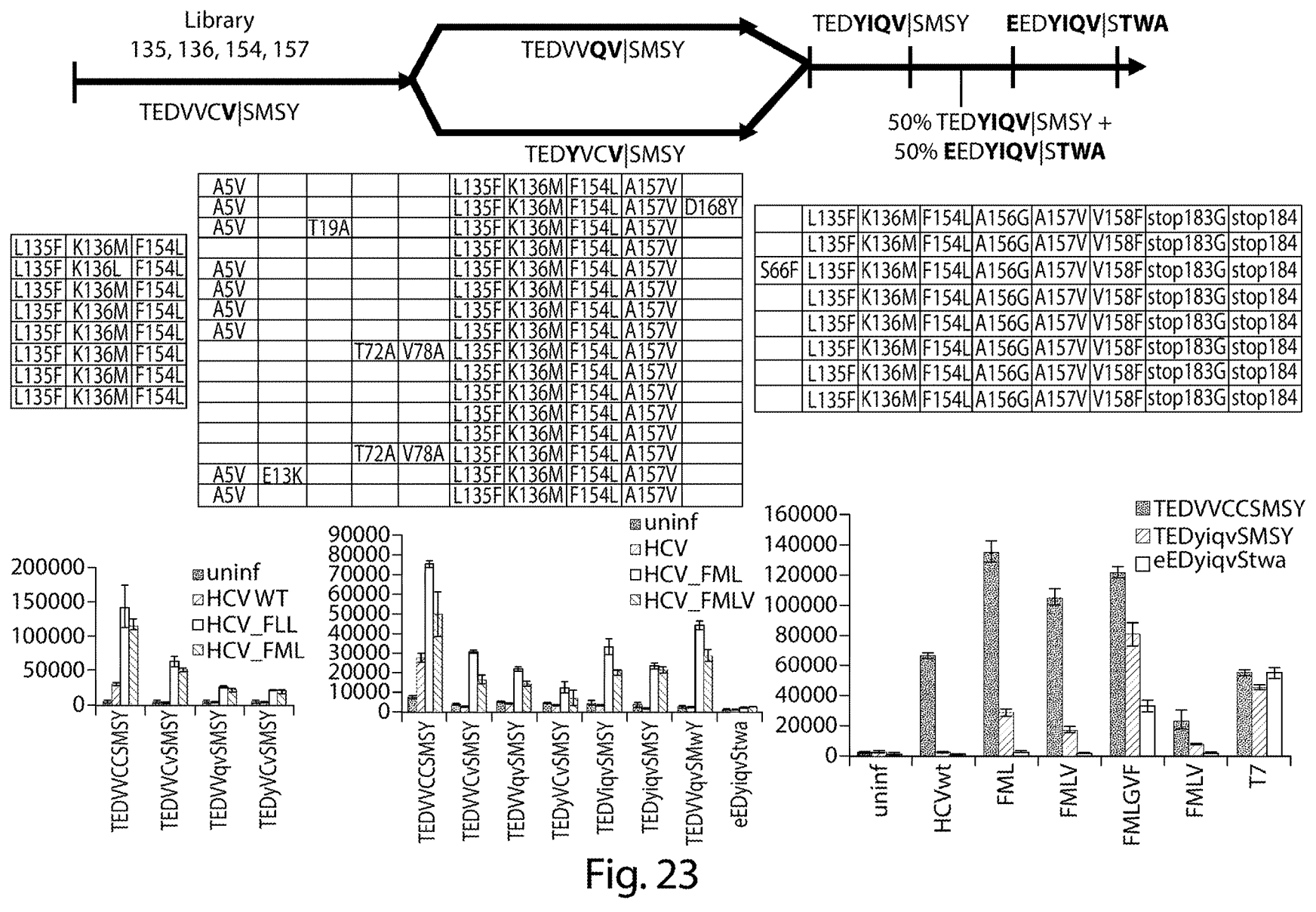

Library
135, 136, 154, 157

TEDVVCV|SMSY

TEDVVQV|SMSY

TEDYVCV|SMSY

TEDYIQV|SMSY

EEDYIQV|STWA

50% TEDYIQV|SMSY +
50% EEDYIQV|STWA

| | | |
|---|---|---|
| L135F | K136M | F154L |
| L135F | K136L | F154L |
| L135F | K136M | F154L |
| L135F | K136M | F154L |
| L135F | K136M | F154L |
| L135F | K136M | F154L |
| L135F | K136M | F154L |
| L135F | K136M | F154L |

| | | | | | | | | | |
|---|---|---|---|---|---|---|---|---|---|
| A5V | | | | | L135F | K136M | F154L | A157V | |
| A5V | | | | | L135F | K136M | F154L | A157V | D168Y |
| A5V | | T19A | | | L135F | K136M | F154L | A157V | |
| | | | | | L135F | K136M | F154L | A157V | |
| A5V | | | | | L135F | K136M | F154L | A157V | |
| A5V | | | | | L135F | K136M | F154L | A157V | |
| A5V | | | | | L135F | K136M | F154L | A157V | |
| A5V | | | | | L135F | K136M | F154L | A157V | |
| | | | T72A | V78A | L135F | K136M | F154L | A157V | |
| | | | | | L135F | K136M | F154L | A157V | |
| | | | | | L135F | K136M | F154L | A157V | |
| | | | | | L135F | K136M | F154L | A157V | |
| | | | | | L135F | K136M | F154L | A157V | |
| | | | T72A | V78A | L135F | K136M | F154L | A157V | |
| A5V | E13K | | | | L135F | K136M | F154L | A157V | |
| A5V | | | | | L135F | K136M | F154L | A157V | |

| | | | | | | | | |
|---|---|---|---|---|---|---|---|---|
| | L135F | K136M | F154L | A156G | A157V | V158F | stop183G | stop184 |
| | L135F | K136M | F154L | A156G | A157V | V158F | stop183G | stop184 |
| S66F | L135F | K136M | F154L | A156G | A157V | V158F | stop183G | stop184 |
| | L135F | K136M | F154L | A156G | A157V | V158F | stop183G | stop184 |
| | L135F | K136M | F154L | A156G | A157V | V158F | stop183G | stop184 |
| | L135F | K136M | F154L | A156G | A157V | V158F | stop183G | stop184 |
| | L135F | K136M | F154L | A156G | A157V | V158F | stop183G | stop184 |
| | L135F | K136M | F154L | A156G | A157V | V158F | stop183G | stop184 |

200000
150000
100000
50000
0
uninf
HCV WT
HCV_FLL
HCV_FML
TEDVVCCSMSY
TEDVVCvSMSY
TEDVVqvSMSY
TEDyVCvSMSY 90000
80000
70000
60000
50000
40000
30000
20000
10000
0
uninf
HCV
HCV_FML
HCV_FMLV
TEDVVCCSMSY
TEDVVCvSMSY
TEDVVqvSMSY
TEDyVCvSMSY
TEDViqvSMSY
TEDyiqvSMSY
TEDVVqvSMwY
eEDyiqvStwa 160000
140000
120000
100000
80000
60000
40000
20000
0
TEDVVCCSMSY
TEDyiqvSMSY
eEDyiqvStwa
uninf
HCVwt
FML
FMLV
FMLGVF
FMLV
T7

Fig. 23

EVOLUTION OF PROTEASES

RELATED APPLICATION

This application is a national stage filing under 35 U.S.C. § 371 of international PCT application, PCT/US2015/057012, filed Oct. 22, 2015, which claims priority under 35 U.S.C. § 119(e) to U.S. provisional patent application, U.S. Ser. No. 62/067,194, filed Oct. 22, 2014, each of which is incorporated herein by reference.

GOVERNMENT SUPPORT

This invention was made with Government support under grant T32 GM008313 awarded by the National Institutes of Health (NIH) and grants HR0011-11-2-0003 and N66001-12-C-4207 awarded by the Defense Advanced Research Projects Agency (DARPA). The Government has certain rights in this invention.

BACKGROUND

Proteases are ubiquitous enzymes that play important roles in many aspects of cell and tissue biology. Proteases can also be harnessed for biotechnological and biomedical applications. Among the more than 600 naturally occurring proteases that have been described) are enzymes that have proven to be important catalysts of industrial processes, essential tools for proteome analysis, and life-saving pharmaceuticals[2-5]. Recombinant human proteases including thrombin, factor VIIa, and tissue plasminogen activator are widely used drugs for the treatment of blood clotting diseases[4]. In addition, the potential of protease-based therapeutics to address disease in a manner analogous to that of antibody drugs,[6,7] but with catalytic turnover, has been recognized for several decades[4,8].

Natural proteases, however, typically target only a narrowly defined set of substrates, limiting their therapeutic potential. The directed evolution of proteases in principle could generate enzymes with tailor-made specificities, but laboratory-evolved proteases are frequently non-specific, weakly active, or only modestly altered in their substrate specificity, limiting their utility[9-14].

In addition to their importance as current and future therapeutic agents, proteases have also proven to be major drug targets for diseases including cardiovascular illness, infectious disease, and cancer[15,16]. While drug specificity and potency are characterized and optimized during preclinical studies, the evolution of drug resistance is often not well understood until it arises in patients, despite the strong relationship between drug resistance vulnerability and a lack of therapeutic efficacy. For example, resistance to HIV and HCV protease inhibitors can arise in as few as two days of clinical use[17] and frequently leads to viral rebound and poor treatment outcomes[18-21]. The speed with which drug resistance can arise in the clinic endangers patients and puts years of drug development efforts prior to such a determination at risk.

Characterizing the potential of protease inhibitors to be overcome by the evolution of drug resistance using methods such as mammalian cell culture, animal models, or yeast display-based laboratory evolution is time- and labor-intensive[22,23]. As a result, identifying drug resistance vulnerabilities of early-stage preclinical candidates is not common practice.

SUMMARY

The laboratory evolution of protease enzymes has the potential to generate proteases with therapeutically relevant specificities, and to assess the vulnerability of protease inhibitor drug candidates to the evolution of drug resistance. Some aspects of this disclosure describe a system for the continuous directed evolution of proteases using phage-assisted continuous evolution (PACE) that links the proteolysis of a target peptide to phage propagation through a protease-activated RNA polymerase (PA-RNAP). Some aspects of this disclosure describe the engineering of an expression system that directly links protease activity to phage propagation, for example, by fusing a transcriptional activator to an inhibitory domain via a protease-cleavable linker. The continuous evolution technology provided herein is useful for evolving proteases with altered substrate preferences, specificities, and cleavage efficiencies. In addition, the technology provided herein can also be used to analyze how therapeutically targeted proteases acquire resistance to therapeutic protease inhibitors, to evaluate a candidate protease inhibitor regarding the potential of the target protease to develop resistance, and to design improved protease inhibitors that are not rendered ineffective simply as a result of one or two mutations in their target protease.

Phage-assisted continuous evolution (PACE) can serve as a rapid, high-throughput method to evolve a protease to reveal resistance to protease inhibitor drug candidates, analogous to previous uses of stepwise protein evolution to study antibiotic resistance[24]. One advantage of the PACE technology described herein is that both the time and human effort required to evolve a protease or to evaluate the likelihood of protease inhibitor resistance to develop are dramatically decreased as compared to conventional iterative evolution methods.

The general concept of PACE technology has been described, for example in International PCT Application, PCT/US2009/056194, filed Sep. 8, 2009, published as WO 2010/028347 on Mar. 11, 2010; International PCT Application, PCT/US2011/066747, filed Dec. 22, 2011, published as WO 2012/088381 on Jun. 28, 2012; and U.S. Application, U.S. Ser. No. 13/922,812, filed Jun. 20, 2013, each of which is incorporated herein by reference. During PACE, a phage vector carrying a gene encoding the protease of interest replicates in a flow of host cells through a fixed-volume vessel (a "lagoon"). For example, in some embodiments of PACE described herein, a population of bacteriophage vectors replicates in a continuous flow of bacterial host cells through the lagoon, wherein the flow rate of the host cells is adjusted so that the average time a host cell remains in the lagoon is shorter than the average time required for host cell division, but longer than the average life cycle of the vector, e.g., shorter than the average M13 bacteriophage life cycle. As a result, the population of vectors replicating in the lagoon can be varied by inducing mutations, and then enriching the population for desired variants by applying selective pressure, while the host cells do not effectively replicate in the lagoon.

Once the appropriate selective pressure is applied, for example, by linking a desired protease activity to the production of a gene for the generation of infectious phage particles as described in more detail elsewhere herein, phage with genes encoding proteases with the desired target activity acquire a selective advantage and thus replicate preferentially. For example, in the context of M13 phage PACE, selective pressure can be engineered by linking a desired target activity to the production of pIII, an essential component in the bacteriophage life cycle[25]. Because the lagoon is continuously diluted by a constant influx of fresh host cells, phage encoding inactive variants that do not trigger expression of the gene required for the generation of infectious phage particles are not packaged into infectious phage particles and are rapidly diluted out of the lagoon. Dilution occurs faster than cell division but slower than phage replication, ensuring that mutations only accumulate in the phage genome. Because evolution during PACE can take place continuously without researcher intervention, hundreds of rounds of evolution can be performed in a single PACE experiment within days or weeks, as compared to the performance of typically a single round of iterative evolution methods per day or per week.

Some aspects of this disclosure are based on the recognition that PACE is well-suited for the directed evolution of proteases, which, depending on the circumstances, may require many successive mutations to remodel complex networks of contacts with polypeptide substrates[26,27]. Moreover, the speed and efficiency of PACE may enable the rapid identification of mutations that confer resistance to protease inhibitors. Previously, PACE has been reported to evolve RNA polymerase enzymes[25,28-30]. The development of new reagents and vectors that efficiently link protease activity to phage replication efficiency as described herein enable the rapid evolution of proteases with desired characteristics and the identification of protease mutations that confer resistance to protease inhibitors. In addition, this disclosure provides method for evaluating candidate protease inhibitors for the likelihood of a target protease developing a resistance, which may hamper clinical application of the inhibitor. Such evaluations cannot readily be performed with conventional techniques. As a result, resistances of proteases that are targeted by therapeutic protease inhibitors are often only recognized after an inhibitor is used in the clinic. The technology provided herein can be used to interrogate resistance formation to protease inhibitors before a candidate inhibitor is developed in a clinical setting, thus streamlining the evaluation of candidate protease inhibitors for drug development.

The utility of the PACE technology provided herein in the identification of resistance-mediating protease mutations is demonstrated herein by two exemplary protease PACE experiments, that evolve and analyze hepatitis C virus (HCV) protease variants in the presence of danoprevir or asunaprevir, two hepatitis C virus (HCV) protease inhibitor drug candidates in clinical trials. The evolved HCV protease variants exhibited up to 30-fold drug resistance after only 1 to 3 days of PACE. Predominant mutations in resistant variants were identified, and these predominant mutations matched those observed to arise in human patients treated with danoprevir or asunaprevir, demonstrating that PACE of a protease can rapidly identify the vulnerabilities of drug candidates to the evolution of clinically relevant drug resistance.

Some aspects of this disclosure provide methods for protease evolution. In some embodiments, such methods comprise providing a phage encoding a protease of interest, contacting a population of host cells with the phage, incubating the phage in a flow of host cells under circumstances that allow for the phage to mutate, replicate in the host cells, and infect fresh host cells. Typically, the host cells harbor an engineered expression system that links expression of a gene required for the generation of infectious phage particles (e.g., pIII) to a desired protease activity to be evolved, and thus confers a selective advantage to those phage encoding mutated variants of the protease that exhibit the desired activity in the pool of replicating and mutating phages, resulting in an enrichment of desired mutations over time, as such mutations replicate more efficiently in and escape dilution and washout from the flow of host cells. The methods provided herein may also include a step of isolating a replicated vector from the host cell population at the end of the PACE experiment, encoding a mutated version of a protease having a desired activity.

The linkage of a desired protease activity to a selective replication advantage of phage encoding protease variants exhibiting such desired activity is typically provided by an expression system in the host cells in which the expression level of a gene required for the generation of infectious phage depends on the desired protease activity. This can be achieved, for example, by providing a gene required for the generation of infectious phage particles in the host cells under the control of a conditional promoter, and additionally providing a transcriptional activator in the host cells that can drive transcription from the conditional promoter. In some embodiments, the transcriptional activator is provided in an inactive form that is converted into an active form by the desirable protease activity. For example, in some embodiments, a transcriptional activator, such as an RNA polymerase, is provided as a fusion protein with a transcriptional inhibitor, for example, an RNA-pol lysozyme, wherein the activator and inhibitor domains are connected by a linker comprising a protease cleavage site. Upon cleavage of the linker by an evolved protease, the inhibition of the transcriptional activator is released, and the transcriptional activator can drive expression of the gene for the generation of infectious phage particles.

Some aspects of this disclosure provide methods for generating protease variants that are resistant to a protease inhibitor. Such methods are similar in general to the protease-evolution methods described herein, but protease evolution is typically performed in the presence of a protease inhibitor. The methods may include a step of isolating mutated variants of a protease at the end of the PACE experiment and analyzing mutations that confer resistance to the protease inhibitor. In some embodiments, the methods comprise analyzing a plurality of resistant protease variants and determining common or dominant mutations amongst such variants to determine which mutations can be causally linked to resistance to the inhibitor. In some embodiments, the methods comprise comparing the evolution of inhibitor-resistant protease variants using a plurality of candidate inhibitors. For example, in some embodiments, the evolution of inhibitor-resistant protease variants is determined in several parallel experiments using the same protease but different protease inhibitors. In some embodiments, the methods include selecting an inhibitor from a plurality of inhibitors based on a PACE experiment yielding no resistant protease variants to the inhibitor or based on the selected inhibitor having the highest number of mutations required for a target protease to gain resistance.

Some aspects of this disclosure provide fusion proteins that link protease activity to transcriptional activation. Typically, such fusion proteins comprise a transcriptional activator in an inactive form, for example, fused to an inhibitor of the transcriptional activator via a linker comprising a protease cleavage site. In some embodiments, proteolytic cleavage of the linker results in release of the inhibitor from the transcriptional activator and thus for a release of the inhibition of the activator. Some aspects of this disclosure provide nucleic acid constructs encoding a fusion protein as provided herein.

Some aspects of this disclosure provide mutagenesis plasmids that enhance the mutagenesis rate in the host cells during a PACE experiment. In some embodiments, the mutagenesis plasmids comprise a gene expression cassette encoding a component of *E. coli* translesion synthesis polymerase V, a deoxyadenosine methylase, and/or a hemimethylated-GATC binding domain, or any combination thereof. In some embodiments, the component of *E. coli* translesion synthesis polymerase V is umuC. In some embodiments, the deoxyadenosine methylase is dam. In some embodiments, the hemimethylated-GATC binding domain is seqA.

Some aspects of this disclosure provide kits comprising reagents and materials useful for the use of PACE for protease evolution. In some embodiments, the kit comprises (a) a phage vector encoding a phage backbone, e.g., an M13 phage backbone, and a multiple cloning site for insertion of a nucleic acid sequence encoding a protease. In some embodiments, the vector or a replication product thereof can be packaged into infectious phage particles in the presence of other phage functions by suitable host cells, but lacks at least one gene required for the generation of infectious particles. In some embodiments, the kit comprises (b) an accessory plasmid comprising a nucleic acid sequence encoding the at least one gene of interest under the control of a promoter that is activated by a transcriptional activator. In some embodiments, the kit comprises (c) an expression construct encoding a fusion protein of the transcriptional activator that activates the promoter of (b) fused to an inhibitor of the transcriptional activator via a linker, and a multiple cloning site for insertion of a nucleic acid sequence encoding a protease cleavage site. In some embodiments, the kit further comprises a helper phage providing all phage functions except for the at least one gene required for the generation of infectious phage particles provided by the accessory plasmid of (b). In some embodiments, the kit comprises suitable host cells. In some embodiments, the kit further comprises a mutagenesis plasmid.

Some aspects of this disclosure provide a system for protease evolution, comprising an apparatus or bioreactor through which a flow of host cells can be directed at a flow rate that results in an average time of the host cells remaining in the lagoon that is sufficient for a phage vector to replicate, but not sufficiently long for the host cell to divide and proliferate, wherein the host cells comprise an expression system linking the expression level of a gene required for the generation of infectious phage to a desired protease activity as described herein. In some embodiments, the host cells in the apparatus comprise a gene required for the generation of infectious phage particles under the control of a conditional promoter, for example, on an accessory plasmid. In some embodiment, the host cells further comprise a transcriptional activator that can drive transcription from the conditional promoter, and in some such embodiments, the transcriptional activator is provided in an inactive form that is converted into an active form by the desirable protease activity.

The summary above is meant to illustrate and outline, in a non-limiting manner, some of the embodiments, advantages, features, and uses of the technology disclosed herein. The disclosure is, however, not limited to the embodiments described in the summary above. Other embodiments, advantages, features, and uses of the technology disclosed herein will be apparent from the Detailed Description, the Drawings, the Examples, and the Claims.

BRIEF DESCRIPTION OF THE DRAWINGS

FIG. 23. Directed evolution of HCV protease variants that cleave macaque MAVS. SEQ ID NOs: 75-81 are shown in the top panel, and SEQ ID NOs: 82-96 are shown in the bottom panels (left to right).

DEFINITIONS

Figures 1A, 1B:
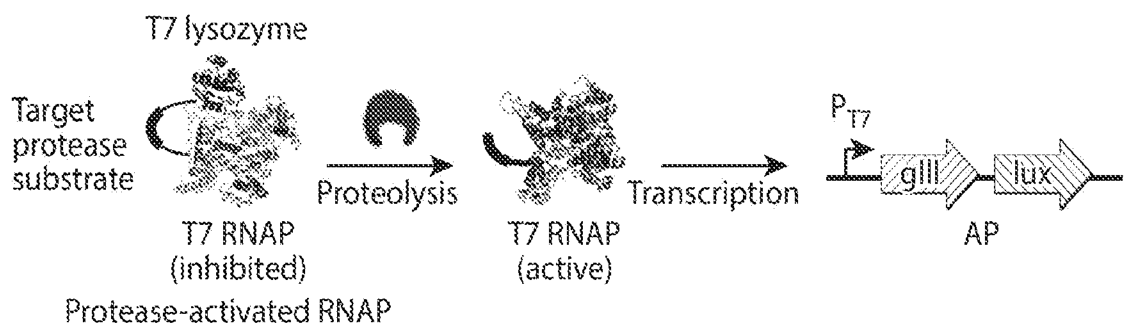
FIGS. 1A-D. Development of a system to link protease activity to gene expression. (A) Protease-activated RNA polymerase (PA-RNAP). T7 RNAP is fused to the natural inhibitor T7 lysozyme through a linker containing a protease target substrate sequence. While the linker is intact, the complex preferentially adopts the lysozyme-bound, RNAP-inactive state. Proteolysis of the target sequence favors dissociation of the complex, freeing active T7 RNAP to transcribe genes downstream of the T7 promoter. This example used an accessory plasmid (AP) in which the T7 promoter drives a tandem gIII-luciferase (lux) cassette. (B) Sequences of the protein linkers containing a target protease substrate used for each PA-RNAP, with T7 lysozyme residues in blue, protease substrates in red, T7 RNAP residues in green, and linker regions in black. SEQ ID NOs: 72-74 are shown. (C) Plasmids used for protease PACE. An accessory plasmid (AP) that has gIII and luciferase (lux) under the control of the T7 promoter serves as the source of gIII in the cells. A complementary plasmid (CP) constitutively expresses a PA-RNAP variant with a protease target substrate sequence embedded in the linker. (D) PA-RNAP gene expression response in *E. coli* cells. Host cells were transformed with (i) an AP containing the T7 promoter driving gIII-lux; (ii) a CP that constitutively expresses a PA-RNAP including the TEV protease substrate, the HCV protease substrate, or the HRV protease substrate; and (iii) a plasmid that expresses TEV protease (orange bars), HCV protease (purple bars), or HRV protease (gray bars). Gene expression is activated only when the expressed protease cleaves the amino acid sequence on the PA-RNAP sensor. The luminescence experiment was performed in triplicate with error bars indicating the standard deviation.

The term "accessory plasmid," as used herein, refers to a plasmid comprising a gene required for the generation of infectious viral particles under the control of a conditional promoter. In the context of continuous evolution of proteases described herein, transcription from the conditional promoter of the accessory plasmid is typically activated by a function of the protease to be evolved. Accordingly, the accessory plasmid serves the function of conveying a competitive advantage to those viral vectors in a given population of viral vectors that carry a gene of interest able to activate the conditional promoter. Only viral vectors carrying an "activating" version of the protease of interest will be able to induce expression of the gene required to generate infectious viral particles in the host cell, and, thus, allow for packaging and propagation of the viral genome in the flow of host cells. Vectors carrying non-activating versions of the protease of interest, on the other hand, will not induce expression of the gene required to generate infectious viral vectors, and, thus, will not be packaged into viral particles that can infect fresh host cells.

The term "cellstat," as used herein, refers to a culture vessel comprising host cells, in which the number of cells is substantially constant over time.

The term "continuous evolution," as used herein, refers to an evolution process, in which a population of nucleic acids encoding a protease of interest is subjected to multiple rounds of (a) replication, (b) mutation, and (c) selection to produce a desired evolved protease that is different from the original protease of interest, for example, in that it cuts a target site not cut by the original protease, cuts its target site in the presence of an inhibitor of the original protease, or cuts its target site at an increased efficiency. The multiple rounds can be performed without investigator intervention, and the steps (a)-(c) can be carried out simultaneously. Typically, the evolution procedure is carried out in vitro, for example, using cells in culture as host cells. In general, a continuous evolution process provided herein relies on a system in which a gene encoding a protease of interest is provided in a nucleic acid vector that undergoes a life-cycle including replication in a host cell and transfer to another host cell, wherein a critical component of the life-cycle is deactivated and reactivation of the component is dependent upon an activity of the protease of interest that is a result of a mutation in the nucleic acid vector.

The term "flow", as used herein in the context of host cells, refers to a stream of host cells, wherein fresh host cells not harboring the transfer vector (e.g., the viral vector encoding the protease of interest) are being introduced into a host cell population, for example, a host cell population in a lagoon, remain within the population for a limited time, and are then removed from the host cell population. In a simple form, a host cell flow may be a flow through a tube, or a channel, for example, at a controlled rate. In other embodiments, a flow of host cells is directed through a lagoon that holds a volume of cell culture media and comprises an inflow and an outflow. The introduction of fresh host cells may be continuous or intermittent and removal may be passive, e.g., by overflow, or active, e.g., by active siphoning or pumping. Removal further may be random, for example, if a stirred suspension culture of host cells is provided, removed liquid culture media will contain freshly introduced host cells as well as cells that have been a member of the host cell population within the lagoon for some time. Even though, in theory, a cell could escape removal from the lagoon indefinitely, the average host cell will remain only for a limited period of time within the lagoon, which is determined mainly by the flow rate of the culture media (and suspended cells) through the lagoon. Since the viral vectors replicate in a flow of host cells, in which fresh, uninfected host cells are provided while infected cells are removed, multiple consecutive viral life cycles can occur without investigator interaction, which allows for the accumulation of multiple advantageous mutations in a single evolution experiment.

The term "fresh," as used herein in the context of host cells, and used interchangeably with the terms "non-infected" or "uninfected" in the context of host cells of viral vectors, refers to a host cell that does not harbor the vector or, in the context of viral vectors, has not been infected by the viral vector comprising a gene encoding a protease of interest as used in a continuous evolution process provided herein. A fresh host cell can, however, have been infected by a viral vector unrelated to the vector to be evolved or by a vector of the same or a similar type but not carrying the gene of interest.

The term "fusion protein" as used herein refers to a hybrid polypeptide which comprises protein sequences or domains from at least two different proteins. One protein may be located at the amino-terminal (N-terminal) portion of the fusion protein or at the carboxy-terminal (C-terminal) protein thus forming an "amino-terminal fusion protein" or a "carboxy-terminal fusion protein," respectively. In the context of protease evolution using a transcriptional activator fused to an inhibitor, a fusion protein typically comprises a transcriptional activator domain that can bind to and drive gene expression from the conditional promoter of the accessory plasmid. Such a transcriptional activator domain may be able to drive gene expression by itself (e.g., an RNA polymerase domain) or may recruit transcriptional machinery to the promoter (e.g., a transcription factor domain). The fusion proteins provided herein may be produced by any method known in the art. For example, the proteins provided herein may be produced via recombinant methods. Methods for recombinant protein generation and expression are well known and include those described by Green and Sambrook, *Molecular Cloning: A Laboratory Manual* ($4^{th}$ ed., Cold Spring Harbor Laboratory Press, Cold Spring Harbor, N.Y. (2012)), the entire contents of which are incorporated herein by reference.

The term "gene of interest" or "gene encoding a protease of interest," as used herein, refers to a nucleic acid construct comprising a nucleotide sequence encoding a gene product, e.g., a protease, of interest to be evolved in a continuous evolution process as provided herein. The term includes any variations of a gene of interest that are the result of a continuous evolution process according to methods provided herein. For example, in some embodiments, a gene of interest is a nucleic acid construct comprising a nucleotide sequence encoding a protease to be evolved, cloned into a viral vector, for example, a phage genome, so that the expression of the encoding sequence is under the control of one or more promoters in the viral genome. In other embodiments, a gene of interest is a nucleic acid construct comprising a nucleotide sequence encoding a protease to be evolved and a promoter operably linked to the encoding sequence. When cloned into a viral vector, for example, a phage genome, the expression of the encoding sequence of such genes of interest is under the control of the heterologous promoter and, in some embodiments, may also be influenced by one or more promoters comprised in the viral genome.

The term "helper phage," as used herein interchangeable with the terms "helper phagemid" and "helper plasmid," refers to a nucleic acid construct comprising a phage gene required for the phage life cycle, or a plurality of such genes, but lacking a structural element required for genome packaging into a phage particle. For example, a helper phage may provide a wild-type phage genome lacking a phage origin of replication. In some embodiments, a helper phage is provided that comprises a gene required for the generation of phage particles, but lacks a gene required for the generation of infectious particles, for example, a full-length pIII gene. In some embodiments, the helper phage provides only some, but not all, genes for the generation of infectious phage particles. Helper phages are useful to allow modified phages that lack a gene for the generation of infectious phage particles to complete the phage life cycle in a host cell. Typically, a helper phage will comprise the genes for the generation of infectious phage particles that are lacking in the phage genome, thus complementing the phage genome. In the continuous evolution context, the helper phage typically complements the selection phage, but both lack a phage gene required for the production of infectious phage particles.

The terms "high copy number plasmid" and "low copy number plasmid" are art-recognized, and those of skill in the art will be able to ascertain whether a given plasmid is a high or low copy number plasmid. In some embodiments, a low copy number accessory plasmid is a plasmid exhibiting an average copy number of plasmid per host cell in a host cell population of about 5 to about 100. In some embodiments, a very low copy number accessory plasmid is a plasmid exhibiting an average copy number of plasmid per host cell in a host cell population of about 1 to about 10. In some embodiments, a very low copy number accessory plasmid is a single-copy per cell plasmid. In some embodiments, a high copy number accessory plasmid is a plasmid exhibiting an average copy number of plasmid per host cell in a host cell population of about 100 to about 5000.

The term "host cell," as used herein, refers to a cell that can host, replicate, and transfer a phage vector useful for a continuous evolution process as provided herein. In embodiments where the vector is a viral vector, a suitable host cell is a cell that can be infected by the viral vector, can replicate it, and can package it into viral particles that can infect fresh host cells. A cell can host a viral vector if it supports expression of genes of viral vector, replication of the viral genome, and/or the generation of viral particles. One criterion to determine whether a cell is a suitable host cell for a given viral vector is to determine whether the cell can support the viral life cycle of a wild-type viral genome that the viral vector is derived from. For example, if the viral vector is a modified M13 phage genome, as provided in some embodiments described herein, then a suitable host cell would be any cell that can support the wild-type M13 phage life cycle. Suitable host cells for viral vectors useful in continuous evolution processes are well known to those of skill in the art, and the disclosure is not limited in this respect.

The term "infectious viral particle," as used herein, refers to a viral particle able to transport the viral genome it comprises into a suitable host cell. Not all viral particles are able to transfer the viral genome to a suitable host cell. Particles unable to accomplish this are referred to as non-infectious viral particles. In some embodiments, a viral particle comprises a plurality of different coat proteins, wherein one or some of the coat proteins can be omitted without compromising the structure of the viral particle. In some embodiments, a viral particle is provided in which at least one coat protein cannot be omitted without the loss of infectivity. If a viral particle lacks a protein that confers infectivity, the viral particle is not infectious. For example, an M13 phage particle that comprises a phage genome packaged in a coat of phage proteins (e.g., pVIII) but lacks pIII (protein III) is a non-infectious M13 phage particle because pIII is essential for the infectious properties of M13 phage particles.

The term "lagoon," as used herein, refers to a culture vessel or bioreactor through which a flow of host cells is directed. When used for a continuous evolution process as provided herein, a lagoon typically holds a population of host cells and a population of viral vectors replicating within the host cell population, wherein the lagoon comprises an outflow through which host cells are removed from the lagoon and an inflow through which fresh host cells are introduced into the lagoon, thus replenishing the host cell population.

The term "mutagen," as used herein, refers to an agent that induces mutations or increases the rate of mutation in a given biological system, for example, a host cell, to a level above the naturally occurring level of mutation in that system. Some exemplary mutagens useful for continuous evolution procedures are provided elsewhere herein, and other useful mutagens will be evident to those of skill in the art. Useful mutagens include, but are not limited to, ionizing radiation, ultraviolet radiation, base analogs, deaminating agents (e.g., nitrous acid), intercalating agents (e.g., ethidium bromide), alkylating agents (e.g., ethylnitrosourea), transposons, bromine, azide salts, psoralen, benzene,3-Chloro-4-(dichloromethyl)-5-hydroxy-2(5H)-furanone (MX) (CAS no. 77439-76-0), O,O-dimethyl-S-(phthalimidomethyl)phosphorodithioate (phos-met) (CAS no. 732-11-6), formaldehyde (CAS no. 50-00-0), 2-(2-furyl)-3-(5-nitro-2-furyl)acrylamide (AF-2) (CAS no. 3688-53-7), glyoxal (CAS no. 107-22-2), 6-mercaptopurine (CAS no. 50-44-2), N-(trichloromethylthio)-4-cyclohexane-1,2-dicarboximide (captan) (CAS no. 133-06-2), 2-aminopurine (CAS no. 452-06-2), methyl methane sulfonate (MMS) (CAS No. 66-27-3), 4-nitroquinoline 1-oxide (4-NQO) (CAS No. 56-57-5), N4-Aminocytidine (CAS no. 57294-74-3), sodium azide (CAS no. 26628-22-8), N-ethyl-N-nitrosourea (ENU) (CAS no. 759-73-9), N-methyl-N-nitrosourea (MNU) (CAS no. 820-60-0), 5-azacytidine (CAS no. 320-67-2), cumene hydroperoxide (CHP) (CAS no. 80-15-9), ethyl methanesulfonate (EMS) (CAS no. 62-50-0), N-ethyl-N-nitro-N-nitrosoguanidine (ENNG) (CAS no. 4245-77-6), N-methyl-N-nitro-N-nitrosoguanidine (MNNG) (CAS no. 70-25-7), 5-diazouracil (CAS no. 2435-76-9), and t-butyl hydroperoxide (BHP) (CAS no. 75-91-2). Additional mutagens can be used in continuous evolution procedures as provided herein, and the invention is not limited in this respect.

The term "mutagenesis plasmid," as used herein, refers to a plasmid comprising a nucleic acid sequence encoding a gene product or a combination of gene products that act(s) as a mutagen. In some embodiments, a mutagenesis plasmid may encode a DNA polymerase lacking a proofreading capability. In some embodiments, the mutagenesis plasmid may encode a gene product involved in the bacterial SOS stress response, for example, a component of a bacterial translesion synthesis polymerase V. In some embodiments, the mutagenesis plasmid may encode a deoxyadenosine methylase. In some embodiments, the mutagenesis plasmid may encode a hemimethylated-GATC binding domain. In some non-limiting embodiments, the mutagenesis plasmid encodes UmuC (a component of *E. coli* translesion synthesis polymerase V), dam (deoxyadenosine methylase), and/or seqA (hemimethylated-GATC binding domain), or any combination thereof.

The term "nucleic acid," as used herein, refers to a polymer of nucleotides. The polymer may include natural nucleosides (i.e., adenosine, thymidine, guanosine, cytidine, uridine, deoxyadenosine, deoxythymidine, deoxyguanosine, and deoxycytidine), nucleoside analogs (e.g., 2-aminoadenosine, 2-thiothymidine, inosine, pyrrolo-pyrimidine, 3-methyl adenosine, 5-methylcytidine, C5-bromouridine, C5-fluorouridine, C5-iodouridine, C5-propynyl-uridine, C5-propynyl-cytidine, C5-methylcytidine, 7-deazaadenosine, 7-deazaguanosine, 8-oxoadenosine, 8-oxoguanosine, O(6)-methylguanine, 4-acetylcytidine, 5-(carboxyhydroxymethyl)uridine, dihydrouridine, methylpseudouridine, 1-methyl adenosine, 1-methyl guanosine, N6-methyl adenosine, and 2-thiocytidine), chemically modified bases, biologically modified bases (e.g., methylated bases), intercalated bases, modified sugars (e.g., 2'-fluororibose, ribose, 2'-deoxyribose, 2"-O-methylcytidine, arabinose, and hexose), or modified phosphate groups (e.g., phosphorothioates and 5'-N-phosphoramidite linkages).

The term "phage," as used herein interchangeably with the term "bacteriophage," refers to a virus that infects bacterial cells. Typically, phages consist of an outer protein capsid enclosing genetic material. The genetic material can be ssRNA, dsRNA, ssDNA, or dsDNA, in either linear or circular form. Phages and phage vectors are well known to those of skill in the art and non-limiting examples of phages that are useful for carrying out the methods provided herein are λ (Lysogen), T2, T4, T7, T12, R17, M13, MS2, G4, P1, P2, P4, Phi X174, N4, Φ6, and Φ29. In certain embodiments, the phage utilized in the present invention is M13. Additional suitable phages and host cells will be apparent to those of skill in the art and the invention is not limited in this aspect. For an exemplary description of additional suitable phages and host cells, see Elizabeth Kutter and Alexander Sulakvelidze: *Bacteriophages: Biology and Applications*. CRC Press; 1st edition (December 2004), ISBN: 0849313368; Martha R. J. Clokie and Andrew M. Kropinski: *Bacteriophages: Methods and Protocols, Volume 1: Isolation, Characterization, and Interactions* (*Methods in Molecular Biology*) Humana Press; 1st edition (December, 2008), ISBN: 1588296822; Martha R. J. Clokie and Andrew M. Kropinski: *Bacteriophages: Methods and Protocols, Volume 2: Molecular and Applied Aspects* (*Methods in Molecular Biology*) Humana Press; 1st edition (December 2008), ISBN: 1603275649; all of which are incorporated herein in their entirety by reference for disclosure of suitable phages and host cells as well as methods and protocols for isolation, culture, and manipulation of such phages).

The term "phage-assisted continuous evolution (PACE)," as used herein, refers to continuous evolution that employs phage as viral vectors. PACE technology has been described previously, for example, in International PCT Application, PCT/US2009/056194, filed Sep. 8, 2009, published as WO 2010/028347 on Mar. 11, 2010; International PCT Application, PCT/US2011/066747, filed Dec. 22, 2011, published as WO 2012/088381 on Jun. 28, 2012; and U.S. application, U.S. Ser. No. 13/922,812, filed Jun. 20, 2013, each of which is incorporated herein by reference.

The term "promoter" is art-recognized and refers to a nucleic acid molecule with a sequence recognized by the cellular transcription machinery and able to initiate transcription of a downstream gene. A promoter can be constitutively active, meaning that the promoter is always active in a given cellular context, or conditionally active, meaning that the promoter is only active in the presence of a specific condition. For example, a conditional promoter may only be active in the presence of a specific protein that connects a protein associated with a regulatory element in the promoter to the basic transcriptional machinery, or only in the absence of an inhibitory molecule. A subclass of conditionally active promoters are inducible promoters that require the presence of a small molecule "inducer" for activity. Examples of inducible promoters include, but are not limited to, arabinose-inducible promoters, Tet-on promoters, and tamoxifen-inducible promoters. A variety of constitutive, conditional, and inducible promoters are well known to the skilled artisan, and the skilled artisan will be able to ascertain a variety of such promoters useful in carrying out the instant invention, which is not limited in this respect.

The term "protease inhibitor," as used herein, refers to a molecule that inhibits the activity of a protease. Many naturally occurring protease inhibitors are known to those of skill in the art. The term also embraces non-naturally occurring protease inhibitors, including, but not limited to, small molecule protease inhibitors. Suitable protease inhibitors will be apparent to those of skill in the art and include, without limitation, protease inhibitors listed in the MEROPS database, accessible at merops.sanger.ac.uk and described in Rawlings et al., (2014) MEROPS: the database of proteolytic enzymes, their substrates and inhibitors. *Nucleic Acids Res* 42, D503-D509, the entire contents of each of which are incorporated herein by reference.

The term "protease," as used herein, refers to an enzyme that catalyzes the hydrolysis of a peptide bond linking amino acid residues together within a protein. The term embraces both naturally occurring and engineered proteases. Many proteases are known in the art. Proteases can be classified by their catalytic residue, and protease classes include, without limitation, serine proteases (serine alcohol), threonine proteases (threonine secondary alcohol), cysteine proteases (cysteine thiol), aspartate proteases (aspartate carboxylic acid), glutamic acid proteases (glutamate carboxylic acid), and metalloproteases (metal ion, e.g., zinc). The structures in parentheses correlate to the respective catalytic moiety of proteases of each class. Some proteases are highly promiscuous and cleave a wide range of protein substrates, e.g., trypsin or pepsin. Other proteases are highly specific and only cleave substrates with a specific sequence. Some blood clotting proteases such as, for example, thrombin, and some viral proteases such as, for example, HCV or TEV protease, are highly specific proteases. Proteases that cleave in a very specific manner typically bind to multiple amino acid residues of their substrate. Suitable proteases and protease cleavage sites, also sometimes referred to as "protease substrates," will be apparent to those of skill in the art and include, without limitation, proteases listed in the MEROPS database, accessible at merops.sanger.ac.uk and described in Rawlings et al., (2014) MEROPS: the database of proteolytic enzymes, their substrates and inhibitors. *Nucleic Acids Res* 42, D503-D509, the entire contents of each of which are incorporated herein by reference. The disclosure is not limited in this respect.

The term "protein," as used herein refers to a polymer of amino acid residues linked together by peptide bonds. The term, as used herein, refers to proteins, polypeptides, and peptide of any size, structure, or function. Typically, a protein will be at least three amino acids long. A protein may refer to an individual protein or a collection of proteins. Inventive proteins preferably contain only natural amino acids, although non-natural amino acids (i.e., compounds that do not occur in nature but that can be incorporated into a polypeptide chain; see, for example, cco.caltech.edu/~dadgrp/Unnatstruct.gif, which displays structures of non-natural amino acids that have been successfully incorporated into functional ion channels) and/or amino acid analogs as are known in the art may alternatively be employed. Also, one or more of the amino acids in an inventive protein may be modified, for example, by the addition of a chemical entity such as a carbohydrate group, a hydroxyl group, a phosphate group, a farnesyl group, an isofarnesyl group, a fatty acid group, a linker for conjugation, functionalization, or other modification, etc. A protein may also be a single molecule or may be a multi-molecular complex. A protein may be just a fragment of a naturally occurring protein or peptide. A protein may be naturally occurring, recombinant, or synthetic, or any combination of these.

The term "replication product," as used herein, refers to a nucleic acid that is the result of viral genome replication by a host cell. This includes any viral genomes synthesized by the host cell from a viral genome inserted into the host cell. The term includes non-mutated as well as mutated replication products.

The term "selection phage," as used herein interchangeably with the term "selection plasmid," refers to a modified phage that comprises a gene of interest to be evolved and lacks a full-length gene encoding a protein required for the generation of infectious phage particles. For example, some M13 selection phages provided herein comprise a nucleic acid sequence encoding a protease to be evolved, e.g., under the control of an M13 promoter, and lack all or part of a phage gene encoding a protein required for the generation of infectious phage particles, e.g., gI, gII, gIII, gIV, gV, gVI, gVII, gVIII, gIX, or gX, or any combination thereof. For example, some M13 selection phages provided herein comprise a nucleic acid sequence encoding a protease to be evolved, e.g., under the control of an M13 promoter, and lack all or part of a gene encoding a protein required for the generation of infective phage particles, e.g., the gIII gene encoding the pIII protein.

The terms "small molecule" and "organic compound" are used interchangeably herein and refer to molecules, whether naturally-occurring or artificially created (e.g., via chemical synthesis) that have a relatively low molecular weight. Typically, an organic compound contains carbon. An organic compound may contain multiple carbon-carbon bonds, stereocenters, and other functional groups (e.g., amines, hydroxyl, carbonyls, or heterocyclic rings). In some embodiments, organic compounds are monomeric and have a molecular weight of less than about 1500 g/mol. In certain embodiments, the molecular weight of the small molecule is less than about 1000 g/mol or less than about 500 g/mol. In certain embodiments, the small molecule is a therapeutic drug or drug candidate, for example, a drug or drug candidate that is in clinical or pre-clinical trials or that has already been deemed safe and effective for use in humans or animals by the appropriate governmental agency or regulatory body.

The term "turbidostat," as used herein, refers to a culture vessel comprising host cells in suspension culture, in which the turbidity of the culture medium is substantially essentially constant over time. In some embodiments, the turbidity of a suspension culture, for example, of bacterial cells, is a measure for the cell density in the culture medium. In some embodiments, a turbidostat comprises an inflow of fresh media and an outflow, and a controller that regulates the flow into and/or out of the turbidostat based on the turbidity of the suspension culture in the turbidostat.

The term "vector," as used herein, refers to a nucleic acid that can be modified to encode a protease of interest and that is able to enter into a host cell, mutate and replicate within the host cell, and then transfer a replicated form of the vector into another host cell. Exemplary suitable vectors include viral vectors, such as retroviral vectors or bacteriophages, and conjugative plasmids. Additional suitable vectors will be apparent to those of skill in the art based on the instant disclosure.

The term "viral life cycle," as used herein, refers to the viral reproduction cycle comprising insertion of the viral genome into a host cell, replication of the viral genome in the host cell, and packaging of a replication product of the viral genome into a viral particle by the host cell.

The term "viral particle," as used herein, refers to a viral genome, for example, a DNA or RNA genome, that is associated with a coat of a viral protein or proteins, and, in some cases, with an envelope of lipids. For example, a phage particle comprises a phage genome packaged into a protein encoded by the wild type phage genome.

The term "viral vector," as used herein, refers to a nucleic acid comprising a viral genome that, when introduced into a suitable host cell, can be replicated and packaged into viral particles able to transfer the viral genome into another host cell. The term viral vector extends to vectors comprising truncated or partial viral genomes. For example, in some embodiments, a viral vector is provided that lacks a gene encoding a protein essential for the generation of infectious viral particles. In suitable host cells, for example, host cells comprising the lacking gene under the control of a conditional promoter, however, such truncated viral vectors can replicate and generate viral particles able to transfer the truncated viral genome into another host cell. In some embodiments, the viral vector is a phage, for example, a filamentous phage (e.g., an M13 phage). In some embodiments, a viral vector, for example, a phage vector, is provided that comprises a gene encoding the protease of interest to be evolved.

DETAILED DESCRIPTION

Introduction

Among the more than 600 naturally occurring proteases that have been described) are enzymes that have proven to be important catalysts of industrial processes, tools for proteome analysis, and life-saving pharmaceuticals[2-5]. Recombinant human proteases including thrombin, factor VIIa, and tissue plasminogen activator are widely used drugs for the treatment of blood clotting diseases[4]. In addition, the potential of protease-based therapeutics to address disease in a manner analogous to that of antibody drugs,[6,7] but with catalytic turnover, has been recognized for several decades[4,8]. Natural proteases, however, typically target only a narrowly defined set of substrates, limiting their therapeutic potential. The directed evolution of proteases in principle could generate enzymes with tailor-made specificities, but laboratory-evolved proteases are frequently nonspecific, weakly active, or only modestly altered in their substrate specificity, limiting their utility[9-14].

In addition to their importance as current and future therapeutic agents, proteases have also proven to be major drug targets for diseases including cardiovascular disease, infectious disease, and cancer[15,16]. While drug specificity and potency are characterized and optimized during preclinical studies, the evolution of drug resistance is often not well understood until it arises in patients, despite the strong relationship between drug resistance vulnerability and a lack of therapeutic efficacy.

For example, resistance to HIV and HCV protease inhibitors can arise in as few as two days of clinical use[17] and frequently leads to viral rebound and poor treatment outcomes[18-21]. The speed with which drug resistance can arise in the clinic endangers patients and puts years of drug development efforts prior to such a determination at risk. Characterizing the potential of protease inhibitors to be overcome by the evolution of drug resistance using methods such as mammalian cell culture, animal models, or yeast display-based laboratory evolution, is time- and labor-intensive[22,23]. As a result, identifying drug resistance vulnerabilities of early-stage preclinical candidates is not common practice.

Phage-assisted continuous evolution (PACE) can serve as a rapid, high-throughput method to evolve protease enzymes and to reveal resistance to protease inhibitor drug candidates, analogous to previous uses of stepwise protein evolution to study antibiotic resistance[24]. During PACE, continuously replicating viral vectors, e.g., bacteriophage vectors, in a fixed-volume vessel (a "lagoon") carry an evolving gene of interest. Phage with genes encoding proteins with the desired target activity preferentially replicate because target activity triggers the production of a gene required for the transfer of the vector from one cell to another, e.g., a gene required for the generation of infectious phage particles, such as, for example, pIII, an essential component in the bacteriophage life cycle[25]. Because the lagoon is continuously diluted by a constant influx of host cells, e.g., *E. coli* cells, phage vectors encoding inactive variants produce non-infectious progeny that are rapidly diluted out of the lagoon. Dilution occurs faster than cell division but slower than phage replication, ensuring that mutations only accumulate in the phage genome. Because evolution during PACE takes place continuously without researcher intervention, hundreds of rounds of evolution can be performed per day or per week.

Some aspects of this disclosure are based on the recognition that PACE can be employed for the directed evolution of proteases. Proteases may require many successive mutations to remodel complex networks of contacts with polypeptide substrates[26,27], and are thus not readily manipulated by conventional, iterative evolution methods. The ability of PACE to perform the equivalent of hundreds of rounds of iterative evolution methods within days enables complex protease evolution experiments, that are impractical with conventional methods. Some aspects of this disclosure are based on the recognition that the speed of PACE also enables the rapid identification of mutations that confer resistance to protease inhibitors, for example, to therapeutic protease inhibitors. Such insights translate into methods for selecting drug candidates based on a determination of the likelihood of a target protease targeted by the drug evolving into a resistant mutant, and informs the design of new protease inhibitors for therapeutic and research use.

This disclosure provides data illustrating the feasibility of PACE-mediated protease evolution for non-limiting examples of the continuous directed evolution of proteases. The exemplary systems described in the Examples section employ an engineered protease-activated RNA polymerase (PA-RNAP) to transduce protease-mediated polypeptide cleavage events into changes in gene expression that support phage propagation during PACE. The successful link of the phage lifecycle to protease activity using PA-RNAP was validated for three distinct proteases. Protease PACE was also performed in the presence of therapeutic protease inhibitors, for example, danoprevir and asunaprevir, two hepatitis C virus (HCV) protease inhibitor drug candidates currently in clinical trials. Under those conditions, protease PACE rapidly evolved HCV protease variants that are resistant to each drug candidate. The PACE-evolved HCV protease variants were observed to be dominated by mutations previously observed in patients treated with these drug candidates, indicating that protease PACE can be used to recapitulate or predict the emergence of resistant protease variants in a clinical context and thus to support the selection of drug candidates for clinical development. Together, the proof-of-concept findings described herein establish a new platform to rapidly generate proteases with novel properties through continuous evolution, and to reveal the vulnerability of protease inhibitors to the evolution of drug resistance.

PACE technology has been described previously, for example, in International PCT Application, PCT/US2009/056194, filed Sep. 8, 2009, published as WO 2010/028347 on Mar. 11, 2010; International PCT Application, PCT/US2011/066747, filed Dec. 22, 2011, published as WO 2012/088381 on Jun. 28, 2012; and U.S. application, U.S. Ser. No. 13/922,812, filed Jun. 20, 2013, each of which is incorporated herein by reference. Those of skill in the art will understand that the PACE technology, strategies, methods, and reagents provided herein can be used in combination with many aspects of the PACE technology described in those applications, for example, with the apparatuses, lagoons, host cell types, cell flow parameters, negative selection strategies, etc., disclosed in these applications.

Continuous Evolution Methods

Some aspects of this disclosure provide methods for evolution of a protease. In some embodiments, a method of evolution of a protease is provided that comprises (a) contacting a population of host cells with a population of vectors comprising a gene encoding a protease. The vectors are typically deficient in at least one gene required for the transfer of the phage vector from one cell to another, e.g., a gene required for the generation of infectious phage particles. In some embodiments of the provided methods, (1) the host cells are amenable to transfer of the vector; (2) the vector allows for expression of the protease in the host cell, can be replicated by the host cell, and the replicated vector can transfer into a second host cell; and (3) the host cell expresses a gene product encoded by the at least one gene for the generation of infectious phage particles (a) in response to the activity of the protease, and the level of gene product expression depends on the activity of the protease. The methods of protease evolution provided herein typically comprise (b) incubating the population of host cells under conditions allowing for mutation of the gene encoding the protease, and the transfer of the vector comprising the gene encoding the protease of interest from host cell to host cell. The host cells are removed from the host cell population at a certain rate, e.g., at a rate that results in an average time a host cell remains in the cell population that is shorter than the average time a host cell requires to divide, but long enough for the completion of a life cycle (uptake, replication, and transfer to another host cell) of the vector. The population of host cells is replenished with fresh host cells that do not harbor the vector. In some embodiments, the rate of replenishment with fresh cells substantially matches the rate of removal of cells from the cell population, resulting in a substantially constant cell number or cell density within the cell population. The methods of protease evolution provided herein typically also comprise (c) isolating a replicated vector from the host cell population in (b), wherein the replicated vector comprises a mutated version of the gene encoding the protease.

In some embodiments, a gene encoding a protease of interest is transferred from host cell to host cell in a manner dependent on the activity of the protease of interest. In some embodiments, the transfer vector is a virus infecting and replicating in the host cells, for example, a bacteriophage or a retroviral vector. In some embodiments, the viral vector is a phage vector infecting bacterial host cells. In some embodiments, the transfer vector is a retroviral vector, for example, a lentiviral vector or a vesicular stomatitis virus vector, infecting human or mouse cells. In some embodiments, the transfer vector is a conjugative plasmid transferred from a donor bacterial cell to a recipient bacterial cell.

In some embodiments, the nucleic acid vector comprising the gene encoding a protease of interest is a phage, a viral vector, or naked DNA (e.g., a mobilization plasmid). In some embodiments, transfer of the gene encoding the protease of interest from cell to cell is via infection, transfect ion, transduction, conjugation, or uptake of naked DNA, and efficiency of cell-to-cell transfer (e.g., transfer rate) is dependent on an activity of the protease of interest or a mutated version thereof. For example, in some embodiments, the nucleic acid vector is a phage harboring the gene encoding a protease of interest, and the efficiency of phage transfer (via infection) is dependent on the activity of the protease of interest in that a protein for the generation of infectious phage particles (e.g., pIII for M13 phage) is expressed in the host cells only in the presence of a desired protease activity, such as the cleavage of a specific protease cleavage site or the cleavage of a target site under specific circumstances, e.g., in the presence of a protease inhibitor.

Some embodiments provide a continuous evolution system, in which a population of viral vectors, e.g., M13 phage vectors, comprising a gene encoding a protease of interest to be evolved replicates in a flow of host cells, e.g., a flow through a lagoon, wherein the viral vectors are deficient in a gene encoding a protein that is essential for the generation of infectious viral particles, and wherein that gene is in the host cell under the control of a conditional promoter the activity of which depends on the activity of the protease of interest. In some embodiments, transcription from the conditional promoter may be activated by cleavage of a fusion protein comprising a transcription factor and an inhibitory protein fused to the transcriptional activator via a linker comprising a target site of the protease.

Viral vectors, in which the gene encoding the protease of interest has not acquired a mutation conferring the desired function, will not activate the conditional promoter, or only achieve minimal activation, while any mutation in the gene of interest that confers the desired mutation will result in activation of the conditional promoter. Since the conditional promoter controls an essential protein for the viral life cycle, activation of this promoter directly corresponds to an advantage in viral spread and replication for those vectors that have acquired an advantageous mutation.

In some embodiments, the viral vector provided is a phage In some embodiments, the phage is a filamentous phage. In some embodiments, the phage is an M13 phage. M13 phages are well known to those in the art and the biology of M13 phages has extensively been studied. A schematic representation of the wild-type M13 genome is provided in FIG. 16. Wild type M13 phage particles comprise a circular, single-stranded genome of approximately 6.4 kb. The wilt-type genome includes ten genes, gI-gX, which, in turn, encode the ten M13 proteins, pI-pX, respectively. gVIII encodes pVIII, also often referred to as the major structural protein of the phage particles, while gIII encodes pIII, also referred to as the minor coat protein, which is required for infectivity of M13 phage particles.

The M13 life cycle includes attachment of the phage to the sex pilus of a suitable bacterial host cell via the pIII protein and insertion of the phage genome into the host cell. The circular, single-stranded phage genome is then converted to a circular, double-stranded DNA, also termed the replicative form (RF), from which phage gene transcription is initiated. The wild type M13 genome comprises nine promoters and two transcriptional terminators as well as an origin of replication. This series of promoters provides a gradient of transcription such that the genes nearest the two transcriptional terminators (gVIII and W) are transcribed at the highest levels. In wild-type M13 phage, transcription of all 10 genes proceeds in same direction. One of the phage-encode proteins, pII, initiates the generation of linear, single-stranded phage genomes in the host cells, which are subsequently circularized, and bound and stabilized by pV. The circularized, single-stranded M13 genomes are then bound by pVIII, while pV is stripped off the genome, which initiates the packaging process. At the end of the packaging process, multiple copies of pIII are attached to wild-type M13 particles, thus generating infectious phage ready to infect another host cell and concluding the life cycle.

The M13 phage genome can be manipulated, for example, by deleting one or more of the wild type genes, and/or inserting a heterologous nucleic acid construct into the genome. M13 does not have stringent genome size restrictions, and insertions of up to 42 kb have been reported. This allows M13 phage vectors to be used in continuous evolution experiments to evolve genes of interest without imposing a limitation on the length of the gene to be involved.

The M13 phage has been well characterized and the genomic sequence of M13 has been reported. Representative M13 genomic sequences can be retrieved from public databases, and an exemplary sequence is provided in entry V00604 of the National Center for Biotechnology Information (NCBI) database (www.ncbi.nlm.nih.gov):

Phage M13 genome:

```
>gi|56713234|emb|V00604.2|Phage M13 genome
                                        (SEQ ID NO: 1)
AACGCTACTACTATTAGTAGAATTGATGCCACCTTTTCAGCTCGCGCCCC
AAATGAAAATATAGCTAAACAGGTTATTGACCATTTGCGAAATGTATCTA
ATGGTCAAACTAAATCTACTCGTTCGCAGAATTGGGAATCAACTGTTACA
TGGAATGAAACTTCCAGACACCGTACTTTAGTTGCATATTTAAAACATGT
TGAGCTACAGCACCAGATTCAGCAATTAAGCTCTAAGCCATCCGCAAAAA
TGACCTCTTATCAAAAGGAGCAATTAAAGGTACTCTCTAATCCTGACCTG
TTGGAGTTTGCTTCCGGTCTGGTTCGCTTTGAAGCTCGAATTAAAACGCG
ATATTTGAAGTCTTTCGGGCTTCCTCTTAATCTTTTTGATGCAATCCGCT
TTGCTTCTGACTATAATAGTCAGGGTAAAGACCTGATTTTTGATTTATGG
TCATTCTCGTTTTCTGAACTGTTTAAAGCATTTGAGGGGGATTCAATGAA
TATTTATGACGATTCCGCAGTATTGGACGCTATCCAGTCTAAACATTTTA
CTATTACCCCCTCTGGCAAAACTTCTTTTGCAAAAGCCTCTCGCTATTTT
GGTTTTTATCGTCGTCTGGTAAACGAGGGTTATGATAGTGTTGCTCTTAC
TATGCCTCGTAATTCCTTTTGGCGTTATGTATCTGCATTAGTTGAATGTG
GTATTCCTAAATCTCAACTGATGAATCTTTCTACCTGTAATAATGTTGTT
CCGTTAGTTCGTTTTATTAACGTAGATTTTTCTTCCCAACGTCCTGACTG
GTATAATGAGCCAGTTCTTAAAATCGCATAAGGTAATTCACAATGATTAA
AGTTGAAATTAAACCATCTCAAGCCCAATTTACTACTCGTTCTGGTGTTT
CTCGTCAGGGCAAGCCTTATTCACTGAATGAGCAGCTTTGTTACGTTGAT
TTGGGTAATGAATATCCGGTTCTTGTCAAGATTACTCTTGATGAAGGTCA
GCCAGCCTATGCGCCTGGTCTGTACACCGTTCATCTGTCCTCTTTCAAAG
TTGGTCAGTTCGGTTCCCTTATGATTGACCGTCTGCGCCTCGTTCCGGCT
AAGTAACATGGAGCAGGTCGCGGATTTCGACACAATTTATCAGGCGATGA
TACAAATCTCCGTTGTACTTTGTTTCGCGCTTGGTATAATCGCTGGGGGT
```

-continued

```
CAAAGATGAGTGTTTTAGTGTATTCTTTCGCCTCTTTCGTTTTAGGTTGG
TGCCTTCGTAGTGGCATTACGTATTTTACCCGTTTAATGGAAACTTCCTC
ATGAAAAAGTCTTTAGTCCTCAAAGCCTCTGTAGCCGTTGCTACCCTCGT
TCCGATGCTGTCTTTCGCTGCTGAGGGTGACGATCCCGCAAAAGCGGCCT
TTAACTCCCTGCAAGCCTCAGCGACCGAATATATCGGTTATGCGTGGGCG
ATGGTTGTTGTCATTGTCGGCGCAACTATCGGTATCAAGCTGTTTAAGAA
ATTCACCTCGAAAGCAAGCTGATAAACCGATACAATTAAAGGCTCCTTTT
GGAGCCTTTTTTTTTGGAGATTTTCAACATGAAAAAATTATTATTCGCAA
TTCCTTTAGTTGTTCCTTTCTATTCTCACTCCGCTGAAACTGTTGAAAGT
TGTTTAGCAAAACCCCATACAGAAAATTCATTTACTAACGTCTGGAAAGA
CGACAAAACTTTAGATCGTTACGCTAACTATGAGGGTTGTCTGTGGAATG
CTACAGGCGTTGTAGTTTGTACTGGTGACGAAACTCAGTGTTACGGTACA
TGGGTTCCTATTGGGCTTGCTATCCCTGAAAATGAGGGTGGTGGCTCTGA
GGGTGGCGGTTCTGAGGGTGGCGGTTCTGAGGGTGGCGGTACTAAACCTC
CTGAGTACGGTGATACACCTATTCCGGGCTATACTTATATCAACCCTCTC
GACGGCACTTATCCGCCTGGTACTGAGCAAAACCCCGCTAATCCTAATCC
TTCTCTTGAGGAGTCTCAGCCTCTTAATACTTTCATGTTTCAGAATAATA
GGTTCCGAAATAGGCAGGGGGCATTAACTGTTTATACGGGCACTGTTACT
CAAGGCACTGACCCCGTTAAAACTTATTACCAGTACACTCCTGTATCATC
AAAAGCCATGTATGACGCTTACTGGAACGGTAAATTCAGAGACTGCGCTT
TCCATTCTGGCTTTAATGAGGATCCATTCGTTTGTGAATATCAAGGCCAA
TCGTCTGACCTGCCTCAACCTCCTGTCAATGCTGGCGGCGGCTCTGGTGG
TGGTTCTGGTGGCGGCTCTGAGGGTGGTGGCTCTGAGGGTGGCGGTTCTG
AGGGTGGCGGCTCTGAGGGAGGCGGTTCCGGTGGTGGCTCTGGTTCCGGT
GATTTTGATTATGAAAAGATGGCAAACGCTAATAAGGGGGCTATGACCGA
AAATGCCGATGAAAACGCGCTACAGTCTGACGCTAAAGGCAAACTTGATT
CTGTCGCTACTGATTACGGTGCTGCTATCGATGGTTTCATTGGTGACGTT
TCCGGCCTTGCTAATGGTAATGGTGCTACTGGTGATTTTGCTGGCTCTAA
TTCCCAAATGGCTCAAGTCGGTGACGGTGATAATTCACCTTTAATGAATA
ATTTCCGTCAATATTTACCTTCCCTCCCTCAATCGGTTGAATGTCGCCCT
TTTGTCTTTAGCGCTGGTAAACCATATGAATTTTCTATTGATTGTGACAA
AATAAACTTATTCCGTGGTGTCTTTGCGTTTCTTTTATATGTTGCCACCT
TTATGTATGTATTTTCTACGTTTGCTAACATACTGCGTAATAAGGAGTCT
TAATCATGCCAGTTCTTTTGGGTATTCCGTTATTATTGCGTTTCCTCGGT
TTCCTTCTGGTAACTTTGTTCGGCTATCTGCTTACTTTTCTTAAAAAGGG
CTTCGGTAAGATAGCTATTGCTATTTCATTGTTTCTTGCTCTTATTATTG
GGCTTAACTCAATTCTTGTGGGTTATCTCTCTGATATTAGCGCTCAATTA
CCCTCTGACTTTGTTCAGGGTGTTCAGTTAATTCTCCCGTCTAATGCGCT
TCCCTGTTTTTATGTTATTCTCTCTGTAAAGGCTGCTATTTTCATTTTTG
ACGTTAAACAAAAAATCGTTTCTTATTTGGATTGGGATAAATAATATGGC
TGTTTATTTTGTAACTGGCAAATTAGGCTCTGGAAAGACGCTCGTTAGCG
```

TTGGTAAGATTCAGGATAAAATTGTAGCTGGGTGCAAAATAGCAACTAAT

CTTGATTTAAGGCTTCAAAACCTCCCGCAAGTCGGGAGGTTCGCTAAAAC

GCCTCGCGTTCTTAGAATACCGGATAAGCCTTCTATATCTGATTTGCTTG

CTATTGGGCGCGGTAATGATTCCTACGATGAAAATAAAAACGGCTTGCTT

GTTCTCGATGAGTGCGGTACTTGGTTTAATACCCGTTCTTGGAATGATAA

GGAAAGACAGCCGATTATTGATTGGTTTCTACATGCTCGTAAATTAGGAT

GGGATATTATTTTTCTTGTTCAGGACTTATCTATTGTTGATAAACAGGCG

CGTTCTGCATTAGCTGAACATGTTGTTTATTGTCGTCGTCTGGACAGAAT

TACTTTACCTTTTGTCGGTACTTTATATTCTCTTATTACTGGCTCGAAAA

TGCCTCTGCCTAAATTACATGTTGGCGTTGTTAAATATGGCGATTCTCAA

TTAAGCCCTACTGTTGAGCGTTGGCTTTATACTGGTAAGAATTTGTATAA

CGCATATGATACTAAACAGGCTTTTTCTAGTAATTATGATTCCGGTGTTT

ATTCTTATTTAACGCCTTATTTATCACACGGTCGGTATTTCAAACCATTA

AATTTAGGTCAGAAGATGAAATTAACTAAAATATATTTGAAAAAGTTTTC

TCGCGTTCTTTGTCTTGCGATTGGATTTGCATCAGCATTTACATATAGTT

ATATAACCCAACCTAAGCCGGAGGTTAAAAAGGTAGTCTCTCAGACCTAT

GATTTTGATAAATTCACTATTGACTCTTCTCAGCGTCTTAATCTAAGCTA

TCGCTATGTTTTCAAGGATTCTAAGGGAAAATTAATTAATAGCGACGATT

TACAGAAGCAAGGTTATTCACTCACATATATTGATTTATGTACTGTTTCC

ATTAAAAAAGGTAATTCAAATGAAATTGTTAAATGTAATTAATTTTGTTT

TCTTGATGTTTGTTTCATCATCTTCTTTTGCTCAGGTAATTGAAATGAAT

AATTCGCCTCTGCGCGATTTTGTAACTTGGTATTCAAAGCAATCAGGCGA

ATCCGTTATTGTTTCTCCCGATGTAAAAGGTACTGTTACTGTATATTCAT

CTGACGTTAAACCTGAAAATCTACGCAATTTCTTTATTTCTGTTTTACGT

GCTAATAATTTTGATATGGTTGGTTCAATTCCTTCCATAATTCAGAAGTA

TAATCCAAACAATCAGGATTATATTGATGAATTGCCATCATCTGATAATC

AGGAATATGATGATAATTCCGCTCCTTCTGGTGGTTTCTTTGTTCCGCAA

AATGATAATGTTACTCAAACTTTTAAAATTAATAACGTTCGGGCAAAGGA

TTTAATACGAGTTGTCGAATTGTTTGTAAAGTCTAATACTTCTAAATCCT

CAAATGTATTATCTATTGACGGCTCTAATCTATTAGTTGTTAGTGCACCT

AAAGATATTTTAGATAACCTTCCTCAATTCCTTTCTACTGTTGATTTGCC

AACTGACCAGATATTGATTGAGGGTTTGATATTTGAGGTTCAGCAAGGTG

ATGCTTTAGATTTTTCATTTGCTGCTGGCTCTCAGCGTGGCACTGTTGCA

GGCGGTGTTAATACTGACCGCCTCACCTCTGTTTTATCTTCTGCTGGTGG

TTCGTTCGGTATTTTTAATGGCGATGTTTTAGGGCTATCAGTTCGCGCAT

TAAAGACTAATAGCCATTCAAAAATATTGTCTGTGCCACGTATTCTTACG

CTTTCAGGTCAGAAGGGTTCTATCTCTGTTGGCCAGAATGTCCCTTTTAT

TACTGGTCGTGTGACTGGTGAATCTGCCAATGTAAATAATCCATTTCAGA

CGATTGAGCGTCAAAATGTAGGTATTTCCATGAGCGTTTTTCCTGTTGCA

ATGGCTGGCGGTAATATTGTTCTGGATATTACCAGCAAGGCCGATAGTTT

GAGTTCTTCTACTCAGGCAAGTGATGTTATTACTAATCAAAGAAGTATTG

CTACAACGGTTAATTTGCGTGATGGACAGACTCTTTTACTCGGTGGCCTC

ACTGATTATAAAAACACTTCTCAAGATTCTGGCGTACCGTTCCTGTCTAA

AATCCCTTTAATCGGCCTCCTGTTTAGCTCCCGCTCTGATTCCAACGAGG

AAAGCACGTTATACGTGCTCGTCAAAGCAACCATAGTACGCGCCCTGTAG

CGGCGCATTAAGCGCGGCGGGTGTGGTGGTTACGCGCAGCGTGACCGCTA

CACTTGCCAGCGCCCTAGCGCCCGCTCCTTTCGCTTTCTTCCCTTCCTTT

CTCGCCACGTTCGCCGGCTTTCCCCGTCAAGCTCTAAATCGGGGGCTCCC

TTTAGGGTTCCGATTTAGTGCTTTACGGCACCTCGACCCCAAAAAACTTG

ATTTGGGTGATGGTTCACGTAGTGGGCCATCGCCCTGATAGACGGTTTTT

CGCCCTTTGACGTTGGAGTCCACGTTCTTTAATAGTGGACTCTTGTTCCA

AACTGGAACAACACTCAACCCTATCTCGGGCTATTCTTTTGATTTATAAG

GGATTTTGCCGATTTCGGCCTATTGGTTAAAAAATGAGCTGATTTAACAA

AAATTTAACGCGAATTTTAACAAAATATTAACGTTTACAATTTAAATATT

TGCTTATACAATCTTCCTGTTTTTGGGGCTTTTCTGATTATCAACCGGGG

TACATATGATTGACATGCTAGTTTTACGATTACCGTTCATCGATTCTCTT

GTTTGCTCCAGACTCTCAGGCAATGACCTGATAGCCTTTGTAGACCTCTC

AAAAATAGCTACCCTCTCCGGCATGAATTTATCAGCTAGAACGGTTGAAT

ATCATATTGATGGTGATTTGACTGTCTCCGGCCTTTCTCACCCTTTTGAA

TCTTTACCTACACATTACTCAGGCATTGCATTTAAAATATATGAGGGTTC

TAAAAATTTTTATCCTTGCGTTGAAATAAAGGCTTCTCCCGCAAAAGTAT

TACAGGGTCATAATGTTTTTGGTACAACCGATTTAGCTTTATGCTCTGAG

GCTTTATTGCTTAATTTTGCTAATTCTTTGCCTTGCCTGTATGATTTATT

GGATGTT

GENE II: join(6006 . . . 6407, 1 . . . 831)

(SEQ ID NO: 2)

translation = MIDMLVLRLPFIDSLVCSRLSGNDLIAFVDLSKIAT

LSGMNLSARTVEYHIDGDLTVSGLSHPFESLPTHYSGIAFKIYEGSKNFY

PCVEIKASPAKVLQGHNVFGTTDLALCSEALLLNFANSLPCLYDLLDVNA

TTISRIDATFSARAPNENIAKQVIDHLRNVSNGQTKSTRSQNWESTVTWN

ETSRHRTLVAYLKHVELQHQIQQLSSKPSAKMTSYQKEQLKVLSNPDLLE

FASGLVRFEARIKTRYLKSFGLPLNLFDAIRFASDYNSQGKDLIFDLWSF

SFSELFKAFEGDSMNIYDDSAVLDAIQSKHFTITPSGKTSFAKASRYFGF

YRRLVNEGYDSVALTMPRNSFWRYVSALVECGIPKSQLMNLSTCNNVVPL

VRFINVDFSSQRPDWYNEPVLKIA

GENE X: 496 . . . 831

(SEQ ID NO: 3)

translation = MNIYDDSAVLDAIQSKHFTITPSGKTSFAKASRYFG

FYRRLVNEGYDSVALTMPRNSFWRYVSALVECGIPKSQLMNLSTCNNVVP

LVRFINVDFSSQRPDWYNEPVLKIA

-continued

GENE V: 843 . . . 1106

(SEQ ID NO: 4)

translation = MIKVEIKPSQAQFTTRSGVSRQGKPYSLNEQLCYVD LGNEYPVLVKITLDEGQPAYAPGLYTVHLSSFKVGQFGSLMIDRLRLVPA K

GENE VII: 1108 . . . 1209

(SEQ ID NO: 5)

translation = MEQVADFDTIYQAMIQISVVLCFALGIIAGGQR

GENE IX: 1206 . . . 1304

(SEQ ID NO: 6)

translation = MSVLVYSFASFVLGWCLRSGITYFTRLMETSS

GENE VIII: 1301 . . . 1522

(SEQ ID NO: 7)

translation = MKKSLVLKASVAVATLVPMLSFAAEGDDPAKAAFNS LQASATEYIGYAWAMVVVIVGATIGIKLFKKFTSKAS

GENE III: 1579 . . . 2853

(SEQ ID NO: 8)

translation = MKKLLFAIPLVVPFYSHSAETVESCLAKPHTENSFT NVWKDDKTLDRYANYEGCLWNATGVVVCTGDETQCYGTWVPIGLAIPENE GGGSEGGGSEGGGSEGGGTKPPEYGDTPIPGYTYINPLDGTYPPGTEQNP ANPNPSLEESQPLNTFMFQNNRFRNRQGALTVYTGTVTQGTDPVKTYYQY TPVSSKAMYDAYWNGKFRDCAFHSGFNEDPFVCEYQGQSSDLPQPPVNAG GGSGGGSGGGSEGGGSEGGGSEGGGSEGGGSGGGSGSGDFDYEKMANANK GAMTENADENALQSDAKGKLDSVATDYGAAIDGFIGDVSGLANGNGATGD FAGSNSQMAQVGDGDNSPLMNNFRQYLPSLPQSVECRPFVFSAGKPYEFS IDCDKINLFRGVFAFLLYVATFMYVFSTFANILRNKES

GENE VI: 2856 . . . 3194

(SEQ ID NO: 9)

translation = MPVLLGIPLLLRFLGFLLVTLFGYLLTFLKKGFGKI AIAISLFLALIIGLNSILVGYLSDISAQLPSDFVQGVQLILPSNALPCFY VILSVKAAIFIFDVKQKIVSYLDWDK

GENE I: 3196 . . . 4242

(SEQ ID NO: 10)

translation = MAVYFVTGKLGSGKTLVSVGKIQDKIVAGCKIATNL DLRLQNLPQVGRFAKTPRVLRIPDKPSISDLLAIGRGNDSYDENKNGLLV LDECGTWFNTRSWNDKERQPIIDWFLHARKLGWDIIFLVQDLSIVDKQAR SALAEHVVYCRRLDRITLPFVGTLYSLITGSKMPLPKLHVGVVKYGDSQL SPTVERWLYTGKNLYNAYDTKQAFSSNYDSGVYSYLTPYLSHGRYFKPLN LGQKMKLTKIYLKKFSRVLCLAIGFASAFTYSYITQPKPEVKKVVSQTYD FDKFTIDSSQRLNLSYRYVFKDSKGKLINSDDLQKQGYSLTYIDLCTVSI KKGNSNEIVKCN

GENE IV: 4220 . . . 5500

(SEQ ID NO: 11)

translation = MKLLNVINFVFLMFVSSSSFAQVIEMNNSPLRDFVT WYSKQSGESVIVSPDVKGTVTVYSSDVKPENLRNFFISVLRANNFDMVGS IPSIIQKYNPNNQDYIDELPSSDNQEYDDNSAPSGGFFVPQNDNVTQTFK INNVRAKDLIRVVELFVKSNTSKSSNVLSIDGSNLLVVSAPKDILDNLPQ FLSTVDLPTDQILIEGLIFEVQQGDALDFSFAAGSQRGTVAGGVNTDRLT -continued SVLSSAGGSFGIFNGDVLGLSVRALKTNSHSKILSVPRILTLSGQKGSIS VGQNVPFITGRVTGESANVNNPFQTIERQNVGISMSVFPVAMAGGNIVLD ITSKADSLSSSTQASDVITNQRSIATTVNLRDGQTLLLGGLTDYKNTSQD SGVPFLSKIPLIGLLFSSRSDSNEESTLYVLVKATIVRAL Some embodiments of the protease PACE technology described herein utilize a “selection phage,” a modified phage that comprises a gene of interest to be evolved and lacks a full-length gene encoding a protein required for the generation of infectious phage particles. In some such embodiments, the selection phage serves as the vector that replicates and evolves in the flow of host cells. For example, some M13 selection phages provided herein comprise a nucleic acid sequence encoding a protease to be evolved, e.g., under the control of an M13 promoter, and lack all or part of a phage gene encoding a protein required for the generation of infectious phage particles, e.g., gI, gII, gIII, gIV, gV, gVI, gVII, gVIII, gIX, or gX, or any combination thereof. For example, some M13 selection phages provided herein comprise a nucleic acid sequence encoding a protease to be evolved, e.g., under the control of an M13 promoter, and lack all or part of a gene encoding a protein required for the generation of infective phage particles, e.g., the gIII gene encoding the pIII protein. An exemplary, non-limiting selection plasmid sequence, SP-MCS, comprising a multiple cloning site, into which a nucleic acid sequence encoding a protease to be evolved can be cloned, is provided below:

(SEQ ID NO: 30)

ATGATTGACATGCTAGTTTTACGATTACCGTTCATCGATTCTCTTGTTTG CTCCAGACTCTCAGGCAATGACCTGATAGCCTTTGTAGACCTCTCAAAAA TAGCTACCCTCTCCGGCATGAATTTATCAGCTAGAACGGTTGAATATCAT GTTGATGGTGATTTGACTGTCTCCGGCCTTTCTCACCCTTTTGAATCTTT ACCTACACATTACTCAGGCATTGCATTTAAAATATATGAGGGTTCTAAAA ATTTTTATCCTTGCGTTGAAATAAAGGCTTCTCCCGCAAAAGTATTACAG GGTCATAATGTTTTTGGTACAACCGATTTAGCTTTATGCTCTGAGGCTTT ATTGCTTAATTTTGCTAATTCTTTGCCTTGCCTGTATGATTTATTGGATG TTAACGCTACTACTATTAGTAGAATTGATGCCACCTTTTCAGCTCGCGCC CCAAATGAAAATATAGCTAAACAGGTTATTGACCATTTGCGAAATGTATC TAATGGTCAAACTAAATCTACTCGTTCGCAGAATTGGGAATCAACTGTTA CATGGAATGAAACTTCCAGACACCGTACTTTAGTTGCATATTTAAAACAT GTTGAGCTACAGCACCAGATTCAGCAATTAAGCTCTAAGCCATCCGCAAA AATGACCTCTTATCAAAAGGAGCAATTAAAGGTACTCTCTAATCCTGACC TGTTGGAGTTTGCTTCCGGGCTGGTTCGCTTTGAAGCTCGAATTAGAACG CGATATTTGAAGTCTTTCGGGCTTCCTCTTAATCTTTTTGATGCAATCCG CTTTGCTTCTGACTATAATAGTCAGGGTAAAGACCTGATTTTTGATTTAT GGTCATTCTCGTTTTCTGAACTGTTTAAAGCATTTGAGGGGGATTCAATG AATATTTATGACGATTCCGCAGTATTGGACGCTATCCAGTCTAAACATTT TACTATTACCCCCTCTGGCAAAACTTCTTTTGCAAAAGCCTCTCGCTATT TTGGTTTTTATCGTCGTCTGGTAAACGAGGGTTATGATAGTGTTGCTCTT

-continued

ACTATGCCTCGTAATTCCTTTTGGCGTTATGTATCTGCATTAGTTGAATG

TGGTATTCCTAAATCTCAACTGATGAATCTTTCTACCTGTAATAATGTTG

TTCCGTTAGTTCGTTTTATTAACGTAGATTTTTCTTCCCAACGTCCTGAC

TGGTATAATGAGCCAGTTCTTAAAATCGCATAAGGTAATTCACAATGATT

AAAGTTGAAATTAAACCATCTCAAGCCCAATTTACTACTCGTTCTGGTGT

TTCTCGTCAGGGCAAGCCTTATTCACTGAATGAGCAGCTTTGTTACGTTG

ATTTGGGTAATGAATATCCGGTTCTTGTCAAGATTACTCTTGATGAAGGT

CAGCCAGCCTATGCGCCTGGTCTGTACACCGTTCATCTGTCCTCTTTCAA

AGTTGGTCAGTTCGGTTCCCTTATGATTGACCGTCTGCGCCTCGTTCCGG

CTAAGTAACATGGAGCAGGTCGCGGATTTCGACACAATTTATCAGGCGAT

GATACAAATCTCCGTTGTACTTTGTTTCGCGCTTGGTATAATCGCTGGGG

GTCAAAGATGAGTGTTTTAGTGTATTCTTTCGCCTCTTTCGTTTTAGGTT

GGTGCCTTCGTAGTGGCATTACGTATTTTACCCGTTTAATGGAAACTTCC

TCATGAAAAAGTCTTTAGTCCTCAAAGCCTCTGTAGCCGTTGCTACCCTC

GTTCCGATGCTGTCTTTCGCTGCTGAGGGTGACGATCCCGCAAAAGCGGC

CTTTAACTCCCTGCAAGCCTCAGCGACCGAATATATCGGTTATGCGTGGG

CGATGGTTGTTGTCATTGTCGGCGCAACTATCGGTATCAAGCTGTTTAAG

AAATTCACCTCGAAAGCAAGCTGATAAACCGATACAATTAAAGGCTCCTT

TTGGAGCCTTTTTTTTCGCGCCAGAAGGAGACCAAGCTTGCATGCCTGCA

GGTCGACTCTAGAGGATCCCCGGGTACCGAGCTCGAATTCTGGAGATTTT

CAACATGCTCCCTCAATCGGTTGAATGTCGCCCTTTTGTCTTTAGCGCTG

GTAAACCATATGAATTTTCTATTGATTGTGACAAAATGAACTTATTCCGT

GGTGTCTTTGCGTTTCTTTTATATGTTGCCACCTTTATGTATGTATTTTC

TACGTTTGCTAACATACTGCGTAATAAGGAGTCTTAATCATGCCAGTTCT

TTTGGGTATTCCGTTATTATTGCGTTTCCTCGGTTTCCTTCTGGTAACTT

TGTTCGGCTATCTGCTTACTTTTCTTAAAAAGGGCTTCGGTAAGATAGCT

ATTGCTATTTCATTGTTTCTTGCTCTTATTATTGGGCTTAACTCAATTCT

TGTGGGTTATCTCTCTGATATTAGCGCTCAATTACCCTCTGACTTTGTTC

AGGGTGTTCAGTTAATTCTCCCGTCTAATGCGCTTCCCTGTTTTTATGTT

ATTCTCTCTGTAAAGGCTGCTATTTTCATTTTTGACGTTAAACAAAAAAT

CGTTTCTTATTTGGATTGGGATAAATAATATGGCTGTTTATTTTGTAACT

GGCAAATTAGGCTCTGGAAAGACGCTCGTTAGCGTTGGTAAGATTCAGGA

TAAAATTGTAGCTGGGTGCAAAATAGCAACTAATCTTGATTTAAGGCTTC

AAAACCTCCCGCAAGTCGGGAGGTTCGCTAAAACGCCTCGCGTTCTTAGA

ATACCGGATAAGCCTTCTATATCTGATTTGCTTGCTATTGGGCGCGGTAA

TGATTCCTACGATGAAAATAAAAACGGCTTGCTTGTTCTCGATGAGTGCG

GTACTTGGTTTAATACCCGTTCTTGGAATGATAAGGAAAGACAGCCGATT

ATTGATTGGTTTCTACATGCTCGTAAATTAGGATGGGATATTATTTTTCT

TGTTCAGGACTTATCTATTGTTGATAAACAGGCGCGTTCTGCATTAGCTG

AACATGTTGTTTATTGTCGTCGTCTGGACAGAATTACTTTACCTTTTGTC

GGTACTTTATATTCTCTTATTACTGGCTCGAAAATGCCTCTGCCTAAATT

-continued

ACATGTTGGCGTTGTTAAATATGGCGATTCTCAATTAAGCCCTACTGTTG

AGCGTTGGCTTTATACTGGTAAGAATTTGTATAACGCATATGATACTAAA

CAGGCTTTTTCTAGTAATTATGATTCCGGTGTTTATTCTTATTTAACGCC

TTATTTATCACACGGTCGGTATTTCAAACCATTAAATTTAGGTCAGAAGA

TGAAATTAACTAAAATATATTTGAAAAAGTTTTCTCGCGTTCTTTGTCTT

GCGATTGGATTTGCATCAGCATTTACATATAGTTATATAACCCAACCTAA

GCCGGAGGTTAAAAAGGTAGTCTCTCAGACCTATGATTTTGATAAATTCA

CTATTGACTCTTCTCAGCGTCTTAATCTAAGCTATCGCTATGTTTTCAAG

GATTCTAAGGGAAAATTAATTAATAGCGACGATTTACAGAAGCAAGGTTA

TTCACTCACATATATTGATTTATGTACTGTTTCCATTAAAAAAGGTAATT

CAAATGAAATTGTTAAATGTAATTAATTTTGTTTTCTTGATGTTTGTTTC

ATCATCTTCTTTTGCTCAGGTAATTGAAATGAATAATTCGCCTCTGCGCG

ATTTTGTAACTTGGTATTCAAAGCAATCAGGCGAATCCGTTATTGTTTCT

CCCGATGTAAAAGGTACTGTTACTGTATATTCATCTGACGTTAAACCTGA

AAATCTACGCAATTTCTTTATTTCTGTTTTACGTGCAAGTAATTTTGATA

TGGTTGGTTCTAACCCTTCCATTATTCAGAAGTATAATCCAAACAATCAG

GATTATATTGATGAATTGCCATCATCTGATAATCAGGAATATGATGATAA

TTCCGCTCCTTCTGGTGGTTTCTTTGTTCCGCAAAATGATAATGTTACTC

AAACTTTTAAAATTAATAACGTTCGGGCAAAGGATTTAATACGAGTTGTC

GAATTGTTTGTAAAGTCTAATACTTCTAAATCCTCAAATGTATTATCTAT

TGACGGCTCTAATCTATTAGTTGTTAGTGCACCTAAAGATATTTTAGATA

ACCTTCCTCAATTCCTTTCTACTGTTGATTTGCCAACTGACCAGATATTG

ATTGAGGGTTTGATATTTGAGGTTCAGCAAGGTGATGCTTTAGATTTTTC

ATTTGCTGCTGGCTCTCAGCGTGGCACTGTTGCAGGCGGTGTTAATACTG

ACCGCCTCACCTCTGTTTTATCTTCTGCTGGTGGTTCGTTCGGTATTTTT

AATGGCGATGTTTTAGGGCTATCAGTTCGCGCATTAAAGACTAATAGCCA

TTCAAAAATATTGTCTGTGCCACGTATTCTTACGCTTTCAGGTCAGAAGG

GTTCTATCTTTGTTGGCCAGAATGTCCCTTTTATTACTGGTCGTGTGACT

GGTGAATCTGCCAATGTAAATAATCCATTTCAGACGATTGAGCGTCAAAA

TGTAGGTATTTCCATGAGCGTTTTTCCTGTTGCAATGGCTGGCGGTAATA

TTGTTCTGGATATTACCAGCAAGGCCGATAGTTTGAGTTCTTCTACTCAG

GCAAGTGATGTTATTACTAATCAAAGAAGTACTGCTACAACGGTTAATTT

GCGTGATGGACAGACTCTTTTACTCGGTGGCCTCACTGATTATAAAAACA

CTTCTCAGGATTCTGGCGTACCGTTCCTGTCTAAAATCCCTTTAATCGGC

CTCCTGTTTAGCTCCCGCTCTGATTCTAACGAGGAAAGCACGTTATACGT

GCTCGTCAAAGCAACCATAGTACGCGCCCTGTAGCGGCGCATTAAGCGCG

GCGGGTGTGGTGGTTACGCGCAGCGTGACCGCTACACTTGCCAGCGCCCT

AGCGCCCGCTCCTTTCGCTTTCTTCCCTTCCTTTCTCGCCACGTTCGCCG

GCTTTCCCCGTCAAGCTCTAAATCGGGGGCTCCCTTTAGGGTTCCGATTT

AGTGCTTTACGGCACCTCGACCCCAAAAAACTTGATTTGGGTGATGGTTC

-continued

```
ACGTAGTGGGCCATCGCCCTGATAGACGGTTTTTCGCCCTTTGACGTTGG

AGTCCACGTTCTTTAATAGTGGACTCTTGTTCCAAACTGGAACAACACTC

AACCCTATCTCGGGCTATTCTTTTGATTTATAAGGGATTTTGCCGATTTC

GGCCTATTGGTTAAAAAATGAGCTGATTTAACAAAAATTTAACGCGAATT

TTAACAAAATATTAACGTTTACAATTTAAATATTTGCTTATACAATCTTC

CTGTTTTTGGGGCTTTTCTTATTATCAACCGGGGTACAT
```

One prerequisite for evolving proteases with a desired activity is to provide a selection system that confers a selective advantage to mutated protease variants exhibiting such an activity. The expression systems and fusion proteins comprising transcriptional activators in an inactive form that are activated by protease activity thus constitute an important feature of some embodiments of the protease PACE technology provided herein.

In some embodiments, the host cell expresses a fusion molecule comprising (i) a transcriptional activator; and (ii) an inhibitor of the transcriptional activator of (i), wherein the inhibitor is fused to the transcriptional activator of (i) via a linker comprising a protease cleavage site that is cleaved by the protease of (a). In some embodiments, the host cell expresses a transcriptional activator that is fused to a polypeptide tag targeting the transcriptional activator for degradation, or directing export of the transcriptional activator from the host cell or into a compartment of the host cell in which the transcriptional activator cannot mediate transcription from a target promoter. Suitable transcriptional activators, inhibitors, and polypeptide tags will be readily apparent to those of skill in the art based on the instant disclosure.

In some embodiments, the transcriptional activator directly drives transcription from a target promoter. For example, in some such embodiments, the transcriptional activator may be an RNA polymerase. Suitable RNA polymerases and promoter sequences targeted by such RNA polymerases are well known to those of skill in the art. Exemplary suitable RNA polymerases include, but are not limited to, T7 polymerases (targeting T7 promoter sequences) and T3 RNA polymerases (targeting T3 promoter sequences). Additional suitable RNA polymerases will be apparent to those of skill in the art based on the instant disclosure, which is not limited in this respect.

In some embodiments, the transcriptional activator does not directly drive transcription, but recruits the transcription machinery of the host cell to a specific target promoter. Suitable transcriptional activators, such as, for example, Gal4 or fusions of the transactivation domain of the VP16 transactivator with DNA-binding domains, will be apparent to those of skill in the art based on the instant disclosure, and the disclosure is not limited in this respect.

In some embodiments, it is advantageous to link protease activity to enhanced phage packaging via a transcriptional activator that is not endogenously expressed in the host cells in order to minimize leakiness of the expression of the gene required for the generation of infectious phage particles through the host cell basal transcription machinery. For example, in some embodiments, it is desirable to drive expression of the gene required for the generation of infectious phage particles from a promoter that is not or is only minimally active in host cells in the absence of an exogenous transcriptional activator, and to provide the exogenous transcriptional activator, such as, for example, T7 RNA polymerase, as part of the expression system linking protease activity to phage packaging efficiency. In some embodiments, the at least one gene for the generation of infectious phage particles is expressed in the host cells under the control of a promoter activated by the transcriptional activator, for example, under the control of a T7 promoter if the transcriptional activator is T7 RNA polymerase, and under the control of a T3 promoter if the transcriptional activator is T3 polymerase, and so on.

In some embodiments, the transcriptional activator is fused to an inhibitor that either directly inhibits or otherwise hinders the transcriptional activity of the transcriptional activator, for example, by directly interfering with DNA binding or transcription, by targeting the transcriptional activator for degradation through the host cells protein degradation machinery, or by directing export from the host cell or localization of the transcriptional activator into a compartment of the host cell in which it cannot activate transcription from its target promoter. In some embodiments, the inhibitor is fused to the transcriptional activator's N-terminus. In other embodiments, it is fused to the activator's C-terminus.

Typically, the fusion proteins employed in the protease PACE methods provided herein comprise a linker connecting the transcriptional activator to the inhibitor and comprising a protease cleavage site. In some embodiments, the transcriptional activity of the fusion protein is inhibited as compared to the activity of the transcriptional activator alone. Such inhibition can be detected by suitable assays well known to those of skill in the art. For example, a reporter assay for assessing the transcriptional activity of a fusion protein and a transcriptional activator alone may comprise a reporter expression construct comprising a nucleic acid encoding a reporter gene under the control of a promoter targeted by the transcriptional activator. The reporter gene may be, for example, a fluorescent protein or a protein that catalyzes a bioluminescent reaction. The transcriptional activity of the respective fusion protein or the transcriptional activator alone can then be determined by fluorescent or bioluminescent readouts. Additional suitable assays for determining the transcriptional activity of the fusion proteins provided herein will be apparent to those of skill in the art and include, without limitation, those described in International PCT Application, PCT/US2011/066747, filed Dec. 22, 2011, published as WO 2012/088381 on Jun. 28, 2012; and U.S. application, U.S. Ser. No. 13/922,812, filed Jun. 20, 2013, the entire contents of each of which are incorporated herein by reference.

In some embodiments, the transcriptional activity of the fusion protein is less than 50%, less than 25%, less than 20%, less than 10%, less than 5%, less than 4%, less than 3%, less than 1%, less than 0.1%, less than 0.01%, or less than 0.001% the activity of the transcriptional activator alone, for example, as measured via a suitable assay, such as one of the exemplary, non-limiting fluorescent or bioluminescent assays provided herein or in International PCT Application, PCT/US2011/066747, filed Dec. 22, 2011, published as WO 2012/088381 on Jun. 28, 2012; and U.S. application, U.S. Ser. No. 13/922,812, filed Jun. 20, 2013, the entire contents of each of which are incorporated herein by reference.

In some embodiments, cleavage of the protease cleavage site comprised in the linker connecting the transcriptional activator and the inhibitor results in release of the inhibitor from the activator and thus activation of the transcriptional activator. In some embodiments, the activity of the transcriptional activator is increased at least 2-fold, at least 5-fold, at least 10-fold, at least 20-fold, at least 25-fold, at least 50-fold, at least 75-fold, at least 100-fold, at least 200-fold, at least 250-fold, at least 500-fold, at least 750-fold, at least 1000-fold, at least 2000-fold, at least 2500-fold, at least 5000-fold, at least 7500-fold, at least 10000-fold, or more upon cleavage of the protease cleavage site of the linker.

In some embodiments, the protease to be evolved is a therapeutic protease. Therapeutic proteases are well known to those of skill in the art and include, without limitation, proteases that are useful for the treatment of cardiovascular disease, sepsis, digestive disorders, inflammation, cystic fibrosis, retinal disorders, psoriasis, and other diseases. Exemplary therapeutic proteases include, without limitation, those proteases described in Craik et al., Proteases as therapeutics. *Biochem J.* 2011 Apr. 1; 435(1):1-16, the entire contents of which are incorporated herein by reference. Some exemplary therapeutic proteases are listed below:

| Protease | Indication |
|---|---|
| Urokinase (u-PA) | Thrombus, catheter clearing |
| t-PA (alteplase, Activase ®) | Myocardial infarction, stroke |
| Reteplase (Retevase) | Myocardial infarction |
| TNK-tPA (tenecteplase, Metalyse ®) | Myocardial infarction |
| Factor IX (BeneFIX ®) | Haemophilia B |
| FVIIa (NovoSeven ®) | Haemophilia A and B |
| Thrombin (Recothrom ®) | Bleeding |
| Activated protein C (drotrecogin alfa, Xigris ®) | Sepsis, septic shock |
| Botulinum toxin A (Botox ®) | Muscle spasms |
| Botulinum toxin B (Myobloc) | Cervical dystonia |
| Zenpep ® (pancrelipase) | Pancreatic Insufficiency |
| Liprotamase (*Aspergillus melleus*) | Cystic fibrosis with exocrine pancreatic insufficiency |
| Microplasmin | Vitreomacular adhesion |
| Glutamine-specific cysteine protease CEP-B2) | |
| Proline-specific prolylendopeptidase (PEP), ALV003 | Coeliac disease |
| Microplasmin | Acute peripheral arterial occlusion, deep vein thrombosis |
| Plasmin | Peripheral arterial disease, thrombosis |
| Recombinant human lysosomal protease | Medical and cosmetic dermatological applications |
| Kallikrein | Thrombosis, peripheral vascular disease, cerebrovascular ischaemia |
| Calpain 3 | Replacement therapy, calpainopathy |
| Penzyme | Psoriasis, eczema and dermatitis |

Additional suitable therapeutic proteases will be apparent to those of skill in the art based on the instant disclosure.

In some embodiments, a therapeutic protease is subjected to PACE to improve the efficiency with which the protease cleaves its target sequence. This may allow achieving the same therapeutic effect with a smaller dose of administered protease or achieving a greater therapeutic effect with the same dose as compared to using a non-evolved protease. In some embodiments, the therapeutic protease may be subjected to PACE to decrease the cleavage of off-target cleavage sites, e.g., by employing negative PACE selection strategies described in more detail elsewhere herein or otherwise known in the art. Decreasing off-target protease cleavage may decrease the toxicity and/or side effects of a therapeutic protease.

In some embodiments, the replicated vector isolated after a protease PACE experiment encodes a mutated protease that cleaves the protease cleavage site with higher efficiency and/or higher specificity than the original version of the protease used at the outset of the PACE experiment. The mutated protease can then be analyzed, and the critical mutations resulting in the observed improvements can be ascertained. For example, a plurality of different evolved proteases isolated from a single PACE experiment or from different PACE experiments starting with the same protease can be analyzed. Shared mutations amongst the evolved proteases are likely to contribute to enhanced protease activity, while mutations that occur only in individual proteases are not likely to contribute to enhanced protease activity. The contribution of an observed mutation after protease PACE may also be followed up in more depth, for example, by introducing the mutation into the original protease and determining the level of improvement conferred by the respective mutation in isolation or in combination with other observed mutations. Those of skill in the art will know suitable methods for generating recombinant proteins to perform such follow-up experiments after protease PACE.

In some embodiments, the protease to be evolved is a target of a protease inhibitor. In some such embodiments, the protease inhibitor is a therapeutic agent. Protease inhibitors are an important class of therapeutic agents and are used, for example, in the treatment of viral infections, protozoal infections, and certain types of cancer. Antiviral protease inhibitors are used, for example, in the context of retroviral infections, and some examples of known antiretroviral protease inhibitors include, without limitation, Saquinavir (e.g., Fortovase, Invirase; see, e.g., U.S. Pat. No. 5,196,438); Ritonavir (e.g., Norvir; see, e.g., U.S. Pat. No. 5,541,206); Indinavir (e.g., Crixivan; see, e.g., U.S. Pat. No. 5,413,999); Nelfinavir (e.g., Viracept; see, e.g., U.S. Pat. No. 5,484,926); Amprenavir (e.g., Agenerase; see, e.g., U.S. Pat. No. 5,585,397); Lopinavir (e.g., Kaletra; see, e.g., U.S. Pat. No. 5,914,332); Atazanavir (e.g., Reyataz; see, e.g., U.S. Pat. No. 5,849,911); Fosamprenavir (e.g., Lexiva, Telzir); Tipranavir (e.g., Aptivus); Darunavir (e.g., Prezista, Tibotec; U.S. Pat. No. 6,248,775); Simeprevir (e.g., Olysio, TMC435; U.S. Pat. No. 7,671,032); Danoprevir; and Asunaprevir. Additional suitable protease inhibitors will be apparent to those of skill in the art based on the instant disclosure, which is not limited in this respect.

In some embodiments, protease PACE is carried out in the presence of the protease inhibitor during all or some of the steps in which the phage encoding the protease mutates and replicates in the flow of host cells. In some embodiments, the protease inhibitor is used at a concentration that does not completely inhibit the activity of the protease. This results, in some embodiments, in the selective pressure being relieved to a certain extent, which allows a diversification of the protease pool since even mutated variants of the protease that are not active in the presence of the inhibitor will be able to propagate in the flow of host cells at a basal level, e.g., at a level that prevents dilution and/or washout of such protease variants from the population of vectors replicating in the cell flow. Such a diversification may be advantageous in some embodiments, e.g., to provide a more varied initial pool of proteases that can then be subjected to evolution under more stringent selective pressure, e.g., in the presence of a concentration of protease inhibitor that results in complete inactivation of the activity of the original protease. Relieving the selective pressure may also be performed at one or more time points during an ongoing PACE experiment, for example, to achieve re-diversification of an evolved protease pool in order to access additional mutations that could not be reached under constant stringent selection pressure.

For example, in some embodiments, a PACE experiment may include an initial phase, e.g., of 1 hour, 2 hours, 3 hours, 4 hours, 5 hours, or 6 hours, or longer, in which now or only low selective pressure is applied, for example, by providing host cells in which the selection phage can replicate regardless of any advantageous mutations, and a subsequent phase, e.g., of 1 hour, 2 hours, 3 hours, 4 hours, 5 hours, or 6 hours, or longer, in which increased selection pressure is applied, for example, by providing host cells that preferentially support replication of phage comprising beneficial mutations, e.g., host cells harboring an accessory plasmid that links protease activity to phage replication efficiency, as described herein. In some PACE experiments, the selective pressure is increased over time, e.g., by subsequently using more and more selective accessory plasmids, e.g., starting with high copy number accessory plasmids and moving to plasmids with a lower copy number. In some embodiments, phases of no or low stringency of selection are alternated with phases of high selective pressure, in order to create multiple rounds of library diversification and selection.

In some embodiments, the protease inhibitor is used at a concentration that results in an inhibition of at least 50%, at least 75%, at least 80%, at least 90%, at least 95%, at least 97.5%, at least 98%, at least 99%, at least 99.5%, or at least 99.9% of the protease activity. In some embodiments, the protease inhibitor is used at an initial concentration that does not completely inhibit the activity of the protease, and the concentration of the inhibitor is subsequently raised to increase the level of protease inhibition in order to increase the stringency of selective pressure during the PACE experiment.

In some embodiments in which a protease inhibitor is used, a phage vector isolated at the end of a PACE experiment encodes a mutated protease variant that cleaves the protease cleavage site in the presence of the inhibitor. In other words, in some embodiments, a protease variant that is resistant to the protease inhibitor used is isolated. In some embodiments, the vector isolated at the end of a PACE experiment encodes a mutated protease that cleaves the protease cleavage site in the presence of the inhibitor with higher efficiency than the original version of the protease used at the outset of the PACE experiment.

In some embodiments, the protease evolution methods provided herein comprise an initial or intermittent phase of diversifying the population of vectors by mutagenesis, in which the cells are incubated under conditions suitable for mutagenesis of the gene encoding the protease in the absence of stringent selection or in the absence of any selection for evolved protease variants that have acquired a desired activity. Such low-stringency selection or no selection periods may be achieved by supporting expression of the gene for the generation of infectious phage particles in the absence of desired protease activity, for example, by providing an inducible expression construct comprising a gene encoding the respective packaging protein under the control of an inducible promoter and incubating under conditions that induce expression of the promoter, e.g., in the presence of the inducing agent. Suitable inducible promoters and inducible expression systems are described herein and in International PCT Application, PCT/US2011/066747, filed Dec. 22, 2011, published as WO 2012/088381 on Jun. 28, 2012; and U.S. application, U.S. Ser. No. 13/922,812, filed Jun. 20, 2013, the entire contents of each of which are incorporated herein by reference. Additional suitable promoters and inducible gene expression systems will be apparent to those of skill in the art based on the instant disclosure. In some embodiments, the method comprises a phase of stringent selection for a mutated protease version. If an inducible expression system is used to relieve selective pressure, the stringency of selection can be increased by removing the inducing agent from the population of cells in the lagoon, thus turning expression from the inducible promoter off, so that any expression of the gene required for the generation of infectious phage particles must come from the protease activity-dependent expression system.

One aspect of the PACE protease evolution methods provided herein is the mutation of the initially provided vectors encoding a protease of interest. In some embodiments, the host cells within the flow of cells in which the vector replicates are incubated under conditions that increase the natural mutation rate. This may be achieved by contacting the host cells with a mutagen, such as certain types of radiation or to a mutagenic compound, or by expressing genes known to increase the cellular mutation rate in the cells.

In some embodiments, the host cells are exposed to a mutagen. Typically, the concentration of the mutagen will be chosen to maximize the mutation rate while not being toxic to the host cells during the retention time in the lagoon. Ideally, a mutagen is used at a concentration or level of exposure that induces a desired mutation rate in a given host cell or viral vector population, but is not significantly toxic to the host cells used within the average time frame a host cell is exposed to the mutagen or the time a host cell is present in the host cell flow before being replaced by a fresh host cell. In some embodiments, the mutagen is ionizing radiation, ultraviolet radiation, base analogs, deaminating agents (e.g., nitrous acid), intercalating agents (e.g., ethidium bromide), alkylating agents (e.g., ethylnitrosourea), transposons, bromine, azide salts, psoralen, benzene,3-Chloro-4-(dichloromethyl)-5-hydroxy-2(5H)-furanone (MX) (CAS no. 77439-76-0), O,O-dimethyl-S-(phthalimidomethyl)phosphorodithioate (phos-met) (CAS no. 732-11-6), formaldehyde (CAS no. 50-00-0), 2-(2-furyl)-3-(5-nitro-2-furyl)acrylamide (AF-2) (CAS no. 3688-53-7), glyoxal (CAS no. 107-22-2), 6-mercaptopurine (CAS no. 50-44-2), N-(trichloromethylthio)-4-cyclohexane-1,2-dicarboximide (captan) (CAS no. 133-06-2), 2-aminopurine (CAS no. 452-06-2), methyl methane sulfonate (MMS) (CAS No. 66-27-3), 4-nitroquinoline 1-oxide (4-NQO) (CAS No. 56-57-5), N4-Aminocytidine (CAS no. 57294-74-3), sodium azide (CAS no. 26628-22-8), N-ethyl-N-nitrosourea (ENU) (CAS no. 759-73-9), N-methyl-N-nitrosourea (MNU) (CAS no. 820-60-0), 5-azacytidine (CAS no. 320-67-2), cumene hydroperoxide (CHP) (CAS no. 80-15-9), ethyl methanesulfonate (EMS) (CAS no. 62-50-0), N-ethyl-N-nitro-N-nitrosoguanidine (ENNG) (CAS no. 4245-77-6), N-methyl-N-nitro-N-nitrosoguanidine (MNNG) (CAS no. 70-25-7), 5-diazouracil (CAS no. 2435-76-9), or t-butyl hydroperoxide (BHP) (CAS no. 75-91-2). Additional suitable mutagens will be known to those of skill in the art, and the disclosure is not limited in this respect.

In some embodiments, the mutation rate of the host cells is increased by contacting the cells with a mutagenesis plasmid encoding gene products known to increase the frequency of mutations in the host cells. In some embodiments, the host cells are contacted with a mutagenesis plasmid. In some embodiments, the mutagenesis plasmid comprises a gene expression cassette encoding a mutagenesis-promoting gene product. In some embodiments, the mutagenesis plasmid comprises a gene expression cassette encoding umuC (a component of *E. coli* translesion synthesis polymerase V, e.g., as set forth in GenBank M10107.1), dam (deoxyadenosine methylase, e.g., as set forth in GenBank J01600.1), or seqA (a hemimethylated-GATC binding domain, e.g., as set forth in GenBank U07651.1), or any combination thereof. In some embodiments, the mutagenesis plasmid further comprises a nucleic acid encoding UmuD', and/or RecA.

In some embodiments, the mutagenesis-promoting gene is under the control of an inducible promoter. Suitable inducible promoters are well known to those of skill in the art and include, for example, arabinose-inducible promoters, tetracycline or doxycyclin-inducible promoters, and tamoxifen-inducible promoters. In some embodiments, the host cell population is contacted with an inducer of the inducible promoter in an amount sufficient to effect an increased rate of mutagenesis. For example, in some embodiments, a bacterial host cell population is provided in which the host cells comprise a mutagenesis plasmid in which a umuC, dam, and seqA expression cassette is controlled by an arabinose-inducible promoter. In some such embodiments, the population of host cells is contacted with the inducer, for example, arabinose, in an amount sufficient to induce an increased rate of mutation.

The use of an inducible mutagenesis plasmid allows one to generate a population of fresh, uninfected host cells in the absence of the inducer, thus avoiding an increased rate of mutation in the fresh host cells before they are introduced into the population of cells contacted with the viral vector. Once introduced into this population, however, these cells can then be induced to support an increased rate of mutation, which is particularly useful in some embodiments of continuous evolution. For example, in some embodiments, the host cell comprises a mutagenesis plasmid as described herein, which includes an arabinose-inducible promoter driving expression of umuC, dam, and seqA from a pBAD promoter (see, e.g., Khlebnikov A, Skaug T, Keasling J D. *Modulation of gene expression from the arabinose-inducible araBAD promoter*. J Ind Microbiol Biotechnol. 2002 July; 29(1):34-7; incorporated herein by reference for disclosure of a pBAD promoter). In some embodiments, the fresh host cells are not exposed to arabinose, which activates expression of the above-identified genes and, thus, increases the rate of mutations in the arabinose-exposed cells, until the host cells reach the lagoon in which the population of selection phage replicates. Accordingly, in some embodiments, the mutation rate in the host cells is normal until they become part of the host cell population in the lagoon, where they are exposed to the inducer (e.g., arabinose) and, thus, to increased mutagenesis. In some embodiments, a method of continuous evolution is provided that includes a phase of diversifying the population of viral vectors by mutagenesis, in which the cells are incubated under conditions suitable for mutagenesis of the viral vector in the absence of stringent selection for the mutated replication product of the viral vector encoding the evolved protein. This is particularly useful in embodiments in which a desired function to be evolved is not merely an increase in an already present function, for example, an increase in the cleavage activity of a protease towards its original cleavage site, but the acquisition of a function not present in the protease to be evolved at the outset of the evolution procedure, such as, for example, cleavage of a target site not recognized by the original version of the protease to be evolved. A step of diversifying the pool of mutated versions of the gene of interest within the population of viral vectors, for example, of phage, allows for an increase in the chance to find a mutation that conveys the desired function, e.g., new substrate specificity in a protease to be evolved.

In some embodiments, the host cell population is contacted with a mutagen continuously during a PACE experiment. In other embodiments, the host cell population is contacted with the mutagen intermittently, creating phases of increased mutagenesis, and accordingly, of increased viral vector diversification. For example, in some embodiments, the host cells are exposed to a concentration of mutagen sufficient to generate an increased rate of mutagenesis in the gene of interest for about 10%, about 20%, about 30%, about 40%, about 50%, or about 75% of the time. In embodiments where a mutagenesis plasmid is employed, intermittent exposure to the encoded mutagenesis-increasing gene products can be achieved by using inducible promoters and adding or withdrawing the inducing agent from the host cell culture media during the PACE experiment.

In some embodiments, the link between desired protease activity and selective advantage for an encoding phage is provided by an expression system in which at least one gene for the generation of infectious phage particles is expressed in response to the desired protease activity as described in more detail elsewhere herein. In some embodiments, the at least one gene for the generation of infectious phage particles to another host cell is a gene required for the production of infectious phage particles. In some embodiments, the vector is M13 phage, and the at least one gene for the generation of infectious phage particles comprises a full-length M13 pIII gene. In some embodiments, the host cells comprise an accessory plasmid comprising an expression construct encoding the at least one gene for the generation of infectious phage particles, e.g., the full-length pIII protein, under the control of a conditional promoter that is activated by the transcriptional activator comprised in the fusion protein.

In some embodiments, the conditional promoter of the accessory plasmid is a promoter, the transcriptional activity of which can be regulated over a wide range, for example, over 2, 3, 4, 5, 6, 7, 8, 9, or 10 orders of magnitude by the activating function, for example, the function of a protease of interest. In some embodiments, the conditional promoter has a basal activity that allows for baseline packaging of viral vectors even in the absence of the desired protease activity or in the presence of only minimal desired protease activity. This allows for starting a continuous evolution process with a viral vector population comprising versions of the protease of interest that only show minimal activation of the conditional promoter, e.g., of wild-type proteases that are fully inhibited by a therapeutic protease inhibitor. In the process of continuous evolution, any mutation in the gene of interest that increases activity of the conditional promoter directly translates into higher expression levels of the gene required for the generation of infectious viral particles in the host cells harboring the vector comprising such a mutation, and, thus, into a competitive advantage over other viral vectors carrying minimally active or loss-of-function versions of the protease of interest.

One function of the accessory plasmid is to provide a gene for the generation of infectious phage particles under the control of a conditional promoter the activity of which depends on a function of the protease of interest. Accordingly, the accessory plasmid provides a selection mechanism that favors desirable mutations over inconsequential mutations or mutations that are detrimental to the desired function. The stringency of selective pressure imposed by the accessory plasmid in a continuous evolution procedure as provided herein can be modulated. For example, an accessory plasmid may be used at different copy numbers per cell, may comprise a conditional promoter having a base line transcription rate ("leakiness") that prevents washout of unmutated sequences from the lagoon while still providing a selective advantage to desirable mutations. In some embodiments, an accessory plasmid comprising an expression cassette in which the gene for the generation of infectious phage particles is under the control of an inducible promoter that can be activated by a chemical compound (e.g., a tet-on promoter), allowing for titration of the expression of the gene for the generation of infectious phage particles during a continuous evolution experiment.

In some embodiments, the use of low copy number accessory plasmids results in an elevated stringency of selection for versions of the gene encoding a protease of interest that activate the conditional promoter on the accessory plasmid, while the use of high copy number accessory plasmids results in a lower stringency of selection. The copy number of an accessory plasmid will depend to a large part on the origin of replication employed. Those of skill in the art will be able to determine suitable origins of replication in order to achieve a desired copy number. The following table lists some non-limiting examples of vectors of different copy numbers and with different origins of replication:

| Plasmids | Origin of Replication | Copy number | Class |
|---|---|---|---|
| pUC vectors | pMB1* | 500-700 | high copy |
| pBluescript ® vectors | ColE1 | 300-500 | high copy |
| pGEM ® vectors | pMB1* | 300-400 | high copy |
| pTZ vectors | pMB1* | >1000 | high copy |
| pBR322 and derivatives | pMB1* | 15-20 | low copy |
| pACYC and derivatives | p15A | 10-12 | low copy |
| pSC101 and derivatives | pSC101 | ~5 | very low copy |

*The pMB1 origin of replication is closely related to that of ColE1 and falls in the same incompatibility group. The high-copy plasmids listed here contain mutated versions of this origin.

It should be understood that one function of the accessory plasmid, namely to provide a gene for the generation of infectious phage particles under the control of a conditional promoter, the activity of which depends on a function of the gene of interest, can be conferred to a host cell in alternative ways. Such alternatives include, but are not limited to, permanent insertion of a gene construct comprising the conditional promoter and the respective gene into the genome of the host cell, or introducing it into the host cell using a different vector, for example, a phagemid, a cosmid, a phage, a virus, or an artificial chromosome. Additional ways to confer accessory plasmid function to host cells will be evident to those of skill in the art, and the invention is not limited in this respect.

The sequences of two exemplary, non-limiting accessory plasmids, AP-MCS-A, and AP-MCS-P, respectively, are provided below:

AP-MCS-A:

(SEQ ID NO: 31)

GGCTGTTTTGGCGGATGAGAGAAGATTTTCAGCCTGATACAGATTAAATC

AGAACGCAGAAGCGGTCTGATAAAACAGAATTTGCCTGGCGGCAGTAGCG

CGGTGGTCCCACCTGACCCCATGCCGAACTCAGAAGTGAAACGCCGTAGC

GCCGATGGTAGTGTGGGGTCTCCCCATGCGAGAGTAGGGAACTGCCAGGC

ATCAAATAAAACGAAAGGCTCAGTCGAAAGACTGGGCCTTTCGTTTTATC

TGTTGTTTGTCGGTGAACGCTCTCCTGAGTAGGACAAATCCGCCGGGAGC

GGATTTGAACGTTGCGAAGCAACGGCCCGGAGGGTGGCGGGCAGGACGCC

CGCCATAAACTGCCAGGCATCAAATTAAGCAGAAGGCCATCCTGACGGAT

-continued

GGCCTTTTTGCGTTTCTACAAACTCTACTCTGCTAGCAAGTAAGGCCGAC

AAGCTTGCATGCCTGCAGGTCGACTCTAGAGGATCCCCGGGTACCGAGCT

CGAATTCCCTTTTTTTTTGGAGATTTTCAACGTGAAAAAATTATTATTCG

CAATTCCTTTAGTTGTTCCTTTCTATTCTCACTCCGCTGAAACTGTTGAA

AGTTGTTTAGCAAAACCCCATACAGAAAATTCATTTACTAACGTCTGGAA

AGACGACAAAACTTTAGATCGTTACGCTAACTATGAGGGCTGTCTGTGGA

ATGCTACAGGCGTTGTAGTTTGTACTGGTGACGAAACTCAGTGTTACGGT

ACATGGGTTCCTATTGGGCTTGCTATCCCTGAAAATGAGGGTGGTGGCTC

TGAGGGTGGCGGTTCTGAGGGTGGCGGTTCTGAGGGTGGCGGTACTAAAC

CTCCTGAGTACGGTGATACACCTATTCCGGGCTATACTTATATCAACCCT

CTCGACGGCACTTATCCGCCTGGTACTGAGCAAAACCCCGCTAATCCTAA

TCCTTCTCTTGAGGAGTCTCAGCCTCTTAATACTTTCATGTTTCAGAATA

ATAGGTTCCGAAATAGGCAGGGGGCATTAACTGTTTATACGGGCACTGTT

ACTCAAGGCACTGACCCCGTTAAAACTTATTACCAGTACACTCCTGTATC

ATCAAAAGCCATGTATGACGCTTACTGGAACGGTAAATTCAGAGACTGCG

CTTTCCATTCTGGCTTTAATGAGGATCCATTCGTTTGTGAATATCAAGGC

CAATCGTCTGACCTGCCTCAACCTCCTGTCAATGCTGGCGGCGGCTCTGG

TGGTGGTTCTGGTGGCGGCTCTGAGGGTGGTGGCTCTGAGGGTGGCGGTT

CTGAGGGTGGCGGCTCTGAGGGAGGCGGTTCCGGTGGTGGCTCTGGTTCC

GGTGATTTTGATTATGAAAAGATGGCAAACGCTAATAAGGGGGCTATGAC

CGAAAATGCCGATGAAAACGCGCTACAGTCTGACGCTAAAGGCAAACTTG

ATTCTGTCGCTACTGATTACGGTGCTGCTATCGATGGTTTCATTGGTGAC

GTTTCCGGCCTTGCTAATGGTAATGGTGCTACTGGTGATTTTGCTGGCTC

TAATTCCCAAATGGCTCAAGTCGGTGACGGTGATAATTCACCTTTAATGA

ATAATTTCCGTCAATATTTACCTTCCCTCCCTCAATCGGTTGAATGTCGC

CCTTTTGTCTTTGGCGCTGGTAAACCATATGAATTTTCTATTGATTGTGA

CAAAATAAACTTATTCCGTGGTGTCTTTGCGTTTCTTTTATATGTTGCCA

CCTTTATGTATGTATTTTCTACGTTTGCTAACATACTGCGTAATAAGGAG

TCTTAATCATGCCAGTTCTAGCATAACCCCTTGGGGCCTCTAAACGGGTC

TTGAGGGGTTTTTTGCCTTGTCGGCCTTACTTGCTAAATACATTCAAATA

TGTATCCGCTCATGAGACAATAACCCTGATAAATGCTTCAATAATATTGA

AAAAGGAAGAGTATGAGTATTCAACATTTCCGTGTCGCCCTTATTCCCTT

TTTTGCGGCATTTTGCCTTCCTGTTTTTGCTCACCCAGAAACGCTGGTGA

AAGTAAAAGATGCTGAAGATCAGTTGGGTGCACGAGTGGGTTACATCGAA

CTGGATCTCAACAGCGGTAAGATCCTTGAGAGTTTTCGCCCCGAAGAACG

TTTTCCAATGATGAGCACTTTTAAAGTTCTGCTATGTGGCGCGGTATTAT

CCCGTATTGACGCCGGGCAAGAGCAACTCGGTCGCCGCATACACTATTCT

CAGAATGACTTGGTTGAGTACTCACCAGTCACAGAAAAGCATCTTACGGA

TGGCATGACAGTAAGAGAATTATGCAGTGCTGCCATAACCATGAGTGATA

ACACTGCGGCCAACTTACTTCTGACAACGATCGGAGGACCGAAGGAGCTA

ACCGCTTTTTTGCACAACATGGGGGATCATGTAACTCGCCTTGATCGTTG

-continued

GGAACCGGAGCTGAATGAAGCCATACCAAACGACGAGCGTGACACCACGA
TGCCTGTAGCAATGGCAACAACGTTGCGCAAACTATTAACTGGCGAACTA
CTTACTCTAGCTTCCCGGCAACAATTGATAGACTGGATGGAGGCGGATAA
AGTTGCAGGACCACTTCTGCGCTCGGCCCTTCCGGCTGGCTGGTTTATTG
CTGATAAATCTGGAGCCGGTGAGCGTGGCTCTCGCGGTATCATTGCAGCA
CTGGGGCCAGATGGTAAGCCCTCCCGTATCGTAGTTATCTACACGACGGG
GAGTCAGGCAACTATGGATGAACGAAATAGACAGATCGCTGAGATAGGTG
CCTCACTGATTAAGCATTGGTAAGAACCTCAGATCCTTCCGTGATGGTAA
CTTCACTAGTTTAAAAGGATCTAGGTGAAGATCCTTTTTGATAATCTCAT
GACCAAAATCCCTTAACGTGAGTTTTCGTTCCACTGAGCGTCAGAGAACC
TCAGATCCTTCCGTATTTAGCCAGTATGTTCTCTAGTGTGGTTCGTTGTT
TTTGCGTGAGCCATGAGAACGAACCATTGAGATCATGCTTACTTTGCATG
TCACTCAAAAATTTTGCCTCAAAACTGGTGAGCTGAATTTTTGCAGTTAA
AGCATCGTGTAGTGTTTTTCTTAGTCCGTTACGTAGGTAGGAATCTGATG
TAATGGTTGTTGGTATTTTGTCACCATTCATTTTTATCTGGTTGTTCTCA
AGTTCGGTTACGAGATCCATTTGTCTATCTAGTTCAACTTGGAAAATCAA
CGTATCAGTCGGGCGGCCTCGCTTATCAACCACCAATTTCATATTGCTGT
AAGTGTTTAAATCTTTACTTATTGGTTTCAAAACCCATTGGTTAAGCCTT
TTAAACTCATGGTAGTTATTTTCAAGCATTAACATGAACTTAAATTCATC
AAGGCTAATCTCTATATTTGCCTTGTGAGTTTTCTTTTGTGTTAGTTCTT
TTAATAACCACTCATAAATCCTCATAGAGTATTTGTTTTCAAAAGACTTA
ACATGTTCCAGATTATATTTTATGAATTTTTTTAACTGGAAAAGATAAGG
CAATATCTCTTCACTAAAAACTAATTCTAATTTTTCGCTTGAGAACTTGG
CATAGTTTGTCCACTGGAAAATCTCAAAGCCTTTAACCAAAGGATTCCTG
ATTTCCACAGTTCTCGTCATCAGCTCTCTGGTTGCTTTAGCTAATACACC
ATAAGCATTTTCCCTACTGATGTTCATCATCTGAGCGTATTGGTTATAAG
TGAACGATACCGTCCGTTCTTTCCTTGTAGGGTTTTCAATCGTGGGGTTG
AGTAGTGCCACACAGCATAAAATTAGCTTGGTTTCATGCTCCGTTAAGTC
ATAGCGACTAATCGCTAGTTCATTTGCTTTGAAAACAACTAATTCAGACA
TACATCTCAATTGGTCTAGGTGATTTTAATCACTATACCAATTGAGATGG
GCTAGTCAATGATAATTACTAGTCCTTTTCCTTTGAGTTGTGGGTATCTG
TAAATTCTGCTAGACCTTTGCTGGAAAACTTGTAAATTCTGCTAGACCCT
CTGTAAATTCCGCTAGACCTTTGTGTGTTTTTTTTGTTTATATTCAAGTG
GTTATAATTTATAGAATAAAGAAAGAATAAAAAAAGATAAAAAGAATAGA
TCCCAGCCCTGTGTATAACTCACTACTTTAGTCAGTTCCGCAGTATTACA
AAAGGATGTCGCAAACGCTGTTTGCTCCTCTACAAAACAGACCTTAAAAC
CCTAAAGGCTTAAGTAGCACCCTCGCAAGCTCGGGCAAATCGCTGAATAT
TCCTTTTGTCTCCGACCATCAGGCACCTGAGTCGCTGTCTTTTTCGTGAC
ATTCAGTTCGCTGCGCTCACGGCTCTGGCAGTGAATGGGGGTAAATGGCA
CTACAGGCGCCTTTTATGGATTCATGCAAGGAAACTACCCATAATACAAG
AAAAGCCCGTCACGGGCTTCTCAGGGCGTTTTATGGCGGGTCTGCTATGT
GGTGCTATCTGACTTTTTGCTGTTCAGCAGTTCCTGCCCTCTGATTTTCC
AGTCTGACCACTTCGGATTATCCCGTGACAGGTCATTCAGACTGGCTAAT
GCACCCAGTAAGGCAGCGGTATCATCAACT

AP-MCS-P:

(SEQ ID NO: 32)

GGCTGTTTTGGCGGATGAGAGAAGATTTTCAGCCTGATACAGATTAAATC
AGAACGCAGAAGCGGTCTGATAAAACAGAATTTGCCTGGCGGCAGTAGCG
CGGTGGTCCCACCTGACCCCATGCCGAACTCAGAAGTGAAACGCCGTAGC
GCCGATGGTAGTGTGGGGTCTCCCCATGCGAGAGTAGGGAACTGCCAGGC
ATCAAATAAAACGAAAGGCTCAGTCGAAAGACTGGGCCTTTCGTTTTATC
TGTTGTTTGTCGGTGAACGCTCTCCTGAGTAGGACAAATCCGCCGGGAGC
GGATTTGAACGTTGCGAAGCAACGGCCCGGAGGGTGGCGGGCAGGACGCC
CGCCATAAACTGCCAGGCATCAAATTAAGCAGAAGGCCATCCTGACGGAT
GGCCTTTTTGCGTTTCTACAAACTCTACTCTGCTAGCAAGTAAGGCCGAC
AAGCTTGCATGCCTGCAGGTCGACTCTAGAGGATCCCCGGGTACCGAGCT
CGAATTCCCTTTTTTTTTGGAGATTTTCAACGTGAAAAAATTATTATTCG
CAATTCCTTTAGTTGTTCCTTTCTATTCTCACTCCGCTGAAACTGTTGAA
AGTTGTTTAGCAAAACCCCATACAGAAAATTCATTTACTAACGTCTGGAA
AGACGACAAAACTTTAGATCGTTACGCTAACTATGAGGGCTGTCTGTGGA
ATGCTACAGGCGTTGTAGTTTGTACTGGTGACGAAACTCAGTGTTACGGT
ACATGGGTTCCTATTGGGCTTGCTATCCCTGAAAATGAGGGTGGTGGCTC
TGAGGGTGGCGGTTCTGAGGGTGGCGGTTCTGAGGGTGGCGGTACTAAAC
CTCCTGAGTACGGTGATACACCTATTCCGGGCTATACTTATATCAACCCT
CTCGACGGCACTTATCCGCCTGGTACTGAGCAAAACCCCGCTAATCCTAA
TCCTTCTCTTGAGGAGTCTCAGCCTCTTAATACTTTCATGTTTCAGAATA
ATAGGTTCCGAAATAGGCAGGGGGCATTAACTGTTTATACGGGCACTGTT
ACTCAAGGCACTGACCCCGTTAAAACTTATTACCAGTACACTCCTGTATC
ATCAAAAGCCATGTATGACGCTTACTGGAACGGTAAATTCAGAGACTGCG
CTTTCCATTCTGGCTTTAATGAGGATCCATTCGTTTGTGAATATCAAGGC
CAATCGTCTGACCTGCCTCAACCTCCTGTCAATGCTGGCGGCGGCTCTGG
TGGTGGTTCTGGTGGCGGCTCTGAGGGTGGTGGCTCTGAGGGTGGCGGTT
CTGAGGGTGGCGGCTCTGAGGGAGGCGGTTCCGGTGGTGGCTCTGGTTCC
GGTGATTTTGATTATGAAAAGATGGCAAACGCTAATAAGGGGGCTATGAC
CGAAAATGCCGATGAAAACGCGCTACAGTCTGACGCTAAAGGCAAACTTG
ATTCTGTCGCTACTGATTACGGTGCTGCTATCGATGGTTTCATTGGTGAC
GTTTCCGGCCTTGCTAATGGTAATGGTGCTACTGGTGATTTTGCTGGCTC
TAATTCCCAAATGGCTCAAGTCGGTGACGGTGATAATTCACCTTTAATGA
ATAATTTCCGTCAATATTTACCTTCCCTCCCTCAATCGGTTGAATGTCGC
CCTTTTGTCTTTGGCGCTGGTAAACCATATGAATTTTCTATTGATTGTGA
CAAAATAAACTTATTCCGTGGTGTCTTTGCGTTTCTTTTATATGTTGCCA
CCTTTATGTATGTATTTTCTACGTTTGCTAACATACTGCGTAATAAGGAG

-continued

```
TCTTAATCATGCCAGTTCTAGCATAACCCCTTGGGGCCTCTAAACGGGTC
TTGAGGGGTTTTTTGCCTTGTCGGCCTTACTTGCTAAATACATTCAAATA
TGTATCCGCTCATGAGACAATAACCCTGATAAATGCTTCAATAATATTGA
AAAAGGAAGAGTATGAGTATTCAACATTTCCGTGTCGCCCTTATTCCCTT
TTTTGCGGCATTTTGCCTTCCTGTTTTTGCTCACCCAGAAACGCTGGTGA
AAGTAAAAGATGCTGAAGATCAGTTGGGTGCACGAGTGGGTTACATCGAA
CTGGATCTCAACAGCGGTAAGATCCTTGAGAGTTTTCGCCCCGAAGAACG
TTTTCCAATGATGAGCACTTTTAAAGTTCTGCTATGTGGCGCGGTATTAT
CCCGTATTGACGCCGGGCAAGAGCAACTCGGTCGCCGCATACACTATTCT
CAGAATGACTTGGTTGAGTACTCACCAGTCACAGAAAAGCATCTTACGGA
TGGCATGACAGTAAGAGAATTATGCAGTGCTGCCATAACCATGAGTGATA
ACACTGCGGCCAACTTACTTCTGACAACGATCGGAGGACCGAAGGAGCTA
ACCGCTTTTTTGCACAACATGGGGGATCATGTAACTCGCCTTGATCGTTG
GGAACCGGAGCTGAATGAAGCCATACCAAACGACGAGCGTGACACCACGA
TGCCTGTAGCAATGGCAACAACGTTGCGCAAACTATTAACTGGCGAACTA
CTTACTCTAGCTTCCCGGCAACAATTGATAGACTGGATGGAGGCGGATAA
AGTTGCAGGACCACTTCTGCGCTCGGCCCTTCCGGCTGGCTGGTTTATTG
CTGATAAATCTGGAGCCGGTGAGCGTGGCTCTCGCGGTATCATTGCAGCA
CTGGGGCCAGATGGTAAGCCCTCCCGTATCGTAGTTATCTACACGACGGG
GAGTCAGGCAACTATGGATGAACGAAATAGACAGATCGCTGAGATAGGTG
CCTCACTGATTAAGCATTGGTAAGAACCTCAGATCCTTCCGTGATGGTAA
CTTCACTAGTTTAAAAGGATCTAGGTGAAGATCCTTTTTGATAATCTCAT
GACCAAAATCCCTTAACGTGAGTTTTCGTTCCACTGAGCGTCAGAGAACC
TCAGATCCTTCCGTATTTAGCCAGTATGTTCTCTAGTGTGGTTCGTTGTT
TTTGCGTGAGCCATGAGAACGAACCATTGAGATCATGCTTACTTTGCATG
TCACTCAAAAATTTTGCCTCAAAACTGGTGAGCTGAATTTTTGCAGTTAA
AGCATCGTGTAGTGTTTTTCTTAGTCCGTTACGTAGGTAGGAATCTGATG
TAATGGTTGTTGGTATTTTGTCACCATTCATTTTTATCTGGTTGTTCTCA
AGTTCGGTTACGAGATCCATTTGTCTATCTAGTTCAACTTGGAAAATCAA
CGTATCAGTCGGGCGGCCTCGCTTATCAACCACCAATTTCATATTGCTGT
AAGTGTTTAAATCTTTACTTATTGGTTTCAAAACCCATTGGTTAAGCCTT
TTAAACTCATGGTAGTTATTTTCAAGCATTAACATGAACTTAAATTCATC
AAGGCTAATCTCTATATTTGCCTTGTGAGTTTTCTTTTGTGTTAGTTCTT
TTAATAACCACTCATAAATCCTCATAGAGTATTTGTTTTCAAAAGACTTA
ACATGTTCCAGATTATATTTTATGAATTTTTTTAACTGGAAAAGATAAGG
CAATATCTCTTCACTAAAAACTAATTCTAATTTTTCGCTTGAGAACTTGG
CATAGTTTGTCCACTGGAAAATCTCAAAGCCTTTAACCAAAGGATTCCTG
ATTTCCACAGTTCTCGTCATCAGCTCTCTGGTTGCTTTAGCTAATACACC
ATAAGCATTTTCCCTACTGATGTTCATCATCTGAGCGTATTGGTTATAAG
TGAACGATACCGTCCGTTCTTTCCTTGTAGGGTTTTCAATCGTGGGGTTG
```

-continued

```
AGTAGTGCCACACAGCATAAAATTAGCTTGGTTTCATGCTCCGTTAAGTC
ATAGCGACTAATCGCTAGTTCATTTGCTTTGAAAACAACTAATTCAGACA
TACATCTCAATTGGTCTAGGTGATTTTAATCACTATACCAATTGAGATGG
GCTAGTCAATGATAATTACTAGTCCTTTTCCTTTGAGTTGTGGGTATCTG
TAAATTCTGCTAGACCTTTGCTGGAAAACTTGTAAATTCTGCTAGACCCT
CTGTAAATTCCGCTAGACCTTTGTGTGTTTTTTTTGTTTATATTCAAGTG
GTTATAATTTATAGAATAAAGAAAGAATAAAAAAAGATAAAAAGAATAGA
TCCCAGCCCTGTGTATAACTCACTACTTTAGTCAGTTCCGCAGTATTACA
AAAGGATGTCGCAAACGCTGTTTGCTCCTCTACAAAACAGACCTTAAAAC
CCTAAAGGCTTAAGTAGCACCCTCGCAAGCTCGGGCAAATCGCTGAATAT
TCCTTTTGTCTCCGACCATCAGGCACCTGAGTCGCTGTCTTTTTCGTGAC
ATTCAGTTCGCTGCGCTCACGGCTCTGGCAGTGAATGGGGGTAAATGGCA
CTACAGGCGCCTTTTATGGATTCATGCAAGGAAACTACCCATAATACAAG
AAAAGCCCGTCACGGGCTTCTCAGGGCGTTTTATGGCGGGTCTGCTATGT
GGTGCTATCTGACTTTTTGCTGTTCAGCAGTTCCTGCCCTCTGATTTTCC
AGTCTGACCACTTCGGATTATCCCGTGACAGGTCATTCAGACTGGCTAAT
GCACCCAGTAAGGCAGCGGTATCATCAACT
```

Since proteases typically cannot directly drive transcription from a promoter, the linkage of protease activity to viral particle packaging is provided indirectly, for example, by using a transcriptional activator that is expressed in the host cells in an inactive form and a desired activity of the protease, e.g., protease-mediated cleavage, of the inactive form results in activation of the transcriptional activator and thus in an increase in the expression of the gene required for packaging infectious viral particles. In some embodiments, the transcriptional activator is expressed in the form of a fusion protein comprising an inhibitor of the transcriptional activator fused to the transcriptional activator via a linker comprising a protease cleavage site. Cleavage of the protease cleavage site results in a dissociation of the inhibitor from the transcriptional activator and thus a lowering of the effective concentration of inhibitor in the vicinity of the transcriptional activator. In some embodiments, cleavage of the linker by the protease of interest thus results in an increase in the transcriptional activity of the transcriptional activator, e.g., by at least a factor of 2, 5, 10, 20, 50, 100, 200, 500, 1000, 2000, 5000, 10000, or more.

In some embodiments, the host cells comprise all phage genes except for the at least one gene for the generation of infectious phage particles in the form of a helper phage. In some embodiments, the phage genes on the helper phage include pI, pII, pIV, pV, pVI, pVII, pVIII, pIX, and/or pX. Some exemplary helper phages suitable for use in such embodiments are provided herein, and additional suitable helper phages will be apparent to the skilled artisan based on the instant disclosure. The host cell may also provide phage functions based on expression constructs other than helper phage, for example, expression constructs integrated into the host cell genome or provided on artificial chromosomes or on separate plasmids. One advantage of providing phage functions in the host cell, e.g., by using a helper phage, is that the selection phage encoding the protease of interest can be deficient in genes encoding proteins or other functions provided by the host cell and can, accordingly, carry a longer gene encoding the protease of interest.

In some embodiments, the host cells comprise the accessory plasmid encoding the at least one gene for the generation of infectious phage particles, e.g., of the M13 phage, encoding the protease to be evolved and a helper phage, and together, the helper phage and the accessory plasmid comprise all genes required for the generation of infectious phage particles. Accordingly, in some such embodiments, variants of the vector that do not encode a protease variant that can untether the inhibitor from the transcriptional activator will not efficiently be packaged, since they cannot effect an increase in expression of the gene required for the generation of infectious phage particles from the accessory plasmid. On the other hand, variants of the vector that encode a protease variant that can efficiently cleave the inhibitor from the transcriptional activator will effect increased transcription of the at least one gene required for the generation of infectious phage particles from the accessory plasmid and thus be efficiently packaged into infectious phage particles.

In some embodiments, diversifying the vector population is achieved by providing a flow of host cells that does not select for gain-of-function mutations in the gene encoding the protease of interest for replication, mutagenesis, and propagation of the population of vectors. In some embodiments, the host cells are host cells that express all genes required for the generation of infectious viral particles, for example, bacterial cells that express a complete helper phage, and, thus, do not impose selective pressure on the gene of interest. In other embodiments, the host cells comprise an accessory plasmid comprising a conditional promoter with a baseline activity sufficient to support viral vector propagation even in the absence of significant gain-of-function mutations of the gene of interest. This can be achieved by using a "leaky" conditional promoter, by using a high-copy number accessory plasmid, thus amplifying baseline leakiness, and/or by using a conditional promoter on which the initial version of the gene of interest effects a low level of activity while a desired gain-of-function mutation effects a significantly higher activity.

Such methods involving host cells of varying selective stringency or varying the selection stringency in other ways as described herein allow for harnessing the power of continuous evolution methods as provided herein for the evolution of protease functions that are completely absent in the initial version of the protease of interest, for example, for the evolution of proteases that target sequences that the initial protease used at the outset of the respective PACE experiments does not recognize or cleave at all.

In some embodiments, the protease PACE methods provided herein further comprises a negative selection for undesired protease activity in addition to the positive selection for a desired protease activity. Such negative selection methods are useful, for example, in order to maintain protease specificity when increasing the cleavage efficiency of a protease directed towards a specific target site. This can avoid, for example, the evolution of proteases that show a generally increased protease activity, including an increased protease activity towards off-target sites, which is generally undesired in the context of therapeutic proteases.

In some embodiments, negative selection is applied during a continuous evolution process as described herein, by penalizing the undesired activities of evolved proteases. This is useful, for example, if the desired evolved protease is an enzyme with high specificity for a target site, for example, a protease with altered, but not broadened, specificity. In some embodiments, negative selection of an undesired activity, e.g., off-target protease activity, is achieved by causing the undesired activity to interfere with pIII production, thus inhibiting the propagation of phage genomes encoding gene products with an undesired activity. In some embodiments, expression of a dominant-negative version of pIII or expression of an antisense RNA complementary to the gIII RBS and/or gIII start codon is linked to the presence of an undesired protease activity. Suitable negative selection strategies and reagents useful for negative selection, such as dominant-negative versions of M13 pIII, are described herein and in International PCT Application, PCT/US2011/066747, filed Dec. 22, 2011, published as WO 2012/088381 on Jun. 28, 2012; and U.S. application, U.S. Ser. No. 13/922,812, filed Jun. 20, 2013, the entire contents of each of which are incorporated herein by reference.

In some embodiments, counter-selection against activity on non-target substrates is achieved by linking undesired evolved protease activities to the inhibition of phage propagation. In some embodiments, a dual selection strategy is applied during a continuous evolution experiment, in which both positive selection and negative selection constructs are present in the host cells. In some such embodiments, the positive and negative selection constructs are situated on the same plasmid, also referred to as a dual selection accessory plasmid.

One advantage of using a simultaneous dual selection strategy is that the selection stringency can be fine-tuned based on the activity or expression level of the negative selection construct as compared to the positive selection construct. Another advantage of a dual selection strategy is that the selection is not dependent on the presence or the absence of a desired or an undesired activity, but on the ratio of desired and undesired activities, and, thus, the resulting ratio of pIII and pIII-neg that is incorporated into the respective phage particle.

For example, in some embodiments, the host cells comprise an expression construct encoding a dominant-negative form of the at least one gene for the generation of infectious phage particles, e.g., a dominant-negative form of the pIII protein (pIII-neg), under the control of an inducible promoter that is activated by a transcriptional activator other than the transcriptional activator driving the positive selection system. Expression of the dominant-negative form of the gene diminishes or completely negates any selective advantage an evolved phage may exhibit and thus dilutes or eradicates any variants exhibiting undesired activity from the lagoon.

For example, if the positive selection system comprises a T7 promoter driving the expression of the at least one gene for the generation of infectious phage particles, and a T7 RNA polymerase fused to a T7-RNA polymerase inhibitor via a linker comprising a protease target site that is cleaved by a desired protease activity, the negative selection system should be a non-T7 based system. For example, in some such embodiments, the negative selection system could be based on T3 polymerase activity, e.g., in that it comprises a T3 promoter driving the expression of a dominant-negative form of the at least one gene for the generation of infectious phage particles, and a T3 RNA polymerase fused to a T3-RNA polymerase inhibitor via a linker comprising a protease target site that is cleaved by an undesired protease activity. When used together, such positive-negative PACE selection results in the evolution of proteases that exhibit the desired activity but not the undesired activity. In some embodiments, the undesired function is cleavage of an off-target protease cleavage site. In some embodiments, the undesired function is cleavage of the linker sequence of the fusion protein outside of the protease cleavage site.

Some aspects of this invention provide or utilize a dominant negative variant of pIII (pIII-neg). These aspects are based on the recognition that a pIII variant that comprises the two N-terminal domains of pIII and a truncated, termination-incompetent C-terminal domain is not only inactive but is a dominant-negative variant of pIII. A pIII variant comprising the two N-terminal domains of pIII and a truncated, termination-incompetent C-terminal domain was described in Bennett, N. J.; Rakonjac, J., Unlocking of the filamentous bacteriophage virion during infection is mediated by the C domain of pIII. *Journal of Molecular Biology* 2006, 356 (2), 266-73; the entire contents of which are incorporated herein by reference. The dominant negative property of such pIII variants has been described in more detail in PCT Application PCT/US2011/066747, published as WO2012/088381 on Jun. 28, 2012, the entire contents of which are incorporated herein by reference.

The pIII-neg variant as provided in some embodiments herein is efficiently incorporated into phage particles, but it does not catalyze the unlocking of the particle for entry during infection, rendering the respective phage noninfectious even if wild type pIII is present in the same phage particle. Accordingly, such pIII-neg variants are useful for devising a negative selection strategy in the context of PACE, for example, by providing an expression construct comprising a nucleic acid sequence encoding a pIII-neg variant under the control of a promoter comprising a recognition motif, the recognition of which is undesired. In other embodiments, pIII-neg is used in a positive selection strategy, for example, by providing an expression construct in which a pIII-neg encoding sequence is controlled by a promoter comprising a nuclease target site or a repressor recognition site, the recognition of either one is desired.

In some embodiments, the vector or phage encoding the protease to be evolved is a filamentous phage, for example, an M13 phage, such as an M13 selection phage as described in more detail elsewhere herein. In some embodiments, the host cells are cells amenable to infection by the filamentous phage, e.g., by M13 phage, such as, for example, *E. coli* cells. In some such embodiments, the gene required for the production of infectious viral particles is the M13 gene III (gIII) encoding the M13 protein III (pIII).

Typically, the vector/host cell combination is chosen in which the life cycle of the vector is significantly shorter than the average time between cell divisions of the host cell. Average cell division times and vector life cycle times are well known in the art for many cell types and vectors, allowing those of skill in the art to ascertain such host cell/vector combinations. In certain embodiments, host cells are being removed from the population of host cells in which the vector replicates at a rate that results in the average time of a host cell remaining in the host cell population before being removed to be shorter than the average time between cell divisions of the host cells, but to be longer than the average life cycle of the viral vector employed. The result of this is that the host cells, on average, do not have sufficient time to proliferate during their time in the host cell population while the viral vectors do have sufficient time to infect a host cell, replicate in the host cell, and generate new viral particles during the time a host cell remains in the cell population. This assures that the only replicating nucleic acid in the host cell population is the vector encoding the protease to be evolved, and that the host cell genome, the accessory plasmid, or any other nucleic acid constructs cannot acquire mutations allowing for escape from the selective pressure imposed.

For example, in some embodiments, the average time a host cell remains in the host cell population is about 10, about 11, about 12, about 13, about 14, about 15, about 16, about 17, about 18, about 19, about 20, about 21, about 22, about 23, about 24, about 25, about 30, about 35, about 40, about 45, about 50, about 55, about 60, about 70, about 80, about 90, about 100, about 120, about 150, or about 180 minutes.

In some embodiments, the average time a host cell remains in the host cell population depends on how fast the host cells divide and how long infection (or conjugation) requires. In general, the flow rate should be faster than the average time required for cell division, but slow enough to allow viral (or conjugative) propagation. The former will vary, for example, with the media type, and can be delayed by adding cell division inhibitor antibiotics (FtsZ inhibitors in *E. coli*, etc.). Since the limiting step in continuous evolution is production of the protein required for gene transfer from cell to cell, the flow rate at which the vector washes out will depend on the current activity of the gene(s) of interest. In some embodiments, titrable production of the protein required for the generation of infectious particles, as described herein, can mitigate this problem. In some embodiments, an indicator of phage infection allows computer-controlled optimization of the flow rate for the current activity level in real-time.

In some embodiments, a protease PACE experiment according to methods provided herein is run for a time sufficient for at least 10, at least 20, at least 30, at least 40, at least 50, at least 100, at least 200, at least 300, at least 400, at least, 500, at least 600, at least 700, at least 800, at least 900, at least 1000, at least 1250, at least 1500, at least 1750, at least 2000, at least 2500, at least 3000, at least 4000, at least 5000, at least 7500, at least 10000, or more consecutive viral life cycles. In certain embodiments, the viral vector is an M13 phage, and the length of a single viral life cycle is about 10-20 minutes.

In some embodiments, the host cells are contacted with the vector and/or incubated in suspension culture. For example, in some embodiments, bacterial cells are incubated in suspension culture in liquid culture media. Suitable culture media for bacterial suspension culture will be apparent to those of skill in the art, and the invention is not limited in this regard. See, for example, *Molecular Cloning: A Laboratory Manual,* 2nd Ed., ed. by Sambrook, Fritsch, and Maniatis (Cold Spring Harbor Laboratory Press: 1989); Elizabeth Kutter and Alexander Sulakvelidze: *Bacteriophages: Biology and Applications*. CRC Press; 1st edition (December 2004), ISBN: 0849313368; Martha R. J. Clokie and Andrew M. Kropinski: *Bacteriophages: Methods and Protocols, Volume 1: Isolation, Characterization, and Interactions (Methods in Molecular Biology)* Humana Press; 1st edition (December, 2008), ISBN: 1588296822; Martha R. J. Clokie and Andrew M. Kropinski: *Bacteriophages: Methods and Protocols, Volume 2: Molecular and Applied Aspects (Methods in Molecular Biology)* Humana Press; 1st edition (December 2008), ISBN: 1603275649; all of which are incorporated herein in their entirety by reference for disclosure of suitable culture media for bacterial host cell culture).

Suspension culture typically requires the culture media to be agitated, either continuously or intermittently. This is achieved, in some embodiments, by agitating or stirring the vessel comprising the host cell population. In some embodiments, the outflow of host cells and the inflow of fresh host cells is sufficient to maintain the host cells in suspension. This in particular, if the flow rate of cells into and/or out of the lagoon is high.

In some embodiments, the flow of cells through the lagoon is regulated to result in an essentially constant number of host cells within the lagoon. In some embodiments, the flow of cells through the lagoon is regulated to result in an essentially constant number of fresh host cells within the lagoon. Typically, the lagoon will hold host cells in liquid media, for example, cells in suspension in a culture media. However, lagoons in which adherent host cells are cultured on a solid support, such as on beads, membranes, or appropriate cell culture surfaces are also envisioned. The lagoon may comprise additional features, such as a stirrer or agitator for stirring or agitating the culture media, a cell densitometer for measuring cell density in the lagoon, one or more pumps for pumping fresh host cells into the culture vessel and/or for removing host cells from the culture vessel, a thermometer and/or thermocontroller for adjusting the culture temperature, as well as sensors for measuring pH, osmolarity, oxygenation, and other parameters of the culture media. The lagoon may also comprise an inflow connected to a holding vessel comprising a mutagen or a transcriptional inducer of a conditional gene expression system, such as the arabinose-inducible expression system of the mutagenesis plasmid described in more detail elsewhere herein.

In some embodiments, the host cell population is continuously replenished with fresh, uninfected host cells. In some embodiments, this is accomplished by a steady stream of fresh host cells into the population of host cells. In other embodiments, however, the inflow of fresh host cells into the lagoon is semi-continuous or intermittent (e.g., batch-fed). In some embodiments, the rate of fresh host cell inflow into the cell population is such that the rate of removal of cells from the host cell population is compensated. In some embodiments, the result of this cell flow compensation is that the number of cells in the cell population is substantially constant over the time of the continuous evolution procedure. In some embodiments, the portion of fresh, uninfected cells in the cell population is substantially constant over the time of the continuous evolution procedure. For example, in some embodiments, about 10%, about 15%, about 20%, about 25%, about 30%, about 40%, about 50%, about 60%, about 70%, about 75%, about 80%, or about 90% of the cells in the host cell population are not infected by virus. In general, the faster the flow rate of host cells is, the smaller the portion of cells in the host cell population that are infected will be. However, faster flow rates allow for more transfer cycles, e.g., viral life cycles, and, thus, for more generations of evolved vectors in a given period of time, while slower flow rates result in a larger portion of infected host cells in the host cell population and therefore a larger library size at the cost of slower evolution. In some embodiments, the range of effective flow rates is invariably bounded by the cell division time on the slow end and vector washout on the high end In some embodiments, the viral load, for example, as measured in infectious viral particles per volume of cell culture media is substantially constant over the time of the continuous evolution procedure.

Typically, the fresh host cells introduced into the lagoon comprise the protease selection system, e.g., the accessory plasmid encoding the at least one gene for the generation of infectious phage particles, the expression construct encoding the fusion protein of the transcriptional activator fused to an inhibitor via a protease-cleavable linker, and an expression construct providing other phage functions, such as, for example, a helper phage. In some embodiments, the host cells also comprise a mutagenesis plasmid. In some embodiments, the host cells are generated by contacting an uninfected host cell with the relevant vectors, for example, the accessory plasmid, a construct encoding the protease-cleavable fusion protein, the helper phage, and the mutagenesis plasmid, and growing an amount of host cells sufficient for the replenishment of the host cell population in a continuous evolution experiment. Methods for the introduction of plasmids and other gene constructs into host cells are well known to those of skill in the art and the invention is not limited in this respect. For bacterial host cells, such methods include, but are not limited to electroporation and heat-shock of competent cells. In some embodiments, the accessory plasmid comprises a selection marker, for example, an antibiotic resistance marker, and the fresh host cells are grown in the presence of the respective antibiotic to ensure the presence of the plasmid in the host cells. Where multiple plasmids are present, different markers are typically used. Such selection markers and their use in cell culture are known to those of skill in the art, and the invention is not limited in this respect.

In some embodiments, the host cell population in a continuous evolution experiment is replenished with fresh host cells growing in a parallel, continuous culture. In some embodiments, the cell density of the host cells in the host cell population contacted with the viral vector and the density of the fresh host cell population is substantially the same.

Typically, the cells being removed from the cell population contacted with the vector comprise cells that are infected with the vector and uninfected cells. In some embodiments, cells are being removed from the cell populations continuously, for example, by effecting a continuous outflow of the cells from the population. In other embodiments, cells are removed semi-continuously or intermittently from the population. In some embodiments, the replenishment of fresh cells will match the mode of removal of cells from the cell population, for example, if cells are continuously removed, fresh cells will be continuously introduced. However, in some embodiments, the modes of replenishment and removal may be mismatched, for example, a cell population may be continuously replenished with fresh cells, and cells may be removed semi-continuously or in batches.

In some embodiments, the rate of fresh host cell replenishment and/or the rate of host cell removal is adjusted based on quantifying the host cells in the cell population. For example, in some embodiments, the turbidity of culture media comprising the host cell population is monitored and, if the turbidity falls below a threshold level, the ratio of host cell inflow to host cell outflow is adjusted to effect an increase in the number of host cells in the population, as manifested by increased cell culture turbidity. In other embodiments, if the turbidity rises above a threshold level, the ratio of host cell inflow to host cell outflow is adjusted to effect a decrease in the number of host cells in the population, as manifested by decreased cell culture turbidity. Maintaining the density of host cells in the host cell population within a specific density range ensures that enough host cells are available as hosts for the evolving viral vector population, and avoids the depletion of nutrients at the cost of viral packaging and the accumulation of cell-originated toxins from overcrowding the culture.

In some embodiments, the cell density in the host cell population and/or the fresh host cell density in the inflow is about $10^2$ cells/ml to about $10^{12}$ cells/ml. In some embodiments, the host cell density is about $10^2$ cells/ml, about $10^3$ cells/ml, about $10^4$ cells/ml, about $10^5$ cells/ml, about $5 \cdot 10^5$ cells/ml, about $10^6$ cells/ml, about $5 \cdot 10^6$ cells/ml, about $10^7$ cells/ml, about $5 \cdot 10^7$ cells/ml, about $10^8$ cells/ml, about $5 \cdot 10^8$ cells/ml, about $10^9$ cells/ml, about $5 \cdot 10^9$ cells/ml, about $10^{10}$ cells/ml, or about $5 \cdot 10^{10}$ cells/ml. In some embodiments, the host cell density is more than about $10^{10}$ cells/ml.

The protease PACE methods provided herein are typically carried out in a lagoon. Suitable lagoons and other laboratory equipment for carrying out protease PACE methods as provided herein have been described in detail elsewhere. See, for example, International PCT Application, PCT/US2011/066747, published as WO2012/088381 on Jun. 28, 2012, the entire contents of which are incorporated herein by reference. In some embodiments, the lagoon comprises a cell culture vessel comprising an actively replicating population of vectors, for example, phage vectors comprising a gene encoding the protease of interest, and a population of host cells, for example, bacterial host cells. In some embodiments, the lagoon comprises an inflow for the introduction of fresh host cells into the lagoon and an outflow for the removal of host cells from the lagoon. In some embodiments, the inflow is connected to a turbidostat comprising a culture of fresh host cells. In some embodiments, the outflow is connected to a waste vessel, or a sink. In some embodiments, the lagoon further comprises an inflow for the introduction of a mutagen into the lagoon. In some embodiments that inflow is connected to a vessel holding a solution of the mutagen. In some embodiments, the lagoon comprises an inflow for the introduction of an inducer of gene expression into the lagoon, for example, of an inducer activating an inducible promoter within the host cells that drives expression of a gene promoting mutagenesis (e.g., as part of a mutagenesis plasmid), as described in more detail elsewhere herein. In some embodiments, that inflow is connected to a vessel comprising a solution of the inducer, for example, a solution of arabinose.

In some embodiments, the lagoon comprises a controller for regulation of the inflow and outflow rates of the host cells, the inflow of the mutagen, and/or the inflow of the inducer. In some embodiments, a visual indicator of phage presence, for example, a fluorescent marker, is tracked and used to govern the flow rate, keeping the total infected population constant. In some embodiments, the visual marker is a fluorescent protein encoded by the phage genome, or an enzyme encoded by the phage genome that, once expressed in the host cells, results in a visually detectable change in the host cells. In some embodiments, the visual tracking of infected cells is used to adjust a flow rate to keep the system flowing as fast as possible without risk of vector washout.

In some embodiments, the controller regulates the rate of inflow of fresh host cells into the lagoon to be substantially the same (volume/volume) as the rate of outflow from the lagoon. In some embodiments, the rate of inflow of fresh host cells into and/or the rate of outflow of host cells from the lagoon is regulated to be substantially constant over the time of a continuous evolution experiment. In some embodiments, the rate of inflow and/or the rate of outflow is from about 0.1 lagoon volumes per hour to about 25 lagoon volumes per hour. In some embodiments, the rate of inflow and/or the rate of outflow is approximately 0.1 lagoon volumes per hour (lv/h), approximately 0.2 lv/h, approximately 0.25 lv/h, approximately 0.3 lv/h, approximately 0.4 lv/h, approximately 0.5 lv/h, approximately 0.6 lv/h, approximately 0.7 lv/h, approximately 0.75 lv/h, approximately 0.8 lv/h, approximately 0.9 lv/h, approximately 1 lv/h, approximately 2 lv/h, approximately 2.5 lv/h, approximately 3 lv/h, approximately 4 lv/h, approximately 5 lv/h, approximately 7.5 lv/h, approximately 10 lv/h, or more than 10 lv/h.

In some embodiments, the inflow and outflow rates are controlled based on a quantitative assessment of the population of host cells in the lagoon, for example, by measuring the cell number, cell density, wet biomass weight per volume, turbidity, or cell growth rate. In some embodiments, the lagoon inflow and/or outflow rate is controlled to maintain a host cell density of from about $10^2$ cells/ml to about $10^{12}$ cells/ml in the lagoon. In some embodiments, the inflow and/or outflow rate is controlled to maintain a host cell density of about $10^2$ cells/ml, about $10^3$ cells/ml, about $10^4$ cells/ml, about $10^5$ cells/ml, about $5\times10^5$ cells/ml, about $10^6$ cells/ml, about $5\times10^6$ cells/ml, about $10^7$ cells/ml, about $5\times10^7$ cells/ml, about $10^8$ cells/ml, about $5\times10^8$ cells/ml, about $10^9$ cells/ml, about $5\times10^9$ cells/ml, about $10^{10}$ cells/ml, about $5\times10^{10}$ cells/ml, or more than $5\times10^{10}$ cells/ml, in the lagoon. In some embodiments, the density of fresh host cells in the turbidostat and the density of host cells in the lagoon are substantially identical.

In some embodiments, the lagoon inflow and outflow rates are controlled to maintain a substantially constant number of host cells in the lagoon. In some embodiments, the inflow and outflow rates are controlled to maintain a substantially constant frequency of fresh host cells in the lagoon. In some embodiments, the population of host cells is continuously replenished with fresh host cells that are not infected by the phage. In some embodiments, the replenishment is semi-continuous or by batch-feeding fresh cells into the cell population.

In some embodiments, the lagoon volume is from approximately 1 ml to approximately 100 l, for example, the lagoon volume is approximately 1 ml, approximately 10 ml, approximately 50 ml, approximately 100 ml, approximately 200 ml, approximately 250 ml, approximately 500 ml, approximately 750 ml, approximately 1 l, approximately 2 ml, approximately 2.5 l, approximately 3 l, approximately 4 l, approximately 5 l, approximately 10 l, approximately 1 ml-10 ml, approximately 10 ml-50 ml, approximately 50 ml-100, approximately 100 ml-250 ml, approximately 250 ml-500 ml, approximately 500 ml-1 l, approximately 1 l-2 l, approximately 2 l-5 l, approximately 5 l-10 l, approximately 10-50 l, approximately 50-100 l, or more than 100 l.

In some embodiments, the lagoon and/or the turbidostat further comprises a heater and a thermostat controlling the temperature. In some embodiments, the temperature in the lagoon and/or the turbidostat is controlled to be from about 4° C. to about 55° C., preferably from about 25° C. to about 39° C., for example, about 37° C.

In some embodiments, the inflow rate and/or the outflow rate is controlled to allow for the incubation and replenishment of the population of host cells for a time sufficient for at least 10, at least 20, at least 30, at least 40, at least 50, at least 100, at least 200, at least 300, at least 400, at least, 500, at least 600, at least 700, at least 800, at least 900, at least 1000, at least 1250, at least 1500, at least 1750, at least 2000, at least 2500, at least 3000, at least 4000, at least 5000, at least 7500, at least 10000, or more consecutive vector or phage life cycles. In some embodiments, the time sufficient for one phage life cycle is about 10, 15, 20, 25, or 30 minutes.

Therefore, in some embodiments, the time of the entire evolution procedure is about 12 hours, about 18 hours, about 24 hours, about 36 hours, about 48 hours, about 50 hours, about 3 days, about 4 days, about 5 days, about 6 days, about 7 days, about 10 days, about two weeks, about 3 weeks, about 4 weeks, or about 5 weeks.

In some embodiments, a PACE method as provided herein is performed in a suitable apparatus as described herein. For example, in some embodiments, the apparatus comprises a lagoon that is connected to a turbidostat comprising a host cell as described herein. In some embodiments, the host cell is an *E. coli* host cell. In some embodiments, the host cell comprises an accessory plasmid as described herein, a helper plasmid as described herein, a mutagenesis plasmid as described herein, and/or an expression construct encoding a fusion protein as described herein, or any combination thereof. In some embodiments, the lagoon further comprises a selection phage as described herein, for example, a selection phage encoding a protease of interest. In some embodiments, the lagoon is connected to a vessel comprising an inducer for a mutagenesis plasmid, for example, arabinose. In some embodiments, the host cells are *E. coli* cells comprising the F' plasmid, for example, cells of the genotype F'proA$^+$B$^+$ Δ(lacIZY) zzf::Tn10(TetR)/endA1 recA1 galE15 galK16 nupG rpsL ΔlacIZYA araD139 Δ(ara,leu) 7697 mcrA Δ(mrr-hsdRMS-mcrBC) proBA::pir116λ$^-$.

For example, in some embodiments, a PACE method as provided herein is carried out in an apparatus comprising a lagoon of about 100 ml, or about 1 l volume, wherein the lagoon is connected to a turbidostat of about 0.5 l, 1 l, or 3 l volume, and to a vessel comprising an inducer for a mutagenesis plasmid, for example, arabinose, wherein the lagoon and the turbidostat comprise a suspension culture of *E. coli* cells at a concentration of about $5\times10^8$ cells/ml. In some embodiments, the flow of cells through the lagoon is regulated to about 3 lagoon volumes per hour. In some embodiments, cells are removed from the lagoon by continuous pumping, for example, by using a waste needle set at a height of the lagoon vessel that corresponds to a desired volume of fluid (e.g., about 100 ml, in the lagoon. In some embodiments, the host cells are *E. coli* cells comprising the F' plasmid, for example, cells of the genotype F'proA$^+$B$^+$ Δ(lacIZY) zzf:Tn10(TetR)/endA1 recA1 galE15 galK16 nupG rpsL ΔlacIZYA araD139 Δ(ara,leu)7697 mcrA Δ(mrr-hsdRMS-mcrBC) proBA::pir116λ$^-$.

Evaluation and Selection of Protease Inhibitors

Some aspects of this disclosure provide method for generating protease variants that are resistant to a protease inhibitor. Such methods are useful, for example, in the evaluation of the likelihood of encountering inhibitor-resistant protease variants after administration of an inhibitor to a subject or a population of subjects. In the context of therapeutic protease inhibitors, the occurrence of resistant protease variants may render a protease inhibitor drug ineffective, as seen with some of the antiviral protease inhibitors described herein. The protease PACE methods provided herein allow for an evaluation of the occurrence of inhibitor-resistant protease variants in vitro, e.g., before a drug candidate is tested in a clinical setting, thus contributing to saving time and expense during drug development and avoiding the development of protease inhibitor drugs that later become ineffective.

In some embodiments, a protease inhibitor inhibits the activity of its target protease in a dose-dependent manner. In some embodiments, the inhibitory potential of a protease inhibitor referred to herein is its maximum level of inhibition or its maximum level of inhibition at a non-toxic concentration. In some embodiments, a protease inhibitor inhibits the activity of a target protease by at least 50%, at least 60%, at least 70%, at least 75%, at least 80%, at least 90%, at least 95%, at least 97.5%, at least 98%, at least 99%, at least 99.5%, at least 99.9%, or by at least 99.99%. In some embodiments, a protease inhibitor inhibits the activity of a protease below measurable levels.

In some embodiments, the protease PACE methods for evaluating and selecting protease inhibitors are similar to the protease PACE methods provided elsewhere herein, with the main difference being that they are carried out in the presence of a protease inhibitor. Accordingly, in some embodiments, such methods comprise (a) contacting a population of host cells with a population of phage vectors comprising a gene encoding a protease and deficient in at least one gene for the generation of infectious phage particles, wherein (1) the host cells are amenable to transfer of the vector; (2) the vector allows for expression of the protease in the host cell, can be replicated by the host cell, and the replicated vector can transfer into a second host cell; (3) the host cell expresses a gene product encoded by the at least one gene for the generation of infectious phage particles of (a) in response to the activity of the protease, and the level of gene product expression depends on the activity of the protease; (b) incubating the population of host cells in the presence of a protease inhibitor and under conditions allowing for mutation of the gene encoding the protease and the transfer of the vector comprising the gene encoding the protease of interest from host cell to host cell, wherein host cells are removed from the host cell population, and the population of host cells is replenished with fresh host cells that do not harbor the vector; and (c) isolating a replicated vector from the host cell population of step (b). The replicated vector isolated in step (c) thus encodes a mutated protease variant that exhibits protease activity in the presence of the protease inhibitor and/or increased protease activity in the presence of the inhibitor as compared to the original version of the protease.

In some embodiments, the method comprises analyzing the mutation(s) present in a plurality of protease variants isolated in step (c), and comparing the observed mutations to identify shared and non-shared mutations. In some embodiments, the shared mutations are identified as resistance-conferring mutations, and in some embodiments, the non-shared mutations are identified as background mutations that do confer resistance by themselves or do not contribute to resistance at all. In some embodiments, the method further comprises confirming the identification of a mutation identified to confer resistance, for example, by generating a protease variant based on the original protease version by introducing only the mutation identified as conferring resistance and then measuring the effect of the mutation on the protease activity of the protease of interest.

In some embodiments, the method further comprises testing a plurality of individual protease inhibitors in separate experiments under identical conditions, and identifying the protease inhibitor to which no inhibitor-resistant protease variant could be identified. While a negative PACE experiment with a protease inhibitor as provided herein does not guarantee that no inhibitor-resistant protease variants will form after an inhibitor is used in a clinical setting, such an observation provides evidence that the range of mutations that are accessible in a PACE experiment are not sufficient to generate a resistant protease variant. With other parameters, such as toxicity and pharmacodynamics parameters, being equal or similar to other inhibitor candidates that yield inhibitor-resistant protease variants in the PACE experiments provided herein, such a "PACE-negative" inhibitor candidate constitutes a preferable lead compound, since the likelihood of the emergence of inhibitor-resistant proteases in the clinic is lower as compared to the "PACE-positive" comparison candidates.

In some embodiments, the method further comprises testing a plurality of individual protease inhibitors in separate experiments under identical conditions, and identifying the protease inhibitor that required the highest number of mutations in the protease to create an inhibitor-resistant protease variant. Such methods are useful, for example, if during a comparison of inhibitor candidates no candidate for which no inhibitor-resistant protease variants could be generated was identified. In the clinical context, it is less likely for an inhibitor-resistant protease to emerge, if multiple mutations are required in order for the protease to gain resistance as compared to proteases that gain resistance from a single point mutation.

In some embodiments, the method may be repeated multiple times, for example, in that a first round of protease PACE experiments is conducted in which a number of candidate inhibitors is compared. At the end of the first round, a candidate inhibitor with a low or with the lowest likelihood of the emergence of resistant proteases is selected, e.g., a candidate inhibitor that did not yield resistant protease variants in the PACE experiment, or that yielded resistant proteases requiring the highest number of mutations as compared to the other candidate inhibitors. A plurality of candidate inhibitor variants is then generated based on the general structure of the selected candidate from the first round, and the candidate variants are subjected to a round of protease PACE. The candidate variant with no incidence of resistant protease variants or with the highest number of required mutations for the emergence of resistant proteases is then selected. This process may be repeated several times, resulting in a more and more refined and optimized version of the inhibitor candidate. As the emergence of resistant protease variants becomes less and less likely in subsequent round, the stringency of selection may be reduced in order to still be able to measure further improvements in the design of the inhibitor.

In some embodiments, the host cells, accessory plasmids, lagoons, flow rates, culture conditions, mutagens, etc., can be chosen for the methods provided herein as described in more detail for other protease PACE methods herein.

Fusion Proteins

One important aspect of this disclosure is the provision of fusion proteins that link protease activity to transcriptional activity and thus translate protease activity into regulation of gene expression and thus phage packaging efficiency in the context of protease PACE. Typically, this link is provided by a fusion protein comprising a domain able to activate transcription from a target promoter and an inhibitory domain that inhibits this transcriptional activity. The two domains are fused via a linker comprising a protease target site that is cleaved by a desired protease activity to be evolved, and the severance of the inhibitory domain from the transcriptional activator domain relieves the inhibition of the activator, which in turn can drive expression from the target promoter.

Accordingly, some aspects of this disclosure provide fusion proteins comprising (a) a transcriptional activator; and (b) an inhibitor of the transcriptional activator of (a), wherein the inhibitor is fused to the transcriptional activator of (a) via a linker comprising a protease cleavage site. In some embodiments, the inhibitor of (ii) is fused to the N-terminus of the transcriptional activator of (i). In some embodiments, the inhibitor of (ii) is fused to the C-terminus of the transcriptional activator of (i). Some suitable pairs of transcriptional activator and inhibitor for the generation of fusion proteins according to some aspects of this disclosure are provided herein and additional suitable pairs and fusion proteins comprising such pairs will be apparent to those of skill in the art based on the instant disclosure. In some embodiments, the inhibitor may be a protein degradation tag that leads to rapid degradation of the tagged protein (e.g., the transcriptional activator) unless the tag is cleaved off by a protease. In other embodiments, the inhibitor may be a signal peptide that targets the fusion protein for export out of the cell or into a cellular compartment in which the transcriptional activator cannot activate transcription of the target gene. Upon cleavage of the signal peptide from the transcriptional activator by a protease, the untagged activator is not exported from the cell and can activate transcription from the target promoter. Suitable signal peptides include, without limitation, periplasmic export tags, e.g., those from PelB, OmpA, PhoA, pIII, and other exported proteins known to those of skill in the art. Suitable transcriptional activators include, without limitation, RNA polymerases, e.g., from bacteriophages other than T7 (e.g., T3, T4, etc.) and from other organisms, as well as sequence specific transcriptional activators such as, for example, Gal4.

In some embodiments, the transcriptional activity of the fusion protein is inhibited as compared to the activity of the transcriptional activator alone. In some embodiments, the transcriptional activity of the fusion protein is less than 50%, less than 25%, less than 20%, less than 10%, less than 5%, less than 4%, less than 3%, less than 1%, less than 0.1%, less than 0.01%, or less than 0.001% the activity of the transcriptional activator alone.

In some embodiments, cleavage of the protease cleavage site results in an activation of the transcriptional activator. In some embodiments, the transcriptional activator regains 100% of the transcriptional activity upon cleavage of the protease cleavage site as compared to the transcriptional activator alone (e.g., in its original form not fused to an inhibitor). In some embodiments, the activity of the transcriptional activator comprised in the fusion protein is increased at least 2-fold, at least 5-fold, at least 10-fold, at least 20-fold, at least 25-fold, at least 50-fold, at least 75-fold, at least 100-fold, at least 200-fold, at least 250-fold, at least 500-fold, at least 750-fold, at least 1000-fold, at least 2000-fold, at least 2500-fold, at least 5000-fold, at least 7500-fold, or at least 10000-fold upon cleavage of the protease cleavage site of the linker.

Those of skill in the art will be able to readily envision suitable methods and assays for determining the transcriptional activity of a given protein, e.g., of a transcriptional activator bound to an inhibitor or alone, e.g., after cleavage of a fusion protein as provided herein. Such assays typically include the use of a reporter construct harboring a promoter targeted by the transcriptional activator (e.g., a T7 promoter if the transcriptional activator is a T7 RNA polymerase) and a reporter gene, e.g., a gene encoding a fluorescent protein or an enzyme catalyzing a bioluminescent reaction. Some exemplary methods and assays are provided herein and additional suitable methods and assays will be apparent to those of skill in the art based on the instant disclosure.

In some embodiments, the linker connecting the transcriptional activator and the inhibitor comprises a stretch of small residues, such as, for example, glycine, serine and/or alanine. Without wishing to be bound by theory, it is presumed that such stretches are highly flexible and thus provide the flexibility required in some embodiments, e.g., in embodiments, in which a linker connects a transcriptional activator and an inhibitor that binds the transcriptional activator at a specific site or in a specific orientation. In some embodiments, a stretch of 2, 3, 4, 5, 6, 7, 8, 9, 10, 11, 12, 13, 14, 15, 16, 17, 18, 19, 20, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, or at least 20 small residues (e.g., glycine, serine, and/or alanine, or any combination thereof), is comprised in the linker sequence, for example, on one or on both sides of the protease cleavage sequence.

Vectors and Reagents

Some aspects of this disclosure provide vectors and reagents for carrying out the inventive continuous protease evolution processes.

In some embodiments, a selection phage is provided that comprises a phage genome deficient in at least one gene required for the generation of infectious phage particles and a gene encoding a protease of interest to be evolved.

For example, in some embodiments, a selection phage as described in PCT Application PCT/US2009/056194, published as WO2010/028347 on Mar. 11, 2010; PCT Application PCT/US2011/066747, published as WO2012/088381 on Jun. 28, 2012; and U.S. Nonprovisional application Ser. No. 13/922,812, filed on Jun. 20, 2013, the entire contents of each of which are incorporated herein by reference, is provided, that comprises a multiple cloning site for insertion of a nucleic acid sequence encoding a protease of interest.

Such selection phage vectors typically comprise an M13 phage genome deficient in a gene required for the generation of infectious M13 phage particles, for example, a full-length gIII. In some embodiments, the selection phage comprises a phage genome providing all other phage functions required for the phage life cycle except the gene required for generation of infectious phage particles. In some such embodiments, an M13 selection phage is provided that comprises a gI, gII, gIV, gV, gVI, gVII, gVIII, gIX, and a gX gene, but not a full-length gIII. In some embodiments, the selection phage comprises a 3'-fragment of gIII, but no full-length gIII. The 3'-end of gIII comprises a promoter and retaining this promoter activity is beneficial, in some embodiments, for an increased expression of gVI, which is immediately downstream of the gIII 3'-promoter, or a more balanced (wild-type phage-like) ratio of expression levels of the phage genes in the host cell, which, in turn, can lead to more efficient phage production. In some embodiments, the 3'-fragment of gIII gene comprises the 3'-gIII promoter sequence. In some embodiments, the 3'-fragment of gIII comprises the last 180 bp, the last 150 bp, the last 125 bp, the last 100 bp, the last 50 bp, or the last 25 bp of gIII. In some embodiments, the 3'-fragment of gIII comprises the last 180 bp of gIII. In some embodiments, the multiple cloning site for insertion of the gene encoding the protease of interest is located downstream of the gVIII 3'-terminator and upstream of the gIII-3'-promoter.

Some aspects of this disclosure provide nucleic acid constructs encoding a fusion protein as provided herein. For example, some aspects of this disclosure provide nucleic acid constructs comprising (a) a nucleic acid sequence encoding a transcriptional activator; (b) a nucleic acid sequence encoding an inhibitor of the of the transcriptional activator of (a); and (c) a nucleic acid sequence separating the nucleic acid sequences of (a) and (b), wherein the nucleic acid sequence of (c) encodes a linker and comprises a multiple cloning site allowing for the insertion of a nucleic acid sequence encoding a protease cleavage site. In some embodiments, the nucleic acid sequence of (c) further encodes a linker connecting the transcriptional activator and the inhibitor. In some embodiments, the linker comprises a stretch of at least two consecutive glycine residues on each side of the protease cleavage site.

Some aspects of this invention provide a vector system for continuous evolution procedures, comprising of a viral vector, for example, a selection phage, a nucleic acid encoding a fusion protein as provided herein, and a matching accessory plasmid. In some embodiments, a vector system for phage-based continuous directed evolution is provided that comprises (a) a selection phage comprising a multiple cloning site for insertion of a gene encoding a protease of interest to be evolved, wherein the phage genome is deficient in at least one gene required to generate infectious phage; (b) a nucleic acid construct comprising a nucleic acid sequence encoding a transcriptional activator fused to an inhibitor of the of the transcriptional activator via a linker sequence and comprising a multiple cloning site for insertion of a nucleic acid sequence encoding a protease cleavage site into the linker sequence; and (c) an accessory plasmid comprising the at least one gene required to generate infectious phage particle under the control of a conditional promoter that can be activated by the transcriptional activator upon cleavage of the protease cleavage site.

In some embodiments, the selection phage is an M13 phage as described herein. For example, in some embodiments, the selection phage comprises an M13 genome including all genes required for the generation of phage particles, for example, gI, gII, gIV, gV, gVI, gVII, gVIII, gIX, and gX gene, but not a full-length gIII gene. In some embodiments, the selection phage genome comprises an F1 or an M13 origin of replication. In some embodiments, the selection phage genome comprises a 3'-fragment of gIII gene. In some embodiments, the selection phage comprises a multiple cloning site upstream of the gIII 3'-promoter and downstream of the gVIII 3'-terminator for insertion of a gene encoding a protease of interest.

The vector system may further comprise a helper phage, wherein the selection phage does not comprise all genes for the generation of infectious phage particles, and wherein the helper phage complements the genome of the selection phage, so that the helper phage genome and the selection phage genome together comprise at least one functional copy of all genes for the generation of phage particles, but are deficient in at least one gene required for the generation of infectious phage particles, which is provided by an accessory plasmid.

In some embodiments, the vector system further comprises a mutagenesis plasmid, for example, an arabinose-inducible mutagenesis plasmid as described herein. In some embodiments, the mutagenesis plasmid comprises a gene expression cassette encoding a component of *E. coli* translesion synthesis polymerase V, a deoxyadenosine methylase, and/or a hemimethylated-GATC binding domain, or any combination thereof. In some embodiments, the component of *E. coli* translesion synthesis polymerase V is umuC. In some embodiments, the deoxyadenosine methylase is dam. In some embodiments, the hemimethylated-GATC binding domain is seqA.

Evolved Proteases and Used Thereof

Some aspects of this invention provide evolved protease variants produced via the PACE methods and systems described herein. In some embodiments, the evolved protease variants exhibit a desirable protease activity, for example, in that they cleave their original target site with higher efficiency, in that they cleave an altered cleavage site, and/or in that they do not cleave an undesirable off-target site. In addition, protease variants that are resistant to protease inhibitors are provided herein. Such resistant variants are useful in determining whether a given candidate protease inhibitor is a viable candidate for clinical development or should be discarded or modified because of a high likelihood of inhibitor-resistant proteases emerging during clinical use.

For example, some aspects of this invention provide evolved tobacco etch virus (TEV) protease variants, HCV protease variants, and human rhinovirus-14 3C (HRV) protease variants, e.g., variants comprising at least one of the mutations described herein. In some embodiments, the variants provided herein comprise at least 1, at least 2, at least 3, at least 4, at least 5, at least 6, at least 7, at least 8, at least 9, or at least 10 mutations as described herein. In some embodiments, the term "protease variant" refers to a non-naturally occurring protease, i.e., comprising an amino acid sequence that is not found in nature. Such non-naturally occurring protease variants are also referred to herein as recombinant proteases.

In some embodiments, a protease variant provided herein is a recombinant (not naturally occurring) protease variant that is at least about 70% identical, at least about 80% identical, at least about 90% identical, at least about 95% identical, at least about 98% identical, at least about 99% identical, at least about 99.5% identical, or at least about 99.9% to a naturally-occurring, wild-type protease, and comprises at least 1, at least 2, at least 3, at least 4, at least 5, at least 6, at least 7, at least 8, at least 9 or at least 10 mutations as described herein.

Naturally occurring, wild-type protease sequences that can serve as a basis or a starting point for the directed evolution strategies described herein or for the generation of protease variants described herein are well known to those of ordinary skill in the art.

For example, in some embodiments, a suitable TEV protease sequence comprises the following sequence:

```
                                       (SEQ ID NO: 12)
GESLFKGPRD YNPISSTICH LTNESDGHTT SLYGIGFGPF

IITNKHLFRR NNGTLLVQSL HGVFKVKNTT TLQQHLIDGR

DMIIIRMPKD FPPFPQKLKF REPQREERIC LVTTNFQTKS

MSSMVSDTSC TFPSSDGIFW KHWIQTKDGQ CGSPLVSTRD

GFIVGIHSAS NFTNTNNYFT SVPKNFMELL TNQEAQQWVS

GWRLNADSVL WGGHKVFMSK PEEPFQPVKE ATQLMNELVY SQ.
```

For example, in some embodiments, a suitable TEV protease sequence comprises the following sequence:

```
                                       (SEQ ID NO: 13)
APITAYAQQT RGLLGCIITS LTGRDKNQVE GEVQVVSTAT

QSFLASCVNG VCWTVFHGAG SKTLAGPKGP VTQMYTNVDQ

DLVGWPAPPG ARSLTPCTCG SSDLYLVTRH ADVIPVRRRG

DSRGALLSPR PVSYLKGSSG GPLLCPSGHA VGIFRAAVCT

RGVAKAVDFI PVESMETTMR SP.
```

For example, in some embodiments, a suitable human rhinovirus-14 3C (HRV) protease variant protease sequence comprises the following sequence:

```
                                       (SEQ ID NO: 14)
GPNTEFALSL LRKNIMTITT SKGEFTGLGI HDRVCVIPTH

AQPGDDVLVN GQKIRVKDKY KLVDPENINL ELTVLTLDRN

EKFRDIRGFI SEDLEGVDAT LVVHSNNFTN TILEVGPVTM

AGLINLSSTP TNRMIRYDYA TKTGQCGGVL CATGKIFGIH

VGGNGRQGFS AQLKKQYFVE KQ.
```

Those of ordinary skill in the art will understand that the sequences provided here are exemplary and not meant to limit the scope of this disclosure. Additional suitable protease sequences will be apparent to those of ordinary skill in the art.

Some aspects of this invention provide methods and strategies to use proteases that have been evolved via the PACE methods provided herein to identify protease inhibitors. For example, in some embodiments, a therapeutically targeted protease, such as a viral protease, is evolved in the presence of a therapeutic protease inhibitor, such as a candidate protease inhibitor or a clinically used protease inhibitor. In some such embodiments, a protease is evolved that exhibits protease activity in the presence of the inhibitor, and thus is resistant to the inhibitor. In some embodiments, the inhibitor-resistant evolved protease comprises at least one mutation observed in inhibitor-resistant proteases in the context of clinical use of the inhibitor. Such evolved proteases are useful for screening compound libraries for inhibitors that are able to inhibit the evolved protease, and can thus serve as therapeutic drugs that inhibit the protease even in its evolved form that is resistant to the initial protease inhibitor.

Accordingly, some embodiments of this disclosure provide methods for drug screening, comprising providing an evolved protease, contacting it with a candidate protease inhibitor, and determining the activity of the evolved protease in the presence of the candidate inhibitor. The activity of the protease can be determined by any suitable assay, for example, one of the fluorescent or bioluminescent assays described herein. Additional suitable assays for determining protease activity will be apparent to those of skill in the art based on the instant disclosure. In some embodiments, if the activity of the evolved protease is decreased in the presence of the candidate inhibitor as compared to the activity of the protease in the absence of the inhibitor, then the candidate inhibitor is identified as an inhibitor of the evolved protease. In some embodiments, the candidate inhibitor is identified as an inhibitor of the evolved protease if the inhibition in the presence of the candidate inhibitor is at least 30%, at least 40%, at least 50%, at least 60%, at least 70%, at least 80%, at least 90%, at least 95%, at least 98%, at least 99%, or at least 99.9% as compared to the activity of the protease in the absence of the candidate inhibitor, or if the protease activity in the presence of the inhibitor is below the detection threshold of the assay used to determine protease activity.

Some aspects of this disclosure provide methods for using a protease provided herein. In some embodiments, such methods include contacting a protein comprising a protease target cleavage sequence with the protease. In some embodiments, the protein contacted with the protease is a therapeutic target. Exemplary suitable therapeutic targets are provided herein, including, but not limited to, C-C chemokine receptor type 5 (CCR5), Programmed death-ligand 1

(PDL1), Tumor Necrosis Factor alpha (TNFa), Insulin-Degrading Enzyme (IDE), membrane metallo-endopeptidase (MME, Neprilysin), and Interleukin 23 alpha subunit P19 (IL23aP19). Additional suitable proteins that can be targeted with the evolved proteases provided herein will be apparent to those of ordinary skill in the art, and the disclosure is not limited in this respect.

Sequences of the exemplary proteins listed above and of additional suitable proteins that can be contacted with the evolved proteases provided herein will be apparent to those of ordinary skill in the art. Exemplary sequences include, without limitation:

>gi|7706702|ref|NP_057668.1|interleukin-23 subunit alpha precursor [*Homo sapiens*]

(SEQ ID NO: 33)

MLGSRAVMLLLLLPWTAQGRAVPGGSSPAWTQCQQLSQKLCTLAWSAHPL

VGHMDLREEGDEETTNDVPHIQCGDGCDPQGLRDNSQFCLQRIHQGLIFY

EKLLGSDIFTGEPSLLPDSPVGQLHASLLGLSQLLQPEGHHWETQQIPSL

SPSQPWQRLLLRFKILRSLQAFVAVAARVFAHGAATLSP

>gi|154091328|ref|NP_001093638.1|C-C chemokine receptor type 5 [*Homo sapiens*]

(SEQ ID NO: 34)

MDYQVSSPIYDINYYTSEPCQKINVKQIAARLLPPLYSLVFIFGFVGNML

VILILINCKRLKSMTDIYLLNLAISDLFFLLTVPFWAHYAAAQWDFGNTM

CQLLTGLYFIGFFSGIFFIILLTIDRYLAVVHAVFALKARTVTFGVVTSV

ITWVVAVFASLPGIIFTRSQKEGLHYTCSSHFPYSQYQFWKNFQTLKIVI

LGLVLPLLVMVICYSGILKTLLRCRNEKKRHRAVRLIFTIMIVYFLFWAP

YNIVLLLNTFQEFFGLNNCSSSNRLDQAMQVTETLGMTHCCINPIIYAFV

GEKFRNYLLVFFQKHIAKRFCKCCSIFQQEAPERASSVYTRSTGEQEISV

GL

>gi|930425329|ref|NP_001300958.1|programmed cell death 1 ligand 1 isoform c precursor [*Homo sapiens*]

(SEQ ID NO: 35)

MRIFAVFIFMTYWHLLNAFTVTVPKDLYVVEYGSNMTIECKFPVEKQLDL

AALIVYWEMEDKNIIQFVHGEEDLKVQHSSYRQRARLLKDQLSLGNAALQ

ITDVKLQDAGVYRCMISYGGADYKRITVKVNAPYNKINQRILVVDPVTSE

HELTCQAEGYPKAEVIWTSSDHQVLSGKTTTTNSKREEKLFNVTSTLRIN

TTTNEIFYCTFRRLDPEENHTAELVIPGNILNVSIKICLTLSPST

>gi|25952111|ref|NP_000585.2|tumor necrosis factor [*Homo sapiens*]

(SEQ ID NO: 36)

MSTESMIRDVELAEEALPKKTGGPQGSRRCLFLSLFSFLIVAGATTLFCL

LHFGVIGPQREEFPRDLSLISPLAQAVRSSSRTPSDKPVAHVVANPQAEG

QLQWLNRRANALLANGVELRDNQLVVPSEGLYLIYSQVLFKGQGCPSTHV

LLTHTISRIAVSYQTKVNLLSAIKSPCQRETPEGAEAKPWYEPIYLGGVF

QLEKGDRLSAEINRPDYLDFAESGQVYFGIIAL

>gi|155969707|ref|NP_004960.2|insulin-degrading enzyme isoform 1 [*Homo sapiens*]

(SEQ ID NO: 37)

MRYRLAWLLHPALPSTFRSVLGARLPPPERLCGFQKKTYSKMNNPAIKRI

GNHITKSPEDKREYRGLELANGIKVLLISDPTTDKSSAALDVHIGSLSDP

-continued

PNIAGLSHFCEHMLFLGTKKYPKENEYSQFLSEHAGSSNAFTSGEHTNYY

FDVSHEHLEGALDRFAQFFLCPLFDESCKDREVNAVDSEHEKNVMNDAWR

LFQLEKATGNPKHPFSKFGTGNKYTLETRPNQEGIDVRQELLKFHSAYYS

SNLMAVCVLGRESLDDLTNLVVKLFSEVENKNVPLPEFPEHPFQEEHLKQ

LYKIVPIKDIRNLYVTFPIPDLQKYYKSNPGHYLGHLIGHEGPGSLLSEL

KSKGWVNTLVGGQKEGARGFMFFIINVDLTEEGLLHVEDIILHMFQYIQK

LRAEGPQEWVFQECKDLNAVAFRFKDKERPRGYTSKIAGILHYYPLEEVL

TAEYLLEEFRPDLIEMVLDKLRPENVRVAIVSKSFEGKTDRTEEWYGTQY

KQEAIPDEVIKKWQNADLNGKFKLPTKNEFIPTNFEILPLEKEATPYPAL

IKDTAMSKLWFKQDDKFFLPKACLNFEFFSPFAYVDPLHCNMAYLYLELL

KDSLNEYAYAAELAGLSYDLQNTIYGMYLSVKGYNDKQPILLKKIIEKMA

TFEIDEKRFEIIKEAYMRSLNNFRAEQPHQHAMYYLRLLMTEVAWTKDEL

KEALDDVTLPRLKAFIPQLLSRLHIEALLHGNITKQAALGIMQMVEDTLI

EHAHTKPLLPSQLVRYREVQLPDRGWFVYQQRNEVHNNCGIEIYYQTDMQ

STSENMFLELFCQIISEPCFNTLRTKEQLGYIVFSGPRRANGIQGLRFII

QSEKPPHYLESRVEAFLITMEKSIEDMTEEAFQKHIQALAIRRLDKPKKL

SAECAKYWGEIISQQYNFDRDNTEVAYLKTLTKEDIIKFYKEMLAVDAPR

RHKVSVHVLAREMDSCPVVGEFPCQNDINLSQAPALPQPEVIQNMTEFKR

GLPLFPLVKPHINFMAAKL

>gi|116256333|ref|NP_009220.2|neprilysin [*Homo sapiens*]

(SEQ ID NO: 38)

MGKSESQMDITDINTPKPKKKQRWTPLEISLSVLVLLLTIIAVTMIALYA

TYDDGICKSSDCIKSAARLIQNMDATTEPCTDFFKYACGGWLKRNVIPET

SSRYGNFDILRDELEVVLKDVLQEPKTEDIVAVQKAKALYRSCINESAID

SRGGEPLLKLLPDIYGWPVATENWEQKYGASWTAEKAIAQLNSKYGKKVL

INLFVGTDDKNSVNHVIHIDQPRLGLPSRDYYECTGIYKEACTAYVDFMI

SVARLIRQEERLPIDENQLALEMNKVMELEKEIANATAKPEDRNDPMLLY

NKMTLAQIQNNFSLEINGKPFSWLNFTNEIMSTVNISITNEEDVVVYAPE

YLTKLKPILTKYSARDLQNLMSWRFIMDLVSSLSRTYKESRNAFRKALYG

TTSETATWRRCANYVNGNMENAVGRLYVEAAFAGESKHVVEDLIAQIREV

FIQTLDDLTWMDAETKKRAEEKALAIKERIGYPDDIVSNDNKLNNEYLEL

NYKEDEYFENIIQNLKFSQSKQLKKLREKVDKDEWISGAAVVNAFYSSGR

NQIVFPAGILQPPFFSAQQSNSLNYGGIGMVIGHEITHGFDDNGRNFNKD

GDLVDWWTQQSASNFKEQSQCMVYQYGNFSWDLAGGQHLNGINTLGENIA

DNGGLGQAYRAYQNYIKKNGEEKLLPGLDLNHKQLFFLNFAQVWCGTYRP

EYAVNSIKTDVHSPGNFRIIGTLQNSAEFSEAFHCRKNSYMNPEKKCRVW

It will be understood that these sequences are exemplary, that additional C-C chemokine receptor type 5 (CCR5), Programmed death-ligand 1 (PDL1), Tumor Necrosis Factor alpha (TNFa), Insulin-Degrading Enzyme (IDE), membrane metallo-endopeptidase (MME, Neprilysin), and Interleukin 23 alpha subunit P19 (IL23aP19) sequences exist, e.g., sequences in other species and sequences comprising SNPs, and that the sequences provided here are not meant to limit the scope of the disclosure.

In some embodiments, the methods provided herein comprise contacting the target protein with the protease in vitro. In some embodiments, the methods provided herein comprise contacting the target protein with the protease in vivo. In some embodiments, the methods provided herein comprise contacting the target protein with the protease in a cell, e.g., by delivering the protease or a nucleic acid molecule encoding the protease to the cell. In some embodiments, the methods provided herein comprise contacting the target protein with the protease in a subject, e.g., by administering the protease to the subject, either locally or systemically. In some such embodiments, the methods is administered to the subject in an amount effective to result in a measurable decrease in the level of full-length target protein in the subject, or in a measurable increase in the level of a cleavage product generated by the protease upon cleavage of the target protein. In some embodiments, the target protein is associated with a disease or disorder and the administration of the protease results in the amelioration of at least one symptom of the disease or disorder.

Host Cells

Some aspects of this invention relate to host cells for continuous evolution processes as described herein. In some embodiments, a host cell is provided that comprises at least one viral gene encoding a protein required for the generation of infectious viral particles under the control of a conditional promoter, and a fusion protein comprising a transcriptional activator targeting the conditional promoter and fused to an inhibitor via a linker comprising a protease cleavage site. For example, some embodiments provide host cells for phage-assisted continuous evolution processes, wherein the host cell comprises an accessory plasmid comprising a gene required for the generation of infectious phage particles, for example, M13 gIII, under the control of a conditional promoter, as described herein. In some embodiments, the host cells comprises an expression construct encoding a fusion protein as described herein, e.g., on the same accessory plasmid or on a separate vector. In some embodiments, the host cell further provides any phage functions that are not contained in the selection phage, e.g., in the form of a helper phage. In some embodiments, the host cell provided further comprises an expression construct comprising a gene encoding a mutagenesis-inducing protein, for example, a mutagenesis plasmid as provided herein.

In some embodiments, modified viral vectors are used in continuous evolution processes as provided herein. In some embodiments, such modified viral vectors lack a gene required for the generation of infectious viral particles. In some such embodiments, a suitable host cell is a cell comprising the gene required for the generation of infectious viral particles, for example, under the control of a constitutive or a conditional promoter (e.g., in the form of an accessory plasmid, as described herein). In some embodiments, the viral vector used lacks a plurality of viral genes. In some such embodiments, a suitable host cell is a cell that comprises a helper construct providing the viral genes required for the generation of infectious viral particles. A cell is not required to actually support the life cycle of a viral vector used in the methods provided herein. For example, a cell comprising a gene required for the generation of infectious viral particles under the control of a conditional promoter may not support the life cycle of a viral vector that does not comprise a gene of interest able to activate the promoter, but it is still a suitable host cell for such a viral vector.

In some embodiments, the host cell is a prokaryotic cell, for example, a bacterial cell. In some embodiments, the host cell is an *E. coli* cell. In some embodiments, the host cell is a eukaryotic cell, for example, a yeast cell, an insect cell, or a mammalian cell. The type of host cell, will, of course, depend on the viral vector employed, and suitable host cell/viral vector combinations will be readily apparent to those of skill in the art.

In some embodiments, the viral vector is a phage and the host cell is a bacterial cell. In some embodiments, the host cell is an *E. coli* cell. Suitable *E. coli* host strains will be apparent to those of skill in the art, and include, but are not limited to, New England Biolabs (NEB) Turbo, Top10F', DH12S, ER2738, ER2267, and XL1-Blue MRF'. These strain names are art recognized and the genotype of these strains has been well characterized. It should be understood that the above strains are exemplary only and that the invention is not limited in this respect.

In some PACE embodiments, for example, in embodiments employing an M13 selection phage, the host cells are *E. coli* cells expressing the Fertility factor, also commonly referred to as the F factor, sex factor, or F-plasmid. The F-factor is a bacterial DNA sequence that allows a bacterium to produce a sex pilus necessary for conjugation and is essential for the infection of *E. coli* cells with certain phage, for example, with M13 phage. For example, in some embodiments, the host cells for M13-PACE are of the genotype F'proA$^+$B$^+$ Δ(lacIZY) zzf::Tn10(TetR)/endA1 recA1 galE15 galK16 nupG rpsL ΔlacIZYA araD139 Δ(ara, leu)7697 mcrA Δ(mrr-hsdRMS-mcrBC) proBA::pir116λ.

Kits and Apparatuses

Some aspects of this invention provide kits for continuous protease evolution as described herein. In some embodiments, the kit comprises (a) a vector encoding a phage backbone, for example, an M13 phage backbone, and a multiple cloning site for insertion of a nucleic acid sequence encoding a protease. In some embodiments, the vector or a replication product thereof can be packaged into infectious phage particles in the presence of other phage functions by suitable host cells. In some embodiments, the vector or a replication product thereof lacks at least one gene required for the generation of infectious particles.

In some embodiments, the kit comprises (b) an accessory plasmid comprising a nucleic acid sequence encoding the at least one gene required for the generation of infectious particles under the control of a conditional promoter that is activated by a transcriptional activator.

In some embodiments, the kit comprises (c) an expression construct encoding a fusion protein of the transcriptional activator that activates the promoter of (b) fused to an inhibitor of the transcriptional activator via a linker, and a multiple cloning site for insertion of a nucleic acid sequence encoding a protease cleavage site.

In some embodiments, the kit further comprises a helper phage providing all phage functions except for the at least one gene required for the generation of infectious phage particles provided by the accessory plasmid of (b). In some embodiments, the helper phage or a replication product thereof cannot be packaged into infectious phage particles.

In some embodiments, the kit comprises suitable host cells. In some embodiments, the host cells are *E. coli* host cells. In some embodiments, the kit further comprises a mutagenesis plasmid. In some embodiments, the mutagenesis plasmid comprising a gene expression cassette encoding umuC (a components of *E. coli* translesion synthesis polymerase V), dam (deoxyadenosine methylase), and/or seqA (a hemimethylated-GATC binding domain), or any combination thereof.

In some embodiments, a PACE apparatus is provided, comprising a lagoon that is connected to a turbidostat comprising a host cell as described herein. In some embodiments, the host cell is an *E. coli* host cell. In some embodiments, the host cell comprises an accessory plasmid as described herein, a helper plasmid as described herein, a mutagenesis plasmid as described herein, and/or an expression construct encoding a fusion protein as described herein, or any combination thereof. In some embodiments, the lagoon further comprises a selection phage as described herein, for example, a selection phage encoding a protease of interest. In some embodiments, the lagoon is connected to a vessel comprising an inducer for a mutagenesis plasmid, for example, arabinose. In some embodiments, the host cells are *E. coli* cells comprising the F' plasmid, for example, cells of the genotype F'proA$^+$B$^+$ Δ(lacIZY) zzf::Tn10(TetR)/endA1 recA1 galE15 galK16 nupG rpsL ΔlacIZYA araD139 Δ(ara,leu)7697 mcrA Δ(mrr-hsdRMS-mcrBC) proBA::pir116λ$^-$.

For example, in some embodiments, a PACE apparatus is provided, comprising a lagoon of about 100 ml, or about 1 l volume, wherein the lagoon is connected to a turbidostat of about 0.5 l, 1 l, or 3 l volume, and to a vessel comprising an inducer for a mutagenesis plasmid, for example, arabinose, wherein the lagoon and the turbidostat comprise a suspension culture of *E. coli* cells at a concentration of about $5\times10^8$ cells/ml. In some embodiments, the flow of cells through the lagoon is regulated to about 3 lagoon volumes per hour. In some embodiments, cells are removed from the lagoon by continuous pumping, for example, by using a waste needle set at a height of the lagoon vessel that corresponds to a desired volume of fluid (e.g., about 100 ml, in the lagoon. In some embodiments, the host cells are *E. coli* cells comprising the F' plasmid, for example, cells of the genotype F'proA$^+$B$^+$ Δ(lacIZY) zzf::Tn10(TetR)/endA1 recA1 galE15 galK16 nupG rpsL ΔlacIZYA araD139 Δ(ara,leu)7697 mcrA Δ(mrr-hsdRMS-mcrBC) proBA::pir116λ$^-$.

Some of the embodiments, advantages, features, and uses of the technology disclosed herein will be more fully understood from the Examples below. The Examples are intended to illustrate some of the benefits of the present disclosure and to describe particular embodiments, but are not intended to exemplify the full scope of the disclosure and, accordingly, do not limit the scope of the disclosure.

EXAMPLES

Example 1: Phage-Assisted Directed Evolution of Proteases

Transducing Protease Activity into Gene Expression

PACE requires that a target activity be linked to changes in the expression of an essential phage gene such as gene III (gIII). To couple the cleavage of a polypeptide substrate to increases in gene expression, we engineered a PA-RNAP that transduces proteolytic activity into changes in gene expression that are sufficiently strong and rapid to support PACE. T7 RNA polymerase (T7 RNAP) is naturally inhibited when bound to T7 lysozyme[31]. We envisioned that T7 lysozyme could be tethered to T7 RNAP through a flexible linker containing a target protease cleavage site. Without wishing to be bound by theory, it is believed that the effective concentration of the tethered T7 lysozyme with respect to T7 RNAP would be sufficiently high that the T7 RNAP subunit would exist predominantly in the T7 lysozyme-bound, RNAP-inactive state. Proteolysis of the target sequence would disfavor the bound T7 RNAP:T7 lysozyme complex, resulting in the liberation of an active T7 RNAP and expression of gIII placed downstream of a T7 promoter (FIG. 1A).

Figure 5:
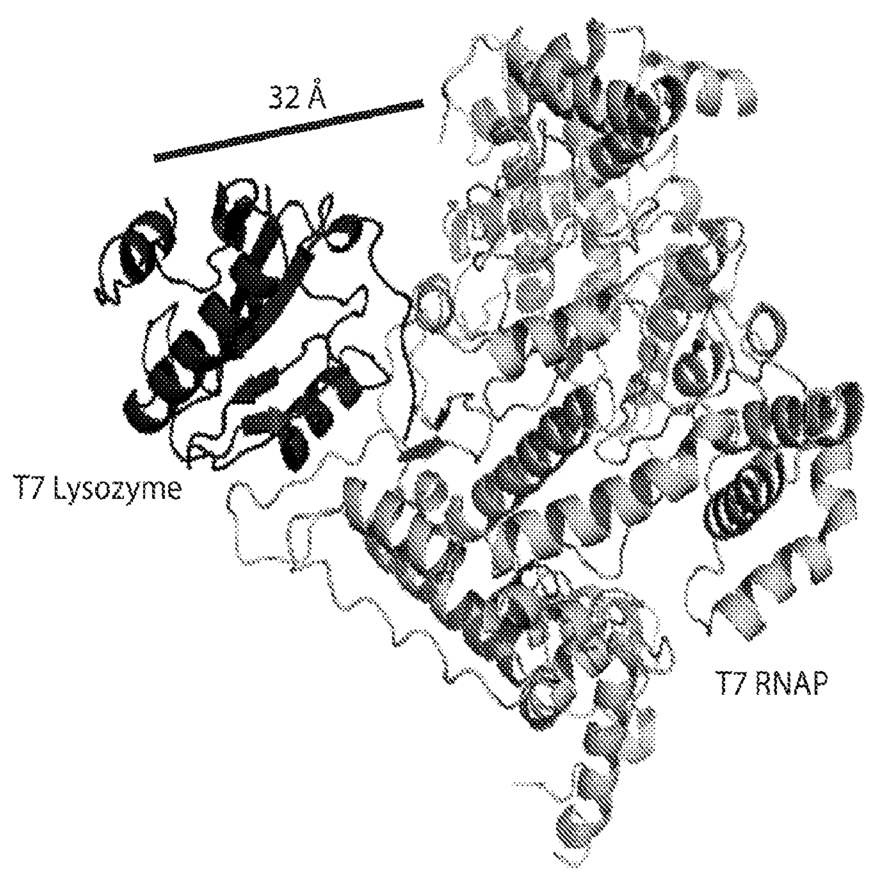
FIG. 5. Crystal structure of T7 lysozyme bound to T7 RNAP. Generated from PDB-1ARO[32].

N-terminal fusions to T7 RNAP are known to be well tolerated, and in the crystal structure of T7 RNAP bound to T7 lysozyme, the C-terminus of T7 lysozyme is only 32 Å from the N-terminus of T7 RNAP, separated by a solvent-exposed channel[32] (FIG. 5). In light of this structural information, we linked the two proteins through these proximal termini. Since T7 lysozyme activity is toxic to host *E. coli* cells, we characterized catalytically inactive lysozyme variants and found that the inactive C131S lysozyme mutant retained its ability to inhibit T7 RNAP without impairing host cell viability.

To identify T7 RNAP-T7 lysozyme linkers that promote complex formation and result in an inactive polymerase subunit yet permit efficient proteolysis, we screened a small set of linkers consisting of Gly, Ser, and Ala ranging in length from three to ten residues flanking each side of a target protease substrate. We designed PA-RNAP constructs containing linker peptide sequences known to be cleaved by tobacco etch virus (TEV) protease, HCV protease, or human rhinovirus-14 3C (HRV) protease. We assayed T7 RNAP activity using a luciferase reporter and observed that T7 lysozyme linked to T7 RNAP through at least 28 residues including the target protease substrate resulted in significant inhibition of RNAP activity (FIG. 1B). To assay RNAP activation, we coexpressed each PA-RNAP variant from a plasmid (the complementary plasmid or CP, FIG. 1C and FIG. 6) together with each of the three proteases (expressed from the expression plasmid or EP, FIG. 7) in *E. coli* cells that also harbored a plasmid encoding gIII and luciferase under control of the T7 promoter (the accessory plasmid or AP, FIG. 1C and FIG. 8).

Figure 1C:
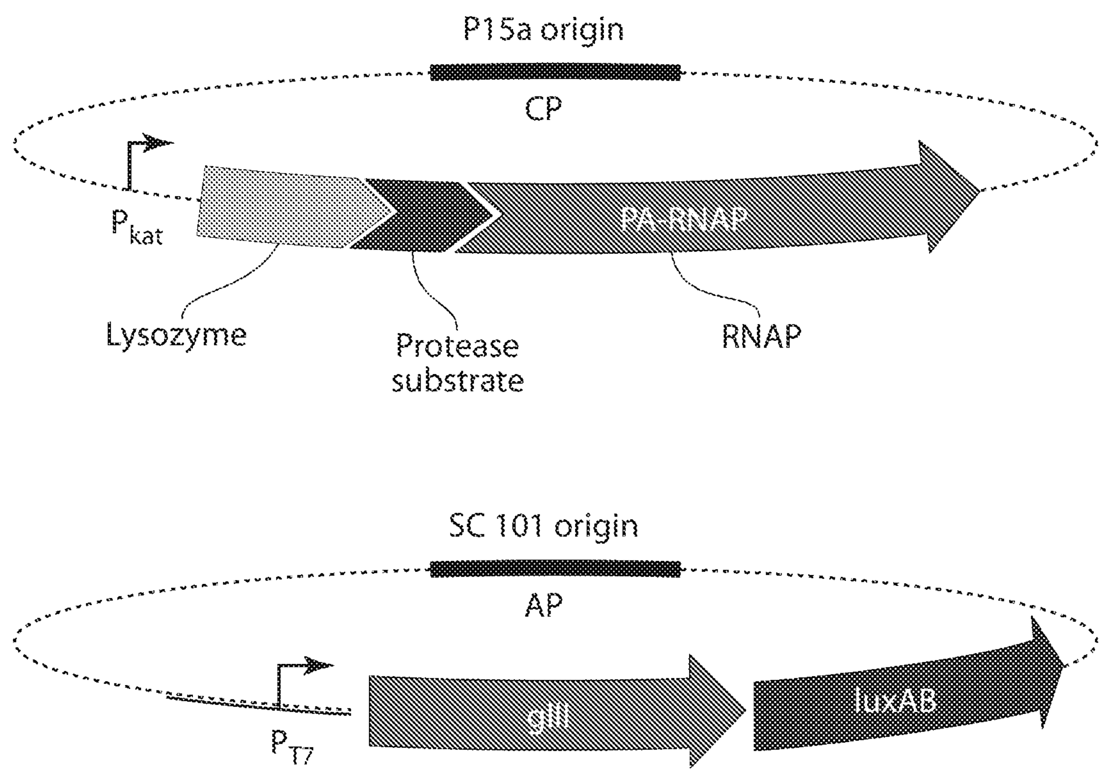
Figure 1D:
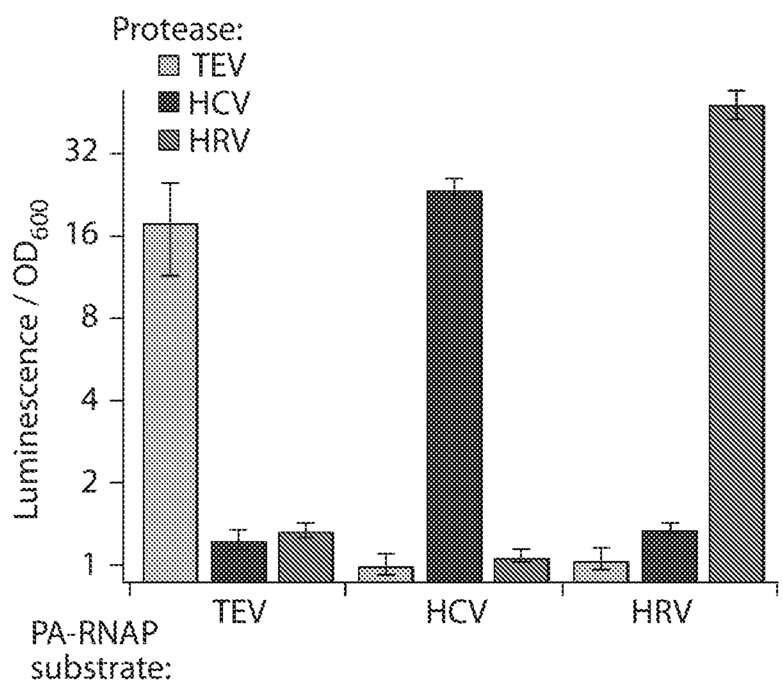

Expression of a protease that is not known to cleave the target amino acid sequence in a coexpressed PA-RNAP did not result in enhanced gene expression as measured by luciferase activity (FIG. 1D). In contrast, expression of a protease that is known to cleave the target sequence within the PA-RNAP resulted in 18- to 49-fold increase in gene expression for all three cognate combinations of protease and substrate. These data indicate that PA-RNAPs are capable of transducing specific proteolytic cleavage activities into large changes in target gene expression.

Linking Protease Activity to Phage Propagation

Figure 9:
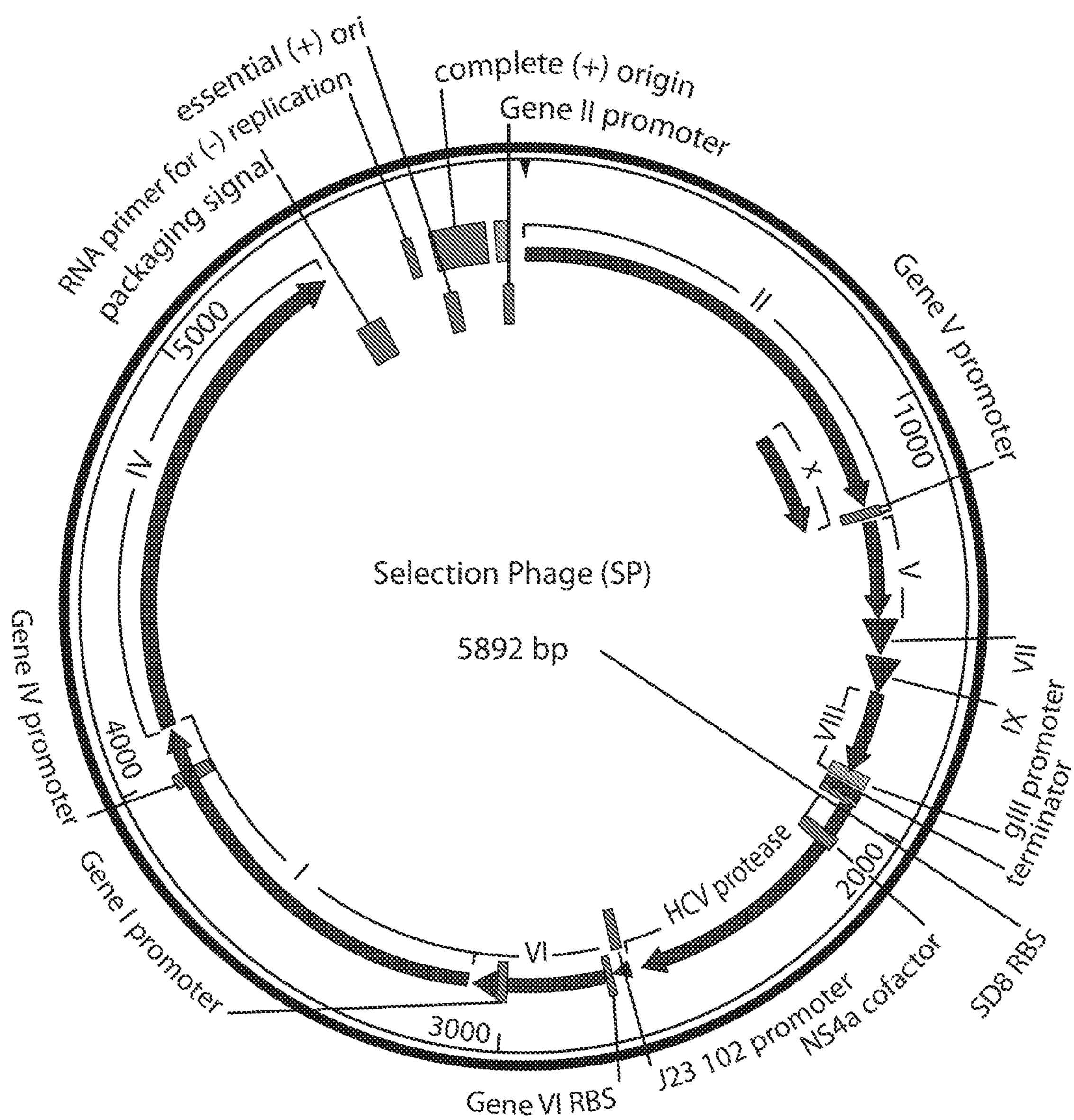
FIG. 9. Vector map of selection phage (SP) used in Example 1.
Figure 11:
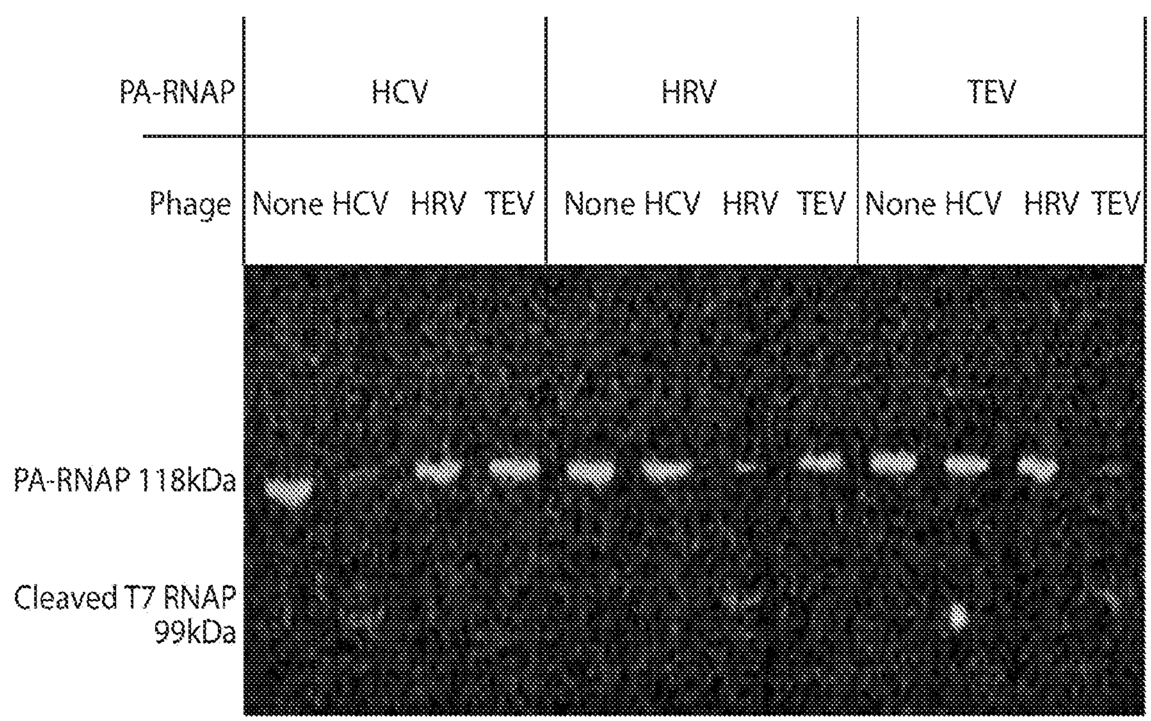
FIG. 11. Western blot showing PA-RNAP is cleaved only by the protease that is known to recognize the target sequence. Band sizes of ~120 kDa and ~100 kDa correspond to the full PA-RNAP construct and the cleaved RNAP, respectively.

Next we sought to use PA-RNAPs to link the life cycle of M13 bacteriophage to protease activity. We generated selection phage (SP) in which gIII was replaced by a gene encoding TEV protease, HCV protease, or HRV protease (FIG. 9). Without pIII, these phage are unable to propagate on wild-type *E. coli* cells. We engineered host *E. coli* cells containing two plasmids: (i) an AP that contains gIII and luciferase under the control of the T7 promoter, and (ii) a CP that constitutively expresses a PA-RNAP (FIG. 1C). To be sure that the PA-RNAP selection scheme work as intended we analyzed the cleavage of the sensor by Western blot. We observed the loss of the Lysozyme-RNAP fusion and the formation of a new protein that corresponds to the size of T7 RNAP exclusively in the presence of protease phage that recognizes the host encoded PA-RNAP (FIG. 11). To assay whether the host cells could support phage propagation in a protease-dependent manner, we performed activity-dependent plaque assays. We observed that plaque formation, a consequence of phage replication in solid media, only occurred with phage encoding a protease that can cleave the PA-RNAP within the host cells. Phage with mismatched protease/PA-RNAP combinations did not form plaques, indicating that phage encoding non-cognate proteases do not replicate, or replicate at a significantly reduced rate. These observations together establish that the PA-RNAP system is capable of transducing protease activity of a phage-encoded protease into phage production.

Figure 2A:
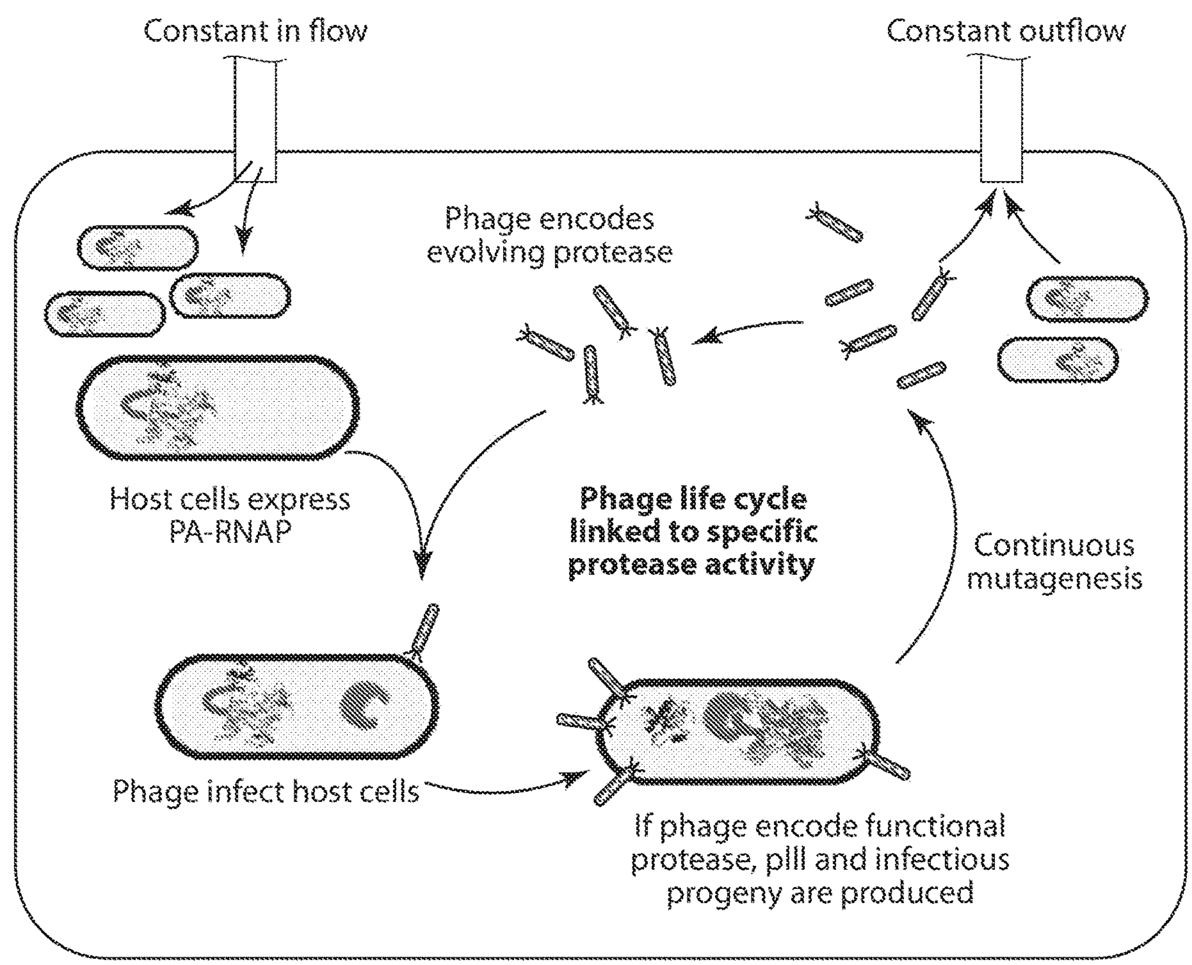
FIGS. 2A-D. PA-RNAPs link protease activity to phage propagation. (A) The protease PACE system. Fixed volume vessels (lagoons) contain phage in which gIII is replaced with a gene encoding an evolving protease. The lagoon is fed with host cells that contain an AP with the T7 promoter driving gIII and a CP that expresses a PA-RNAP. Phage infect incoming cells and inject their genome containing a protease variant. Only if the protease variant can activate the PA-RNAP by cleaving the linker encoding the target protease substrate, gIII is expressed and that SP can propagate. (B-D) Enrichment of active proteases from mixed populations using PACE. At time 0, a lagoon was seeded with a 1,000-fold excess of non-cognate protease-encoding phage over cognate protease-encoding phage. The lagoon was continuously diluted with host cells containing a PA-RNAP with either the HCV (B), TEV (C), or HRV (D) protease substrates. Lagoon samples were periodically analyzed by PCR. In all three cases, phage encoding the cognate protease were rapidly enriched in the lagoon while phage encoding the non-cognate protease were depleted.

We next tested if the PA-RNAP-based selection supports the continuous propagation of phage encoding active proteases in the continuous liquid culture format required for PACE (FIG. 2A). We maintained three host cell cultures, each harboring a CP expressing a PA-RNAP containing one of the three protease cleavage sites (TEV, HCV, or HRV protease substrates), using chemostats diluted with fresh growth media at a fixed rate[30]. Each of these host cell cultures continuously diluted lagoons seeded with various combinations of phage containing TEV, HCV, or HRV protease. Lagoons seeded with phage encoding cognate proteases that can cleave the PA-RNAP within the host cells robustly propagated ($10^8$-$10^{10}$ pfu $mL^{-1}$ after 72 hours of continuous dilution at 1.0 lagoon volume per hour), while lagoons seeded with phage encoding proteases that do not match the PA-RNAP of incoming host cells washed out ($<10^4$ pfu $mL^{-1}$), demonstrating protease activity-dependent propagation in continuous liquid culture.

Figure 2B:
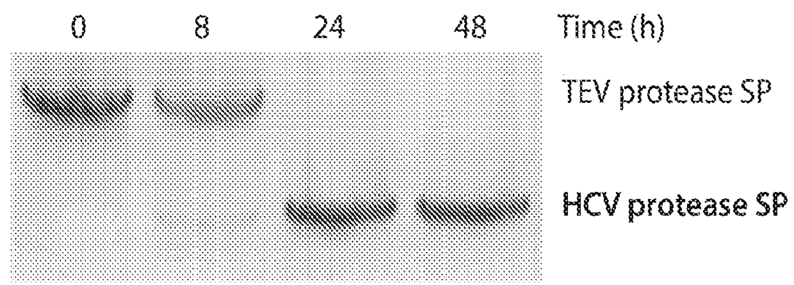
Figure 2C:
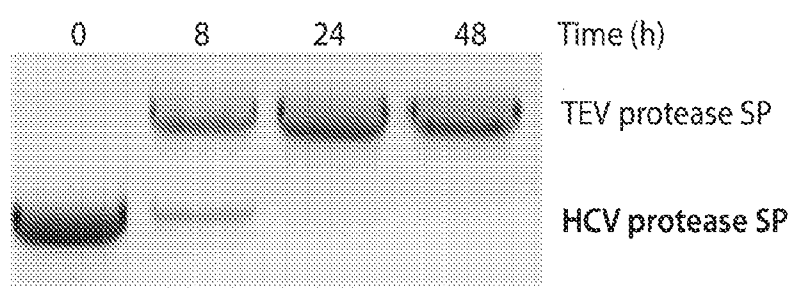

In order to determine if this system can selectively replicate phage carrying protease genes with a desired activity at the expense of phage encoding proteases that are unable to cleave the host-cell PA-RNAP, we performed protease phage enrichment experiments in a PACE format. We seeded a lagoon with a 1,000:1 ratio of TEV SP:HCV SP, then allowed the phage to propagate in the lagoon while being continuously diluted with host cells containing a PA-RNAP with the HCV protease recognition site. We periodically sampled the waste line of the lagoon and amplified by PCR the region of the phage containing the protease genes. The TEV protease and HCV protease genes are readily distinguishable as PCR amplicons of distinct lengths. At the start of the experiment the HCV protease phage were virtually undetectable by PCR amplification of the starting population and gel electrophoresis, while TEV protease dominated the lagoon (FIG. 2B). After just 24 h of continuous propagation on host cells containing the HCV PA-RNAP, the TEV protease SPs were undetectable, while the HCV protease SPs were strongly enriched (≥100,000-fold enrichment over 24 hours).

Figure 2D:
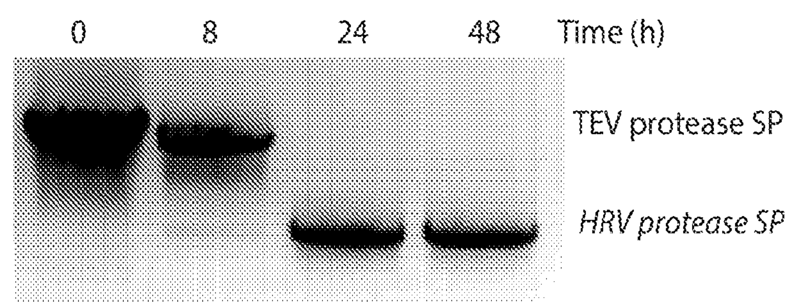

We repeated this experiment with a 1,000-fold excess of HCV protease phage over TEV protease phage using host cells containing the TEV protease PA-RNAP (FIG. 2C), and a third time using a 1,000-fold excess of TEV protease phage over HRV phage and host cells containing the HRV protease PA-RNAP (FIG. 2D). In all three of the enrichment experiments, continuous propagation rapidly and dramatically enriched phage encoding each cognate protease from a minute fraction of the starting phage mixture, while non-cognate proteases washed out of the lagoon (FIGS. 2A-D). Collectively, these results indicate that this protease PACE system successfully links specific protease activity to the phage life cycle in a continuous flow format and can strongly and rapidly enrich phage that encode proteases with the ability to cleave a target polypeptide substrate.

Continuous Evolution of Resistance to HCV Protease Inhibitors

Figure 3A:
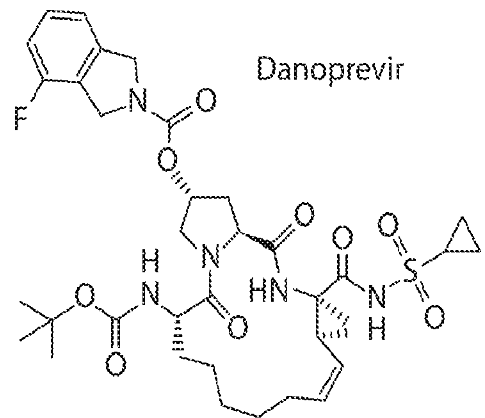
FIGS. 3A-B. HCV PA-RNAP response to protease inhibitors in *E. coli* cells. Host cells expressing the HCV PA-RNAP were incubated with the HCV protease inhibitors danoprevir (A) or asunaprevir (B) for 90 min, followed by inoculation with HCV protease encoding phage. After 3 hours, luminescence assays were used to quantify relative gene activation resulting from the PA-RNAP Luminescence experiments were performed in triplicate with error bars depicting the standard deviation.
Figure 3A:
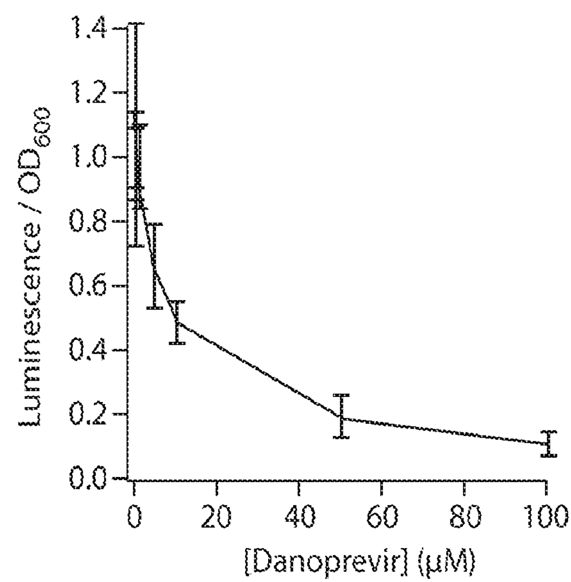
Figure 3B:
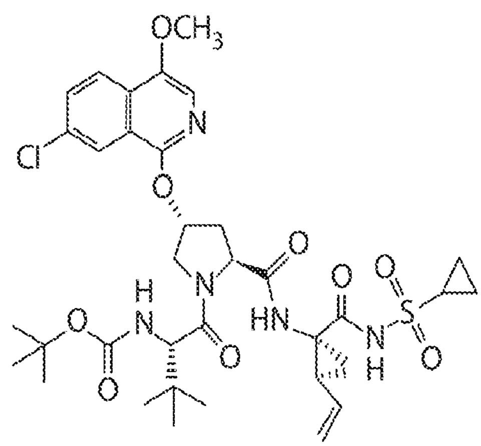
Figure 3B:
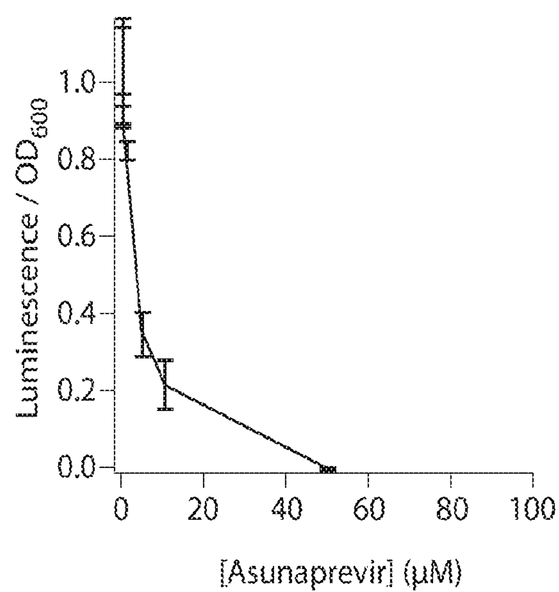

As an initial application of protease PACE, we continuously evolved protease enzymes to rapidly assess the drug resistance susceptibility of small-molecule protease inhibitors. Several HCV protease inhibitors are in late-stage clinical trials or are awaiting FDA approval[33,34]. For some HCV protease inhibitor drug candidates, clinically isolated drug resistance mutations are known[20]. First we tested whether small-molecule HCV protease inhibitors can modulate protease activity in the protease PACE system. We observed that the incubation of host cells with either danoprevir ($IC_{50}$=~0.3 nM)[35] or asunaprevir ($IC_{50}$=~1.0 nM)[36], two second-generation HCV protease inhibitors, inhibited the cellular gene expression arising from the activity of HCV protease on the HCV PA-RNAP in a dose-dependent manner (FIGS. 3A-B). These observations suggest that protease inhibitors can create selection pressure during PACE favoring the evolution of protease mutants that retain their ability to cleave a cognate substrate despite the presence of the drug candidates.

Based on the relationship between protease inhibitor concentration and gene expression in our system (FIGS. 3A-B) and initial trial PACE experiments, we selected 20 μM danoprevir as the final concentration to use in the culture media during attempts to continuously evolve drug-resistant HCV proteases. We inoculated two separate lagoons with HCV protease SP and propagated the phage on host cells containing the HCV protease PA-RNAP in the absence of any inhibitor for 6 h to allow the accumulation of mutations in HCV protease genes. Next, we added 20 μM danoprevir to the media that feeds into the host cell culture, and eventually into each of the two replicate lagoons. As a control, we propagated two replicate lagoons of HCV protease phage on HCV protease PA-RNAP host cells with no added protease inhibitor for the same time period. Throughout all of these experiments, we induced enhanced mutagenesis of the phage genome by activating an improved mutagenesis plasmid (MP) in the host cells with 0.5% arabinose (see Methods and Materials for a description and Table 1 below for characterization of the improved MP).

TABLE 1

Frequency of rifampin resistant colonies using the improved MP.

| | Glucose | Arabinose | Fold above pJC184 |
|---|---|---|---|
| None | 1.21 ± 1.25 | 0.26 ± 0.13 | — |
| pJC184 | 29.6 ± 32.5 | 2146 ± 2062 | 1 |
| pAB086k8 | 10.4 ± 18.5 | 10330 ± 13862 | 4.8 |

Figure 4:
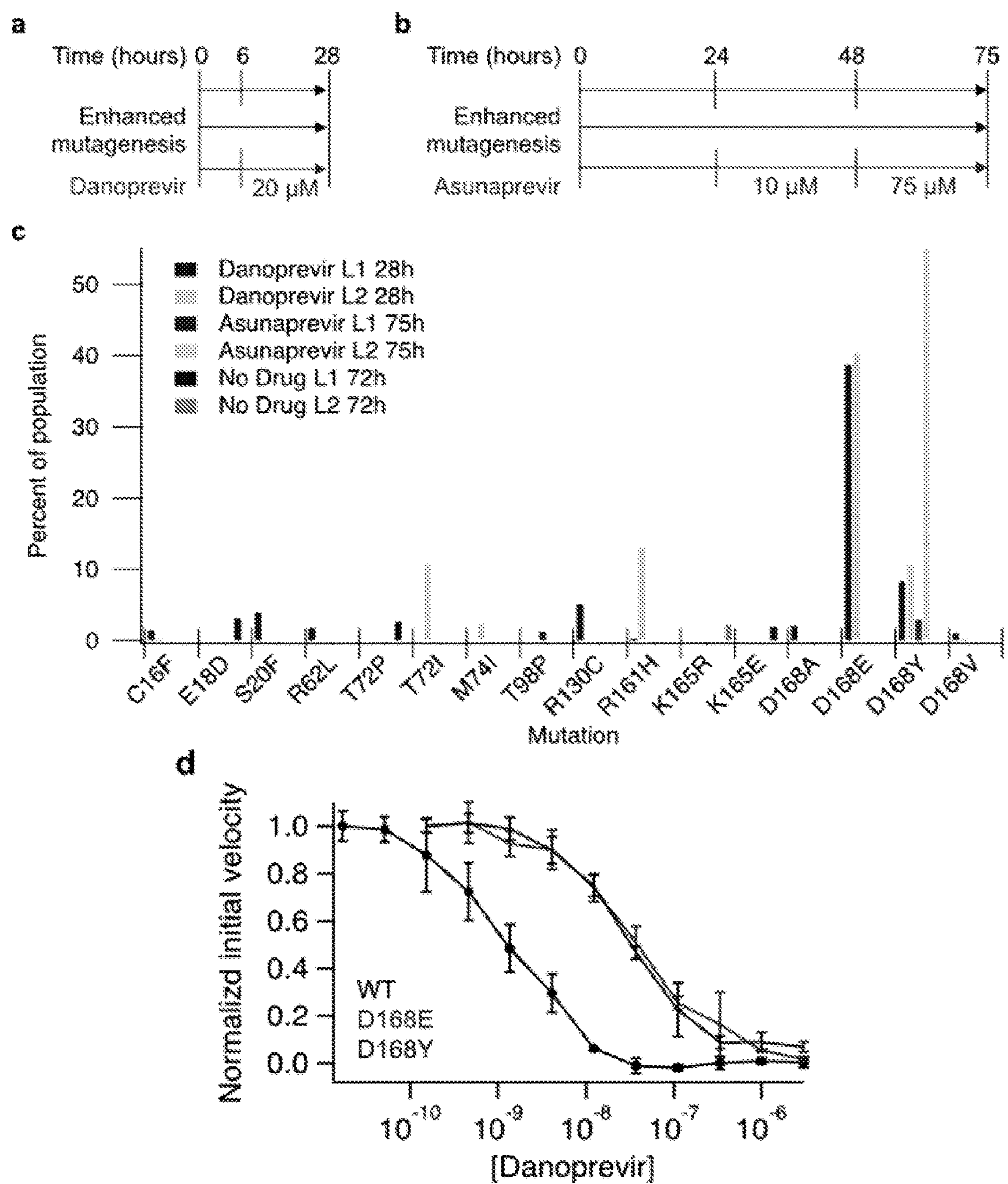
FIGS. 4A-E. Continuous evolution of drug resistance in HCV protease. (A, B) PACE condition timeline for evolution in the presence of danoprevir (A) or asunaprevir (B). The blue arrows indicate arabinose-induced enhanced mutagenesis, and the red arrow shows the timing and dosing of HCV protease inhibitors. PACE condition timeline for evolution in the presence of asunaprevir. (C) High-throughput sequencing data from phage populations in replicate lagoons (L1 and L2) subjected to danoprevir treatment at 28 h, asunaprevir treatment at 75 h, and no drug at 72 h. All mutations with frequencies more than 1% above the allele-specific error rate are shown. (D) In vitro analysis of danoprevir inhibition of mutant HCV proteases that evolved during PACE. (E) In vitro analysis of asunaprevir inhibition of mutant HCV proteases that evolved during PACE. For (D) and (E), evolved HCV protease variants were expressed and purified, then assayed using an internally quenched fluorescent-substrate (Anaspec). In vitro analyses were performed in triplicate with error bars calculated as the standard deviation.
Figure 4:
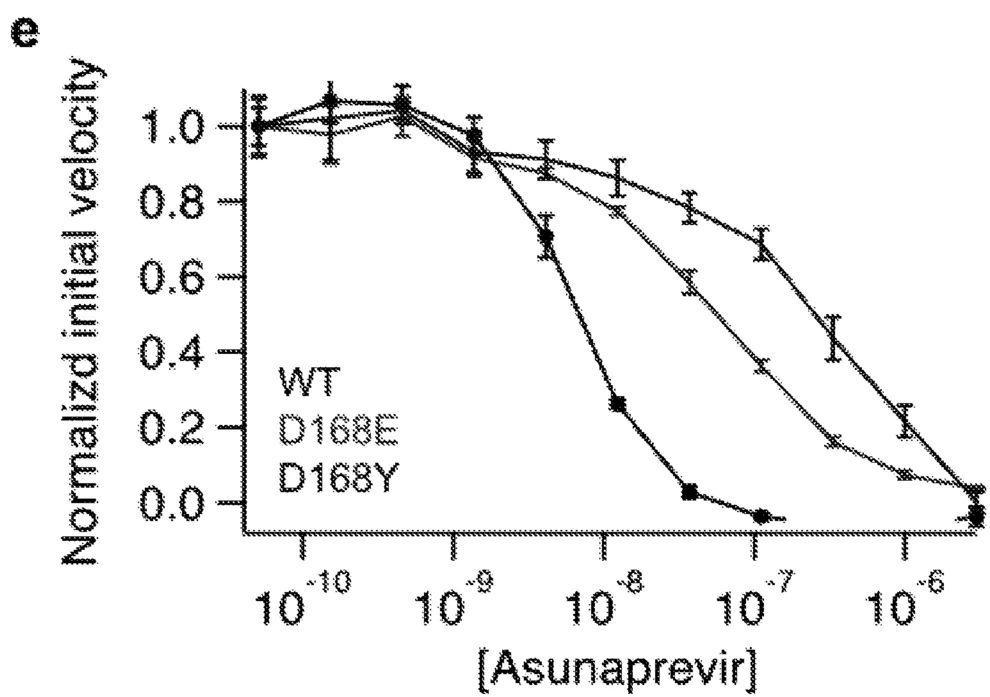

Phage populations at 6 and 28 h from replicate lagoons were analyzed by high-throughput DNA sequencing. No mutations were substantially enriched in the control lagoons propagated in the absence of any drug candidate (FIG. 4C). In contrast, several mutations rapidly evolved in both replicate lagoons in the presence of danoprevir. Mutations at position D168 were predominant among these mutations. By 28 h, lagoon 1 with danoprevir contained 38.8% D168E, 8.3% D168Y, 2.1% D168A, and 1.1% D168V, while lagoon 2 with danoprevir contained 40.3% D168E and 10.7% D168Y (FIG. 4C). Other genetic differences between the SPs of these two replicate populations suggest that cross-contamination did not lead to the observed protease variants in these experiments. These findings reveal that the presence of danoprevir caused the population of continuously evolving proteases to rapidly acquire mutations at D168.

To assay whether the PACE-evolved mutations confer danoprevir drug resistance in HCV protease, we purified recombinant HCV protease variants containing either of the two most highly enriched mutations, D168E and D168Y. Each of these two mutations increase the $IC_{50}$ of danoprevir by ~30-fold (wild-type HCV protease $IC_{50}$=1.3±0.1 nM; HCV protease D168E $IC_{50}$=38.9±2.4 nM; HCV protease D168Y $IC_{50}$=34.4±2.8 nM; $IC_{50}$±standard deviation) (FIG.

4D). Importantly, the D168E, D168A, and D168V mutations emerging from protease PACE have been previously identified as common drug-resistance mutations in HCV isolated from patients treated with danoprevir[20,37].

To validate that protease PACE in the presence of a different HCV protease inhibitor can also result in the rapid evolution of drug-resistance mutations, we repeated PACE of HCV protease in the presence of asunaprevir, an HCV protease inhibitor in phase III clinical trials, instead of danoprevir. We selected 75 μM asunaprevir as the final target concentration to use in the culture media based on dose-dependent gene expression assays (FIGS. 3A-B). In order to allow diversity to emerge in the protease population, we first propagated HCV protease phage for 24 h without any inhibitor. Next, to ensure that the populations had sufficient time to evolve mutations that confer drug resistance, we propagated the populations for 24 h with 10 μM asunaprevir, Finally, the asunaprevir concentration was increased to 75 μM for 27 h in order to enrich those mutations that conferred robust drug resistance. HCV protease phage were also propagated for an identical amount of time without any added drug candidate for comparison. High-throughput DNA sequencing of phage populations at the end of the experiment revealed that mutations evolved at substantial levels in the asunaprevir-treated lagoons but not in the control samples (FIG. 4C). In this experimental condition as well, mutations at position D168 were highly enriched. In the case of asunaprevir, however, the only substitution at this position to emerge at substantial levels from protease PACE was D168Y, in contrast with the evolution of both D168E and D168Y during protease PACE with danoprevir.

In vitro assays of HCV proteases containing either mutation provides an explanation underlying the strong apparent preference of D168Y over D168E within asunaprevir-treated lagoons. D168Y increases the $IC_{50}$ of asunaprevir by 30-fold, while D168E only increases the $IC_{50}$ of asunaprevir by ~10-fold (wild-type HCV protease $IC_{50}$=6.9±0.6 nM; HCV protease D168E $IC_{50}$=53.5±3.4 nM; HCV protease D168Y $IC_{50}$=214.8±31.9 nM; $IC_{50}$±standard deviation) (FIG. 4E). Mutations at position D168 have been previously identified in replicon-based asunaprevir resistance experiments[38] and the specific D168Y mutation has been observed to arise in hepatitis C patients treated with asunaprevir[39], Data from patients also reveals that D168E, D168V, and D168A mutations favor viral escape from danoprevir therapy[37], further supporting that D168 is an important residue for viral escape. Collectively, these results establish that protease PACE in the presence of protease inhibitor drug candidates can very rapidly (1-3 days) reveal clinically relevant mutants that confer strong resistance to the drug candidates, without requiring extensive laboratory or clinical experiments.

Discussion

Previous efforts to use laboratory evolution to study HCV protease inhibitor resistance have relied on time- and labor-intensive approaches such as viral replication in mammalian cell culture or conventional protein evolution methods, which typically require months to complete[22]. By comparison, the continuous evolution of proteases can reveal key resistance mutations in as little as ~1 day of PACE. The speed of PACE and its ability to be multiplexed using many lagoons in parallel, each receiving a different drug candidate, and analyzed by high-throughput DNA sequencing of bar-coded lagoon samples, raises the possibility of screening future early-stage hit or lead compounds for their vulnerability to the evolution of drug resistance, before more resource-intensive optimization of in vivo properties or clinical trials take place. Rapid and cost-effective access to drug resistance susceptibility enabled by PACE may enhance the more informed selection of more promising early-stage drug candidates for further development. This technique could also be applied to quickly screen a drug candidate across many distinct genotypic variants of a protease target (such as the six major HCV protease genotypes) to reveal each target variant's potential to evolve mutations that abrogate the effectiveness of the drug candidate. As HCV patient isolates and replicon assays have already demonstrated differing drug resistance profiles among different HCV genotypes,[40] this capability could also be used to rapidly identify patient-specific drug treatments that are more likely to offer long-term therapeutic effects on patients infected with specific HCV strains, even in the absence of previous data relating strain genotypes to drug effectiveness.

The development of protease PACE also expands the scope of PACE to evolve diverse biochemical activities. Prior PACE studies have only evolved RNA polymerases, which have activities that can be directly linked to changes in gIII expression. This study demonstrates how other types of enzymatic activities with no obvious direct connection to gene expression can nevertheless be evolved using PACE by establishing an indirect, but robust, linkage between the activity of interest and gIII expression.

The protease PACE system provides a strong foundation for the continuous evolution of proteases with reprogrammed specificities. Previous work on reprogramming the DNA substrate selectivity of T7 RNAP enzymes[25,28-30] demonstrated the ability of PACE to rapidly evolve enzymes that accept substrates very different from the native substrate. These reprogramming experiments relied on a "stepping-stone" strategy in which selection phage are transitioned between a series of intermediate substrates[28], and are enhanced by the recent development of modulated selection stringency and negative selection during PACE[30]. In principle these strategies coupled with protease PACE should also enable the continuous evolution of protease enzymes with the tailor-made ability to selectively cleave proteins implicated in human diseases.

Materials and Methods

PA-RNAP Gene Expression Response In Vivo.

All plasmids were constructed by Gibson Assembly 2× Master Mix (NEB); all PCR products were generated using Q5 Hot Start 2× Master Mix (NEB). *E. coli* strain S1030[30] were transformed by electroporation with three plasmids: (i) a complementary plasmid (CP) that constitutively expresses a PA-RNAP with one of the three protease cut sites (FIG. 6), (ii) an accessory plasmid (AP, FIG. 8) that encodes gIII-luciferase (translationally coupled) under control of the T7 promoter, and (iii) an arabinose-inducible expression plasmid for one of the three proteases (EP, FIG. 7). The HRV protease gene was purchased as IDT gblocks and cloned into the expression vector. The MBP-TEV fusion protein was amplified by PCR from pRK793[41]. The MBP fusion was necessary for expression and solubility. The HCV protease gene was generously provided by the Schiffer lab as a constitutively active construct that includes the NS4a cofactor peptide. Cells were grown in 2×YT media to saturation in the presence of antibiotics and 1 mM glucose, then inoculated into 1 mL fresh media containing 1 mM glucose and antibiotics in a 96 well culture plate. After 4.5 h, 150 μL of the cultures were transferred to a black-wall clear-bottom assay plate and luciferase and $OD_{600}$ measurements were taken using a Tecan Infinite Pro plate. The luminescence data was normalized to cell density by dividing by $OD_{600}$.

Protease Activity-Dependent Plaque Assays.

Protease phage were cloned using Gibson assembly and the aforementioned expression plasmids as templates. *E. coli* strain S1030 were transformed by electroporation with an AP and a CP. After the transformed host cells were grown in 2×YT to $OD_{600}$~1.0, 100 μL of cells were added to 50 μL of serial dilutions of protease-encoding phage. After one minute, 800 μL of top agar (7 g/L agar in 2×YT) was added, mixed and transferred to quarter-plates containing bottom agar (15 g/L agar in 2×YT). After overnight incubation at 37° C., the plates were examined for plaques, which represent zones of slowed growth and diminished turbidity due to phage propagation.

PACE Propagations and Enrichment Experiments.

*E. coli* strain S1030 were transformed by electroporation with an AP, CP (one for each of the three PA-RNAPs), and a mutagenesis plasmid (MP, FIG. 10, Table 1) encoding arabinose-inducible expression of a dominant-negative mutator variant of dnaQ, wild-type dam, and wild-type seqA[42-44]. Starter cultures were grown overnight in 2×YT supplemented with antibiotics and 1 mM glucose to prevent induction of mutagenesis prior to the PACE experiment. Host cell culture chemostats containing 80 mL of Davis rich media[30] were inoculated with 2 mL of starter culture and grown at 37° C. with magnetic stir-bar agitation. At approximately $OD_{600}$ 1.0, fresh Davis rich media was pumped in at 80-100 mL $h^{-1}$, with a chemostat waste needle set at 80 mL. This fixed dilution rate maintains the chemostat culture in late log phase growth, at which point it can be flowed into lagoons seeded with protease phage (initial titers were ~$10^5$ pfu $mL^{-1}$). For these experiments, lagoon waste needles were set to maintain a lagoon volume of 15 mL, and host cell cultures were flowed in at 15-17 mL $h^{-1}$. Arabinose (10% w/v in water) was added directly to lagoons via syringe pump at 0.7 mL $h^{-1}$ to induce mutagenesis. Test propagations were conducted with cognate protease phage as well as non-cognate protease phage. Enrichment experiment lagoons were seeded with 1,000-fold excess of non-cognate protease phage. Lagoon samples were sterile-filtered at least every 24 h, and titers were assessed by plaque assay. Plaque assays were performed with S1030 carrying pJC175e, a plasmid that supplies gIII under control of the phage-shock promoter[30]. Mock selections were monitored by PCR of the protease gene using filtered samples as template and the primers listed below. The distinct sizes of amplicons containing protease genes enabled evaluation of the relative abundance of cognate and non-cognate protease-encoding phage.

```
Forward primer (BCD582):
                                    (SEQ ID NO: 15)
TGTTTTAGTGTATTCTTTCGCCTCTTTCGTT

Reverse primer (BCD578):
                                    (SEQ ID NO: 16)
CCCACAAGAATTGAGTTAAGCCCAATAATAAGAGC
```

Inhibition of PA-RNAP Response in Host *E. coli* Cells.

Host cells were prepared by electroporation with an AP and the CP encoding the HCV-site PA-RNAP. We prepared 2×YT media with serial dilutions of inhibitors (danoprevir and asunaprevir, MedChemExpress) from stock solutions made in DMSO, and inoculated with a saturated starter culture of host cells. 150 μL cell cultures in a 96-well assay plate were incubated at 37° C. for 1.5 h to allow uptake of inhibitors, then infected with ~10 μL HCV protease phage (multiplicity of infection~10). After 3 h of incubation at 37° C., the luminescence of each culture was measured on a Tecan Infinite Pro plate reader and normalized to $OD_{600}$. In the absence of inhibitor, phage-encoded protease will activate the PA-RNAP leading to robust production of luciferase. Relative dose responses to inhibitors compared to control cells without drug were measured in triplicate.

Evolution of Drug Resistance in HCV Protease Using PACE.

Host cells were the same as those in the HCV test propagation and enrichment experiments. Chemostats were established in an identical manner as mentioned previously, but with the volume and flow rate halved (40 mL; 40-50 mL $h^{-1}$). This adjustment was made to provide enough cell culture to feed two lagoons while also conserving media that contained small-molecule inhibitors. Lagoons were seeded with HCV protease phage and run in duplicate. After 6 h of propagation without any inhibitor, a filtered lagoon sample was taken, and danoprevir was added directly to the chemostat media at 20 μM with 2.5% DMSO to enhance solubility. A final time point was taken after 22 additional hours, and titers were measured by plaque assay on strain S1030 carrying pJC175e. For the asunaprevir experiment, samples were taken every 12 h. After 24 h of propagation with no inhibitor, asunaprevir was added directly to the chemostat media at 10 μM with 2.5% DMSO. After an additional 24 h, asunaprevir dosage was increased to 75 μM and 5% DMSO. Titers were measured by plaque assay on strain S1030 carrying pJC175e.

High-Throughput Sequencing of Evolved Populations.

Strain S1030 carrying pJC175e were grown to saturation and used to inoculate fresh media. Host cells were infected with phage samples from the above PACE experiments and incubated for 5 h at 37° C. DNA from infected cells was extracted using miniprep kits to yield concentrated template phage DNA (Epoch Life Science). PCR reactions were performed using Q5 Hot Start 2× Master Mix (NEB) with a set of tiled primers. The PCR product from the first reaction was diluted ten-fold and 1 μL served as the template for the second PCR. The second PCR added Illumina adapters as well as barcodes; PCR products were purified from agarose gel (Qiagen) and quantified using the Quant-IT Picogreen assay (Invitrogen). Samples were normalized and pooled together to create a sequencing library at approximately 4 nM. The library was quantified by qPCR (KapaBiosystems) and processed by an Illumina MiSeq using the MiSeq Reagent Kit v3 and the 2×300 paired-end protocol. A single paired-end read of 600 bp is sufficient to cover the entire HCV protease gene. Data was analyzed in MATLAB using a custom script that aligned reads to the wild type gene, and filtered out bases that were below a Q-score threshold of 31 (Illumina Q-scores range from 1-40). As a control, the wild-type stock of HCV protease phage was sequenced and processed to assess the extent of sequencing error and PCR bias. At each locus within the gene, the error rate was calculated as the fraction of residues that was not wild-type. This error rate was added to 1% to determine the variant threshold for each locus within the gene.

Purification and In Vitro Assays of Evolved HCV Variants.

HCV protease variants were sub-cloned by Gibson assembly out of the phage genome and into the previously mentioned EP. EPs were transformed into NEB BL21 DE3 chemically competent cells. Starter cultures were grown to saturation, and 2 mL was used to inoculate 500 mL LB. At $OD_{600}$=0.6, cultures were transferred to 20° C. and induced with 0.5% arabinose for 6 h. Cells were harvested by centrifugation at 5,000 g for 10 m, and resuspended in lysis/bind buffer (50 mM Tris-HCl pH 8.0, 500 mM NaCl, 10% glycerol, 5 mM imidazole). Cells were lysed by sonication for a total of 2 m, and then centrifuged for 20 m at 18,000 g to clarify the lysate. Supernatant was flowed through 0.2 mL His-pur nickel resin spin columns that were equilibrated with binding buffer (Pierce-Thermo). Resin was washed with 4 column volumes of wash buffer (50 mM Tris-HCl pH 8.0, 500 mM NaCl, 10% glycerol, 20 mM imidazole). HCV protease was eluted in 4 column volumes of 50 mM Tris-HCl pH 8.0, 500 mM NaCl, 10% glycerol, 200 mM imidazole. Samples were further purified by size exclusion chromatography on a SuperDex 75 10/300 GL column (GE Healthcare). Size exclusion was performed in 50 mM Tris-HCl pH 8.0, 100 mM NaCl, 10% glycerol, 1 mM DTT. Protein concentrations were determined by $UV_{280}$ on a Nanodrop machine and calculated using an extinction coefficient of 19,000 $cm^{-1}$ $M^{-1}$ and a molecular weight of 23 kDa.

In vitro assays were performed using the commercial HCV RET Substrate 1 (Anaspec), an internally quenched probe that fluoresces upon proteolytic cleavage, according to the manufacturer's instructions. Protease and inhibitors were incubated in assay buffer at room temperature for 5 m prior to addition of substrate. Fluorescence was measured every 30 s for 20 m by a Tecan Infinite Pro plate reader (excitation/emission=355 nm/495 nm). Assays were performed at 30° C. with 40 nM protease, 7.5 μM substrate, and varying concentration of inhibitors in a final volume of 100 μL per well in black-wall clear-bottom assay plate. The assay buffer contained 50 mM Tris HCl pH 8.0, 100 mM NaCl, 20% glycerol, 5 mM DTT. Assays were performed in triplicate, and initial reaction velocities were calculated and normalized to controls without inhibitor. The data was fit to the Hill Equation using Igor Pro with base and max parameters fixed at one and zero respectively. The resulting fits yielded $IC_{50}$ values and standard deviations of the estimate.

Western Blot of PA-RNAP Sensor Activation.

*E. coli* cells transformed with an AP and a CP were grown to log phase, then infected with a 10-fold excess of protease-encoding phage. After 4.5 h, the cells were harvested by centrifugation at 5000 g for 10 min, and then resuspended in LDS Sample Buffer (Life Technologies). Samples were heated to 95° C. for 5 m and vortexed to shear genomic DNA. 4 μL of each sample was loaded onto a protein gel electrophoresis system (Bolt gel system, Life Technologies). The blot was performed using a PVDF membrane (iBlot 2 system, Life Technologies). The membrane was blocked with 5% BSA TBST then incubated overnight with the primary antibody (5% BSA, TBST, 1:5000 anti-T7 RNAP mouse monoclonal, Novagen #70566). The membrane was washed three times, incubated with the secondary antibody (5% BSA, TBST, 1:5000 donkey anti-mouse, IR-dye conjugate, LI-COR #926-32212) for 60 min, washed three times, then visualized on a LI-COR Odyssey at 800 nm. As seen in FIG. 11, the PA-RNAP sensor is proteolyzed to a smaller band of anticipated molecular weight only in the presence of a cognate protease that can cleave the peptide sequence in each PA-RNAP linker.

Improved Mutagenesis Plasmid (MP).

The previous generation of the mutagenesis plasmid (MP)[25] carried four genes: dnaQ926[43] (a dominant-negative *E. coli* DNA polymerase III proofreading subunit), umuD' and umuC (the components of *E. coli* translesion synthesis polymerase V) and recA730 (an activated recA mutant). The complex of UmuD'$_2$C/RecA730 forms the *E. coli* mutasome complex, a critical requirement for translesion synthesis across predominantly T-T (6-4) photoproducts and pyrimidine dimers[45,46]. Since neither type of mutation is predicted to occur commonly during current PACE experiments, which do not use UV light or chemical mutagens, the genes encoding the mutasome were removed from the MP. To improve the efficiency of mutagenesis, two additional proteins were included on the $P_{BAD}$ transcript: dam (deoxyadenosine methylase) and seqA (a hemimethylated-GATC binding domain), both of which are known mutators when overexpressed in *E. coli*[42,44]. The combination of these three genes yielded higher mutagenesis rates in the presence of arabinose during PACE, and resulted in 5-fold higher mutagenesis of *E. coli* chromosomal DNA as assessed by a rifampin resistance assay (see Table 1).

Rifampin Resistance Assay.

MG1655 ΔrecA *E. coli*[47] (CGSC#: 12492) cells were transformed with the appropriate MPs and plated on 2×YT/agar plates supplemented with 40 μg/mL chloramphenicol and 100 mM glucose to ensure that no induction occurs prior to the assay. After overnight growth, single colonies were picked into liquid Davis Rich Media[48] supplemented with 40 μg/mL chloramphenicol and grown for 12-16 hours with vigorous shaking at 37° C. Cultures were then diluted 1,000-fold in Davis Rich Media and grown until they reached $OD_{600}$=0.5-0.7, at which point the were split into two equal volumes, supplemented with either 100 mM glucose or 100 mM arabinose, and allowed to grow for an additional 24 hours. Saturated cultures were serially diluted and plated on 2×YT/agar supplemented with 100 mM glucose with or without 100 μg/mL rifampin. After overnight growth, colonies were counted from both plates, and the frequency of resistant mutants was calculated. This measurement been widely used in the literature as a metric of mutagenesis[49].

Analysis of High-Throughput Sequencing Data of Evolved Populations of HCV Protease.

FASTQ files were automatically generated by the Illumina MiSeq. These files were already binned by sample barcodes and ready for transfer to a desktop computer for processing via a custom Matlab script. Each read was aligned to the wild-type HCV protease gene in the expected orientation using the Smith-Waterman algorithm. Base calls with Q-scores below a threshold of 31 were converted to ambiguous bases, and the resulting ambiguous codons were turned into a series of three dashes for computationally efficient translation. Ambiguous codons were translated into X's, which were ignored when tabulating allele counts in a matrix. The script automatically cycled through each FASTQ file and saved the resulting allele count matrix in a separate subdirectory. At this stage, matrices for paired-end reads were added together and normalized to yield allele frequencies for each sample.

We relied on a wild-type control sample to assess PCR and sequencing bias. For this sample, we calculated the frequency of alleles that were not wild-type at each locus to yield the locus-specific error rate. We added 0.01 (1%) to the locus-specific error rate to yield our variant call threshold. The allele frequency matrix for each sample was scanned for mutant alleles above the variant call threshold.

Matlab Scripts

Alignment and Tallying Script

```
filename2='ntdHCV.txt';
filename3='aaHCV.txt';
for d=1:48
      orient=orientations{d};
      seqsFile=filenames{d};
      [header,seqs,qscore] = fastqread(seqsFile);
      seqsLength = length(seqs);
      seqsFile = strrep(seqsFile,'.fastq','');
      if exist(seqsFile,'dir');
            error('Directory already exists. Please rename or move it before
moving on.');
      end
      mkdir(seqsFile);
      wtID = −1;
      while wtID < 0
            wtID = fopen(filename2);
      end
      wt = fscanf(wtID, '%s');
      fclose(wtID);
      wtLength = length(wt);
      aaID = −1;
      while aaID < 0
            aaID = fopen(filename3);
      end
      aa = fscanf(aaID,'%s');
      fclose(aaID);
      aaLength = length (aa);
      sBLength = length(seqs);
      nSkips = 0;
      ALN=repmat(' ',[sBLength wtLength]);
      ALNaa=repmat(' ',[sBLength aaLength]);
      for i = 1:sBLength
            if orient=='F'
                  [score,alignment,start] = swalign(seqs{i},wt,'Alphabet','NT');
            elseif orient=='R'
                     reverse = seqrcomplement(seqs{i});
                  [score,alignment,start] = swalign(reverse,wt,'Alphabet','NT');
                  qscore{i}=fliplr(qscore{i});
            end
            len = length(alignment(3,:));
            skip = 0;
            for j = 1:len
                  if (alignment(3,j) == '-' || alignment(1,j) == '-')
                        skip = 1;
                        nSkips = nSkips + 1;
                        break;
                  end
                  if isletter(qscore{i} (start(1)+j−1))
                  else
                        alignment(1,j) = 'N';
                  end
               end
            if skip == 0
                  ALN(i,start(2):(start(2)+length(alignment)−1))=
                  alignment(1,:);
                  if mod(start(2),3)==1
                        frame=1;
                  end
                  if mod(start(2),3)==2;
                        frame=3;
                  end
                  if mod(start(2),3)==0;
                        frame=2;
                  end
                  ntd=alignment(1,frame:length(alignment));
                  index=strfind(ntd,'N');
                  modulus=mod([index],3);
                  for k=1:length(index)
                        ntd(index(k))='-';
                        if modulus(k)==1
                           ntd(index(k)+1)='-';
                           ntd(index(k)+2)='-';
                        elseif modulus(k)==2 && index(k) >1
                           ntd(index(k)+1)='-';
                           ntd(index(k)−1)='-';
                        elseif modulus(k)==0 && index(k) >2
                           ntd(index(k)−2)='-';
                           ntd(index(k)−1)='-';
                        end
                  end
                  aaseq=nt2aa(ntd);
ALNaa(i,round(start(2)/3)+1:round(start(2)/3)+length(aaseq))=aaseq;
            end
      end
      TallyAA=zeros(20,aaLength);
      TallyNTD=zeros(4,wtLength);
      parfor i=1:wtLength
TallyNTD(:,i)=[sum(ALN(:,i)=='A'),sum(ALN(:,i)=='T'),sum(ALN
(:,i)=='C'),sum(ALN(:,i)=='G')];
      end
      parfor i=1:aaLength
TallyAA(:,i)=[sum(ALNaa(:,i)=='A'),sum(ALNaa(:,i)=='R'),sum(ALNaa
(:,i)=='N'),sum(ALNaa(:,i)=='D'),sum(ALNaa(:,i)=='C') ...
                  sum(ALNaa(:,i)=='Q'), sum(ALNaa(:,i)=='E'),
sum(ALNaa(:,i)=='G'), sum(ALNaa(:,i)=='H'), sum(ALNaa(:,i)=='I') ...
                  sum(ALNaa(:,i)=='L'), sum(ALNaa(:,i)=='K'),
sum(ALNaa(:,i)=='M'), sum(ALNaa(:,i)=='F'), sum(ALNaa(:,i)=='P') ...
                  sum(ALNaa(:,i)=='S'), sum(ALNaa(:,i)=='T'),
sum(ALNaa(:,i)=='W'), sum(ALNaa(:,i)=='Y'), sum(ALNaa(:,i)=='V')];
      end
      save(strcat(seqsFile, '/TallyAA'), 'TallyAA');
      save(strcat(seqsFile, '/TallyNTD'), 'TallyNTD');
      dlmwrite(strcat(seqsFile, '/TallyAA.txt'), TallyAA, 'newline', 'pc');
      dlmwrite(strcat(seqsFile, '/TallyNTD.txt'), TallyNTD, 'precision',
'%.3f', 'newline', 'pc');
end
```

Variant calling Script

```
filename2='ntdHCV.txt';
filename3='aaHCV.txt';
      wtID = −1;
      while wtID < 0
            wtID = fopen(filename2);
      end
      wtNTD = fscanf(wtID,'%s');
      fclose(wtID);
      ntdlength = length(wtNTD);
         aaID = −1;
      while aaID < 0
            aaID = fopen(filename3);
      end
      wtAA = fscanf(aaID,'%s');
      fclose(aaID);
      aalength = length(wtAA);
      iwtAA=aa2int(wtAA);
for d=41:44
      seqsFile1=strrep(filenames{2*d−1},'.fastq','');
      seqsFile2=strrep(filenames{2*d},'.fastq','');
AA1=load(strcat('/MATLAB/',seqsFile1,'/TallyAA.mat'));
      NTD1=load(strcat('/MATLAB/', seqsFile1,'/TallyNTD.mat'));
AA2=load(strcat('/MATLAB/',seqsFile2,'/TallyAA.mat'));
      NTD2=load(strcat('/MATLAB/', seqsFile2,'/TallyNTD.mat'));
      AA=AA1.TallyAA+AA2.TallyAA;
      NTD=NTD1.TallyNTD+NTD2.TallyNTD;
      AA = AA*spdiags((1./sum(AA,1))',0,aalength,aalength);
      NTD = NTD*spdiags((1./sum(NTD,1))',0,ntdlength,ntdlength);
      for 1=1:189
            error(i)=1−AA(iwtAA(1),1)+.01;
      end
   save(strcat('/MATLAB/',seqsFile1,'/error'),'error')
end
for d=1:47
      seqsFile1=strrep(filenames{2*d−1},'.fastq','');
      seqsFile2=strrep(filenames{2*d},'.fastq','');
AA1=load(strcat('/MATLAB/',seqsFile1,'/TallyAA.mat'));
      NTD1=load(strcat('/MATLAB/', seqsFile1,'/TallyNTD.mat'));
      AA2=load(strcat('/MATLAB/',seqsFile2,'/TallyAA.mat'));
      NTD2=load(strcat('/MATLAB/', seqsFile2,'/TallyNTD.mat'));
      AA=AA1.TallyAA+AA2.TallyAA;
      NTD=NTD1.TallyNTD+NTD2.TallyNTD;
      AA = AA*spdiags((1./sum(AA,1))',0,aalength,aalength);
      NTD = NTD*spdiags((1./sum(NTD,1))',0,ntdlength,ntdlength);
      mutations='';
      frequencies='';
      for i=1:aalength−1
```

-continued

```
            index=find(AA(:,1)>error(1));
            notwt=index(index~=iwtAA(1));
            residues=int2aa(notwt);
            if ~isempty(residues);
                string=strcat(wtAA(i), num2str(i-7), residues');
                mutations=strcat(mutations,'_',string);
                frequencies=strcat(frequencies,'_', num2str(AA(notwt,i)'));
            end
        end
        save(strcat('/MATLAB/',seqsFile1,'/AA'),'AA')
        save(strcat('/MATLAB/',seqsFile1,'/mutations'),'mutations')
        save(strcat('/MATLAB/',seqsFile1,'/frequencies'),'frequencies')
end
```

Sequences

Figure 6:
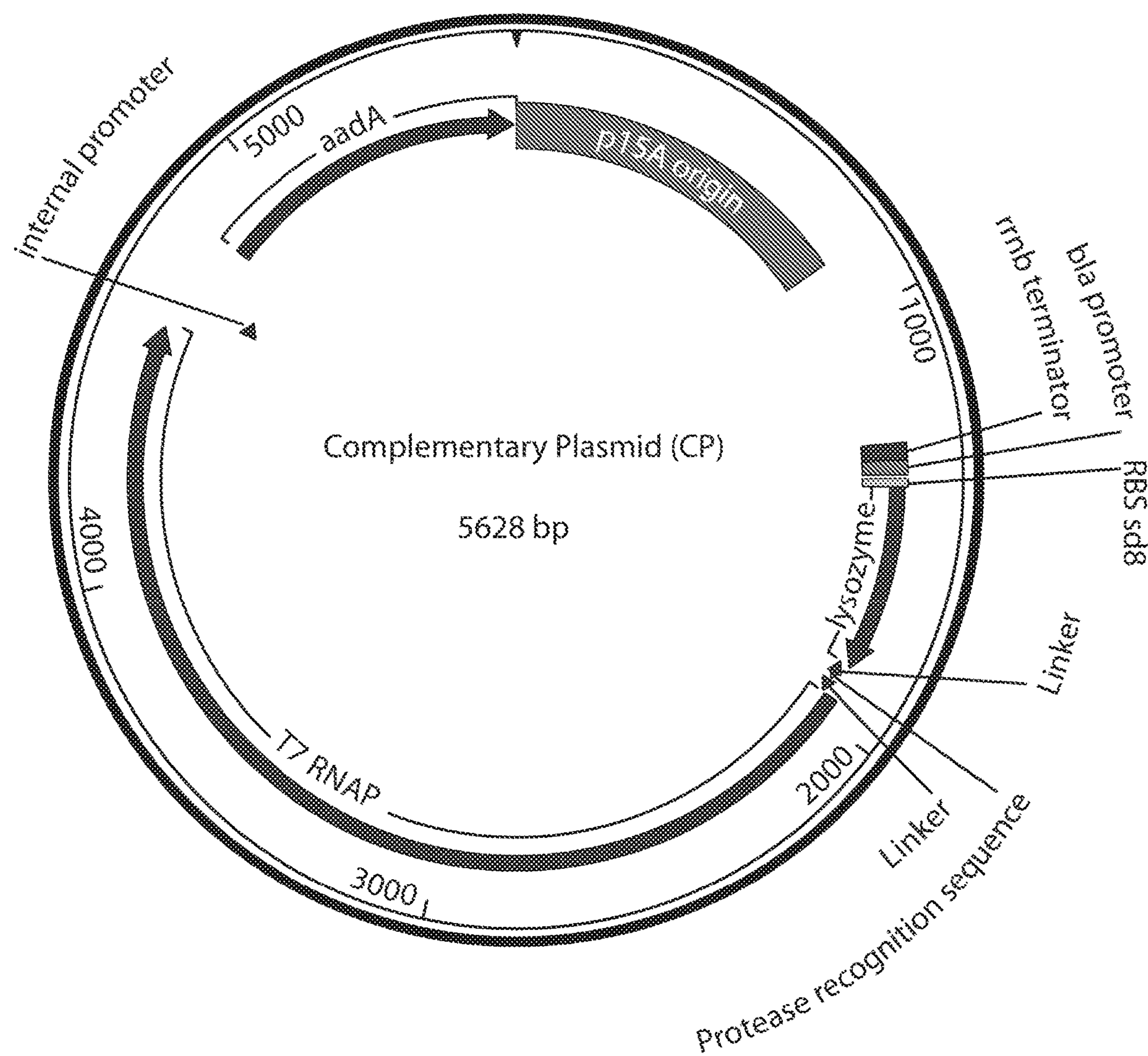
FIG. 6. Vector map of complementary plasmid (CP) used in Example 1.

Sequence of complementary plasmid (CP) illustrated in FIG. 6 (SEQ ID NO: 17):

ACGGATCGCTTCATGTGGCAGGAGAAAAAAGACTGCACCGGTGCGTCAGC

AGAATATGTGATACAGGATATATTCCGCTTCCTCGCTCACTGACTCGCTA

CGCTCGGTCGTTCGACTGCGGCGAGCGGAAATGGCTTACGAACGGGGCGG

AGATTTCCTGGAAGATGCCAGGAAGATACTTAACAGGGAAGTGAGAGGGC

CGCGGCAAAGCCGTTTTTCCATAGGCTCCGCCCCCCTGACAAGCATCACG

AAATCTGACGCTCAAATCAGTGGTGGCGAAACCCGACAGGACTATAAAGA

TACCAGGCGTTTCCCCCTGGCGGCTCCCTCGTGCGCTCTCCTGTTCCTGC

CTTTCGGTTTACCGGTGTCATTCCGCTGTTATGGCCGCGTTTGTCTCATT

CCACGCCTGACACTCAGTTCCGGGTAGGCAGTTCGCTCCAAGCTGGACTG

TATGCACGAACCCCCCGTTCAGTCCGACCGCTGCGCCTTATCCGGTAACT

ATCGTCTTGAGTCCAACCCGGAAAGACATGCAAAAGCACCACTGGCAGCA

GCCACTGGTAATTGATTTAGAGGAGTTAGTCTTGAAGTCATGCGCCGGTT

AAGGCTAAACTGAAAGGACAAGTTTTGGTGACTGCGCTCCTCCAAGCCAG

TTACCTCGGTTCAAAGAGTTGGTAGCTCAGAGAACCTTCGAAAAACCGCC

CTGCAAGGCGGTTTTTTCGTTTTCAGAGCAAGAGATTACGCGCAGACCAA

AACGATCTCAAGAAGATCATCTTATTAAGGGGTCTGACGCTCAGTGGAAC

GAAAACTCACGTTAAGGGATTTTGGTCATGAGATTATCAAAAAGGATCTT

CACCTAGATCCTTTTAAATTAAAAATGAAGTTTTAAATCAATCTAAAGTA

TATATGAGTAAACTTGGTCTGACAGTTACCAATGCTTAATCAGTGAGGCA

CCTATCTCAGCGATCTGTCTATTTCGTTCATCCATAGTTGCCTGACTCCC

CGTCGTGTAGATAACTACGATACGGGAGGGCTTACCATCTGGCCCCAGTG

CTGCAATGATACCGCGAGACCCACGCTCACCGGCTCCAGATTTATCAGCA

ATAAACCAGCCAGCCGATTCGAGCTCGCCCGGGGATCGACCAGTTGGTGA

TTTTGAACTTTTGCTTTGCCACGGAACGGTCTGCGTTGTCGGGAAGATGC

GTGATCTGATCCTTCAACTCAGCAAAAGTTCGATTTATTCAACAAAGCCG

CCGTCCCGTCAAGTCAGCGTAATGCTCTGCCAGTGTTACAACCAATTAAC

CAATTCTGATTTCCGGTCAAATAAAACGAAAGGCTCAGTCGAAAGACTGG

GCCTTTCGTTTTGTTTATACATAGGCGAGTACTCTGTTATGGTTCCTTCC

TCGAAAGGAAAAAAAAAAATGGCTCGTGTACAGTTTAAACAACGTGAATCT

ACTGACGCAATCTTTGTTCACTGCTCGGCTACCAAGCCAAGTCAGAATGT

-continued

TGGTGTCCGTGAGATTCGCCAGTGGCACAAAGAGCAGGGTTGGCTCGATG

TGGGATACCACTTTATCATCAAGCGAGACGGTACTGTGGAGGCAGGACGA

GATGAGATGGCTGTAGGCTCTCACGCTAAGGGTTACAACCACAACTCTAT

CGGCGTCTGCCTTGTTGGTGGTATCGACGATAAAGGTAAGTTCGACGCTA

ACTTTACGCCAGCCCAAATGCAATCCCTTCGCTCACTGCTTGTCACACTG

CTGGCTAAGTACGAAGGCGCTGTGCTTCGCGCCCATCATGAGGTGGCGCC

GAAGGCTTCCCCTTCGTTCGACCTTAAGCGTTGGTGGGAGAAGAACGAAC

TGGTCACTTCTGACCGTGGTAGCGGCGGTGGTGCGAGTGGTGGCGCGCTG

GAGGTCCTGTTCCAGGGCCCGGGCGGTAGCGCAGGCAGTGGAGCGGGCGG

TAACACGATTAACATCGCTAAGAACGACTTCTCTGACATCGAACTGGCTG

CTATCCCGTTCAACACTCTGGCTGACCATTACGGTGAGCGTTTAGCTCGC

GAACAGTTGGCCCTTGAGCATGAGTCTTACGAGATGGGTGAAGCACGCTT

CCGCAAGATGTTTGAGCGTCAACTTAAAGCTGGTGAGGTTGCGGATAACG

CTGCCGCCAAGCCTCTCATCACTACCCTACTCCCTAAGATGATTGCACGC

ATCAACGACTGGTTTGAGGAAGTGAAAGCTAAGCGCGGCAAGCGCCCGAC

AGCCTTCCAGTTCCTGCAAGAAATCAAGCCGGAAGCCGTAGCGTACATCA

CCATTAAGACCACTCTGGCTTGCCTAACCAGTGCTGACAATACAACCGTT

CAGGCTGTAGCAAGCGCAATCGGTCGGGCCATTGAGGACGAGGCTCGCTT

CGGTCGTATCCGTGACCTTGAAGCTAAGCACTTCAAGAAAAACGTTGAGG

AACAACTCAACAAGCGCGTAGGGCACGTCTACAAGAAAGCATTTATGCAA

GTTGTCGAGGCTGACATGCTCTCTAAGGGTCTACTCGGTGGCGAGGCGTG

GTCTTCGTGGCATAAGGAAGACTCTATTCATGTAGGAGTACGCTGCATCG

AGATGCTCATTGAGTCAACCGGAATGGTTAGCTTACACCGCCAAAATGCT

GGCGTAGTAGGTCAAGACTCTGAGACTATCGAACTCGCACCTGAATACGC

TGAGGCTATCGCAACCCGTGCAGGTGCGCTGGCTGGCATCTCTCCGATGT

TCCAACCTTGCGTAGTTCCTCCTAAGCCGTGGACTGGCATTACTGGTGGT

GGCTATTGGGCTAACGGTCGTCGTCCTCTGGCGCTGGTGCGTACTCACAG

TAAGAAAGCACTGATGCGCTACGAAGACGTTTACATGCCTGAGGTGTACA

AAGCGATTAACATTGCGCAAAACACCGCATGGAAAATCAACAAGAAAGTC

CTAGCGGTCGCCAACGTAATCACCAAGTGGAAGCATTGTCCGGTCGAGGA

CATCCCTGCGATTGAGCGTGAAGAACTCCCGATGAAACCGGAAGACATCG

ACATGAATCCTGAGGCTCTCACCGCGTGGAAACGTGCTGCCGCTGCTGTG

TACCGCAAGGACAAGGCTCGCAAGTCTCGCCGTATCAGCCTTGAGTTCAT

GCTTGAGCAAGCCAATAAGTTTGCTAACCATAAGGCCATCTGGTTCCCTT

ACAACATGGACTGGCGCGGTCGTGTTTACGCTGTGTCAATGTTCAACCCG

CAAGGTAACGATATGACCAAAGGACTGCTTACGCTGGCGAAAGGTAAACC

AATCGGTAAGGAAGGTTACTACTGGCTGAAAATCCACGGTGCAAACTGTG

CGGGTGTCGATAAGGTTCCGTTCCCTGAGCGCATCAAGTTCATTGAGGAA

AACCACGAGAACATCATGGCTTGCGCTAAGTCTCCACTGGAGAACACTTG

GTGGGCTGAGCAAGATTCTCCGTTCTGCTTCCTTGCGTTCTGCTTTGAGT

-continued

ACGCTGGGGTACAGCACCACGGCCTGAGCTATAACTGCTCCCTTCCGCTG

GCGTTTGACGGGTCTTGCTCTGGCATCCAGCACTTCTCCGCGATGCTCCG

AGATGAGGTAGGTGGTCGCGCGGTTAACTTGCTTCCTAGTGAAACCGTTC

AGGACATCTACGGGATTGTTGCTAAGAAAGTCAACGAGATTCTACAAGCA

GACGCAATCAATGGGACCGATAACGAAGTAGTTACCGTGACCGATGAGAA

CACTGGTGAAATCTCTGAGAAAGTCAAGCTGGGCACTAAGGCACTGGCTG

GTCAATGGCTGGCTTACGGTGTTACTCGCAGTGTGACTAAGCGTTCAGTC

ATGACGCTGGCTTACGGGTCCAAAGAGTTCGGCTTCCGTCAACAAGTGCT

GGAAGATACCATTCAGCCAGCTATTGATTCCGGCAAGGGTCTGATGTTCA

CTCAGCCGAATCAGGCTGCTGGATACATGGCTAAGCTGATTTGGGAATCT

GTGAGCGTGACGGTGGTAGCTGCGGTTGAAGCAATGAACTGGCTTAAGTC

TGCTGCTAAGCTGCTGGCTGCTGAGGTCAAAGATAAGAAGACTGGAGAGA

TTCTTCGCAAGCGTTGCGCTGTGCATTGGGTAACTCCTGATGGTTTCCCT

GTGTGGCAGGAATACAAGAAGCCTATTCAGACGCGCTTGAACCTGATGTT

CCTCGGTCAGTTCCGCTTACAGCCTACCATTAACACCAACAAAGATAGCG

AGATTGATGCACACAAACAGGAGTCTGGTATCGCTCCTAACTTTGTACAC

AGCCAAGACGGTAGCCACCTTCGTAAGACTGTAGTGTGGGCACACGAGAA

GTACGGAATCGAATCTTTTGCACTGATTCACGACTCCTTCGGTACCATTC

CGGCTGACGCTGCGAACCTGTTCAAAGCAGTGCGCGAAACTATGGTTGAC

ACATATGAGTCTTGTGATGTACTGGCTGATTTCTACGACCAGTTCGCTGA

CCAGTTGCACGAGTCTCAATTGGACAAAATGCCAGCACTTCCGGCTAAAG

GTAACTTGAACCTCCGTGACATCTTAGAGTCGGACTTCGCGTTCGCGTAA

TGGAGATTTTCAACATGCTCCCTCAATCGGTTGAATGTCGCCCTTTTGTC

TTTGGCGCTGGTAAACCATATGAATTTTCTATTGATTGTGACAAAATAAA

CTTATTCCGTGGTGTCTTTGCGTTTCTTTTATATGTTGCCACCTTTATGT

ATGTATTTTCTACGTTTGCTAACATACTGCGTAATAAGGAGTCTTAATCA

TGCCAGTTCTTTTGGGTATTCCGTAGAAAAAGGAAGAGTATGAGGGAAGC

GGTGATCGCCGAAGTATCGACTCAACTATCAGAGGTAGTTGGCGTCATCG

AGCGCCATCTCGAACCGACGTTGCTGGCCGTACATTTGTACGGCTCCGCA

GTGGATGGCGGCCTGAAGCCACACAGTGATATTGATTTGCTGGTTACGGT

GACCGTAAGGCTTGATGAAACAACGCGGCGAGCTTTGATCAACGACCTTT

TGGAAACTTCGGCTTCCCCTGGAGAGAGCGAGATTCTCCGCGCTGTAGAA

GTCACCATTGTTGTGCACGACGACATCATTCCGTGGCGTTATCCAGCTAA

GCGCGAACTGCAATTTGGAGAATGGCAGCGCAATGACATTCTTGCAGGTA

TCTTCGAGCCAGCCACGATCGACATTGATCTGGCTATCTTGCTGACAAAA

GCAAGAGAACATAGCGTTGCCTTGGTAGGTCCAGCGGCGGAGGAACTCTT

TGATCCGGTTCCTGAACAGGATCTATTTGAGGCGCTAAATGAAACCTTAA

CGCTATGGAACTCGCCGCCCGACTGGGCTGGCGATGAGCGAAATGTAGTG

CTTACGTTGTCCCGCATTTGGTACAGCGCAGTAACCGGCAAAATCGCGCC

GAAGGATGTCGCTGCCGACTGGGCAATGGAGCGCCTGCCGGCCCAGTATC

AGCCCGTCATACTTGAAGCTAGACAGGCTTATCTTGGACAAGAAGAAGAT

-continued

CGCTTGGCCTCGCGCGCAGATCAGTTGGAAGAATTTGTCCACTACGTGAA

AGGCGAGATCACCAAGGTAGTCGGCAAA rrnb terminator 1318 . . . 1362; bla promoter 1363 . . . 1392; p15A origin 1 . . . 861; sd8 RBS 1404 . . . 1417; T7 Lysozyme 1418 . . . 1867; Flexible Linker 1868 . . . 1897; Protease recognition sequence 1898 . . . 1921; Flexible Linker 1922 . . . 1951; T7 RNAP 1952 . . . 4600; aadA 4840 . . . 5628.

Figure 7:
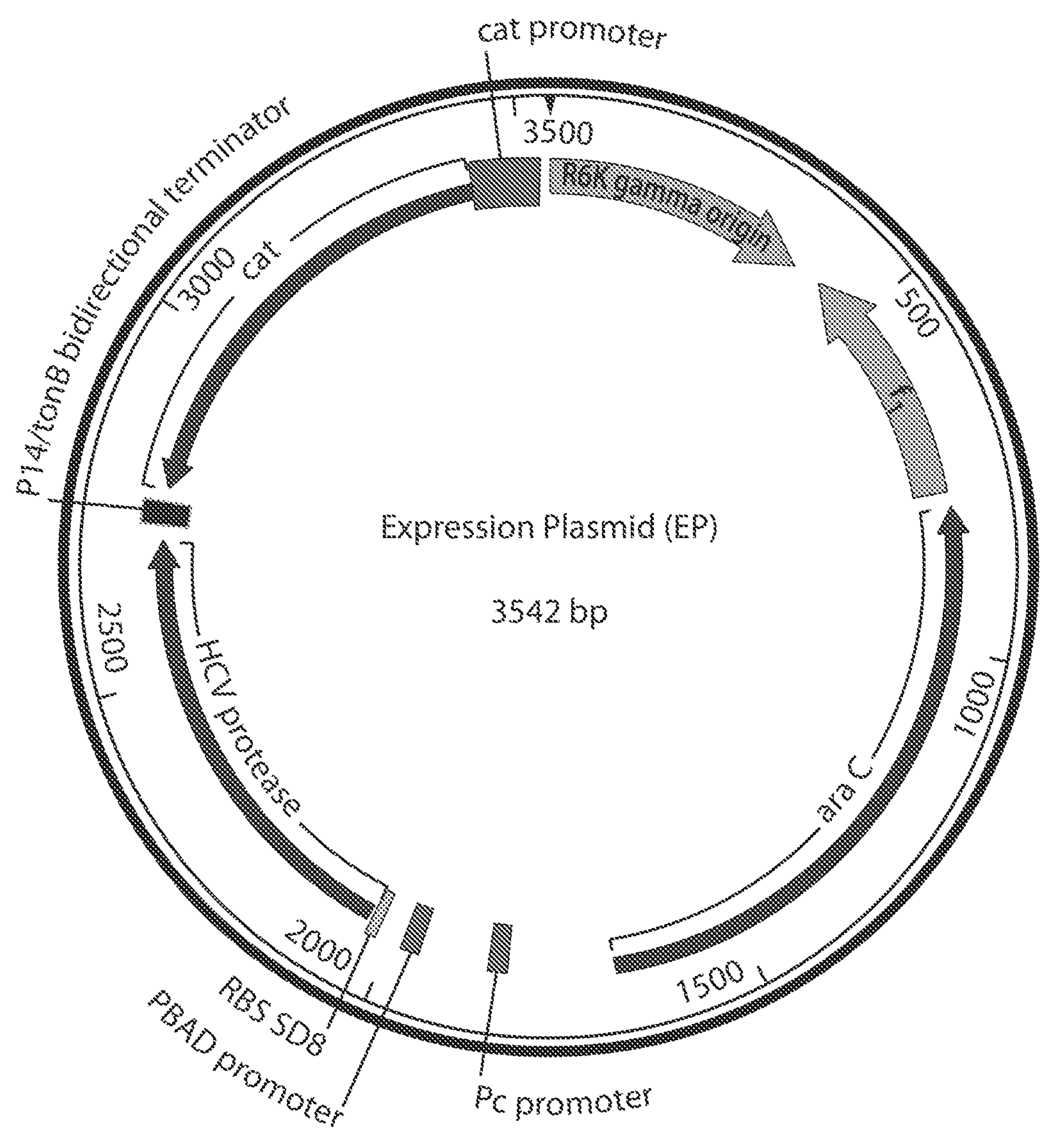
FIG. 7. Vector map of expression plasmid (EP) used in Example 1.

Sequence of expression plasmid (EP) illustrated in FIG. 7 (SEQ ID NO: 18):

TGAGATCCTTTTTTTCTGCGCGTAATCTGCTGCTTGCAAACAAAAAAACC

ACCGCTACCAGCGGTGGTTTGTTTGCCGGATCAAGAGCTACCACCTCTTT

TTCCGAAGGTAACTGGCTTCAGCAGAGCGCAGATACCAAATACTGTCCTT

CTAGTGTAGCCGTAGTTAGGCCACCACTTCAAGAACTCTGTAGCACCGCC

TACATACCTCGCTCTGCTAATCCTGTTACCAGTGGCTGCTGCCAGTGGCG

ATAAGTCGTGTCTTACCGGGTTGGACTCAAGACGATAGTTACCGGATAAG

GCGCAGCGGTCGGGCTGAACGGGGGGTTCGTGCACACAGCCCAGCTTGGA

GCGAACGACCTACACCGAACTGAGATACCTACAGCGTGAGCTATGAGAAA

GCGCCACGCTTCCCGAAGGGAGAAAGGCGGACAGGTATCCGGTAAGCGGC

AGGGTCGGAACAGGAGAGCGCACGAGGGAGCTTCCAGGGGGAAACGCCTG

GTATCTTTATAGTCCTGTCGGGTTTCGCCACCTCTGACTTGAGCGTCGAT

TTTTGTGATGCTCGTCAGGGGGGCGGAGCCTATGGAAAAACGCCAGCAAC

GCGGCCTTTTTACGGTTCCTGGCCTTTTGCTGGCCTTTTGCTCACATGTT

CTTTCCTGCGTTATCCCCTGATTCTGTGGATAACCGTATTACCGCCTTTG

AGTGAGCTGATACCGCTCGCCGCAGCCGAACGACCGAGCGCAGCGAGTCA

GTGAGCGAGGAAGCGGAAGAGCGCCTGATGCGGTATTTTCTCCTTACGCA

TCTGTGCGGTATTTCACACCGCATATGGTGCACTCTCAGTACAATCTGCT

CTGATGCCGCATAGTTAAGCCAGTATACACTCCGCTATCGCTACGTGACT

GGGTCATGGCTGCGCCCCGACACCCGCCAACACCCGCTGACGCGCCCTGA

CGGGCTTGTCTGCTCCCGGCATCCGCTTACAGACAAGCTGTGACCGTCTC

CGGGAGCTGCATGTGTCAGAGGTTTTCACCGTCATCACCGAAACGCGCGA

GGCAGCTGCGGTAAAGCTCATCAGCGTGGTCGTGAAGCGATTCACAGATG

TCTGCCTGTTCATCCGCGTCCAGCTCGTTGAGTTTCTCCAGAAGCGTTAA

TGTCTGGCTTCTGATAAAGCGGGCCATGTTAAGGGCGGTTTTTTCCTGTT

TGGTCACTGATGCCTCCGTGTAAGGGGGATTTCTGTTCATGGGGGTAATG

ATACCGATGAAACGAGAGAGGATGCTCACGATACGGGTTACTGATGATGA

ACAAGAGGACATCCGGTCAAATAAAACGAAAGGCTCAGTCGAAAGACTGG

GCCTTTCGTTTTAGACTTAGGGACCCTTTATGACAACTTGACGGCTACAT

CATTCACTTTTTCTTCACAACCGGCACGGAACTCGCTCGGGCTGGCCCCG

GTGCATTTTTTAAATACCCGCGAGAAATAGAGTTGATCGTCAAAACCAAC

ATTGCGACCGACGGTGGCGATAGGCATCCGGGTGGTGCTCAAAAGCAGCT

TCGCCTGGCTGATACGTTGGTCCTCGCGCCAGCTTAAGACGCTAATCCCT

AACTGCTGGCGGAAAAGATGTGACAGACGCGACGGCGACAAGCAAACATG

CTGTGCGACGCTGGCGATATCAAAATTGCTGTCTGCCAGGTGATCGCTGA

-continued

```
TGTACTGACAAGCCTCGCGTACCCGATTATCCATCGGTGGATGGAGCGAC
TCGTTAATCGCTTCCATGCGCCGCAGTAACAATTGCTCAAGCAGATTTAT
CGCCAGCAGCTCCGAATAGCGCCCTTCCCCTTGCCCGGCGTTAATGATTT
GCCCAAACAGGTCGCTGAAATGCGGCTGGTGCGCTTCATCCGGGCGAAAG
AACCCCGTATTGGCAAATATTGACGGCCAGTTAAGCCATTCATGCCAGTA
GGCGCGCGGACGAAAGTAAACCCACTGGTGATACCATTCGCGAGCCTCCG
GATGACGACCGTAGTGATGAATCTCTCCTGGCGGGAACAGCAAAATATCA
CCCGGTCGGCAAACAAATTCTCGTCCCTGATTTTTCACCACCCCCTGACC
GCGAATGGTGAGATTGAGAATATAACCTTTCATTCCCAGCGGTCGGTCGA
TAAAAAAATCGAGATAACCGTTGGCCTCAATCGGCGTTAAACCCGCCACC
AGATGGGCATTAAACGAGTATCCCGGCAGCAGGGGATCATTTTGCGCTTC
AGCCATACTTTTCATACTCCCACCATTCAGAGAAGAAACCAATTGTCCAT
ATTGCATCAGACATTGCCGTCACTGCGTCTTTTACTGGCTCTTCTCGCTA
ACCCAACCGGTAACCCCGCTTATTAAAAGCATTCTGTAACAAAGCGGGAC
CAAAGCCATGACAAAAACGCGTAACAAAAGTGTCTATAATCACGGCAGAA
AAGTCCACATTGATTATTTGCACGGCGTCACACTTTGCTATGCCATAGCA
TTTTTATCCATAAGATTAGCGGATCCTACCTGACGCTTTTTATCGCAACT
CTCTACTGTTTCTCCATACCCGTTTTTTTACCTGCAGGTGCAGTAAGGAG
GAAAAAAAAATGCATCATCATCATCATCATGGTGAAAACCTGTATTTTCA
GAGTCATATGGCTAGCATGAAAAAAAAAGGATCCGTTGTTATCGTCGGCC
GTATCAACCTGTCCGGTGACACCGCTTACGCTCAGCAGACTCGAGGTGAG
GAGGGTTGCCAAGAAACCTCCCAGACCGGTCGTGACAAAAACCAGGTTGA
AGGTGAAGTTCAGATCGTTTCCACCGCTACCCAGACCTTCCTGGCTACCT
CCATCAACGGTGTTCTGTGGACCGTTTACCACGGTGCTGGTACCCGTACC
ATCGCTTCCCCGAAAGGTCCGGTTACCCAGATGTACACCAACGTTGACAA
AGACCTGGTTGGTTGGCAGGCTCCGCAGGGTTCCCGTTCCCTGACCCCGT
GCACCTGCGGTTCCTCCGACCTGTACCTGGTTACCCGTCACGCTGACGTT
ATCCCGGTTCGTCGTCGTGGTGACTCCCGTGGTTCCCTGCTGTCCCCGCG
TCCGATCTCCTACCTGAAAGGTTCCTCCGGTGGTCCGCTGCTGTGCCCGG
CTGGTCACGCTGTTGGTATCTTCAGGGCTGCTGTTTCCACCCGTGGTGTT
GCTAAAGCTGTTGACTTCATCCCGGTTGAATCCCTGGAAACCACCATGCG
TTCCCCGTGACTTAATTAACGGCACTCCTCAGCAAATATAATGACCCTCT
TGATAACCCAAGAGGGCATTTTTTAATGCCCATGGCGTTTATTTGCCGAC
TACCTTGGTGATCTCGCCTTTCACGTAGTGGACAAATTCTTCCAACTGAT
CTGCGCGCGAGGCCAAGCGATCTTCTTCTTGTCCAAGATAAGCCTGTCTA
GCTTCAAGTATGACGGGCTGATACTGGGCCGGCAGGCGCTCCATTGCCCA
GTCGGCAGCGACATCCTTCGGCGCGATTTTGCCGGTTACTGCGCTGTACC
AAATGCGGGACAACGTAAGCACTACATTTCGCTCATCGCCAGCCCAGTCG
GGCGGCGAGTTCCATAGCGTTAAGGTTTCATTTAGCGCCTCAAATAGATC
CTGTTCAGGAACCGGATCAAAGAGTTCCTCCGCCGCTGGACCTACCAAGG
CAACGCTATGTTCTCTTGCTTTTGTCAGCAAGATAGCCAGATCAATGTCG
ATCGTGGCTGGCTCGAAGATACCTGCAAGAATGTCATTGCGCTGCCATTC
TCCAAATTGCAGTTCGCGCTTAGCTGGATAACGCCACGGAATGATGTCGT
CGTGCACAACAATGGTGACTTCTACAGCGCGGAGAATCTCGCTCTCTCCA
GGGGAAGCCGAAGTTTCCAAAAGGTCGTTGATCAAAGCTCGCCGCGTTGT
TTCATCAAGCCTTACGGTCACCGTAACCAGCAAATCAATATCACTGTGTG
GCTTCAGGCCGCCATCCACTGCGGAGCCGTACAAATGTACGGCCAGCAAC
GTCGGTTCGAGATGGCGCTCGATGACGCCAACTACCTCTGATAGTTGAGT
CGATACTTCGGCGATCACCGCTTCCCTCATACTCTTCCTTTTTCAATATT
ATTGAAGCATTTATCAGGGTTATTGTCTCATGAGCGGATACATATTTGAA
TGTATTTAGAAAAATAGGCCAAATAGGCCGT
```

rrnB1 terminator 1318 . . . 1362; araC complement(1378 . . . 2256); pBAD promoter 2464 . . . 2579; SD8 RBS 2595 . . . 2609; ColE1 rep_origin 1 . . . 588; Rop complement(1016 . . . 1207); aadA complement(3339 . . . 4130); aadA promoter 4131 . . . 4215; tetA/orfL terminator complement(3284 . . . 3325); 6xHis-TEVcutsite-HCV protease 2610 . . . 3260.

Figure 8:
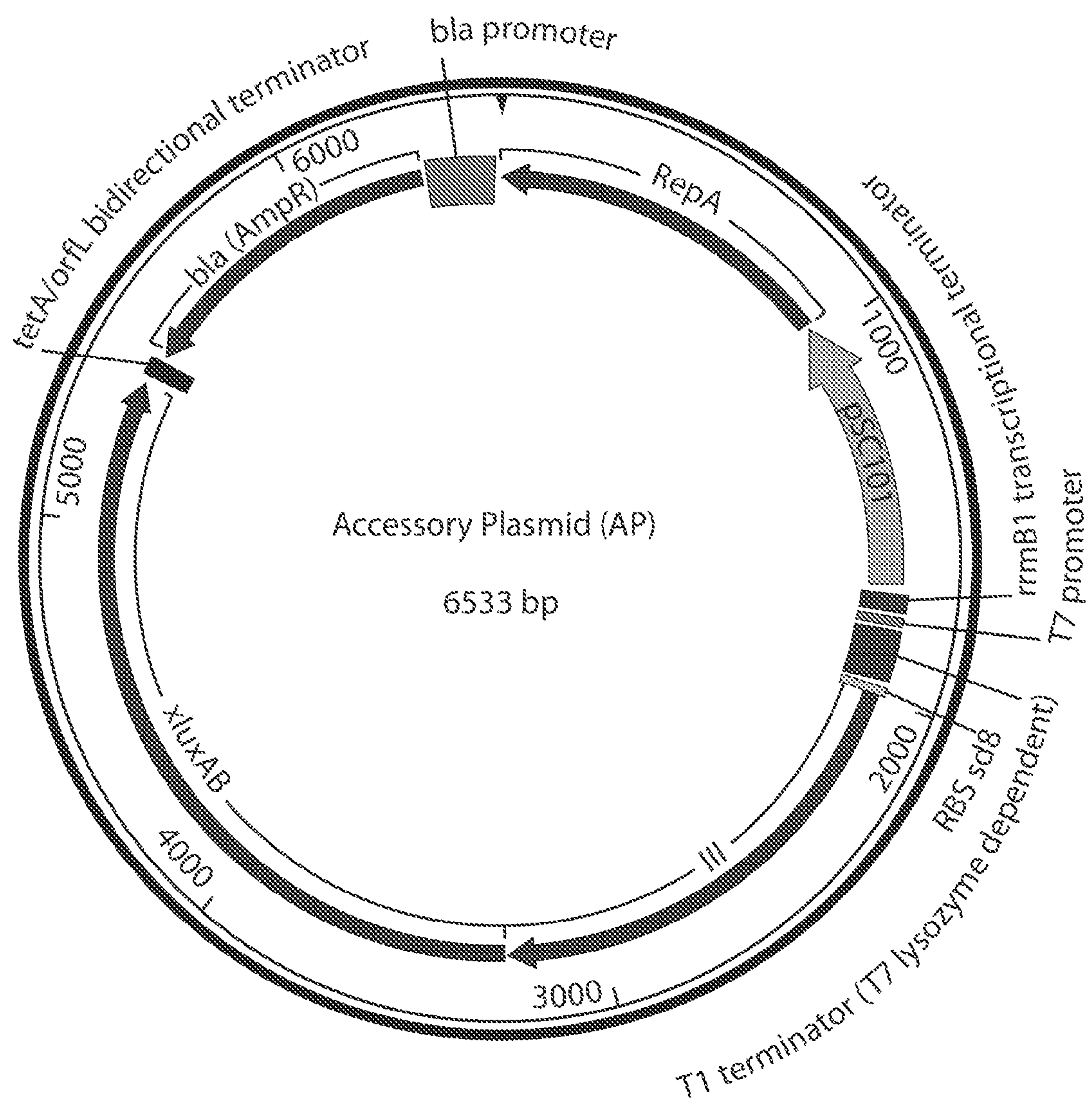
FIG. 8. Vector map of accessory plasmid (AP) used in Example 1.

Sequence of accessory plasmid (AP) illustrated in FIG. 8 (SEQ ID NO: 19):

```
TCAGATCCTTCCGTATTTAGCCAGTATGTTCTCTAGTGTGGTTCGTTGTT
TTTGCGTGAGCCATGAGAACGAACCATTGAGATCATGCTTACTTTGCATG
TCACTCAAAAATTTTGCCTCAAAACTGGTGAGCTGAATTTTTGCAGTTAA
AGCATCGTGTAGTGTTTTTCTTAGTCCGTTACGTAGGTAGGAATCTGATG
TAATGGTTGTTGGTATTTTGTCACCATTCATTTTTATCTGGTTGTTCTCA
AGTTCGGTTACGAGATCCATTTGTCTATCTAGTTCAACTTGGAAAATCAA
CGTATCAGTCGGGCGGCCTCGCTTATCAACCACCAATTTCATATTGCTGT
AAGTGTTTAAATCTTTACTTATTGGTTTCAAAACCCATTGGTTAAGCCTT
TTAAACTCATGGTAGTTATTTTCAAGCATTAACATGAACTTAAATTCATC
AAGGCTAATCTCTATATTTGCCTTGTGAGTTTTCTTTTGTGTTAGTTCTT
TTAATAACCACTCATAAATCCTCATAGAGTATTTGTTTTCAAAAGACTTA
ACATGTTCCAGATTATATTTTATGAATTTTTTTAACTGGAAAAGATAAGG
CAATATCTCTTCACTAAAAACTAATTCTAATTTTTCGCTTGAGAACTTGG
CATAGTTTGTCCACTGGAAAATCTCAAAGCCTTTAACCAAAGGATTCCTG
ATTTCCACAGTTCTCGTCATCAGCTCTCTGGTTGCTTTAGCTAATACACC
ATAAGCATTTTCCCTACTGATGTTCATCATCTGAGCGTATTGGTTATAAG
TGAACGATACCGTCCGTTCTTTCCTTGTAGGGTTTTCAATCGTGGGGTTG
AGTAGTGCCACACAGCATAAAATTAGCTTGGTTTCATGCTCCGTTAAGTC
ATAGCGACTAATCGCTAGTTCATTTGCTTTGAAAACAACTAATTCAGACA
TACATCTCAATTGGTCTAGGTGATTTTAATCACTATACCAATTGAGATGG
GCTAGTCAATGATAATTACTAGTCCTTTTCCTTTGAGTTGTGGGTATCTG
TAAATTCTGCTAGACCTTTGCTGGAAAACTTGTAAATTCTGCTAGACCCT
CTGTAAATTCCGCTAGACCTTTGTGTGTTTTTTTTGTTTATATTCAAGTG
GTTATAATTTATAGAATAAAGAAAGAATAAAAAAAGATAAAAAGAATAGA
```

-continued

TCCCAGCCCTGTGTATAACTCACTACTTTAGTCAGTTCCGCAGTATTACA

AAAGGATGTCGCAAACGCTGTTTGCTCCTCTACAAAACAGACCTTAAAAC

CCTAAAGGCTTAAGTAGCACCCTCGCAAGCTCGGGCAAATCGCTGAATAT

TCCTTTTGTCTCCGACCATCAGGCACCTGAGTCGCTGTCTTTTTCGTGAC

ATTCAGTTCGCTGCGCTCACGGCTCTGGCAGTGAATGGGGGTAAATGGCA

CTACAGGCGCCTTTTATGGATTCATGCAAGGAAACTACCCATAATACAAG

AAAAGCCCGTCACGGGCTTCTCAGGGCGTTTTATGGCGGGTCTGCTATGT

GGTGCTATCTGACTTTTTGCTGTTCAGCAGTTCCTGCCCTCTGATTTTCC

AGTCTGACCACTTCGGATTATCCCGTGACAGGTCATTCAGACTGGCTAAT

GCACCCAGTAAGGCAGCGGTATCATCAACAGGCTTACCCGTCTTACTGTC

AAGAGGACATCCGGTCAAATAAAACGAAAGGCTCAGTCGAAAGACTGGGC

CTTTCGTTTTGCTGAGGAGACTTAGGGACCCTACTAATACGACTCACTAT

AGGGAGAAAGAAGGAGCGACATTGCTCCGTGTATTCACTCGTTGGAATGA

ATACACAGTGCAGTGTTTATTCTGTTATTTATGCCAAAAATAAAGGCCAC

TATCAGGCAGCTTTGTTGTTCTGTTTACCAAGTTCAGGAGGTAACTCATA

AGAAAGACCTGCAGGTGCAGTAAAGGAAAAAAAAAATGAAAAAATTATTA

TTCGCAATTCCTTTAGTTGTTCCTTTCTATTCTCACTCCGCTGAAACTGT

TGAAAGTTGTTTAGCAAAACCCCATACAGAAAATTCATTTACTAACGTCT

GGAAAGACGACAAAACTTTAGATCGTTACGCTAACTATGAGGGCTGTCTG

TGGAATGCTACAGGCGTTGTAGTTTGTACTGGTGACGAAACTCAGTGTTA

CGGTACATGGGTTCCTATTGGGCTTGCTATCCCTGAAAATGAGGGTGGTG

GCTCTGAGGGTGGCGGTTCTGAGGGTGGCGGTTCTGAGGGTGGCGGTACT

AAACCTCCTGAGTACGGTGATACACCTATTCCGGGCTATACTTATATCAA

CCCTCTCGACGGCACTTATCCGCCTGGTACTGAGCAAAACCCCGCTAATC

CTAATCCTTCTCTTGAGGAGTCTCAGCCTCTTAATACTTTCATGTTTCAG

AATAATAGGTTCCGAAATAGGCAGGGGGCATTAACTGTTTATACGGGCAC

TGTTACTCAAGGCACTGACCCCGTTAAAACTTATTACCAGTACACTCCTG

TATCATCAAAAGCCATGTATGACGCTTACTGGAACGGTAAATTCAGAGAC

TGCGCTTTCCATTCTGGCTTTAATGAGGATCCATTCGTTTGTGAATATCA

AGGCCAATCGTCTGACCTGCCTCAACCTCCTGTCAATGCTGGCGGCGGCT

CTGGTGGTGGTTCTGGTGGCGGCTCTGAGGGTGGTGGCTCTGAGGGTGGC

GGTTCTGAGGGTGGCGGCTCTGAGGGAGGCGGTTCCGGTGGTGGCTCTGG

TTCCGGTGATTTTGATTATGAAAAGATGGCAAACGCTAATAAGGGGGCTA

TGACCGAAAATGCCGATGAAAACGCGCTACAGTCTGACGCTAAAGGCAAA

CTTGATTCTGTCGCTACTGATTACGGTGCTGCTATCGATGGTTTCATTGG

TGACGTTTCCGGCCTTGCTAATGGTAATGGTGCTACTGGTGATTTTGCTG

GCTCTAATTCCCAAATGGCTCAAGTCGGTGACGGTGATAATTCACCTTTA

ATGAATAATTTCCGTCAATATTTACCTTCCCTCCCTCAATCGGTTGAATG

TCGCCCTTTTGTCTTTGGCGCTGGTAAACCTTACGAGTTCAGTATCGACT

GCGATAAGATCAACCTGTTCCGCGGTGTCTTTGCGTTTCTTTTATATGTT

GCCACCTTTATGTATGTATTTTCTACGTTTGCTAACATACTGCGTAATAA

-continued

GGAGTCTTAATGAAATTTGGAAACTTTTTGCTTACATACCAACCTCCCCA

ATTTTCCCAAACAGAGGTAATGAAACGTTTGGTTAAATTAGGTCGCATCT

CTGAGGAGTGTGGTTTTGATACCGTATGGTTACTGGAGCATCATTTCACG

GAGTTTGGTTTGCTTGGTAACCCTTATGTCGCTGCTGCATATTTACTTGG

CGCGACTAAAAAATTGAATGTAGGAACTGCCGCTATTGTTCTTCCCACAG

CCCATCCAGTACGCCAACTTGAAGATGTGAATTTATTGGATCAAATGTCA

AAAGGACGATTTCGGTTTGGTATTTGCCGAGGGCTTTACAACAAGGACTT

TCGCGTATTCGGCACAGATATGAATAACAGTCGCGCCTTAGCGGAATGCT

GGTACGGGCTGATAAAGAATGGCATGACAGAGGGATATATGGAAGCTGAT

AATGAACATATCAAGTTCCATAAGGTAAAAGTAAACCCCGCGGCGTATAG

CAGAGGTGGCGCACCGGTTTATGTGGTGGCTGAATCAGCTTCGACGACTG

AGTGGGCTGCTCAATTTGGCCTACCGATGATATTAAGTTGGATTATAAAT

ACTAACGAAAAGAAAGCACAACTTGAGCTTTATAATGAAGTGGCTCAAGA

ATATGGGCACGATATTCATAATATCGACCATTGCTTATCATATATAACAT

CTGTAGATCATGACTCAATTAAAGCGAAAGAGATTTGCCGGAAATTTCTG

GGGCATTGGTATGATTCTTATGTGAATGCTACGACTATTTTTGATGATTC

AGACCAAACAAGAGGTTATGATTTCAATAAAGGGCAGTGGCGTGACTTTG

TATTAAAAGGACATAAAGATACTAATCGCCGTATTGATTACAGTTACGAA

ATCAATCCCGTGGGAACGCCGCAGGAATGTATTGACATAATTCAAAAAGA

CATTGATGCTACAGGAATATCAAATATTTGTTGTGGATTTGAAGCTAATG

GAACAGTAGACGAAATTATTGCTTCCATGAAGCTCTTCCAGTCTGATGTC

ATGCCATTTCTTAAAGAAAAACAACGTTCGCTATTATATTATGGCGGTGG

CGGTAGCGGCGGTGGCGGTAGCGGCGGTGGCGGTAGCGGCGGTGGCGGTA

GCAAATTTGGATTGTTCTTCCTTAACTTCATCAATTCAACAACTGTTCAA

GAACAGAGTATAGTTCGCATGCAGGAAATAACGGAGTATGTTGATAAGTT

GAATTTTGAACAGATTTTAGTGTATGAAAATCATTTTTCAGATAATGGTG

TTGTCGGCGCTCCTCTGACTGTTTCTGGTTTTCTGCTCGGTTTAACAGAG

AAAATTAAAATTGGTTCATTAAATCACATCATTACAACTCATCATCCTGT

CCGCATAGCGGAGGAAGCTTGCTTATTGGATCAGTTAAGTGAAGGGAGAT

TTATTTTAGGGTTTAGTGATTGCGAAAAAAAAGATGAAATGCATTTTTTT

AATCGCCCGGTTGAATATCAACAGCAACTATTTGAAGAGTGTTATGAAAT

CATTAACGATGCTTTAACAACAGGCTATTGTAATCCAGATAACGATTTTT

ATAGCTTCCCTAAAATATCTGTAAATCCCCATGCTTATACGCCAGGCGGA

CCTCGGAAATATGTAACAGCAACCAGTCATCATATTGTTGAGTGGGCGGC

CAAAAAAGGTATTCCTCTCATCTTTAAGTGGGATGATTCTAATGATGTTA

GATATGAATATGCTGAAAGATATAAAGCCGTTGCGGATAAATATGACGTT

GACCTATCAGAGATAGACCATCAGTTAATGATATTAGTTAACTATAACGA

AGATAGTAATAAAGCTAAACAAGAGACGCGTGCATTTATTAGTGATTATG

TTCTTGAAATGCACCCTAATGAAAATTTCGAAAATAAACTTGAAGAAATA

ATTGCAGAAAACGCTGTCGGAAATTATACGGAGTGTATAACTGCGGCTAA

-continued

GTTGGCAATTGAAAAGTGTGGTGCGAAAAGTGTATTGCTGTCCTTTGAAC

CAATGAATGATTTGATGAGCCAAAAAAATGTAATCAATATTGTTGATGAT

AATATTAAGAAGTACCACACGGAATATACCTAAACTTAATTAACGGCACT

CCTCAGCAAATATAATGACCCTCTTGATAACCCAAGAGGGCATTTTTTAA

TGCCCATGGCGTTTACCAATGCTTAATCAGTGAGGCACCTATCTCAGCGA

TCTGTCTATTTCGTTCATCCATAGTTGCCTGACTCCCCGTCGTGTAGATA

ACTACGATACGGGAGGGCTTACCATCTGGCCCCAGTGCTGCAATGATACC

GCGAGACCCACGCTCACCGGCTCCAGATTTATCAGCAATAAACCAGCCAG

CCGGAAGGGCCGAGCGCAGAAGTGGTCCTGCAACTTTATCCGCCTCCATC

CAGTCTATTAATTGTTGCCGGGAAGCTAGAGTAAGTAGTTCGCCAGTTAA

TAGTTTGCGCAACGTTGTTGCCATTGCTACAGGCATCGTGGTGTCACGCT

CGTCGTTTGGTATGGCTTCATTCAGCTCCGGTTCCCAACGATCAAGGCGA

GTTACATGATCCCCCATGTTGTGCAAAAAAGCGGTTAGCTCCTTCGGTCC

TCCGATCGTTGTCAGAAGTAAGTTGGCCGCAGTGTTATCACTCATGGTTA

TGGCAGCACTGCATAATTCTCTTACTGTCATGCCATCCGTAAGATGCTTT

TCTGTGACTGGTGAGTACTCAACCAAGTCATTCTGAGAATAGTGTATGCG

GCGACCGAGTTGCTCTTGCCCGGCGTCAATACGGGATAATACCGCGCCAC

ATAGCAGAACTTTAAAAGTGCTCATCATTGGAAAACGTTCTTCGGGGCGA

AAACTCTCAAGGATCTTACCGCTGTTGAGATCCAGTTCGATGTAACCCAC

TCGTGCACCCAACTGATCTTCAGCATCTTTTACTTTCACCAGCGTTTCTG

GGTGAGCAAAAACAGGAAGGCAAAATGCCGCAAAAAAGGGAATAAGGGCG

ACACGGAAATGTTGAATACTCATACTCTTCCTTTTTCAATATTATTGAAG

CATTTATCAGGGTTATTGTCTCATGAGCGGATACATATTTGAATGTATTT

AGAAAAATAAACAAATAGGGGTTCCGCGCACATTTCCCCGAAAAGTGCCA

CCTGACGTCTAAGAAACCATTATTATCATGACATTAACCTATAAAAATAG

GCGTATCACGAGGCCCTTAGGCCAAATAGGCCGT repA complement(1 . . . 951); pSC101 rep_origin complement(955 . . . 1700); rrnB1 terminator 1716 . . . 1760; T7 promoter 1785 . . . 1804; T1 terminator 1812 . . . 1957; sd8 RBS 1972 . . . 1985; gIII 1986 . . . 3260; xluxAB 3260 . . . 5383; tetA/orfL bidirectional terminator complement(5408 . . . 5449); bla AmpR complement(5463 . . . 6323); bla promoter complement(6324 . . . 6518).

Sequence of selection phage (SP) illustrated in FIG. 9 (SEQ ID NO: 20):

ATGATTGACATGCTAGTTTTACGATTACCGTTCATCGATTCTCTTGTTTG

CTCCAGACTCTCAGGCAATGACCTGATAGCCTTTGTAGACCTCTCAAAAA

TAGCTACCCTCTCCGGCATGAATTTATCAGCTAGAACGGTTGAATATCAT

GTTGATGGTGATTTGACTGTCTCCGGCCTTTCTCACCCTTTTGAATCTTT

ACCTACACATTACTCAGGCATTGCATTTAAAATATATGAGGGTTCTAAAA

ATTTTTATCCTTGCGTTGAAATAAAGGCTTCTCCCGCAAAAGTATTACAG

GGTCATAATGTTTTTGGTACAACCGATTTAGCTTTATGCTCTGAGGCTTT

ATTGCTTAATTTTGCTAATTCTTTGCCTTGCCTGTATGATTTATTGGATG

TTAACGCTACTACTATTAGTAGAATTGATGCCACCTTTTCAGCTCGCGCC

-continued

CCAAATGAAAATATAGCTAAACAGGTTATTGACCATTTGCGAAATGTATC

TAATGGTCAAACTAAATCTACTCGTTCGCAGAATTGGGAATCAACTGTTA

CATGGAATGAAACTTCCAGACACCGTACTTTAGTTGCATATTTAAAACAT

GTTGAGCTACAGCACCAGATTCAGCAATTAAGCTCTAAGCCATCCGCAAA

AATGACCTCTTATCAAAAGGAGCAATTAAAGGTACTCTCTAATCCTGACC

TGTTGGAGTTTGCTTCCGGGCTGGTTCGCTTTGAAGCTCGAATTAGAACG

CGATATTTGAAGTCTTTCGGGCTTCCTCTTAATCTTTTTGATGCAATCCG

CTTTGCTTCTGACTATAATAGTCAGGGTAAAGACCTGATTTTTGATTTAT

GGTCATTCTCGTTTTCTGAACTGTTTAAAGCATTTGAGGGGGATTCAATG

AATATTTATGACGATTCCGCAGTATTGGACGCTATCCAGTCTAAACATTT

TACTATTACCCCCTCTGGCAAAACTTCTTTTGCAAAAGCCTCTCGCTATT

TTGGTTTTTATCGTCGTCTGGTAAACGAGGGTTATGATAGTGTTGCTCTT

ACTATGCCTCGTAATTCCTTTTGGCGTTATGTATCTGCATTAGTTGAATG

TGGTATTCCTAAATCTCAACTGATGAATCTTTCTACCTGTAATAATGTTG

TTCCGTTAGTTCGTTTTATTAACGTAGATTTTTCTTCCCAACGTCCTGAC

TGGTATAATGAGCCAGTTCTTAAAATCGCATAAGGTAATTCACAATGATT

AAAGTTGAAATTAAACCATCTCAAGCCCAATTTACTACTCGTTCTGGTGT

TTCTCGTCAGGGCAAGCCTTATTCACTGAATGAGCAGCTTTGTTACGTTG

ATTTGGGTAATGAATATCCGGTTCTTGTCAAGATTACTCTTGATGAAGGT

CAGCCAGCCTATGCGCCTGGTCTGTACACCGTTCATCTGTCCTCTTTCAA

AGTTGGTCAGTTCGGTTCCCTTATGATTGACCGTCTGCGCCTCGTTCCGG

CTAAGTAACATGGAGCAGGTCGCGGATTTCGACACAATTTATCAGGCGAT

GATACAAATCTCCGTTGTACTTTGTTTCGCGCTTGGTATAATCGCTGGGG

GTCAAAGATGAGTGTTTTAGTGTATTCTTTCGCCTCTTTCGTTTTAGGTT

GGTGCCTTCGTAGTGGCATTACGTATTTTACCCGTTTAATGGAAACTTCC

TCATGAAAAAGTCTTTAGTCCTCAAAGCCTCTGTAGCCGTTGCTACCCTC

GTTCCGATGCTGTCTTTCGCTGCTGAGGGTGACGATCCCGCAAAAGCGGC

CTTTAACTCCCTGCAAGCCTCAGCGACCGAATATATCGGTTATGCGTGGG

CGATGGTTGTTGTCATTGTCGGCGCAACTATCGGTATCAAGCTGTTTAAG

AAATTCACCTCGAAAGCAAGCTGATAAACCGATACAATTAAAGGCTCCTT

TTGGAGCCTTTTTTTTCGCGCCAATAAGGAGGAAAAAAAAATGGGCAGCA

GCCATCATCATCATCATCACAGCAGCGGCCTGGTGCCGCGCGGCAGCCAT

ATGGCTAGCATGAAAAAAAAAGGATCCGTTGTTATCGTCGGCCGTATCAA

CCTGTCCGGTGACACCGCTTACGCTCAGCAGACTCGAGGTGAGGAGGGTT

GCCAAGAAACCTCCCAGACCGGTCGTGACAAAAACCAGGTTGAAGGTGAA

GTTCAGATCGTTTCCACCGCTACCCAGACCTTCCTGGCTACCTCCATCAA

CGGTGTTCTGTGGACCGTTTACCACGGTGCTGGTACCCGTACCATCGCTT

CCCCGAAAGGTCCGGTTACCCAGATGTACACCAACGTTGACAAAGACCTG

GTTGGTTGGCAGGCTCCGCAGGGTTCCCGTTCCCTGACCCCGTGCACCTG

CGGTTCCTCCGACCTGTACCTGGTTACCCGTCACGCTGACGTTATCCCGG

TTCGTCGTCGTGGTGACTCCCGTGGTTCCCTGCTGTCCCCGCGTCCGATC

-continued

TCCTACCTGAAAGGTTCCTCCGGTGGTCCGCTGCTGTGCCCGGCTGGTCA

CGCTGTTGGTATCTTCAAGGCTGCTGTTTCCACCCGTGGTGTTGCTAAAG

CTGTTGACTTCATCCCGGTTGAATCCCTGGAAACCACCATGCGTTCCCCG

TGATGATGATAATAATGGAGATTTTCAACATGGGCTAGCTCAGCCCTAGG

TATTATGCTAGCGTGGTGTCTGCGTAATAAGGAGTCTTAATCATGCCAGT

TCTTTTGGGTATTCCGTTATTATTGCGTTTCCTCGGTTTCCTTCTGGTAA

CTTTGTTCGGCTATCTGCTTACTTTTCTTAAAAAGGGCTTCGGTAAGATA

GCTATTGCTATTTCATTGTTTCTTGCTCTTATTATTGGGCTTAACTCAAT

TCTTGTGGGTTATCTCTCTGATATTAGCGCTCAATTACCCTCTGACTTTG

TTCAGGGTGTTCAGTTAATTCTCCCGTCTAATGCGCTTCCCTGTTTTTAT

GTTATTCTCTCTGTAAAGGCTGCTATTTTCATTTTTGACGTTAAACAAAA

AATCGTTTCTTATTTGGATTGGGATAAATAATATGGCTGTTTATTTTGTA

ACTGGCAAATTAGGCTCTGGAAAGACGCTCGTTAGCGTTGGTAAGATTCA

GGATAAAATTGTAGCTGGGTGCAAAATAGCAACTAATCTTGATTTAAGGC

TTCAAAACCTCCCGCAAGTCGGGAGGTTCGCTAAAACGCCTCGCGTTCTT

AGAATACCGGATAAGCCTTCTATATCTGATTTGCTTGCTATTGGGCGCGG

TAATGATTCCTACGATGAAAATAAAAACGGCTTGCTTGTTCTCGATGAGT

GCGGTACTTGGTTTAATACCCGTTCTTGGAATGATAAGGAAAGACAGCCG

ATTATTGATTGGTTTCTACATGCTCGTAAATTAGGATGGGATATTATTTT

TCTTGTTCAGGACTTATCTATTGTTGATAAACAGGCGCGTTCTGCATTAG

CTGAACATGTTGTTTATTGTCGTCGTCTGGACAGAATTACTTTACCTTTT

GTCGGTACTTTATATTCTCTTATTACTGGCTCGAAAATGCCTCTGCCTAA

ATTACATGTTGGCGTTGTTAAATATGGCGATTCTCAATTAAGCCCTACTG

TTGAGCGTTGGCTTTATACTGGTAAGAATTTGTATAACGCATATGATACT

AAACAGGCTTTTTCTAGTAATTATGATTCCGGTGTTTATTCTTATTTAAC

GCCTTATTTATCACACGGTCGGTATTTCAAACCATTAAATTTAGGTCAGA

AGATGAAATTAACTAAAATATATTTGAAAAAGTTTTCTCGCGTTCTTTGT

CTTGCGATTGGATTTGCATCAGCATTTACATATAGTTATATAACCCAACC

TAAGCCGGAGGTTAAAAAGGTAGTCTCTCAGACCTATGATTTTGATAAAT

TCACTATTGACTCTTCTCAGCGTCTTAATCTAAGCTATCGCTATGTTTTC

AAGGATTCTAAGGGAAAATTAATTAATAGCGACGATTTACAGAAGCAAGG

TTATTCACTCACATATATTGATTTATGTACTGTTTCCATTAAAAAAGGTA

ATTCAAATGAAATTGTTAAATGTAATTAATTTTGTTTTCTTGATGTTTGT

TTCATCATCTTCTTTTGCTCAGGTAATTGAAATGAATAATTCGCCTCTGC

GCGATTTTGTAACTTGGTATTCAAAGCAATCAGGCGAATCCGTTATTGTT

TCTCCCGATGTAAAAGGTACTGTTACTGTATATTCATCTGACGTTAAACC

TGAAAATCTACGCAATTTCTTTATTTCTGTTTTACGTGCAAGTAATTTTG

ATATGGTTGGTTCTAACCCTTCCATTATTCAGAAGTATAATCCAAACAAT

CAGGATTATATTGATGAATTGCCATCATCTGATAATCAGGAATATGATGA

TAATTCCGCTCCTTCTGGTGGTTTCTTTGTTCCGCAAAATGATAATGTTA

-continued

CTCAAACTTTTAAAATTAATAACGTTCGGGCAAAGGATTTAATACGAGTT

GTCGAATTGTTTGTAAAGTCTAATACTTCTAAATCCTCAAATGTATTATC

TATTGACGGCTCTAATCTATTAGTTGTTAGTGCACCTAAAGATATTTTAG

ATAACCTTCCTCAATTCCTTTCTACTGTTGATTTGCCAACTGACCAGATA

TTGATTGAGGGTTTGATATTTGAGGTTCAGCAAGGTGATGCTTTAGATTT

TTCATTTGCTGCTGGCTCTCAGCGTGGCACTGTTGCAGGCGGTGTTAATA

CTGACCGCCTCACCTCTGTTTTATCTTCTGCTGGTGGTTCGTTCGGTATT

TTTAATGGCGATGTTTTAGGGCTATCAGTTCGCGCATTAAAGACTAATAG

CCATTCAAAAATATTGTCTGTGCCACGTATTCTTACGCTTTCAGGTCAGA

AGGGTTCTATCTTTGTTGGCCAGAATGTCCCTTTTATTACTGGTCGTGTG

ACTGGTGAATCTGCCAATGTAAATAATCCATTTCAGACGATTGAGCGTCA

AAATGTAGGTATTTCCATGAGCGTTTTTCCTGTTGCAATGGCTGGCGGTA

ATATTGTTCTGGATATTACCAGCAAGGCCGATAGTTTGAGTTCTTCTACT

CAGGCAAGTGATGTTATTACTAATCAAAGAAGTACTGCTACAACGGTTAA

TTTGCGTGATGGACAGACTCTTTTACTCGGTGGCCTCACTGATTATAAAA

ACACTTCTCAGGATTCTGGCGTACCGTTCCTGTCTAAAATCCCTTTAATC

GGCCTCCTGTTTAGCTCCCGCTCTGATTCTAACGAGGAAAGCACGTTATA

CGTGCTCGTCAAAGCAACCATAGTACGCGCCCTGTAGCGGCGCATTAAGC

GCGGCGGGTGTGGTGGTTACGCGCAGCGTGACCGCTACACTTGCCAGCGC

CCTAGCGCCCGCTCCTTTCGCTTTCTTCCCTTCCTTTCTCGCCACGTTCG

CCGGCTTTCCCCGTCAAGCTCTAAATCGGGGGCTCCCTTTAGGGTTCCGA

TTTAGTGCTTTACGGCACCTCGACCCCAAAAAACTTGATTTGGGTGATGG

TTCACGTAGTGGGCCATCGCCCTGATAGACGGTTTTTCGCCCTTTGACGT

TGGAGTCCACGTTCTTTAATAGTGGACTCTTGTTCCAAACTGGAACAACA

CTCAACCCTATCTCGGGCTATTCTTTTGATTTATAAGGGATTTTGCCGAT

TTCGGCCTATTGGTTAAAAAATGAGCTGATTTAACAAAAATTTAACGCGA

ATTTTAACAAAATATTAACGTTTACAATTTAAATATTTGCTTATACAATC

TTCCTGTTTTTGGGGCTTTTCTTATTATCAACCGGGGTACAT gII 1 . . . 1233; gX898 . . . 1233; gV promoter 1208 . . . 1237; gV 1245 . . . 1508; gVII 1510 . . . 1611; gIX 1608 . . . 1706; gVIII 1703 . . . 1924; gIII promoter 1910 . . . 1939; SD8 RBS 1973 . . . 1990; HCV protease 1994 . . . 2659; J23107 promoter 2683 . . . 2712; gVI RBS 2727 . . . 2742; gVI 2743 . . . 3081; gI promoter 2990 . . . 3019; gI 3083 . . . 4129; gIV promoter 3961 . . . 3990; gIV 4107 . . . 5387; packing signal 5386 . . . 5463; RNA primer for (-) replication complement(5591 . . . 5611); complete (+) origin 5656 . . . 5796; essential (+) ori 5656 . . . 5699; gII promoter 5821 . . . 5849.

Figure 10:
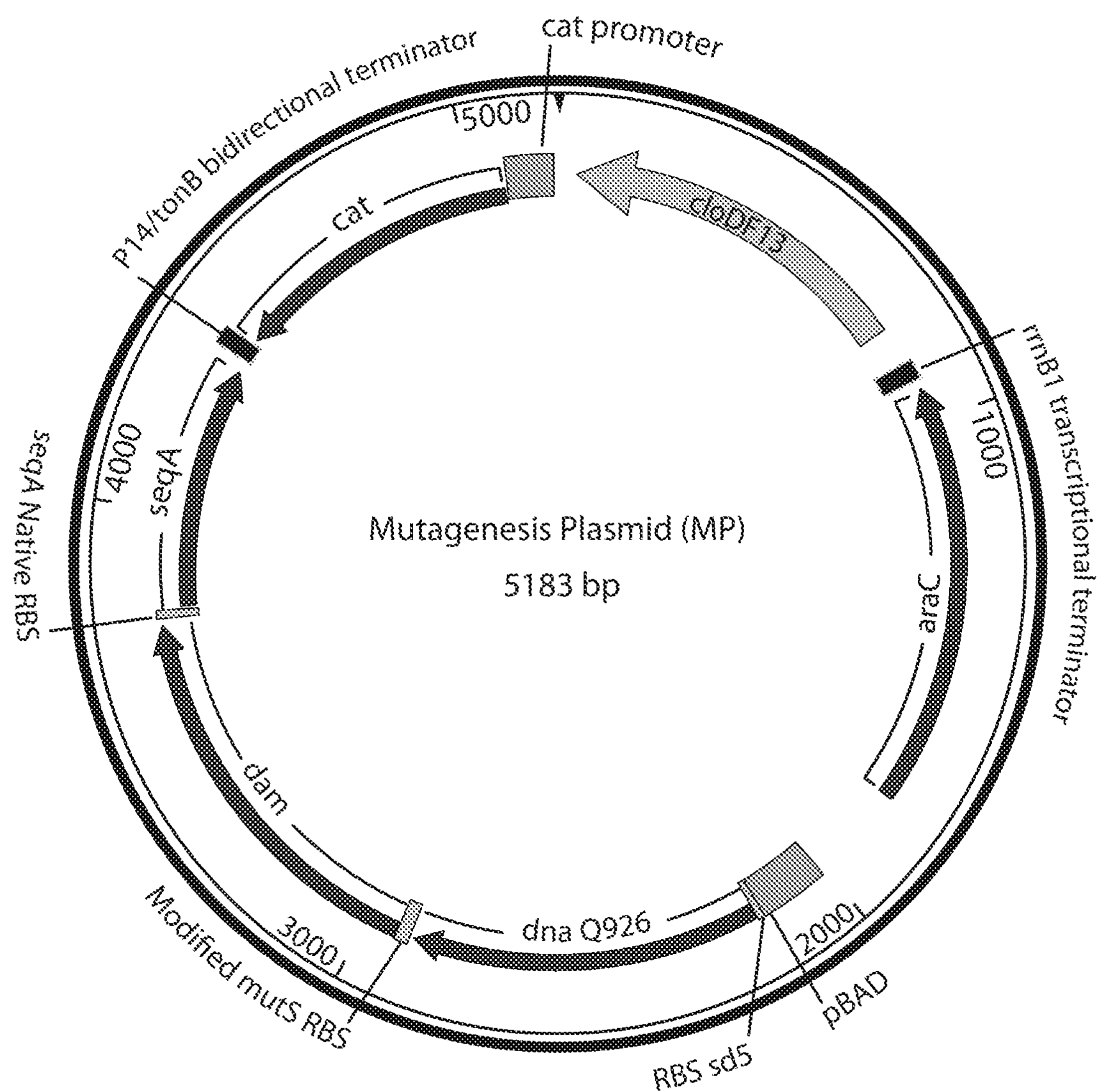
FIG. 10. Vector map of mutagenesis plasmid (MP) used in Example 1.

Sequence of mutagenesis plasmid (MP) as illustrated in FIG. 10 (SEQ ID NO: 21):

CACTCGGTCGCTACGCTCCGGGCGTGAGACTGCGGCGGGCGCTGCGGACA

CATACAAAGTTACCCACAGATTCCGTGGATAAGCAGGGGACTAACATGTG

AGGCAAAACAGCAGGGCCGCGCCGGTGGCGTTTTTCCATAGGCTCCGCCC

TCCTGCCAGAGTTCACATAAACAGACGCTTTTCCGGTGCATCTGTGGGAG

CCGTGAGGCTCAACCATGAATCTGACAGTACGGGCGAAACCCGACAGGAC

-continued

```
TTAAAGATCCCCACCGTTTCCGGCGGGTCGCTCCCTCTTGCGCTCTCCTG
TTCCGACCCTGCCGTTTACCGGATACCTGTTCCGCCTTTCTCCCTTACGG
GAAGTGTGGCGCTTTCTCATAGCTCACACACTGGTATCTCGGCTCGGTGT
AGGTCGTTCGCTCCAAGCTGGGCTGTAAGCAAGAACTCCCCGTTCAGCCC
GACTGCTGCGCCTTATCCGGTAACTGTTCACTTGAGTCCAACCCGGAAAA
GCACGGTAAAACGCCACTGGCAGCAGCCATTGGTAACTGGGAGTTCGCAG
AGGATTTGTTTAGCTAAACACGCGGTTGCTCTTGAAGTGTGCGCCAAAGT
CCGGCTACACTGGAAGGACAGATTTGGTTGCTGTGCTCTGCGAAAGCCAG
TTACCACGGTTAAGCAGTTCCCCAACTGACTTAACCTTCGATCAAACCAC
CTCCCCAGGTGGTTTTTTCGTTTACAGGGCAAAAGATTACGCGCAGAAAA
AAAGGATCTCAAGAAGATCCTTTGATCTTTTCTACTGAACCGCTCTAGAT
TTCAGTGCAATTTATCTCTTCAAATGTAGCACCTGAAGTCAGCCCAGGAG
GAAGAGGACATCCGGTCAAATAAAACGAAAGGCTCAGTCGAAAGACTGGG
CCTTTCGTTTTAGACTTAGGGACCCTTTATGACAACTTGACGGCTACATC
ATTCACTTTTTCTTCACAACCGGCACGGAACTCGCTCGGGCTGGCCCCGG
TGCATTTTTTAAATACCCGCGAGAAATAGAGTTGATCGTCAAAACCAACA
TTGCGACCGACGGTGGCGATAGGCATCCGGGTGGTGCTCAAAAGCAGCTT
CGCCTGGCTGATACGTTGGTCCTCGCGCCAGCTTAAGACGCTAATCCCTA
ACTGCTGGCGGAAAAGATGTGACAGACGCGACGGCGACAAGCAAACATGC
TGTGCGACGCTGGCGATATCAAAATTGCTGTCTGCCAGGTGATCGCTGAT
GTACTGACAAGCCTCGCGTACCCGATTATCCATCGGTGGATGGAGCGACT
CGTTAATCGCTTCCATGCGCCGCAGTAACAATTGCTCAAGCAGATTTATC
GCCAGCAGCTCCGAATAGCGCCCTTCCCCTTGCCCGGCGTTAATGATTTG
CCCAAACAGGTCGCTGAAATGCGGCTGGTGCGCTTCATCCGGGCGAAAGA
ACCCCGTATTGGCAAATATTGACGGCCAGTTAAGCCATTCATGCCAGTAG
GCGCGCGGACGAAAGTAAACCCACTGGTGATACCATTCGCGAGCCTCCGG
ATGACGACCGTAGTGATGAATCTCTCCTGGCGGGAACAGCAAAATATCAC
CCGGTCGGCAAACAAATTCTCGTCCCTGATTTTTCACCACCCCCTGACCG
CGAATGGTGAGATTGAGAATATAACCTTTCATTCCCAGCGGTCGGTCGAT
AAAAAAATCGAGATAACCGTTGGCCTCAATCGGCGTTAAACCCGCCACCA
GATGGGCATTAAACGAGTATCCCGGCAGCAGGGGATCATTTTGCGCTTCA
GCCATACTTTTCATACTCCCACCATTCAGAGAAGAAACCAATTGTCCATA
TTGCATCAGACATTGCCGTCACTGCGTCTTTTACTGGCTCTTCTCGCTAA
CCCAACCGGTAACCCCGCTTATTAAAAGCATTCTGTAACAAAGCGGGACC
AAAGCCATGACAAAAACGCGTAACAAAAGTGTCTATAATCACGGCAGAAA
AGTCCACATTGATTATTTGCACGGCGTCACACTTTGCTATGCCATAGCAT
TTTTATCCATAAGATTAGCGGATCCTACCTGACGCTTTTTATCGCAACTC
TCTACTGTTTCTCCATACCCGTTTTTTTGGACGCGTACAACTCAAGTCTG
ACATAAATGACCGCTATGAGCACTGCAATTACACGCCAGATCGTTCTCGC
TACCGCAACCACCGGTATGAACCAGATTGGTGCGCACTATGAAGGCCACA
```

-continued

```
AGATCATTGAGATTGGTGCCGTTGAAGTGGTGAACCGTCGCCTGACGGGC
AATAACTTCCATGTTTATCTCAAACCCGATCGGCTGGTGGATCCGGAAGC
CTTTGGCGTACATGGTATTGCCGATGAATTTTTGCTCGATAAGCCCACGT
TTGCCGAAGTAGCCGATGAGTTCATGGACTATATTCGCGGCGCGGAGTTG
GTGATCCATAACGCAGCGTTCGATATCGGCTTTATGGACTACGAGTTTTC
GTTGCTTAAGCGCGATATTCCGAAGACCAATACTTTCTGTAAGGTCACCG
ATAGCCTTGCGGTGGCGAGGAAAATGTTTCCCGGTAAGCGCAACAGCCTC
GATGCGTTATGTGCTCGCTACGAAATAGATAACAGTAAACGAACGCTGCA
CGGGGCATTACTCGATGCCCAGATCCTTGCGGAAGTTTATCTGGCGATGA
CCGGTGGTCAAACGTCGATGGCTTTTGCGATGGAAGGAGAGACACAACAG
CAACAAGGTGAAGCAACAATTCAGCGCATTGTACGTCAGGCAAGTAAGTT
ACGCGTTGTTTTTGCGACAGATGAAGAGATTGCAGCTCATGAAGCCCGTC
TCGATCTGGTGCAGAAGAAAGGCGGAAGTTGCCTCTGGCGAGCATAATTT
AATATCAGTAAACCGGACATAACCCATGAAGAAAAATCGCGCTTTTTTGA
AGTGGGCAGGGGGCAAGTATCCCCTGCTTGATGATATTAAACGGCATTTG
CCCAAGGGCGAATGTCTGGTTGAGCCTTTTGTAGGTGCCGGGTCGGTGTT
TCTCAACACCGACTTTTCTCGTTATATCCTTGCCGATATCAATAGCGACC
TGATCAGTCTCTATAACATTGTGAAGATGCGTACTGATGAGTACGTACAG
GCCGCACGCGAGCTGTTTGTTCCCGAAACAAATTGCGCCGAGGTTTACTA
TCAGTTCCGCGAAGAGTTCAACAAAAGCCAGGATCCGTTCCGTCGGGCGG
TACTGTTTTTATATTTGAACCGCTACGGTTACAACGGCCTGTGTCGTTAC
AATCTGCGCGGTGAGTTTAACGTGCCGTTCGGCCGCTACAAAAAACCCTA
TTTCCCGGAAGCAGAGTTGTATCACTTCGCTGAAAAAGCGCAGAATGCCT
TTTTCTATTGTGAGTCTTACGCCGATAGCATGGCGCGCGCAGATGATGCA
TCCGTCGTCTATTGCGATCCGCCTTATGCACCGCTGTCTGCGACCGCCAA
CTTTACGGCGTATCACACAAACAGTTTTACGCTTGAACAACAAGCGCATC
TGGCGGAGATCGCCGAAGGTCTGGTTGAGCGCCATATTCCAGTGCTGATC
TCCAATCACGATACGATGTTAACGCGTGAGTGGTATCAGCGCGCAAAATT
GCATGTCGTCAAAGTTCGACGCAGTATAAGCAGCAACGGCGGCACACGTA
AAAAGGTGGACGAACTGCTGGCTTTGTACAAACCAGGAGTCGTTTCACCC
GCGAAAAAATAATTCAGCTAAGACACTGCACTGGATTAAGATGAAAACGA
TTGAAGTTGATGATGAACTCTACAGCTATATTGCCAGCCACACTAAGCAT
ATCGGCGAGAGCGCATCCGACATTTTACGGCGTATGTTGAAATTTTCCGC
CGCATCACAGCCTGCTGCTCCGGTGACGAAAGAGGTTCGCGTTGCGTCAC
CTGCTATCGTCGAAGCGAAGCCGGTCAAAACGATTAAAGACAAGGTTCGC
GCAATGCGTGAACTTCTGCTTTCGGATGAATACGCAGAGCAAAAGCGAGC
GGTCAATCGCTTTATGCTGCTGTTGTCTACACTATATTCTCTTGACGCCC
AGGCGTTTGCCGAAGCAACGGAATCGTTGCACGGTCGTACACGCGTTTAC
TTTGCGGCAGATGAACAAACGCTGCTGAAAAATGGTAATCAGACCAAGCC
GAAACATGTGCCAGGCACGCCGTATTGGGTGATCACCAACACCAACACCG
GCCGTAAATGCAGCATGATCGAACACATCATGCAGTCGATGCAATTCCCG
```

-continued

```
GCGGAATTGATTGAGAAGGTTTGCGGAACTATCTAAACTTAATTAACGGC
ACTCCTCAGCCAAGTCAAAAGCCTCCGACCGGAGGCTTTTGACTACATGC
CCATGGCGTTTACGCCCCGCCCTGCCACTCATCGCAGTACTGTTGTAATT
CATTAAGCATTCTGCCGACATGGAAGCCATCACAAACGGCATGATGAACC
TGAATCGCCAGCGGCATCAGCACCTTGTCGCCTTGCGTATAATATTTGCC
CATAGTGAAAACGGGGGCGAAGAAGTTGTCCATATTGGCCACGTTTAAAT
CAAAACTGGTGAAACTCACCCAGGGATTGGCTGAGACGAAAAACATATTC
TCAATAAACCCTTTAGGGAAATAGGCCAGGTTTTCACCGTAACACGCCAC
ATCTTGCGAATATATGTGTAGAAACTGCCGGAAATCGTCGTGGTATTCAC
TCCAGAGCGATGAAAACGTTTCAGTTTGCTCATGGAAAACGGTGTAACAA
GGGTGAACACTATCCCATATCACCAGCTCACCGTCTTTCATTGCCATACG
GAACTCCGGATGAGCATTCATCAGGCGGGCAAGAATGTGAATAAAGGCCG
GATAAAACTTGTGCTTATTTTTCTTTACGGTCTTTAAAAAGGCCGTAATA
TCCAGCTGAACGGTCTGGTTATAGGTACATTGAGTAACTGACTGAAATGC
CTCAAAATGTTCTTTACGATGCCATTGGGATATATCAACGGTGGTATATC
CAGTGATTTTTTTCTCCATTTTAGCTTCCTTAGCTCCTGAAAATCTCGAT
AACTCAAAAAATACGCCCGGTAGTGATCTTATTTCATTATGGTGAAAGTT
GGAACCTCTTACGTGCCAAGCCAAATAGGCCGT
rrnB1 terminator 867 . . . 911; cloDF13 rep_origin
complement(39 . . . 777); P14/tonB terminator
complement(4361 . . . 4396); Cat cmR CDS
complement(4410 . . . 5069); cat promoter
5070 . . . 5167; araC complement(927 . . . 1805);
pBAD promoter 2013 . . . 2165; dnaQ926
2166 . . . 2897; sd5 RBS 2156 . . . 2165;
Modified mutS RBS 2907 . . . 2925; dam
(wt) 2926 . . . 3762; seqA (wt) 3791 . . . 4336;
seqA Native RBS 3771 . . . 3790.
```

Example 2: Reprogramming Protease Specificity

Figure 12:
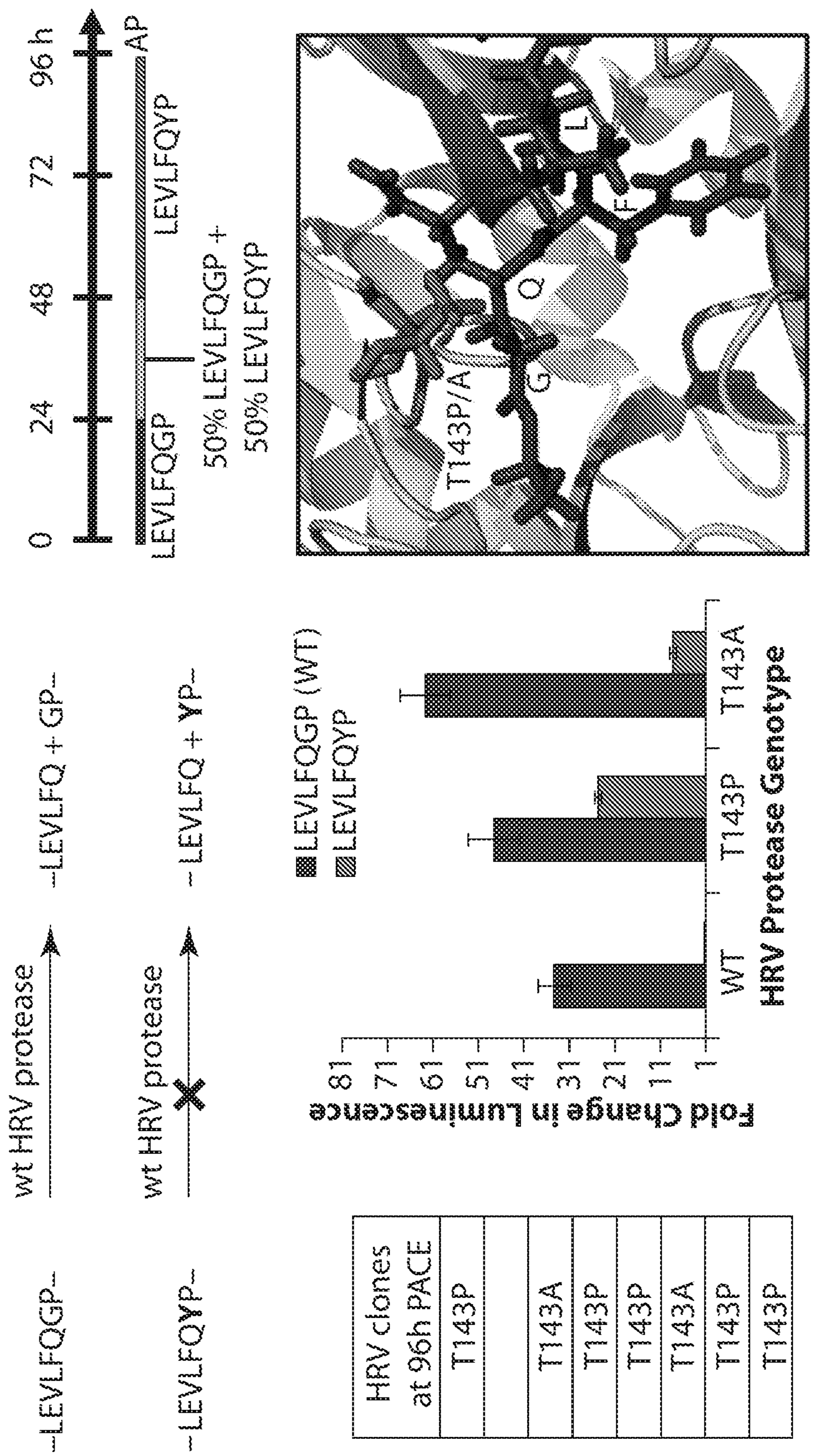
FIG. 12. Directed evolution of a reprogrammed HRV protease.

FIG. 12 shows the directed evolution of a reprogrammed HRV protease. Wild-type HRV protease cleaves the substrate sequence LEVLFQGP (SEQ ID NO: 22), but does not cleave the target substrate sequence LEVLFQYP (SEQ ID NO: 23). A 96 hour PACE experiment was performed starting with the wild-type protease substrate sequence for 24 hours, followed by a 50:50 mixture of wild-type and target substrate sequence for 24 hours and the target sequence only for 48 hours. After 96 hours, clones comprising mutations T143A and T143P were recovered. Activity of mutant clones on wild-type and target substrate were tested.

Figure 13:
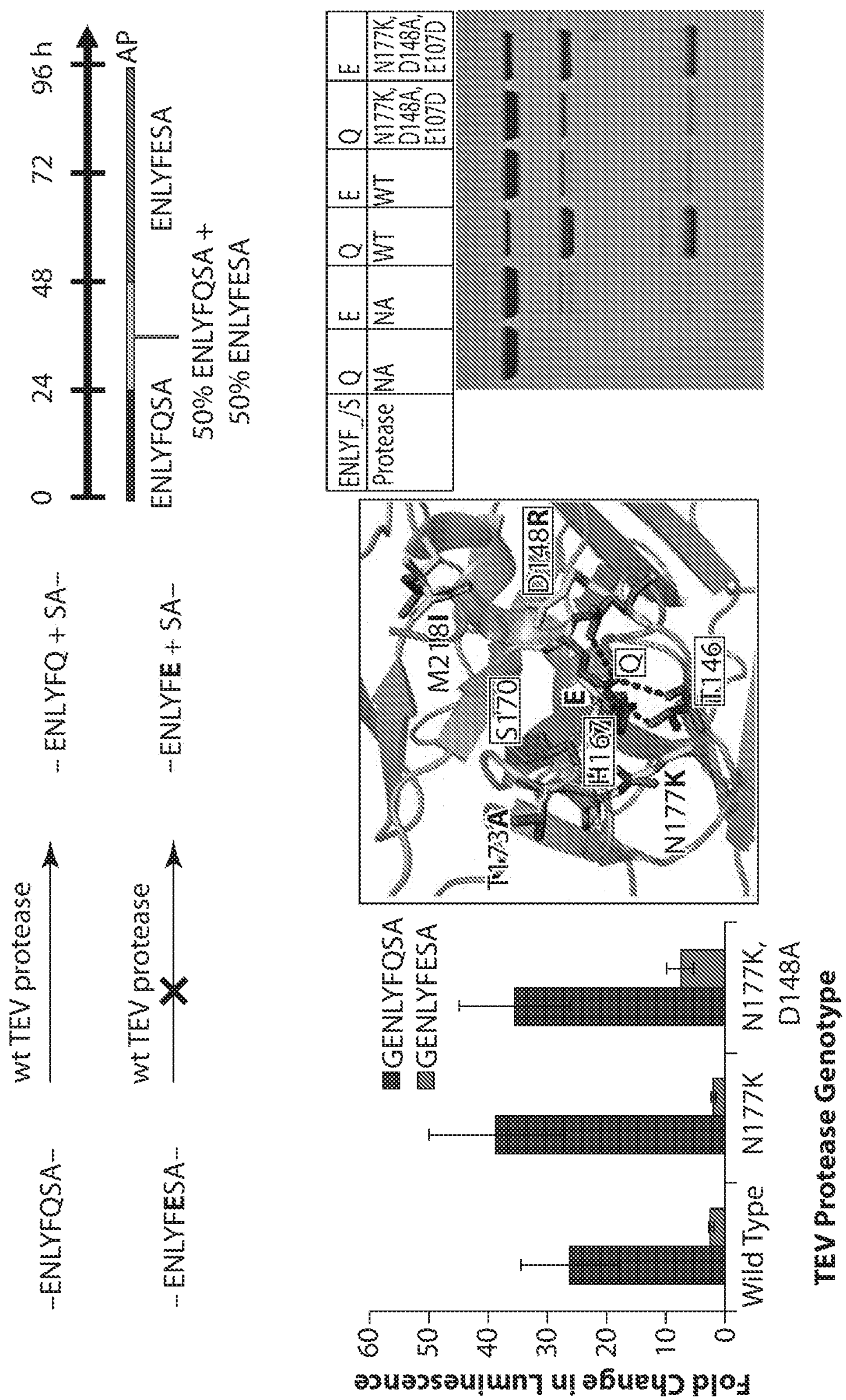
FIG. 13. Directed evolution of a reprogrammed TEV protease.

FIG. 13 shows the directed evolution of a reprogrammed TEV protease. Wild-type TEV protease cleaves the substrate sequence ENLYFQSA (SEQ ID NO: 24), but does not cleave the target substrate sequence ENLYFESA (SEQ ID NO: 25). A 96 hour PACE experiment was performed starting with the wild-type protease substrate sequence for 24 hours, followed by a 50:50 mixture of wild-type and target substrate sequence for 24 hours and the target sequence only for 48 hours. After 96 hours, clones comprising the following mutations were recovered:

| TEV Protease Genotypes at 96 h | | | | | |
|---|---|---|---|---|---|
| | E107D | | D148A | N177K | |
| | | | | N177K | |
| | | | D148A | N177K | |
| | | | | N177K | |
| | | | | N177K | |
| Q73R | | S135F | | | stop223 |
| | | S135F | | | stop223 |
| | | S135F | | | stop223 |

The activity of some mutant TEV clones on wild-type and target substrate were tested.

Figure 14:
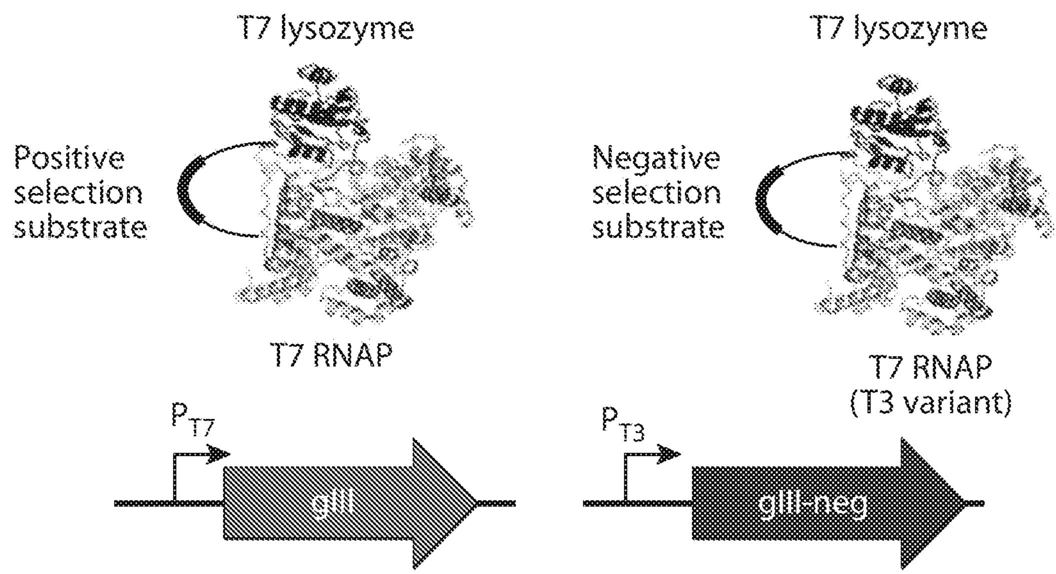
FIG. 14. Directed evolution of TEV variants with improved specificity using negative selection against undesired cleavage target sequences.
Figure 14:
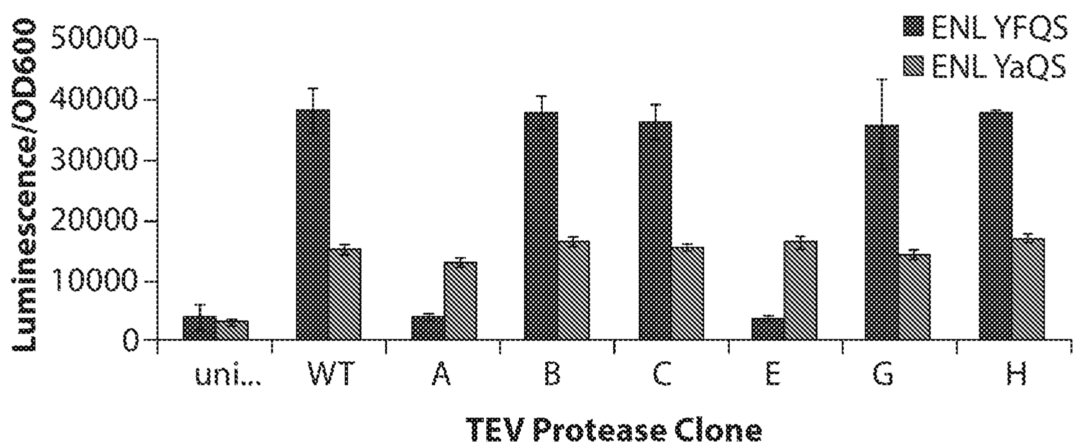
Figure 14:
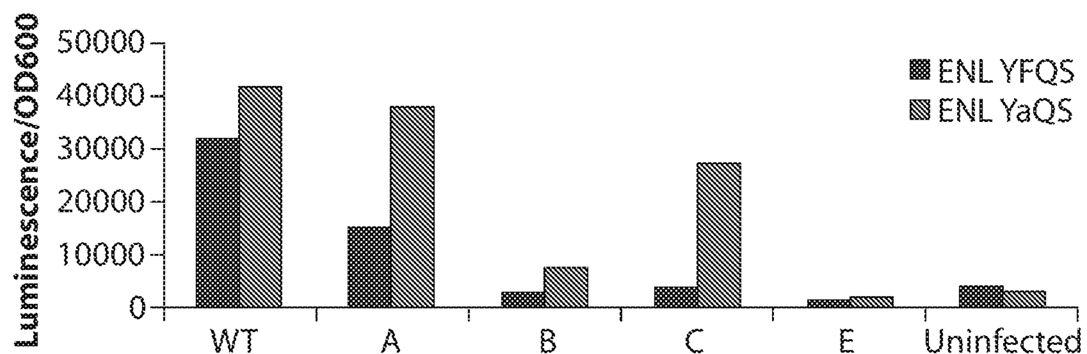

In order to improve the specificity of the evolved proteases, a negative selection scheme was employed. Two orthogonal PA-RNAPs were used in parallel: a positive selection PA-RNAP driving PIII from a T7 promoter, and a negative selection PA-RNAP driving PIII-neg from a T3 promoter (FIG. 14, upper panel). A population of promiscuous and specific clones was obtained after positive selection on substrate ENLYaQS starting from a TEV NNK library. The clones exhibited mutations at residues 209, 211, 216, and 218:

| | | | | | | | |
|---|---|---|---|---|---|---|---|
| A | | | V209F | W211C | V216F | M218L | |
| B | | | V209I | W211I | V216V | M218L | T232P |
| C | | | V209I | W211I | V216V | M218L | |
| D | | | V209I | W211I | V216V | M218L | |
| E | P8C | | V209F | W221C | V216F | M218L | |
| F | | | V209I | W211I | V216V | M218L | |
| G | | P88H | V209I | W211I | V216V | M218L | |
| H | | | V209V | W211I | V216L | M218I | |

The activity of the TEV clones was assessed (FIG. 14, middle panel; "uni . . . "=uninfected).

After combined positive selection on ENLYaQS substrate and negative selection on ENLYFQS, only specific genotypes remained in the population of mutant clones:

| | | | | | | |
|---|---|---|---|---|---|---|
| A | | V209I | W211I | | V216F | M218W |
| B | M121L | V209I | W211I | | V216F | M218L |
| C | | V209I | W211I | | V216F | M218L |
| D | M121L | V209I | W211I | | V216F | M218L |
| E | | V209I | W211I | K215E | V216F | M218L |
| F | M121L | V209I | W211I | | V216F | M218L |
| G | | V209I | W211I | | V216F | M218L |
| H | | V209I | W211I | | V216F | M218L |

The activity of the TEV clones was assessed (FIG. 14, lower panel).

A number of exemplary disease-associated protease target substrate sequences were identified. The target sequences were selected based on exhibiting a high level of homology to a native TEV protease recognition sequence, an extracellular, solvent-exposed localization, conformational flexibility, and conservation of the target substrate sequence between human and animal disease models. A list of monoclonal antibody therapeutics and high-profile targets was compiled, using a TEV specificity matrix to rank all heptapeptides within these proteins. The crystal structures of each of the targets was inspected in order to confirm conformational flexibility and solvent exposure. The following list shows the differences of exemplary target proteins as compared to the native TEV target site (see Dougherty W G et al., *Virology.* 171, 356 (1989).

| TEV site | E | X | L | Y | F | Q | S |
|---|---|---|---|---|---|---|---|
| CCR5 | H | F | P | Y | S | Q | Y |
| PDL1 | H | S | S | Y | R | Q | R |
| TNFa | L | G | G | V | F | Q | L |
| IDE | E | L | L | K | F | H | S |
| MME | E | D | E | Y | F | E | N |

Figure 15:
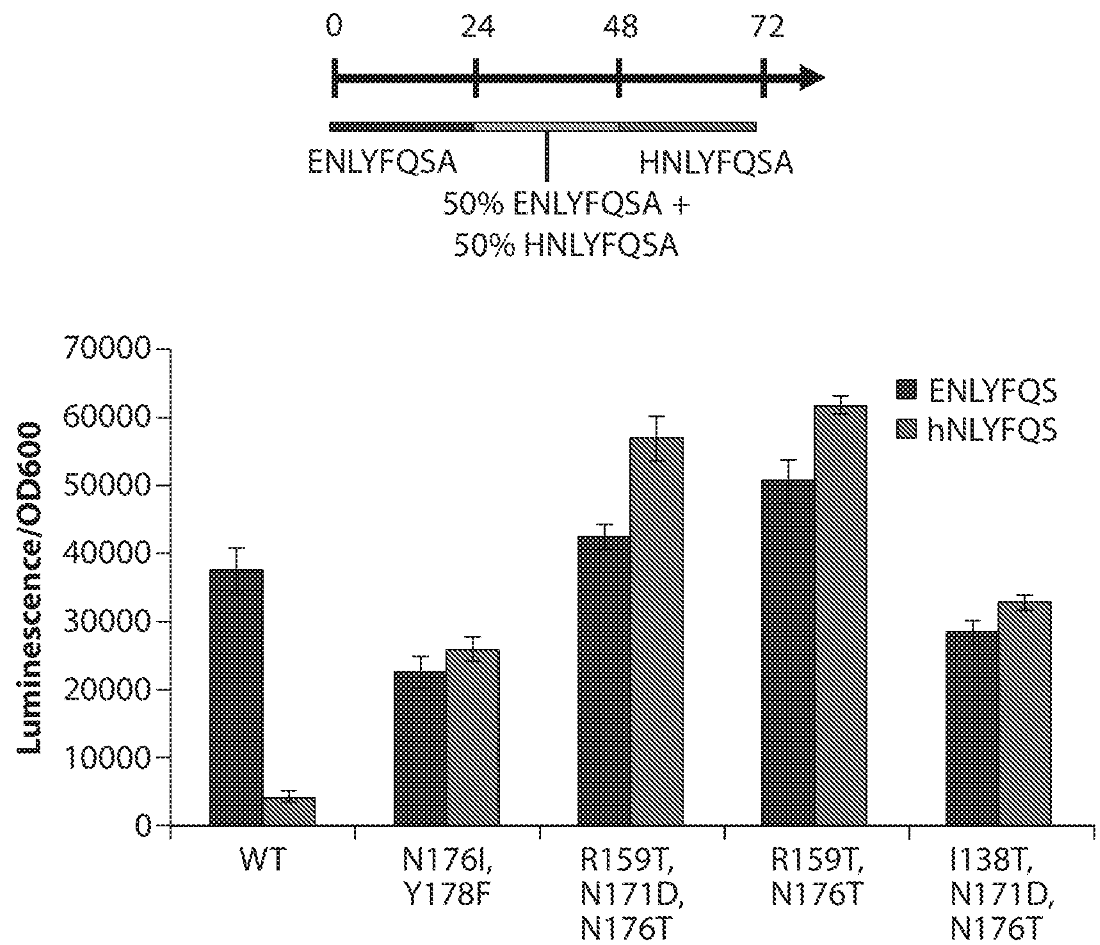
FIG. 15. Directed evolution of TEV variants cleaving single-mutant substrate sequences.

TEV proteases that cleave a single mutant substrate were evolved. FIG. 15 shows a PACE experiment, in which an initial phase of 24 hours on wild-type substrate (EMLYFQSA, SEQ ID NO: 26) was followed by 24 hours on a 50:50 mixture of wild-type and single-mutant substrate (HNLYFQSA, SEQ ID NO: 27). The following TEV genotypes were observed 24 hours after mixing:

| TEV Protease Genotypes 24 h After Mixing | | | | | | | | | |
|---|---|---|---|---|---|---|---|---|---|
| L1 | A | | | | | N176S | | | |
| | B | | | | | | | | Q226Stop |
| | C | | S135F | | | | | | |
| | D | | | | | | | | |
| | E | | S135F | | | | | | |
| | F | | | | | | | | |
| | G | | | | | | | | |
| | H | | S135F | | | | | | |
| L2 | A | D90G | | | | | | N185S | |
| | B | | | | | N176T | | | |
| | C | | | | N171D | | N177Y | | |
| | D | | | | N171D | | N177Y | | |
| | F | | | | | | | | |
| | G | | | D136E | | N176D | | | |

The activity of selected observed TEV genotypes was assessed (FIG. 15 lower panel).

Figure 16:
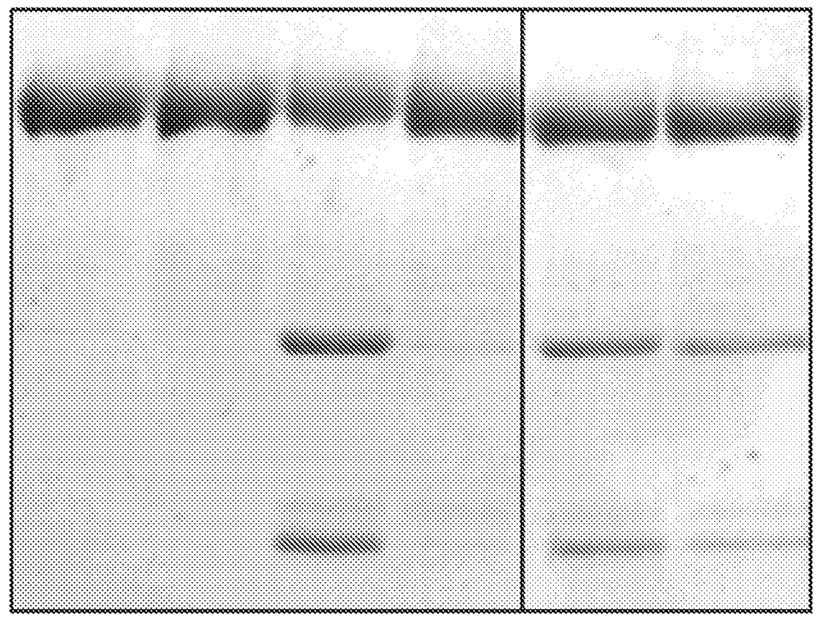
FIG. 16. Directed evolution of TEV variants cleaving single-mutant substrate sequences.

In a separate experiment, TEV proteases that cleave a single mutant substrate were evolved directly for 36 hours on the mutant substrate (FIG. 16). The following TEV genotypes were observed:

| TEV Protease Genotypes 36 h Propagation of NNK Library of Residues 171, 176, 178 | | | | | | |
|---|---|---|---|---|---|---|
| L1 | B | | | | N176I | Y178F |
| | C | | R159T | N171D | N176T | |
| | D | | R159T | | N176T | |
| L2 | A | I138T | | N171D | N176T | |
| | B | I138T | | N171D | N176T | |
| | C | I138T | | N171D | N176T | |
| | D | I138T | | N171D | N176T | |

The activity of selected TEV genotypes on different substrates was assessed (FIG. 16 lower panel).

Figure 17:
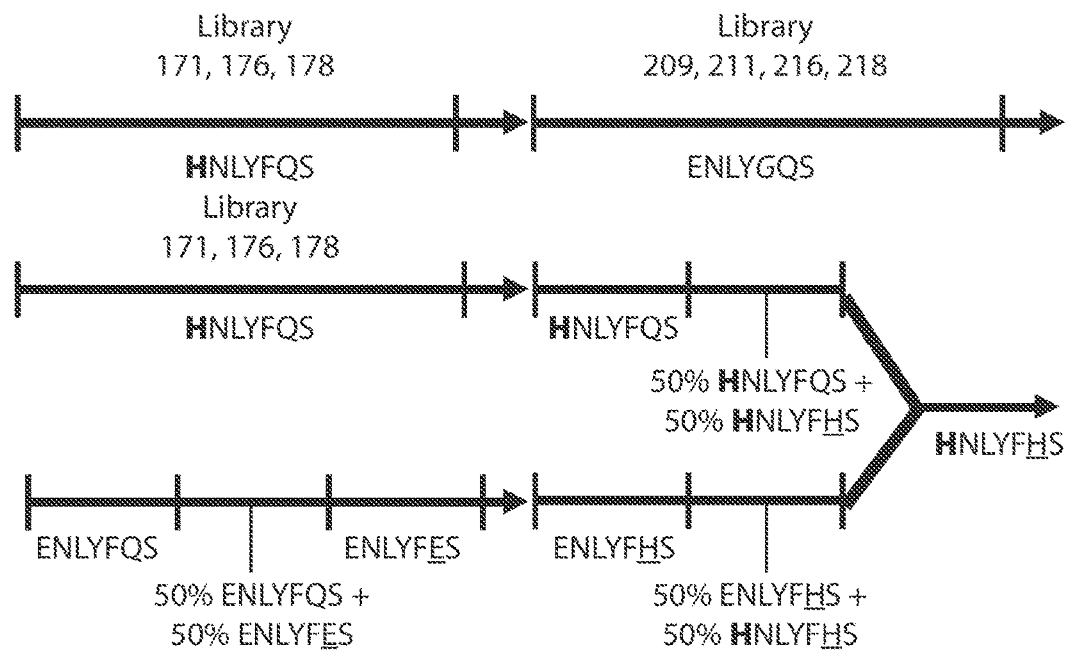
FIG. 17. Directed evolution of TEV variants cleaving double-mutant substrate sequences.
Figure 17:
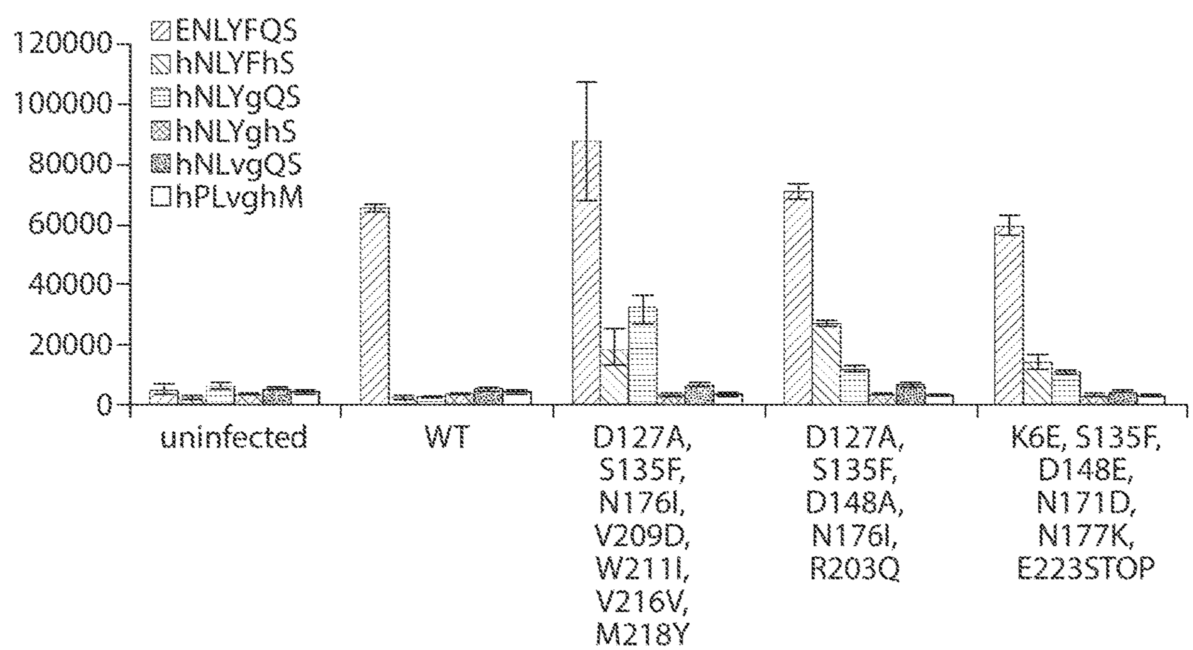

TEV proteases that cleave a double-mutant substrate were evolved using a multi-step evolution strategy as described in FIG. 17. The activity of various mutant TEV clones on double-mutant substrates was assessed (FIG. 17, lower panel). The following mutant TEV clones were observed:

| | | | | | | | | | |
|---|---|---|---|---|---|---|---|---|---|
| L6 | a | | D127A | S135F | N176I | V209D | W211I | V216V | M218Y |
| | b | | D127A | S135F | N176I | V209M | W211I | V216V | M218W |
| | c | | D127A | S135F | N176I | V209D | W211I | V216V | M218Y |
| | d | | D127A | S135F | N176I | V209D | W211I | V216V | M218Y |
| | e | F91V | D127A | S135F | N176I | V209Q | W211I | V216V | M218W |
| | f | | D127A | S135F | N176I | V209D | W211I | V216V | M218Y |

-continued

| | | | | | | | |
|---|---|---|---|---|---|---|---|
| g | D127A | S135F | N176I | V209V | W211M | V216V | M218F |
| h | D127A | S135F | N176I | V209D | W211V | V216V | M218W |

| | | | | | | | | | | |
|---|---|---|---|---|---|---|---|---|---|---|
| L1 | a | | | | | S135F | | D148A | F162S | |
| | b | | | | | S135F | | D148A | | |
| | c | | | | F116C | S135F | | D148A | F162S | |
| | d | | | | | S135F | | D148A | | |
| | e | | | | | S135F | | D148A | | |
| | f | | | | | S135F | | | | |
| | g | | | | | S135F | | D148A | | |
| | h | | | | | S135F | | D148A | | |
| L2 | a | | | | | | I138T | | | |
| | b | | | | | | I138T | | | |
| | c | | | | | | I138T | | | |
| | d | | | | | | I138T | | | |
| | e | | | | | | I138T | | | |
| | f | | | | | | I138T | | | |
| | g | | | | | | I138T | | | |
| | h | | | | | | I138T | | | |
| L3 | a | | | | | S135F | | | | |
| | b | K6E | | C110R | | S135F | I138T | | | |
| | c | | | | | S135F | | | | N171D |
| | d | K6E | | | | S135F | | | | N171D |
| | e | K6E | | | | S135F | | | | |
| | f | | | | | S135F | | | | N171D |
| | g | | | | | S135F | | | | N171D |
| L4 | a | | | | | S135F | | | | |
| | b | | | | | S135F | | | | |
| | c | | S59L | | | S135F | | | | |
| | d | | | | | S135F | | | | |
| | e | | | | | S135F | | | | |
| | f | | | | | S135F | | | | |
| | g | | | | | S135F | | | | |
| | h | | | | | S135F | | | | |

| | | | | | | | | | |
|---|---|---|---|---|---|---|---|---|---|
| L1 | a | N176I | | | | A206T | | | |
| | b | N176I | | | R203Q | | | | |
| | c | N176I | | | | A206T | | | |
| | d | N176I | | | | | | | |
| | e | N176I | | | | | | | |
| | f | N176I | | | R203Q | | | | |
| | g | N176I | | | | | | | |
| | h | N176I | | | | | | | |
| L2 | a | N176T | | | | | | | |
| | b | N176T | | | | | | | |
| | c | N176T | | | | | | | |
| | d | N176T | | | | | | | |
| | e | N176T | | | | | | | |
| | f | N176T | | | | | | | |
| | g | N176T | | S181T | | | | | |
| | h | N176T | | | | | | | |
| L3 | a | | N177K | | | | | | E223stop |
| | b | | N177K | | | | | | E223stop |
| | c | | N177K | | | | | | E223stop |
| | d | | N177K | | | | | | E223stop |
| | e | | N177K | | | | | | E223stop |
| | f | | N177K | | | | | | E223stop |
| | g | | N177K | | | | | | E223stop |
| L4 | a | N176T | | | | | | | |
| | b | N176T | | | | | K215R | | |
| | c | N176T | | | | | | V216stop | |
| | d | N176T | | | | | | | |
| | e | N176T | | | | | | | |
| | f | N176T | | | | | | | |
| | g | N176T | | | | | | | |
| | h | N176T | | | | | | | |

Figure 18:
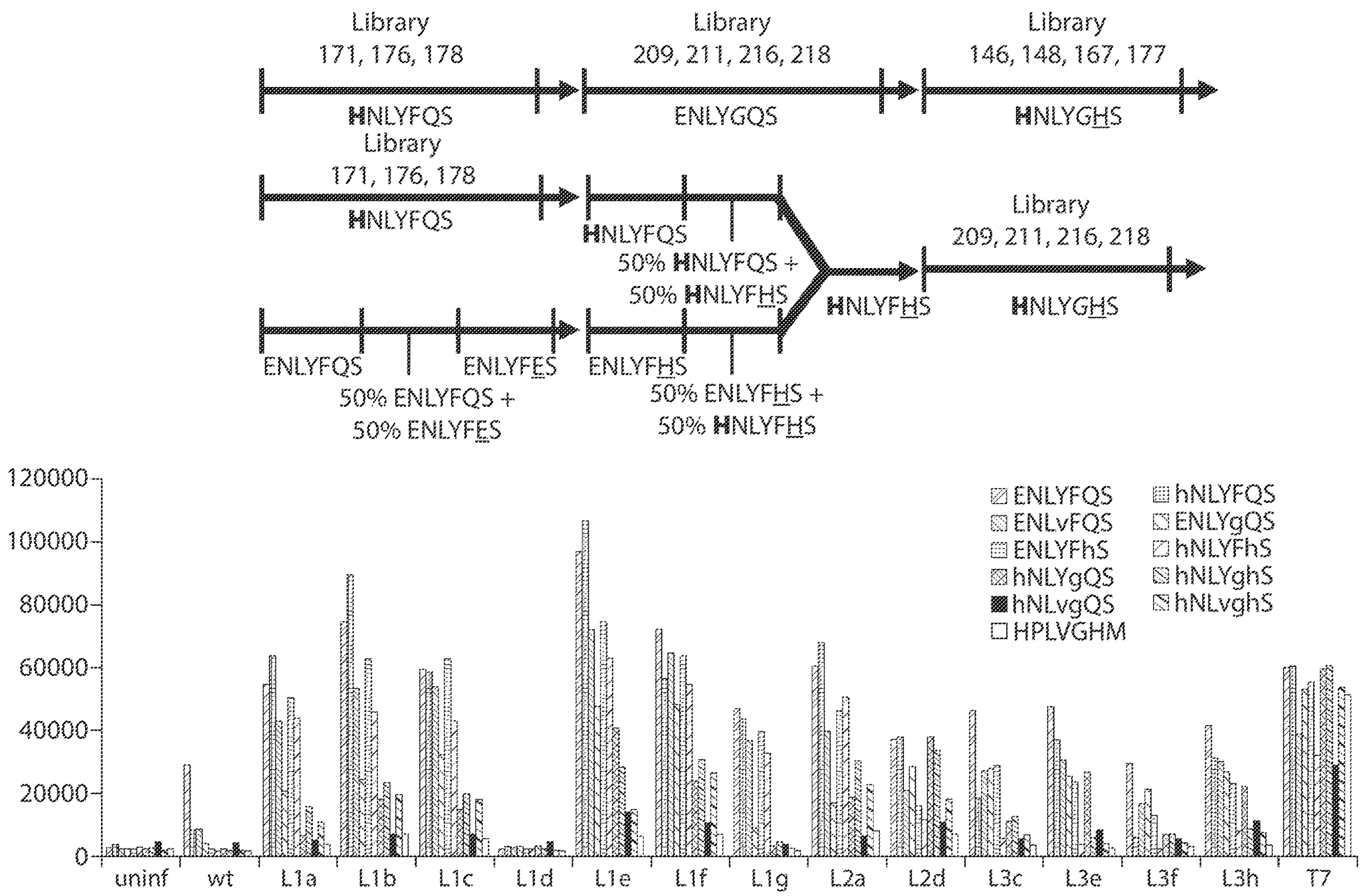
FIG. 18. Directed evolution of TEV variants cleaving triple-mutant substrate sequences.

TEV proteases that cleave a triple-mutant substrate were evolved using a multi-step evolution strategy as described in FIG. 18. The activity of various mutant TEV clones on triple-mutant substrates was assessed (FIG. 18, lower panel). The following mutant TEV clones were observed:

| | | | | | | | | | | | | |
|---|---|---|---|---|---|---|---|---|---|---|---|---|
| L1 | a | | | | | D127A | | S135F | T146A | D148P | | |
| | b | | | E106G | | D127A | | S135F | T146A | D148P | | |
| | c | | | | | D127A | | S135F | T146A | D148P | | |
| | d | | | | | D127A | | S135F | T146R | D148C | H167P | |
| | e | | | | | D127A | | S135F | T146A | D148P | | |
| | f | | | | | D127A | | S135F | T146C | D148P | | |
| | g | | | | | D127A | | S135F | T146C | D146P | | |
| | h | | | | | D127A | | S135F | T146C | D148P | | |
| L2 | a | | | | | D127A | | S135F | T146S | D148P | | N171D |
| | b | | | | | D127A | | S135F | T146C | D148P | | N171D |
| | c | | | | | D127A | | S135F | T146S | D148P | | N171D |
| | d | | | | | D127A | | S135F | T146C | D148P | | N171D |
| | e | | V63I | | | D127A | F132S | S135F | T146S | D148P | | N171D |
| | f | | | | | D127A | | S135F | T146S | D148P | | N171D |
| | g | | | | | D127A | | S135F | T146C | D148P | | N171D |
| | h | | | | | D127A | | S135F | T146C | D148P | | N171D |
| L3 | c | | | | E107D | D127A | | S135F | T146A | D148A | | |
| | d | | | | E107D | D127A | | S135F | | D148A | | |
| | e | | | | E107D | D127A | | S135F | | D148A | | |
| | f | | | | E107D | D127A | | S135F | T146A | D148A | | |
| | g | G32R | | | E107D | D127A | | S135F | T146A | D148A | | |
| | h | | | | E107D | D127A | | S135F | | D148A | | |

| | | | | | | | | | | | |
|---|---|---|---|---|---|---|---|---|---|---|---|
| L1 | a | N176I | N177M | | V209M | W211I | | M218F | | | |
| | b | N176I | N177R | | V209M | W211I | | M218F | | | |
| | c | N176I | N177R | | V209M | W211I | | M218F | | | |
| | d | N1761 | N177G | | V209M | W211I | | M218F | | | |
| | e | N176I | N177W | | V209M | W211I | | M218F | | | |
| | f | N176I | N177M | | V209M | W211I | | M218F | | | |
| | g | | N177M | S200G | V209M | W211I | | M218F | | | |
| | h | N176I | N177M | | V209M | W211I | | M218F | | | |
| L2 | a | N176T | N177M | | V209M | W211I | | M218F | | | K229E |
| | b | N176T | N177M | | V209E | W211L | V216I | M218W | E223stop | | |
| | c | N176T | N177M | | V209M | W211I | | M218F | | | K229E |
| | d | N176T | N177M | | V209E | W211L | V216I | M218W | | | |
| | e | N176T | N177M | | V209M | W211I | | M218F | | | K229E |
| | f | N176T | N177M | | V209M | W211I | | M218F | | | K229E |
| | g | N176T | N177M | | V209E | W211L | V216I | M218W | E223stop | | |
| | h | N176T | N177M | | V209M | W211I | | M218F | | | K229E |
| L3 | c | N176I | | | V209S | W211I | | M218W | | | |
| | d | N176I | | | V209E | W211L | V216I | M218W | | Q226stop | |
| | e | N176I | | | V209S | W211I | | M218W | | | |
| | f | N176I | | | V209E | W211L | V216I | M218W | | | |
| | g | N1761 | | | V209E | W211L | V216I | M218W | | Q226stop | |
| | h | N176I | | | V209F | W211C | | M218L | | | |

Figure 19:
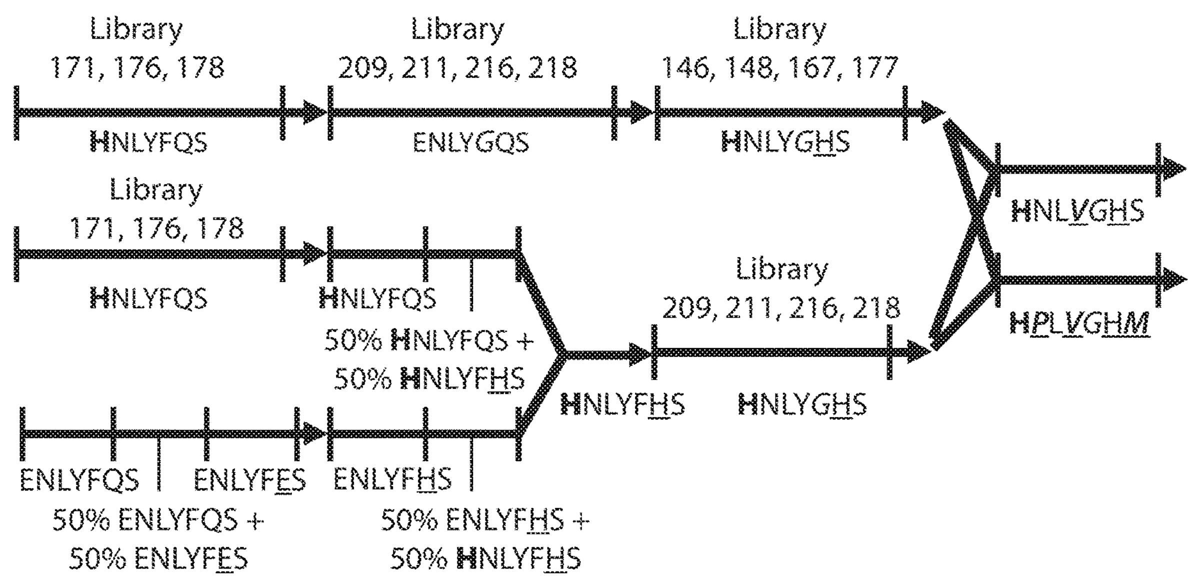
FIG. 19. Directed evolution of TEV variants cleaving a target IL23a peptide.
Figure 19:
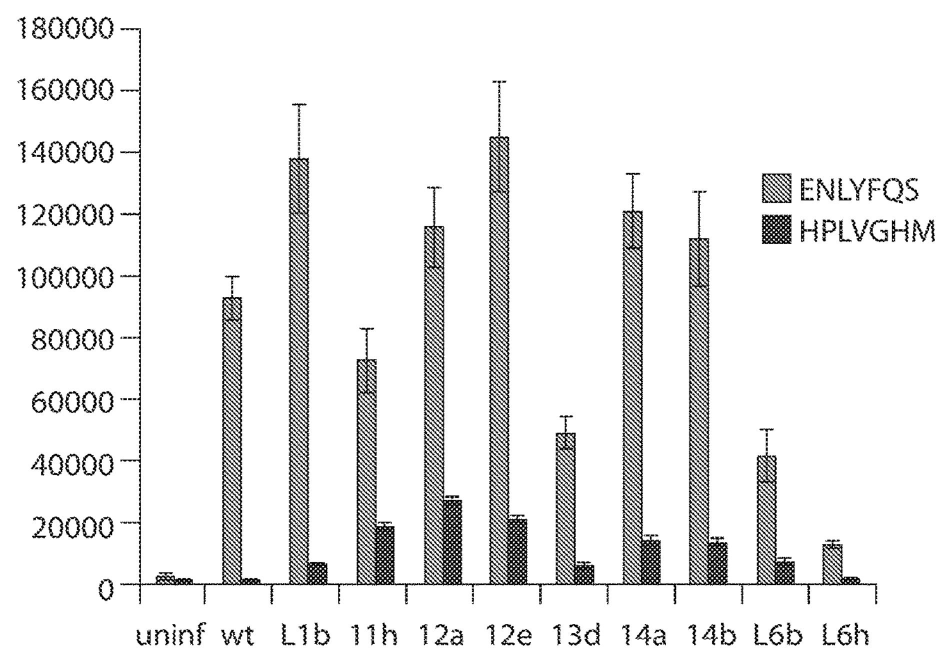

TEV proteases that cleave a target IL23a peptide were evolved using a multi-step evolution strategy as described in FIG. 19. The activity of various mutant TEV clones on IL23a substrates was assessed (FIG. 19, lower panel). The following mutant TEV clones were observed:

| | | |
|---|---|---|
| L1 | a | |
| | b | |
| | c | P8L |
| | d | |
| | e | |
| | f | |
| | g | |
| | h | |
| L2 | a | |
| | b | |
| | c | |
| | d | |
| | e | |
| | f | |
| | g | |
| | h | |

-continued

| | | | | | | | | | | | |
|---|---|---|---|---|---|---|---|---|---|---|---|
| L3 | a | | | | N12H | | | | | | |
| | b | | | | | | | | | | |
| | c | | | | | | | | | | |
| | d | | | | | | | | | | |
| | e | | | | | | | | K67N | | |
| | f | | | | | | | | | | |
| | g | | | | | | | | | | |
| | h | | | | | | | | | | |
| L4 | a | | | | | | | | | | |
| | b | | | | | | | | | | |
| | c | | | | | | | | | | |
| | d | | | | | | | | | | |
| | e | | | | | | | | | | |
| | f | | | | | | | | | | |
| | g | | | | N12T | | | | | | |
| | h | | | | | | | | | | R80G |
| L5 | a | | | | | | | | | | |
| | b | | | | | | | | | | |
| | c | | | | | | | | | | |
| | d | | | | | | | | | | |
| | e | K6E | | | | | | | | | |
| | f | | | | | T17A | | | | | |
| | g | | | | | | | | | N68D | |
| L6 | a | | | | | | | | | | |
| | b | | | | | | | | | | |
| | c | | | | | | T30A | R50K | | | |
| | d | | | | | | | | | | |
| | e | | | | | | | | | | |
| | f | | | | | | | | | | |
| | g | | | R9C | | | | | | | |
| | h | | | | | | | | | | |

| | | | | | | | | | | | |
|---|---|---|---|---|---|---|---|---|---|---|---|
| L1 | a | | | | D127A | S135F | T1464A | D148P | | | |
| | b | | | | D127A | S135F | T1464A | D148P | | | |
| | c | | | | D127A | S135F | T1464A | D148P | | | |
| | d | | | | D127A | S135F | T1464A | D148P | | | |
| | e | | | | D127A | S135F | T1464A | D148P | | | |
| | f | | | | D127A | S135F | T1464A | D148P | | | |
| | g | | | | D127A | S135F | T1464A | D148P | | R159K | |
| | h | | | | D127A | S135F | T1464A | D148P | | | |
| L2 | a | | | | D127A | S135F | T1464S | D148P | | | F162S |
| | b | | | | D127A | S135F | T1464S | D148P | | | F162S |
| | c | | | | D127A | S135F | T1464S | D148P | | | F162S |
| | d | | | | D127A | S135F | T1464S | D148P | | | F162S |
| | e | | | | D127A | S135F | T1464S | D148P | | | |
| | f | | | | D127A | S135F | T1464S | D148P | | | F162S |
| | g | | | | D127A | S135F | T1464S | D148P | | | F162S |
| | h | | | | D127A | S135F | T1464S | D148P | | | F162S |
| L3 | a | | E107D | | D127A | S135F | T1464A | D148A | | | |
| | b | | E107D | | D127A | S135F | T1464A | D148A | | | |
| | c | | E107D | | D127A | S135F | T1464A | D148A | | | |
| | d | | E107D | | D127A | S135F | T1464A | D148A | | | |
| | e | | E107D | | D127A | S135F | T1464A | D148A | S152N | | |
| | f | | E107D | | D127A | S135F | T1464A | D148A | | | |
| | g | | E107D | | D127A | S135F | T1464A | D148A | | | |
| | h | | E107D | | D127A | S135F | T1464A | D148A | | | |
| L4 | a | E106G | | | D127A | S135F | T1464S | D148P | | | |
| | b | | | T118S | D127A | S135F | T1464A | D148P | | | |
| | c | | | | D127A | S135F | T1464A | D148P | | | |
| | d | | | T118S | D127A | S135F | T1464A | D148P | | | |
| | e | | | | D127A | S135F | T1464A | D148P | | | |
| | f | | | | D127A | S135F | T1464A | D148P | | | |
| | g | | | | D127A | S135F | T1464A | D148P | | | |
| | h | | | | D127A | S135F | T1464A | D148P | | | |
| L5 | a | | | | D127A | S135F | T1464S | D148P | | | |
| | b | | | | D127A | S135F | T1464S | D148P | | | |
| | c | | | | D127A | S135F | T1464S | D148P | | | |
| | d | | | | D127A | S135F | T1464S | D148P | | | |
| | e | | | | D127A | S135F | T1464S | D148P | | | |
| | f | | | | D127A | S135F | T1464S | D148P | | | |
| | g | | | | D127A | S135F | T1464S | D148P | | | |
| L6 | a | E106G | E107D | | D127A | S135F | T1464A | D148A | | | |
| | b | | E107D | | D127A | S135F | T1464A | D148A | | | |
| | c | | E107D | | D127A | S135F | T1464A | D148A | | | |
| | d | | E107D | | D127A | S135F | T1464A | D148A | | | |
| | e | | E107D | | D127A | S135F | T1464A | D148A | | | |

-continued

| | | | | | | | | | | | |
|---|---|---|---|---|---|---|---|---|---|---|---|
| | f | | E107D | | D127A | S135F | T1464A | D148A | | | |
| | g | | E107D | | D127A | S135F | T1464A | D148A | | | |
| | h | E106G | E107D | | D127A | S135F | T1464A | D148A | | | |
| L1 | a | | N176I | N177W | V209M | W211I | M218F | | | K229E | Q233stop |
| | b | | N176I | N177W | V209M | W211I | M218F | | | K229E | |
| | c | | N176I | N177W | V209M | W211I | M218F | | | K229E | |
| | d | | N176I | N177W | V209M | W211I | M218F | | | K229E | Q233stop |
| | e | | N176I | N177W | V209M | W211I | M218F | | | K229E | Q233stop |
| | f | | N176I | N177W | V209M | W211I | M218F | | | K229E | Q233stop |
| | g | | N176I | N177R | V209M | W211I | M218F | | | K229E | |
| | h | | N176I | N177R | V209M | W211I | M218F | | | K229E | |
| L2 | a | N171D | N176T | N177M | V209M | W211I | M218F | | | K229E | |
| | b | N171D | N176T | N177M | V209M | W211I | M218F | | | K229E | |
| | c | N171D | N176T | N177M | V209M | W211I | M218F | | | K229E | |
| | d | N171D | N176T | N177M | V209M | W211I | M218F | | | K229E | |
| | e | N171D | N176T | N177M | V209M | W211I | M218F | | | K229E | |
| | f | N171D | N176T | N177M | V209M | W211I | M218F | | | K229E | |
| | g | N171D | N176T | N177M | V209M | W211I | M218F | Q226stop | | K229E | |
| | h | N171D | N176T | N177M | V209M | W211I | M218F | | | K229E | |
| L3 | a | | N176I | | V209F | W211C | M218L | Q226stop | | | |
| | b | | N176I | | V209F | W211C | M218L | | P227S | | |
| | c | | N176I | | V209F | W211C | M218L | | | | |
| | d | | N176I | | V209F | W211C | M218L | | | | |
| | e | | N176I | | V209F | W211C | M218L | | | | |
| | f | | N176I | | V209F | W211C | M218L | | | | |
| | g | | N176I | | V209F | W211C | M218L | | | | |
| | h | | N176I | | V209F | W211C | M218L | | | | |
| L4 | a | | N176I | N177F | V209M | W211I | M218F | | | K229E | |
| | b | | N176I | N177R | V209M | W211I | M218F | | | K229E | |
| | c | | N176I | N177R | V209M | W211I | M218F | | | K229E | |
| | d | | N176I | N177R | V209M | W211I | M218F | | | K229E | |
| | e | | N176I | N177R | V209M | W211I | M218F | | | K229E | |
| | f | | N176I | N177R | V209M | W211I | M218F | | | K229E | |
| | g | | N176I | N177R | V209M | W211I | M218F | | | K229E | |
| | h | | N176I | N177R | V209M | W211I | M218F | | | K229E | |
| L5 | a | N171D | N176T | N177M | V209M | W211I | M218F | | | K229E | |
| | b | N171D | N176T | N177M | V209M | W211I | M218F | | | K229E | |
| | c | N171D | N176T | N177M | V209M | W211I | M218F | | | K229E | |
| | d | N171D | N176T | N177M | V209M | W211I | M218F | | | K229E | |
| | e | N171D | N176T | N177M | V209M | W211I | M218F | | | K229E | |
| | f | N171D | N176T | N177M | V209M | W211I | M218F | | | K229E | |
| | g | N171D | N176T | N177M | V209M | W211I | M218F | | | K229E | |
| L6 | a | | N176I | | V209F | W211C | M218L | | | | |
| | b | | N176I | | | | M218F | Q226stop | | | |
| | c | | N176I | | V209F | W211C | M218L | | | | |
| | d | | N176I | | | | M218F | Q226stop | | | |
| | e | | N176I | | | | M218F | Q226stop | | | |
| | f | | N176I | | | | M218F | Q226stop | | | |
| | g | | N176I | | | | M218F | Q226stop | | | |
| | h | | N176I | | V209F | W211C | M218L | | | | |

Cleavage of MBP-GST Test Substrates.

Figure 20:
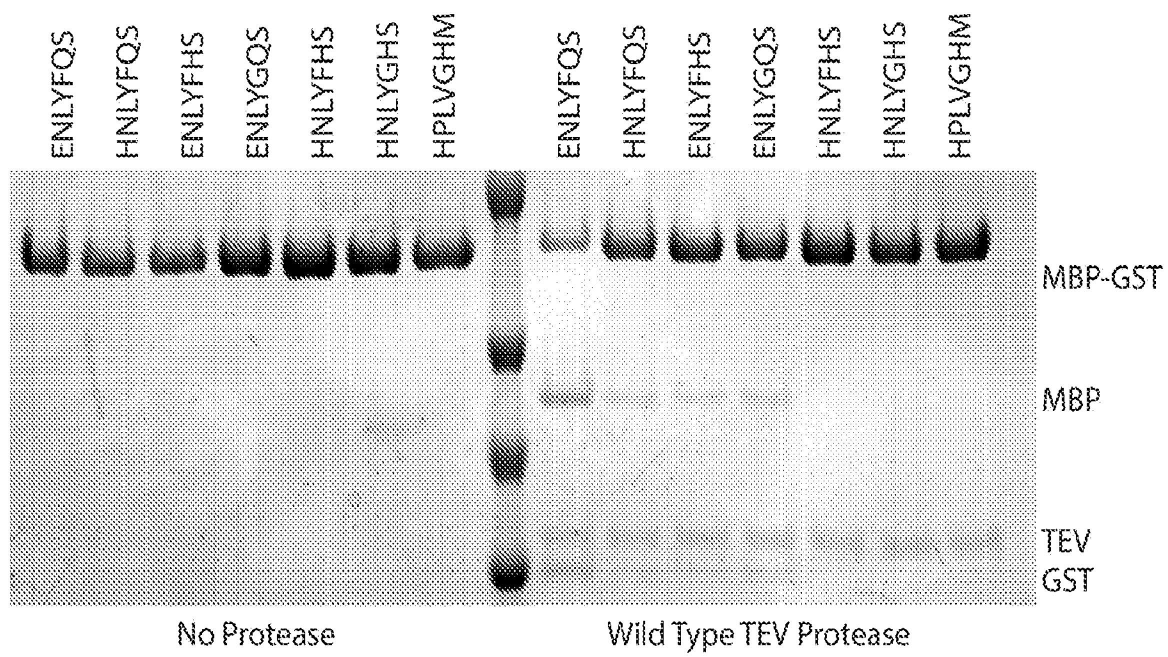
FIG. 20. Cleavage efficiency of wild-type TEV protease on various substrate sequences.
Figure 21:
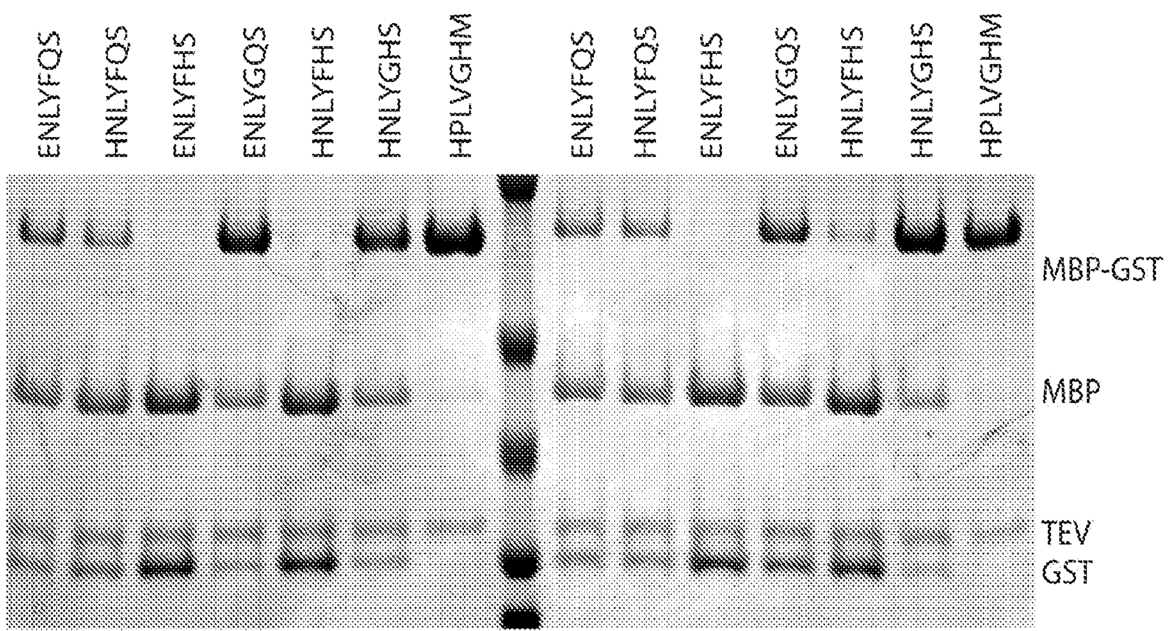
FIG. 21. Cleavage efficiency of two evolved TEV proteases on various substrates sequences.

An MBP-[substrate sequence]-GST fusion protein was digested at 30° C. for 3 hours in 25 mM Tris pH 8.0, 50 mM NaCl, 1 mM EDTA, 20% glycerol. FIG. 20 shows the cleavage efficiency of wild-type TEV protease on various substrate sequences. FIG. 21 shows the cleavage efficiency of two evolved TEV proteases tested on the same substrates under the same conditions. On the left, cleavage results are shown for evolved protease TEV_L2A (D127A, S135F, T146S, D148P, F162S, N171D, N176T, N177M, V209M*, W211I*, M218F*, K229E) are shown. On the right, cleavage results are shown for evolved protease TEV_L1 (D127A, S135F, T146A, D148P, N176I, N177R, V209M*, W211I*, M218F*, K229E). Mutations that improve solubility and expression are underlined. Mutations relating to P1 are in bold, mutations relating to P2 are marked with an asterisk, and mutations relating to P6 are italicized.

Evolution of HCV Proteases that Cleave Macaque MAVS.

Figure 22:
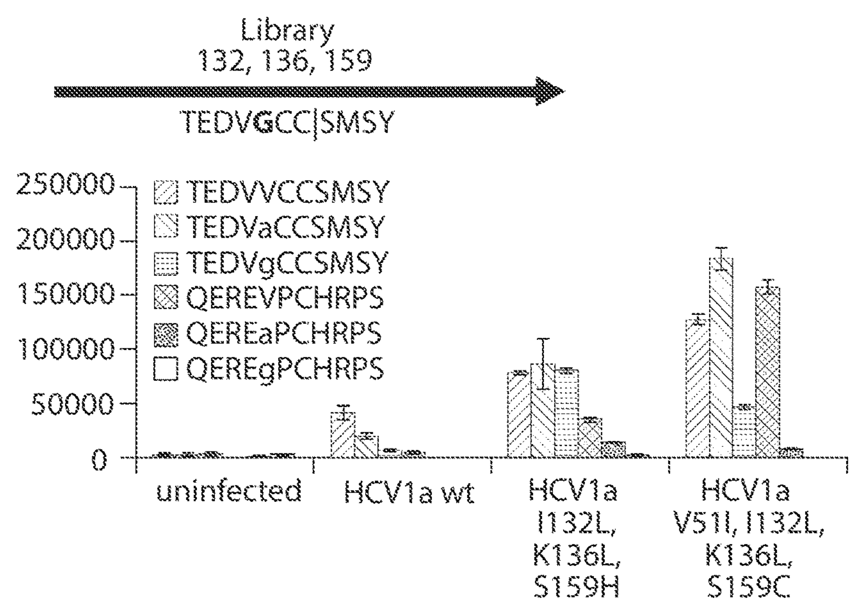
FIG. 22. Directed evolution of HCV protease variants that cleave macaque MAYS.
Figure 22:
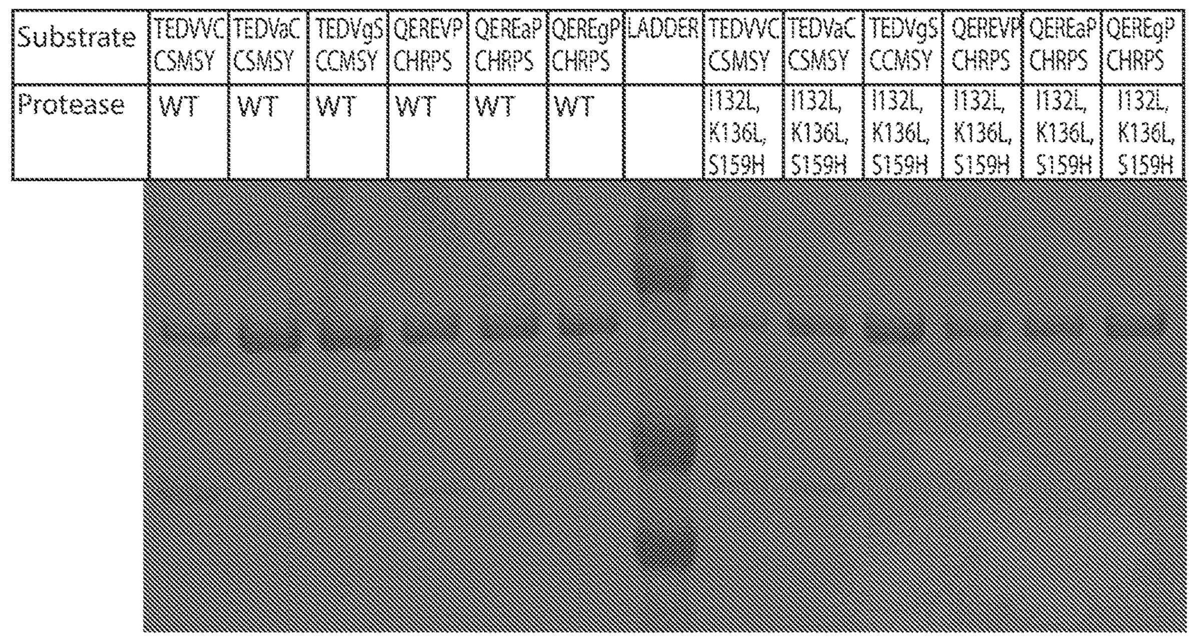

FIG. 22 shows the evolution of HCV protease variants that cleave macaque MAYS. Exemplary genotypes observed after 48 and 96 hours are displayed below:

| | | | | | | |
|---|---|---|---|---|---|---|
| 48 h | a | | | I132L | K136L | S159H |
| | b | | V51I | I132L | K136L | S159C |
| | c | | | I132L | K136L | S159H |
| | d | | | I132L | K136L | S159H |
| | e | | | I132L | K136L | S159H |
| | f | | V51I | I132L | K136L | S159C |
| | g | V33I | V51I | I132L | K136L | S159H |
| | h | | V51I | I132L | K136L | S159C |

-continued

| | | | | | | | | |
|---|---|---|---|---|---|---|---|---|
| 96 h | a | | | V51I | | I132L | K136L | S159C |
| | b | | G->S ns4 | V51I | | I132L | K136L | S159C |
| | c | | | | T76P | I132L | K136L | S159H |
| | d | | | V51I | | I132L | K136L | S159C |
| | e | | | V51I | | I132L | K136L | S159C |
| | f | | | V51I | | I132L | K136L | S159C |
| | g | V->I ns4 | | V51I | | I132L | K136L | S159C |
| | h | | | V51I | | I132L | K136L | S159C |

Evolution of HCV Proteases that Cleave Ferret MAVS.

FIG. 23 shows the evolution of HCV protease variants that cleave ferret MAYS. Exemplary genotypes observed at the various stages during the evolution experiment are displayed.

REFERENCES

1 Schilling, O. & Overall, C. M. Proteome-derived, database-searchable peptide libraries for identifying protease cleavage sites. Nat Biotechnol 26, 685-694, (2008).

2 Walsh, G. Biopharmaceutical benchmarks 2006. Nat Biotechnol 24, 769-776, (2006).

3 Wehr, M. C. et al. Monitoring regulated protein-protein interactions using split TEV. Nat Methods 3, 985-993, (2006).

4 Craik, C. S., Page, M. J. & Madison, E. L. Proteases as therapeutics. Biochem J 435, 1-16, (2011).

Gray, D. C., Mahrus, S. & Wells, J. A. Activation of specific apoptotic caspases with an engineered small-molecule-activated protease. Cell 142, 637-646, (2010).

6 von Mehren, M., Adams, G. P. & Weiner, L. M. Monoclonal antibody therapy for cancer. Annu Rev Med 54, 343-369, (2003).

7 Waldmann, T. A. Immunotherapy: past, present and future. Nat Med 9, 269-277, (2003).

8 Caravella, J. & Lugovskoy, A. Design of next-generation protein therapeutics. Curr Opin Chem Biol 14, 520-528, (2010).

9 Russell, A. J. & Fersht, A. R. Rational modification of enzyme catalysis by engineering surface charge. Nature 328, 496-500, (1987).

10 Varadarajan, N., Gam, J., Olsen, M. J., Georgiou, G. & Iverson, B. L. Engineering of protease variants exhibiting high catalytic activity and exquisite substrate selectivity. Proc Natl Acad Sci USA 102, 6855-6860, (2005).

11 Knight, Z. A., Garrison, J. L., Chan, K., King, D. S. & Shokat, K. M. A remodelled protease that cleaves phosphotyrosine substrates. J Am Chem Soc 129, 11672-11673, (2007).

12 Sellamuthu, S. et al. Engineering of protease variants exhibiting altered substrate specificity. Biochem Biophys Res Commun 371, 122-126, (2008).

13 Varadarajan, N., Rodriguez, S., Hwang, B. Y., Georgiou, G. & Iverson, B. L. Highly active and selective endopeptidases with programmed substrate specificities. Nat Chem Biol 4, 290-294, (2008).

14 Yi, L. et al. Engineering of TEV protease variants by yeast ER sequestration screening (YESS) of combinatorial libraries. Proc Natl Acad Sci USA 110, 7229-7234, (2013).

15 Abbenante, G. & Fairlie, D. P. Protease inhibitors in the clinic. Med Chem 1, 71-104, (2005).

16 Turk, B. Targeting proteases: successes, failures and future prospects. Nat Rev Drug Discov 5, 785-799, (2006).

17 Rong, L., Dahari, H., Ribeiro, R. M. & Perelson, A. S. Rapid emergence of protease inhibitor resistance in hepatitis C virus. Sci Transl Med 2, 30ra32, (2010).

18 Ridky, T. & Leis, J. Development of drug resistance to HW-1 protease inhibitors. J Biol Chem 270, 29621-29623, (1995).

19 Lefebvre, E. & Schiffer, C. A. Resilience to resistance of HIV-1 protease inhibitors: profile of darunavir. AIDS Rev 10, 131-142, (2008).

20 Romano, K. P. et al. The molecular basis of drug resistance against hepatitis C virus NS3/4A protease inhibitors. PLoS Pathog 8, e1002832, (2012).

21 Shang, L., Lin, K. & Yin, Z. Resistance mutations against HCV protease inhibitors and antiviral drug design. Curr Pharm Des 20, 694-703, (2014).

22 Verbinnen, T. et al. Tracking the evolution of multiple in vitro hepatitis C virus replicon variants under protease inhibitor selection pressure by 454 deep sequencing. J Virol 84, 11124-11133, (2010).

23 Billerbeck, E., de Jong, Y., Dorner, M., de la Fuente, C. & Ploss, A. Animal models for hepatitis C. Curr Top Microbiol Immunol 369, 49-86, (2013).

24 Orencia, M. C., Yoon, J. S., Ness, J. E., Stemmer, W. P. & Stevens, R. C. Predicting the emergence of antibiotic resistance by directed evolution and structural analysis. Nat Struct Biol 8, 238-242, (2001).

25 Esvelt, K. M., Carlson, J. C. & Liu, D. R. A system for the continuous directed evolution of biomolecules. Nature 472, 499-503, (2011).

26 Hedstrom, L., Szilagyi, L. & Rutter, W. J. Converting trypsin to chymotrypsin: the role of surface loops. Science 255, 1249-1253, (1992).

27 Kim, J. L. et al. Crystal structure of the hepatitis C virus NS3 protease domain complexed with a synthetic NS4A cofactor peptide. Cell 87, 343-355, (1996).

28 Dickinson, B. C., Leconte, A. M., Allen, B., Esvelt, K. M. & Liu, D. R. Experimental interrogation of the path dependence and stochasticity of protein evolution using phage-assisted continuous evolution. Proc Natl Acad Sci USA, (2013).

29 Leconte, A. M. et al. A population-based experimental model for protein evolution: effects of mutation rate and selection stringency on evolutionary outcomes. Biochemistry 52, 1490-1499, (2013).

30 Carlson, J. C., Badran, A. H., Guggiana-Nilo, D. A. & Liu, D. R. Negative selection and stringency modulation in phage-assisted continuous evolution. Nat Chem Biol 10, 216-222, (2014).

31 Entus, R., Aufderheide, B. & Sauro, H. M. Design and implementation of three incoherent feed-forward motif based biological concentration sensors. Syst Synth Biol 1, 119-128, (2007).

32 Jeruzalmi, D. & Steitz, T. A. Structure of T7 RNA polymerase complexed to the transcriptional inhibitor T7 lysozyme. EMBO J 17, 4101-4113, (1998).

33 Clark, V. C., Peter, J. A. & Nelson, D. R. New therapeutic strategies in HCV: second-generation protease inhibitors. Liver Int 33 Suppl 1, 80-84, (2013).

34 Maims, M. P. & von Hahn, T. Novel therapies for hepatitis C—one pill fits all? Nat Rev Drug Discov 12, 595-610, (2013).

35 Jiang, Y. et al. Discovery of danoprevir (ITMN-191/R7227), a highly selective and potent inhibitor of hepatitis C virus (HCV) NS3/4A protease. J Med Chem 57, 1753-1769, (2014).

36 Scola, P. M. et al. The discovery of asunaprevir (BMS-650032), an orally efficacious NS3 protease inhibitor for the treatment of hepatitis C virus infection. J Med Chem 57, 1730-1752, (2014).

37 Lim, S. R. et al. Virologic escape during danoprevir (ITMN-191/RG7227) monotherapy is hepatitis C virus subtype dependent and associated with R155K substitution. Antimicrob Agents Chemother 56, 271-279, (2012).

38 McPhee, F. et al. Resistance analysis of the hepatitis C virus NS3 protease inhibitor asunaprevir. Antimicrob Agents Chemother 56, 3670-3681, (2012).

39 McPhee, F. et al. Resistance analysis of hepatitis C virus genotype 1 prior treatment null responders receiving daclatasvir and asunaprevir. Hepatology 58, 902-911, (2013).

40 Imhof, I. & Simmonds, P. Genotype differences in susceptibility and resistance development of hepatitis C virus to protease inhibitors telaprevir (VX-950) and danoprevir (ITMN-191). Hepatology 53, 1090-1099, (2011).

41 Kapust, R. B. et al. Tobacco etch virus protease: mechanism of autolysis and rational design of stable mutants with wild-type catalytic proficiency. Protein Eng 14, 993-1000, (2001).

42 Herman, G. E. & Modrich, P. *Escherichia coli* K-12 clones that overproduce dam methylase are hypermutable. J Bacteriol 145, 644-646, (1981).

43 Fijalkowska, I. J. & Schaaper, R. M. Mutants in the Exo I motif of *Escherichia coli* dnaQ: defective proofreading and inviability due to error catastrophe. Proc Natl Acad Sci USA 93, 2856-2861, (1996).

44 Yang, H., Wolff, E., Kim, M., Diep, A. & Miller, J. H. Identification of mutator genes and mutational pathways in *Escherichia coli* using a multicopy cloning approach. Mol Microbiol 53, 283-295, (2004).

45 Bagg, A., Kenyon, C. J. & Walker, G. C. Inducibility of a gene product required for UV and chemical mutagenesis in *Escherichia coli*. Proc Natl Acad Sci USA 78, 5749-5753, (1981).

46 Burckhardt, S. E., Woodgate, R., Scheuermann, R H. & Echols, H. UmuD mutagenesis protein of *Escherichia coli*: overproduction, purification, and cleavage by RecA. Proc Natl Acad Sci USA 85, 1811-1815, (1988).

47 Mandi, A. A., Buckman, C., Harris, L. & Lloyd, R. G. Rep and PriA helicase activities prevent RecA from provoking unnecessary recombination during replication fork repair. Genes Dev 20, 2135-2147, (2006).

48 Carlson, J. C., Badran, A. H., Guggiana-Nilo, D. A. & Liu, D. R. Negative selection and stringency modulation enable phage-assisted continuous evolution (PACE) of enzymes with altered specificity. Accepted, (2013).

49 Cupples, C. G. & Miller, J. H. A set of lacZ mutations in *Escherichia coli* that allow rapid detection of each of the six base substitutions. Proc Natl Acad Sci USA 86, 5345-5349, (1989).

```
"<dam> - Genbank J01600.1 (Accession number.Version number)
                                                    (SEQ ID NO: 97)
   1 ggatcctttt tttctgcgcg taatctgctg cttgcaaaca aaaaaaccac cgc-
taccagc

  61 ggtggtttgt ttgccggatc tgaagtaatc aaggt-
tatct cccgcaatgg tttatcgttg

 121 cgg-
gagttgc ctgaagcgct ggatgctgtc ggagctttct ccacagccgg agaaggtgta

 181 attagttagt cagcatgaag aaaaatcgcg ctttttt-
gaa gtgggcaggg ggcaagtatc

 241 ccctgcttga tgatattaaa cggcat-
ttgc ccaagggcga atgtctggtt gagccttttg

 301 taggtgccgg gtcggtgttt ctcaacaccg acttttctcg ttacatcctt gccga-
tatca

 361 atagcgacct gatcagtctc tataacattg tgaagatgcg tactgatgag tacgta-
cagg

 421 ccgcacgcga gctgtttgtt cccgaaacaa attgcgccga ggtttactat cagttccgcg

 481 aagagttcaa caaaagccag gatccgttcc gtcgggcggt actgttttta tatttgaacc

 541 gctacggtta caacggcctg tgtcgttaca atctgcgcgg tgagtttaac gtgccgttcg

 601 gccgctacaa aaaaccctat ttcccggaag cagagttgta tcacttcgct gaaaaagcgc

 661 agaatgcctt tttctattgt gagtcttacg ccgatagcat ggcgcgcgca gatgatg-
cat

 721 ccgtcgtcta ttgcgatccg ccttatgcac cgctgtctgc gaccgc-
caac tttacggcgt

 781 atcacacaaa cagttttacg cttgaacaac aagcgcatct ggcg-
gagatc gccgaaggtc

 841 tggttgagcg ccatattcca gtgctgatct ccaatcacga tacgatgtta acgcgtgagt
```

-continued 901 ggtatcagcg cgcaaaattg catgtcgtca aagttcgacg cagtataagc agcaacggcg 961 gcacacgtaa aaaggtggac gaactgctgg ctttgtacaa accaggagtc gttt-
cacccg 1021 cgaaaaaata attctcaagg agaagcggat caaacagtat tttgattgcc ccct-
caattc 1081 tgtcggctga ttttgcccgc ctgggtgaag ataccgcaaa agccctggca gctg <seqA> - Genbank U07651.1 (Accession number.Version number)
(SEQ ID NO: 98)

1 aagcttccag atcttctttg ctgctttttg caatgtcatg gacatcggca acgtctt-
tac 61 caagctgttt ttgaatcatt tttgcgatat tttcggt-
att accggtgtcg ctgccgaaaa 121 agatgccagt gatagccatg agtgaaataa cctcttgaaa cttatt-
gaaa tgggggtgga 181 aaattgccca cggataaagg caatcat-
agc agaacaggca gtcttgcgga atcagcaaac 241 gagcaggact gcacactgtg ctacatgaaa gtggaaattt aaacgatgcc ctgac-
tacgc 301 agcgccgcca gttgctgcat taacatctct tcgatcagtt cgctacggct catat-
tgcgc 361 gactccgcca gctcgttcag cgcctcgaca gcttccgcgt tcagcttcag ttcgacacgc 421 ttaaggccac gtactttgtc gcgttttagc tggttgcgtt tat-
taatacg cagctgttca 481 tcgcgcgaaa gcggattagt tttcggtcgt cccggtcgac gctcgtgcgc gaaca-
gatct 541 aatgtcgtac ggtccgtttg ttctttggcc atgatcttgg tgacttcggg ggaaacaatc 601 agccaggcct ctgcccggat ggatagcgcg ccataataca tcagcgcgat gagt-
cacgcc 661 aacgcccacg cgcggaaagc gacgcggacg ctgggttttt aatcagttgc gttaat-
catt 721 gagatagcga cggatagcgc gtaataccgc atccggtttt tcag-
catgga cccagtgacc 781 cgcgcctgca atcacatgcg cccgtgcctg tggaaattga gccagtaaat cat-
cacggta 841 ctgctcgcta acatacggag aattgccgcc agggataaac agggcagggt gatcc-
catgc 901 cgggattttc tcccaaccta caatatgcgg atactgatcc cacaataccg gcacgt-
taaa 961 gcgccactcc ccgtcaacaa aagatttcag cagaaactga atcacccctt cttcat-
taag 1021 atgctggcgc attattgctg ctgcttgctg gcgagtttgt gcgtcc-
gatt cactgaccgc 1081 gttgatagcc gcaaaaatct catcatgacg gcgtacgtga tagtcgaccg gcgcga-
tatc 1141 gatcgccacc agtttatcga tgc-
gatcgga ggctagtgca gtaagtgcca ttaccgcttt 1201 accgcccatg gagtgaccga taaatgttgc tttgtcgatc tgctgtg-
cat ccagagtatc 1261 aacaagatcc tgcgccatcg ccgggtaatt cattaccgga tctctcggtg aaagaccgtg 1321 gttacgcata tcaacctgga tgatattgtg atcgtt-
tacc agatcgcgag ccagtacgcc 1381 aaggttgtcg aggctgccaa acagaccgtg gacaagaacg atgggagaat tat-
tgtgctg 1441 gttttgtgca gtttgcgcgc ggatattcaa ttt-
catggca aagttctttt tttcgcgttg -continued

```
1501 tcgggttagg gtattatgtt gaccattgtg ccacagggct gcaacaaata aggttt-
attc

1561 cgagtttttc tgcaagccag gcttgacgct atccgctgcc gggattt-
att catatactcc

1621 tggcgacttg tattcagcta agacactgca ctggat-
taag atgaaaacga ttgaagttga

1681 tgatgaactc tacagctata ttgccagcca cactaagcat atcggcgaga gcg-
catccga

1741 cattttacgg cgtatgttga aattttccgc cgcatcacag cctgctgctc cggtgacgaa

1801 agaggttcgc gttgcgtcac ctgctatcgt cgaagcgaag ccggtcaaaa cgattaaaga

1861 caaggttcgc gcaatgcgtg aacttctgct ttcggat-
gaa tacgcagagc aaaagcgagc

1921 ggtcaatcgc tttatgctgc tgttgtctac actatattct cttgacgccc aggcgtttgc

1981 cgaagcaacg gaatcgttgc acggtcgtac acgcgtttac tttgcggcag atgaacaaac

2041 gctgctgaaa aatggtaatc agaccaagcc gaaacatgtg ccaggcacgc cgtattgggt

2101 gatcaccaac accaacaccg gccgtaaatg cagcatgatc gaacacatca tgcagtc-
gat

2161 gcaattcccg gcggaattga ttgagaaggt ttgcggaact atctaaaacg ttgca-
gacaa

2221 aggacaaagc aatggcaatc cacaatcgtg caggccaacc tgcacaacag
     agtgatttga ."
```

All publications, patents, patent applications, publication, and database entries (e.g., sequence database entries) mentioned herein, e.g., in the Background, Summary, Detailed Description, Examples, and/or References sections, are hereby incorporated by reference in their entirety as if each individual publication, patent, patent application, publication, and database entry was specifically and individually incorporated herein by reference. In case of conflict, the present application, including any definitions herein, will control.

EQUIVALENTS AND SCOPE

Those skilled in the art will recognize, or be able to ascertain using no more than routine experimentation, many equivalents of the embodiments described herein. The scope of the present disclosure is not intended to be limited to the above description, but rather is as set forth in the appended claims.

Articles such as "a," "an," and "the" may mean one or more than one unless indicated to the contrary or otherwise evident from the context. Claims or descriptions that include "or" between two or more members of a group are considered satisfied if one, more than one, or all of the group members are present, unless indicated to the contrary or otherwise evident from the context. The disclosure of a group that includes "or" between two or more group members provides embodiments in which exactly one member of the group is present, embodiments in which more than one members of the group are present, and embodiments in which all of the group members are present. For purposes of brevity those embodiments have not been individually spelled out herein, but it will be understood that each of these embodiments is provided herein and may be specifically claimed or disclaimed.

It is to be understood that the invention encompasses all variations, combinations, and permutations in which one or more limitation, element, clause, or descriptive term, from one or more of the claims or from one or more relevant portion of the description, is introduced into another claim. For example, a claim that is dependent on another claim can be modified to include one or more of the limitations found in any other claim that is dependent on the same base claim. Furthermore, where the claims recite a composition, it is to be understood that methods of making or using the composition according to any of the methods of making or using disclosed herein or according to methods known in the art, if any, are included, unless otherwise indicated or unless it would be evident to one of ordinary skill in the art that a contradiction or inconsistency would arise.

Where elements are presented as lists, e.g., in Markush group format, it is to be understood that every possible subgroup of the elements is also disclosed, and that any element or subgroup of elements can be removed from the group. It is also noted that the term "comprising" is intended to be open and permits the inclusion of additional elements or steps. It should be understood that, in general, where an embodiment, product, or method is referred to as comprising particular elements, features, or steps, embodiments, products, or methods that consist, or consist essentially of, such elements, features, or steps, are provided as well. For purposes of brevity those embodiments have not been individually spelled out herein, but it will be understood that each of these embodiments is provided herein and may be specifically claimed or disclaimed.

Where ranges are given, endpoints are included. Furthermore, it is to be understood that unless otherwise indicated or otherwise evident from the context and/or the understanding of one of ordinary skill in the art, values that are expressed as ranges can assume any specific value within the stated ranges in some embodiments, to the tenth of the unit of the lower limit of the range, unless the context clearly dictates otherwise. For purposes of brevity, the values in each range have not been individually spelled out herein, but it will be understood that each of these values is provided herein and may be specifically claimed or disclaimed. It is also to be understood that unless otherwise indicated or otherwise evident from the context and/or the understanding of one of ordinary skill in the art, values expressed as ranges can assume any subrange within the given range, wherein the endpoints of the subrange are expressed to the same degree of accuracy as the tenth of the unit of the lower limit of the range.

In addition, it is to be understood that any particular embodiment of the present invention may be explicitly excluded from any one or more of the claims. Where ranges are given, any value within the range may explicitly be excluded from any one or more of the claims. Any embodiment, element, feature, application, or aspect of the compositions and/or methods of the invention, can be excluded from any one or more claims. For purposes of brevity, all of the embodiments in which one or more elements, features, purposes, or aspects is excluded are not set forth explicitly herein.

What is claimed is:

1. A mutagenesis plasmid comprising a gene expression cassette encoding:

(i) a deoxyadenosine methylase, wherein the methylase is dam;

(ii) a hemimethylated-GATC binding domain, wherein the hemimethylated-GATC binding domain is seqA; and (iii) a dominant-negative *E. coli* DNA polymerase III proofreading subunit, wherein the dominant-negative *E. coli* DNA polymerase III proofreading subunit is dnaQ926; wherein the expression cassette does not encode recA730.

2. The mutagenesis plasmid of claim 1, wherein dam is encoded by a nucleic acid sequence comprising the sequence set forth in SEQ ID NO: 97.

3. The mutagenesis plasmid of claim 1, wherein seqA is encoded by a nucleic acid sequence comprising the sequence set forth in SEQ ID NO: 98.

4. The mutagenesis plasmid of claim 1, wherein the expression cassette does not encode UmuD.

5. The mutagenesis plasmid of claim 1, wherein the expression cassette comprises a pBAD promoter.

6. The mutagenesis plasmid of claim 1 comprising the sequence set forth in SEQ ID NO: 21.

7. The mutagenesis plasmid of claim 1, wherein the dnaQ926 is encoded by the sequence set forth in nucleotides 2,166 through 2,897 of SEQ ID NO: 21.

8. The mutagenesis plasmid of claim 1, wherein the dam is encoded by the sequence set forth in nucleotides 2,926 through 3,762 of SEQ ID NO: 21.

9. The mutagenesis plasmid of claim 1, wherein the seqA is encoded by the sequence set forth in nucleotides 3,791 through 4,336 of SEQ ID NO: 21.

10. A cell comprising the mutagenesis plasmid of claim 1.

11. The cell of claim 10, wherein the cell is an *E. coli* cell.

12. A container housing a plurality of cells comprising the mutagenesis plasmid of claim 1.

* * * * *

SEQUENCE LISTING

```
<160> NUMBER OF SEQ ID NOS: 98

<210> SEQ ID NO 1
<211> LENGTH: 6407
<212> TYPE: DNA
<213> ORGANISM: Enterobacteria phage M13

<400> SEQUENCE: 1

aacgctacta ctattagtag aattgatgcc accttttcag ctcgcgcccc aaatgaaaat     60

atagctaaac aggttattga ccatttgcga aatgtatcta atggtcaaac taaatctact    120

cgttcgcaga attgggaatc aactgttaca tggaatgaaa cttccagaca ccgtacttta    180

gttgcatatt taaaacatgt tgagctacag caccagattc agcaattaag ctctaagcca    240

tccgcaaaaa tgacctctta tcaaaaggag caattaaagg tactctctaa tcctgacctg    300

ttggagtttg cttccggtct ggttcgcttt gaagctcgaa ttaaaacgcg atatttgaag    360

tctttcgggc ttcctcttaa tctttttgat gcaatccgct ttgcttctga ctataatagt    420

cagggtaaag acctgatttt tgatttatgg tcattctcgt tttctgaact gtttaaagca    480

tttgaggggg attcaatgaa tatttatgac gattccgcag tattggacgc tatccagtct    540

aaacatttta ctattacccc ctctggcaaa acttcttttg caaaagcctc tcgctatttt    600

ggtttttatc gtcgtctggt aaacgagggt tatgatagtg ttgctcttac tatgcctcgt    660

aattcctttt ggcgttatgt atctgcatta gttgaatgtg gtattcctaa atctcaactg    720

atgaatcttt ctacctgtaa taatgttgtt ccgttagttc gttttattaa cgtagatttt    780

tcttcccaac gtcctgactg gtataatgag ccagttctta aaatcgcata aggtaattca    840

caatgattaa agttgaaatt aaaccatctc aagcccaatt tactactcgt tctggtgttt    900

ctcgtcaggg caagccttat tcactgaatg agcagctttg ttacgttgat ttgggtaatg    960

aatatccggt tcttgtcaag attactcttg atgaaggtca gccagcctat gcgcctggtc   1020

tgtacaccgt tcatctgtcc tctttcaaag ttggtcagtt cggttccctt atgattgacc   1080

gtctgcgcct cgttccggct aagtaacatg gagcaggtcg cggatttcga cacaatttat   1140

caggcgatga tacaaatctc cgttgtactt tgtttcgcgc ttggtataat cgctgggggt   1200

caaagatgag tgttttagtg tattctttcg cctctttcgt tttaggttgg tgccttcgta   1260

gtggcattac gtattttacc cgtttaatgg aaacttcctc atgaaaaagt ctttagtcct   1320

caaagcctct gtagccgttg ctaccctcgt tccgatgctg tctttcgctg ctgagggtga   1380

cgatcccgca aaagcggcct ttaactccct gcaagcctca gcgaccgaat atatcggtta   1440

tgcgtgggcg atggttgttg tcattgtcgg cgcaactatc ggtatcaagc tgtttaagaa   1500

attcacctcg aaagcaagct gataaaccga tacaattaaa ggctcctttt ggagcctttt   1560

tttttggaga ttttcaacat gaaaaaatta ttattcgcaa ttcctttagt tgttcctttc   1620

tattctcact ccgctgaaac tgttgaaagt tgtttagcaa aaccccatac agaaaattca   1680

tttactaacg tctggaaaga cgacaaaact ttagatcgtt acgctaacta tgagggttgt   1740
```

```
ctgtggaatg ctacaggcgt tgtagtttgt actggtgacg aaactcagtg ttacggtaca   1800
tgggttccta ttgggcttgc tatccctgaa aatgagggtg gtggctctga gggtggcggt   1860
tctgagggtg gcggttctga gggtggcggt actaaacctc ctgagtacgg tgatacacct   1920
attccgggct atacttatat caaccctctc gacggcactt atccgcctgg tactgagcaa   1980
aaccccgcta atcctaatcc ttctcttgag gagtctcagc ctcttaatac tttcatgttt   2040
cagaataata ggttccgaaa taggcagggg gcattaactg tttatacggg cactgttact   2100
caaggcactg accccgttaa aacttattac cagtacactc ctgtatcatc aaaagccatg   2160
tatgacgctt actggaacgg taaattcaga gactgcgctt tccattctgg ctttaatgag   2220
gatccattcg tttgtgaata tcaaggccaa tcgtctgacc tgcctcaacc tcctgtcaat   2280
gctggcggcg gctctggtgg tggttctggt ggcggctctg agggtggtgg ctctgagggt   2340
ggcggttctg agggtggcgg ctctgaggga ggcggttccg gtggtggctc tggttccggt   2400
gattttgatt atgaaaagat ggcaaacgct aataaggggg ctatgaccga aaatgccgat   2460
gaaaacgcgc tacagtctga cgctaaaggc aaacttgatt ctgtcgctac tgattacggt   2520
gctgctatcg atggtttcat tggtgacgtt tccggccttg ctaatggtaa tggtgctact   2580
ggtgattttg ctggctctaa ttcccaaatg gctcaagtcg gtgacggtga taattcacct   2640
ttaatgaata atttccgtca atatttacct tccctccctc aatcggttga atgtcgccct   2700
tttgtcttta gcgctggtaa accatatgaa ttttctattg attgtgacaa aataaactta   2760
ttccgtggtg tctttgcgtt tcttttatat gttgccacct ttatgtatgt attttctacg   2820
tttgctaaca tactgcgtaa taaggagtct taatcatgcc agttcttttg ggtattccgt   2880
tattattgcg tttcctcggt ttccttctgg taactttgtt cggctatctg cttacttttc   2940
ttaaaaaggg cttcggtaag atagctattg ctatttcatt gtttcttgct cttattattg   3000
ggcttaactc aattcttgtg ggttatctct ctgatattag cgctcaatta ccctctgact   3060
ttgttcaggg tgttcagtta attctcccgt ctaatgcgct tccctgtttt tatgttattc   3120
tctctgtaaa ggctgctatt ttcatttttg acgttaaaca aaaaatcgtt tcttatttgg   3180
attgggataa ataatatggc tgtttatttt gtaactggca aattaggctc tggaaagacg   3240
ctcgttagcg ttggtaagat tcaggataaa attgtagctg ggtgcaaaat agcaactaat   3300
cttgatttaa ggcttcaaaa cctcccgcaa gtcgggaggt tcgctaaaac gcctcgcgtt   3360
cttagaatac cggataagcc ttctatatct gatttgcttg ctattgggcg cggtaatgat   3420
tcctacgatg aaaataaaaa cggcttgctt gttctcgatg agtgcggtac ttggtttaat   3480
acccgttctt ggaatgataa ggaaagacag ccgattattg attggtttct acatgctcgt   3540
aaattaggat gggatattat ttttcttgtt caggacttat ctattgttga taaacaggcg   3600
cgttctgcat tagctgaaca tgttgtttat tgtcgtcgtc tggacagaat tactttacct   3660
tttgtcggta ctttatattc tcttattact ggctcgaaaa tgcctctgcc taaattacat   3720
gttggcgttg ttaaatatgg cgattctcaa ttaagcccta ctgttgagcg ttggctttat   3780
actggtaaga atttgtataa cgcatatgat actaaacagg ctttttctag taattatgat   3840
tccggtgttt attcttattt aacgccttat ttatcacacg gtcggtattt caaaccatta   3900
aatttaggtc agaagatgaa attaactaaa atatatttga aaaagttttc tcgcgttctt   3960
tgtcttgcga ttggatttgc atcagcattt acatatagtt atataaccca acctaagccg   4020
gaggttaaaa aggtagtctc tcagacctat gattttgata aattcactat tgactcttct   4080
```

-continued

```
cagcgtctta atctaagcta tcgctatgtt ttcaaggatt ctaagggaaa attaattaat   4140
agcgacgatt tacagaagca aggttattca ctcacatata ttgatttatg tactgtttcc   4200
attaaaaaag gtaattcaaa tgaaattgtt aaatgtaatt aattttgttt tcttgatgtt   4260
tgtttcatca tcttcttttg ctcaggtaat tgaaatgaat aattcgcctc tgcgcgattt   4320
tgtaacttgg tattcaaagc aatcaggcga atccgttatt gtttctcccg atgtaaaagg   4380
tactgttact gtatattcat ctgacgttaa acctgaaaat ctacgcaatt tctttatttc   4440
tgttttacgt gctaataatt ttgatatggt tggttcaatt ccttccataa ttcagaagta   4500
taatccaaac aatcaggatt atattgatga attgccatca tctgataatc aggaatatga   4560
tgataattcc gctccttctg gtggtttctt tgttccgcaa aatgataatg ttactcaaac   4620
ttttaaaatt aataacgttc gggcaaagga tttaatacga gttgtcgaat tgtttgtaaa   4680
gtctaatact tctaaatcct caaatgtatt atctattgac ggctctaatc tattagttgt   4740
tagtgcacct aaagatattt tagataacct tcctcaattc ctttctactg ttgatttgcc   4800
aactgaccag atattgattg agggtttgat atttgaggtt cagcaaggtg atgctttaga   4860
tttttcattt gctgctggct ctcagcgtgg cactgttgca ggcggtgtta atactgaccg   4920
cctcacctct gttttatctt ctgctggtgg ttcgttcggt atttttaatg gcgatgtttt   4980
agggctatca gttcgcgcat taaagactaa tagccattca aaaatattgt ctgtgccacg   5040
tattcttacg ctttcaggtc agaagggttc tatctctgtt ggccagaatg tccctttat    5100
tactggtcgt gtgactggtg aatctgccaa tgtaaataat ccatttcaga cgattgagcg   5160
tcaaaatgta ggtatttcca tgagcgtttt tcctgttgca atggctggcg gtaatattgt   5220
tctggatatt accagcaagg ccgatagttt gagttcttct actcaggcaa gtgatgttat   5280
tactaatcaa agaagtattg ctacaacggt taatttgcgt gatggacaga ctcttttact   5340
cggtggcctc actgattata aaaacacttc tcaagattct ggcgtaccgt tcctgtctaa   5400
aatcccttta atcggcctcc tgtttagctc ccgctctgat tccaacgagg aaagcacgtt   5460
atacgtgctc gtcaaagcaa ccatagtacg cgccctgtag cggcgcatta agcgcggcgg   5520
gtgtggtggt tacgcgcagc gtgaccgcta cacttgccag cgccctagcg cccgctcctt   5580
tcgctttctt cccttccttt ctcgccacgt tcgccggctt tccccgtcaa gctctaaatc   5640
gggggctccc tttagggttc cgatttagtg ctttacggca cctcgacccc aaaaaacttg   5700
atttgggtga tggttcacgt agtgggccat cgccctgata gacggttttt cgccctttga   5760
cgttggagtc cacgttcttt aatagtggac tcttgttcca aactggaaca acactcaacc   5820
ctatctcggg ctattctttt gatttataag ggattttgcc gatttcggcc tattggttaa   5880
aaaatgagct gatttaacaa aaatttaacg cgaattttaa caaaatatta acgtttacaa   5940
tttaaatatt tgcttataca atcttcctgt ttttggggct tttctgatta tcaaccgggg   6000
tacatatgat tgacatgcta gttttacgat taccgttcat cgattctctt gtttgctcca   6060
gactctcagg caatgacctg atagcctttg tagacctctc aaaaatagct accctctccg   6120
gcatgaattt atcagctaga acggttgaat atcatattga tggtgatttg actgtctccg   6180
gcctttctca cccttttgaa tctttaccta cacattactc aggcattgca tttaaaatat   6240
atgagggttc taaaaatttt tatccttgcg ttgaaataaa ggcttctccc gcaaaagtat   6300
tacagggtca taatgttttt ggtacaaccg atttagcttt atgctctgag gctttattgc   6360
ttaattttgc taattctttg ccttgcctgt atgatttatt ggatgtt                 6407
```

<210> SEQ ID NO 2
<211> LENGTH: 410
<212> TYPE: PRT
<213> ORGANISM: Enterobacteria phage M13

<400> SEQUENCE: 2

```
Met Ile Asp Met Leu Val Leu Arg Leu Pro Phe Ile Asp Ser Leu Val
1               5                   10                  15

Cys Ser Arg Leu Ser Gly Asn Asp Leu Ile Ala Phe Val Asp Leu Ser
            20                  25                  30

Lys Ile Ala Thr Leu Ser Gly Met Asn Leu Ser Ala Arg Thr Val Glu
        35                  40                  45

Tyr His Ile Asp Gly Asp Leu Thr Val Ser Gly Leu Ser His Pro Phe
    50                  55                  60

Glu Ser Leu Pro Thr His Tyr Ser Gly Ile Ala Phe Lys Ile Tyr Glu
65                  70                  75                  80

Gly Ser Lys Asn Phe Tyr Pro Cys Val Glu Ile Lys Ala Ser Pro Ala
                85                  90                  95

Lys Val Leu Gln Gly His Asn Val Phe Gly Thr Thr Asp Leu Ala Leu
            100                 105                 110

Cys Ser Glu Ala Leu Leu Leu Asn Phe Ala Asn Ser Leu Pro Cys Leu
        115                 120                 125

Tyr Asp Leu Leu Asp Val Asn Ala Thr Thr Ile Ser Arg Ile Asp Ala
    130                 135                 140

Thr Phe Ser Ala Arg Ala Pro Asn Glu Asn Ile Ala Lys Gln Val Ile
145                 150                 155                 160

Asp His Leu Arg Asn Val Ser Asn Gly Gln Thr Lys Ser Thr Arg Ser
                165                 170                 175

Gln Asn Trp Glu Ser Thr Val Thr Trp Asn Glu Thr Ser Arg His Arg
            180                 185                 190

Thr Leu Val Ala Tyr Leu Lys His Val Glu Leu Gln His Gln Ile Gln
        195                 200                 205

Gln Leu Ser Ser Lys Pro Ser Ala Lys Met Thr Ser Tyr Gln Lys Glu
    210                 215                 220

Gln Leu Lys Val Leu Ser Asn Pro Asp Leu Leu Glu Phe Ala Ser Gly
225                 230                 235                 240

Leu Val Arg Phe Glu Ala Arg Ile Lys Thr Arg Tyr Leu Lys Ser Phe
                245                 250                 255

Gly Leu Pro Leu Asn Leu Phe Asp Ala Ile Arg Phe Ala Ser Asp Tyr
            260                 265                 270

Asn Ser Gln Gly Lys Asp Leu Ile Phe Asp Leu Trp Ser Phe Ser Phe
        275                 280                 285

Ser Glu Leu Phe Lys Ala Phe Glu Gly Asp Ser Met Asn Ile Tyr Asp
    290                 295                 300

Asp Ser Ala Val Leu Asp Ala Ile Gln Ser Lys His Phe Thr Ile Thr
305                 310                 315                 320

Pro Ser Gly Lys Thr Ser Phe Ala Lys Ala Ser Arg Tyr Phe Gly Phe
                325                 330                 335

Tyr Arg Arg Leu Val Asn Glu Gly Tyr Asp Ser Val Ala Leu Thr Met
            340                 345                 350

Pro Arg Asn Ser Phe Trp Arg Tyr Val Ser Ala Leu Val Glu Cys Gly
        355                 360                 365

Ile Pro Lys Ser Gln Leu Met Asn Leu Ser Thr Cys Asn Asn Val Val
    370                 375                 380
```

```
Pro Leu Val Arg Phe Ile Asn Val Asp Phe Ser Ser Gln Arg Pro Asp
385                 390                 395                 400

Trp Tyr Asn Glu Pro Val Leu Lys Ile Ala
                405                 410


<210> SEQ ID NO 3
<211> LENGTH: 111
<212> TYPE: PRT
<213> ORGANISM: Enterobacteria phage M13

<400> SEQUENCE: 3

Met Asn Ile Tyr Asp Asp Ser Ala Val Leu Asp Ala Ile Gln Ser Lys
1               5                   10                  15

His Phe Thr Ile Thr Pro Ser Gly Lys Thr Ser Phe Ala Lys Ala Ser
            20                  25                  30

Arg Tyr Phe Gly Phe Tyr Arg Arg Leu Val Asn Glu Gly Tyr Asp Ser
        35                  40                  45

Val Ala Leu Thr Met Pro Arg Asn Ser Phe Trp Arg Tyr Val Ser Ala
    50                  55                  60

Leu Val Glu Cys Gly Ile Pro Lys Ser Gln Leu Met Asn Leu Ser Thr
65                  70                  75                  80

Cys Asn Asn Val Val Pro Leu Val Arg Phe Ile Asn Val Asp Phe Ser
                85                  90                  95

Ser Gln Arg Pro Asp Trp Tyr Asn Glu Pro Val Leu Lys Ile Ala
            100                 105                 110


<210> SEQ ID NO 4
<211> LENGTH: 87
<212> TYPE: PRT
<213> ORGANISM: Enterobacteria phage M13

<400> SEQUENCE: 4

Met Ile Lys Val Glu Ile Lys Pro Ser Gln Ala Gln Phe Thr Thr Arg
1               5                   10                  15

Ser Gly Val Ser Arg Gln Gly Lys Pro Tyr Ser Leu Asn Glu Gln Leu
            20                  25                  30

Cys Tyr Val Asp Leu Gly Asn Glu Tyr Pro Val Leu Val Lys Ile Thr
        35                  40                  45

Leu Asp Glu Gly Gln Pro Ala Tyr Ala Pro Gly Leu Tyr Thr Val His
    50                  55                  60

Leu Ser Ser Phe Lys Val Gly Gln Phe Gly Ser Leu Met Ile Asp Arg
65                  70                  75                  80

Leu Arg Leu Val Pro Ala Lys
                85


<210> SEQ ID NO 5
<211> LENGTH: 33
<212> TYPE: PRT
<213> ORGANISM: Enterobacteria phage M13

<400> SEQUENCE: 5

Met Glu Gln Val Ala Asp Phe Asp Thr Ile Tyr Gln Ala Met Ile Gln
1               5                   10                  15

Ile Ser Val Val Leu Cys Phe Ala Leu Gly Ile Ile Ala Gly Gly Gln
            20                  25                  30

Arg


<210> SEQ ID NO 6
```

```
<211> LENGTH: 32
<212> TYPE: PRT
<213> ORGANISM: Enterobacteria phage M13

<400> SEQUENCE: 6

Met Ser Val Leu Val Tyr Ser Phe Ala Ser Phe Val Leu Gly Trp Cys
1               5                   10                  15

Leu Arg Ser Gly Ile Thr Tyr Phe Thr Arg Leu Met Glu Thr Ser Ser
            20                  25                  30


<210> SEQ ID NO 7
<211> LENGTH: 73
<212> TYPE: PRT
<213> ORGANISM: Enterobacteria phage M13

<400> SEQUENCE: 7

Met Lys Lys Ser Leu Val Leu Lys Ala Ser Val Ala Val Ala Thr Leu
1               5                   10                  15

Val Pro Met Leu Ser Phe Ala Ala Glu Gly Asp Asp Pro Ala Lys Ala
            20                  25                  30

Ala Phe Asn Ser Leu Gln Ala Ser Ala Thr Glu Tyr Ile Gly Tyr Ala
        35                  40                  45

Trp Ala Met Val Val Val Ile Val Gly Ala Thr Ile Gly Ile Lys Leu
    50                  55                  60

Phe Lys Lys Phe Thr Ser Lys Ala Ser
65                  70


<210> SEQ ID NO 8
<211> LENGTH: 424
<212> TYPE: PRT
<213> ORGANISM: Enterobacteria phage M13

<400> SEQUENCE: 8

Met Lys Lys Leu Leu Phe Ala Ile Pro Leu Val Val Pro Phe Tyr Ser
1               5                   10                  15

His Ser Ala Glu Thr Val Glu Ser Cys Leu Ala Lys Pro His Thr Glu
            20                  25                  30

Asn Ser Phe Thr Asn Val Trp Lys Asp Asp Lys Thr Leu Asp Arg Tyr
        35                  40                  45

Ala Asn Tyr Glu Gly Cys Leu Trp Asn Ala Thr Gly Val Val Val Cys
    50                  55                  60

Thr Gly Asp Glu Thr Gln Cys Tyr Gly Thr Trp Val Pro Ile Gly Leu
65                  70                  75                  80

Ala Ile Pro Glu Asn Glu Gly Gly Gly Ser Glu Gly Gly Gly Ser Glu
                85                  90                  95

Gly Gly Gly Ser Glu Gly Gly Gly Thr Lys Pro Pro Glu Tyr Gly Asp
            100                 105                 110

Thr Pro Ile Pro Gly Tyr Thr Tyr Ile Asn Pro Leu Asp Gly Thr Tyr
        115                 120                 125

Pro Pro Gly Thr Glu Gln Asn Pro Ala Asn Pro Asn Pro Ser Leu Glu
    130                 135                 140

Glu Ser Gln Pro Leu Asn Thr Phe Met Phe Gln Asn Asn Arg Phe Arg
145                 150                 155                 160

Asn Arg Gln Gly Ala Leu Thr Val Tyr Thr Gly Thr Val Thr Gln Gly
                165                 170                 175

Thr Asp Pro Val Lys Thr Tyr Tyr Gln Tyr Thr Pro Val Ser Ser Lys
            180                 185                 190
```

```
Ala Met Tyr Asp Ala Tyr Trp Asn Gly Lys Phe Arg Asp Cys Ala Phe
        195                 200                 205

His Ser Gly Phe Asn Glu Asp Pro Phe Val Cys Glu Tyr Gln Gly Gln
    210                 215                 220

Ser Ser Asp Leu Pro Gln Pro Pro Val Asn Ala Gly Gly Gly Ser Gly
225                 230                 235                 240

Gly Gly Ser Gly Gly Gly Ser Glu Gly Gly Gly Ser Glu Gly Gly Gly
                245                 250                 255

Ser Glu Gly Gly Gly Ser Glu Gly Gly Gly Ser Gly Gly Gly Ser Gly
            260                 265                 270

Ser Gly Asp Phe Asp Tyr Glu Lys Met Ala Asn Ala Asn Lys Gly Ala
        275                 280                 285

Met Thr Glu Asn Ala Asp Glu Asn Ala Leu Gln Ser Asp Ala Lys Gly
    290                 295                 300

Lys Leu Asp Ser Val Ala Thr Asp Tyr Gly Ala Ala Ile Asp Gly Phe
305                 310                 315                 320

Ile Gly Asp Val Ser Gly Leu Ala Asn Gly Asn Gly Ala Thr Gly Asp
                325                 330                 335

Phe Ala Gly Ser Asn Ser Gln Met Ala Gln Val Gly Asp Gly Asp Asn
            340                 345                 350

Ser Pro Leu Met Asn Asn Phe Arg Gln Tyr Leu Pro Ser Leu Pro Gln
        355                 360                 365

Ser Val Glu Cys Arg Pro Phe Val Phe Ser Ala Gly Lys Pro Tyr Glu
    370                 375                 380

Phe Ser Ile Asp Cys Asp Lys Ile Asn Leu Phe Arg Gly Val Phe Ala
385                 390                 395                 400

Phe Leu Leu Tyr Val Ala Thr Phe Met Tyr Val Phe Ser Thr Phe Ala
                405                 410                 415

Asn Ile Leu Arg Asn Lys Glu Ser
            420
```

<210> SEQ ID NO 9
<211> LENGTH: 112
<212> TYPE: PRT
<213> ORGANISM: Enterobacteria phage M13

<400> SEQUENCE: 9

```
Met Pro Val Leu Leu Gly Ile Pro Leu Leu Leu Arg Phe Leu Gly Phe
1               5                   10                  15

Leu Leu Val Thr Leu Phe Gly Tyr Leu Leu Thr Phe Leu Lys Lys Gly
            20                  25                  30

Phe Gly Lys Ile Ala Ile Ala Ile Ser Leu Phe Leu Ala Leu Ile Ile
        35                  40                  45

Gly Leu Asn Ser Ile Leu Val Gly Tyr Leu Ser Asp Ile Ser Ala Gln
    50                  55                  60

Leu Pro Ser Asp Phe Val Gln Gly Val Gln Leu Ile Leu Pro Ser Asn
65                  70                  75                  80

Ala Leu Pro Cys Phe Tyr Val Ile Leu Ser Val Lys Ala Ala Ile Phe
                85                  90                  95

Ile Phe Asp Val Lys Gln Lys Ile Val Ser Tyr Leu Asp Trp Asp Lys
            100                 105                 110
```

<210> SEQ ID NO 10
<211> LENGTH: 348
<212> TYPE: PRT
<213> ORGANISM: Enterobacteria phage M13

<400> SEQUENCE: 10

```
Met Ala Val Tyr Phe Val Thr Gly Lys Leu Gly Ser Gly Lys Thr Leu
1               5                   10                  15

Val Ser Val Gly Lys Ile Gln Asp Lys Ile Val Ala Gly Cys Lys Ile
            20                  25                  30

Ala Thr Asn Leu Asp Leu Arg Leu Gln Asn Leu Pro Gln Val Gly Arg
        35                  40                  45

Phe Ala Lys Thr Pro Arg Val Leu Arg Ile Pro Asp Lys Pro Ser Ile
    50                  55                  60

Ser Asp Leu Leu Ala Ile Gly Arg Gly Asn Asp Ser Tyr Asp Glu Asn
65                  70                  75                  80

Lys Asn Gly Leu Leu Val Leu Asp Glu Cys Gly Thr Trp Phe Asn Thr
                85                  90                  95

Arg Ser Trp Asn Asp Lys Glu Arg Gln Pro Ile Ile Asp Trp Phe Leu
            100                 105                 110

His Ala Arg Lys Leu Gly Trp Asp Ile Ile Phe Leu Val Gln Asp Leu
        115                 120                 125

Ser Ile Val Asp Lys Gln Ala Arg Ser Ala Leu Ala Glu His Val Val
    130                 135                 140

Tyr Cys Arg Arg Leu Asp Arg Ile Thr Leu Pro Phe Val Gly Thr Leu
145                 150                 155                 160

Tyr Ser Leu Ile Thr Gly Ser Lys Met Pro Leu Pro Lys Leu His Val
                165                 170                 175

Gly Val Val Lys Tyr Gly Asp Ser Gln Leu Ser Pro Thr Val Glu Arg
            180                 185                 190

Trp Leu Tyr Thr Gly Lys Asn Leu Tyr Asn Ala Tyr Asp Thr Lys Gln
        195                 200                 205

Ala Phe Ser Ser Asn Tyr Asp Ser Gly Val Tyr Ser Tyr Leu Thr Pro
    210                 215                 220

Tyr Leu Ser His Gly Arg Tyr Phe Lys Pro Leu Asn Leu Gly Gln Lys
225                 230                 235                 240

Met Lys Leu Thr Lys Ile Tyr Leu Lys Lys Phe Ser Arg Val Leu Cys
                245                 250                 255

Leu Ala Ile Gly Phe Ala Ser Ala Phe Thr Tyr Ser Tyr Ile Thr Gln
            260                 265                 270

Pro Lys Pro Glu Val Lys Lys Val Val Ser Gln Thr Tyr Asp Phe Asp
        275                 280                 285

Lys Phe Thr Ile Asp Ser Ser Gln Arg Leu Asn Leu Ser Tyr Arg Tyr
    290                 295                 300

Val Phe Lys Asp Ser Lys Gly Lys Leu Ile Asn Ser Asp Asp Leu Gln
305                 310                 315                 320

Lys Gln Gly Tyr Ser Leu Thr Tyr Ile Asp Leu Cys Thr Val Ser Ile
                325                 330                 335

Lys Lys Gly Asn Ser Asn Glu Ile Val Lys Cys Asn
            340                 345
```

<210> SEQ ID NO 11
<211> LENGTH: 426
<212> TYPE: PRT
<213> ORGANISM: Enterobacteria phage M13

<400> SEQUENCE: 11

```
Met Lys Leu Leu Asn Val Ile Asn Phe Val Phe Leu Met Phe Val Ser
1               5                   10                  15
```

```
Ser Ser Ser Phe Ala Gln Val Ile Glu Met Asn Asn Ser Pro Leu Arg
            20                  25                  30

Asp Phe Val Thr Trp Tyr Ser Lys Gln Ser Gly Glu Ser Val Ile Val
        35                  40                  45

Ser Pro Asp Val Lys Gly Thr Val Thr Val Tyr Ser Ser Asp Val Lys
    50                  55                  60

Pro Glu Asn Leu Arg Asn Phe Phe Ile Ser Val Leu Arg Ala Asn Asn
65                  70                  75                  80

Phe Asp Met Val Gly Ser Ile Pro Ser Ile Ile Gln Lys Tyr Asn Pro
                85                  90                  95

Asn Asn Gln Asp Tyr Ile Asp Glu Leu Pro Ser Ser Asp Asn Gln Glu
            100                 105                 110

Tyr Asp Asp Asn Ser Ala Pro Ser Gly Gly Phe Phe Val Pro Gln Asn
        115                 120                 125

Asp Asn Val Thr Gln Thr Phe Lys Ile Asn Asn Val Arg Ala Lys Asp
    130                 135                 140

Leu Ile Arg Val Val Glu Leu Phe Val Lys Ser Asn Thr Ser Lys Ser
145                 150                 155                 160

Ser Asn Val Leu Ser Ile Asp Gly Ser Asn Leu Leu Val Val Ser Ala
                165                 170                 175

Pro Lys Asp Ile Leu Asp Asn Leu Pro Gln Phe Leu Ser Thr Val Asp
            180                 185                 190

Leu Pro Thr Asp Gln Ile Leu Ile Glu Gly Leu Ile Phe Glu Val Gln
        195                 200                 205

Gln Gly Asp Ala Leu Asp Phe Ser Phe Ala Ala Gly Ser Gln Arg Gly
    210                 215                 220

Thr Val Ala Gly Gly Val Asn Thr Asp Arg Leu Thr Ser Val Leu Ser
225                 230                 235                 240

Ser Ala Gly Gly Ser Phe Gly Ile Phe Asn Gly Asp Val Leu Gly Leu
                245                 250                 255

Ser Val Arg Ala Leu Lys Thr Asn Ser His Ser Lys Ile Leu Ser Val
            260                 265                 270

Pro Arg Ile Leu Thr Leu Ser Gly Gln Lys Gly Ser Ile Ser Val Gly
        275                 280                 285

Gln Asn Val Pro Phe Ile Thr Gly Arg Val Thr Gly Glu Ser Ala Asn
    290                 295                 300

Val Asn Asn Pro Phe Gln Thr Ile Glu Arg Gln Asn Val Gly Ile Ser
305                 310                 315                 320

Met Ser Val Phe Pro Val Ala Met Ala Gly Gly Asn Ile Val Leu Asp
                325                 330                 335

Ile Thr Ser Lys Ala Asp Ser Leu Ser Ser Ser Thr Gln Ala Ser Asp
            340                 345                 350

Val Ile Thr Asn Gln Arg Ser Ile Ala Thr Thr Val Asn Leu Arg Asp
        355                 360                 365

Gly Gln Thr Leu Leu Leu Gly Gly Leu Thr Asp Tyr Lys Asn Thr Ser
    370                 375                 380

Gln Asp Ser Gly Val Pro Phe Leu Ser Lys Ile Pro Leu Ile Gly Leu
385                 390                 395                 400

Leu Phe Ser Ser Arg Ser Asp Ser Asn Glu Glu Ser Thr Leu Tyr Val
                405                 410                 415

Leu Val Lys Ala Thr Ile Val Arg Ala Leu
            420                 425
```

<210> SEQ ID NO 12
<211> LENGTH: 242
<212> TYPE: PRT
<213> ORGANISM: Artificial Sequence
<220> FEATURE:
<223> OTHER INFORMATION: Synthetic Polypeptide

<400> SEQUENCE: 12

```
Gly Glu Ser Leu Phe Lys Gly Pro Arg Asp Tyr Asn Pro Ile Ser Ser
1               5                   10                  15

Thr Ile Cys His Leu Thr Asn Glu Ser Asp Gly His Thr Thr Ser Leu
            20                  25                  30

Tyr Gly Ile Gly Phe Gly Pro Phe Ile Ile Thr Asn Lys His Leu Phe
        35                  40                  45

Arg Arg Asn Asn Gly Thr Leu Leu Val Gln Ser Leu His Gly Val Phe
    50                  55                  60

Lys Val Lys Asn Thr Thr Thr Leu Gln Gln His Leu Ile Asp Gly Arg
65                  70                  75                  80

Asp Met Ile Ile Ile Arg Met Pro Lys Asp Phe Pro Pro Phe Pro Gln
                85                  90                  95

Lys Leu Lys Phe Arg Glu Pro Gln Arg Glu Glu Arg Ile Cys Leu Val
            100                 105                 110

Thr Thr Asn Phe Gln Thr Lys Ser Met Ser Ser Met Val Ser Asp Thr
        115                 120                 125

Ser Cys Thr Phe Pro Ser Ser Asp Gly Ile Phe Trp Lys His Trp Ile
    130                 135                 140

Gln Thr Lys Asp Gly Gln Cys Gly Ser Pro Leu Val Ser Thr Arg Asp
145                 150                 155                 160

Gly Phe Ile Val Gly Ile His Ser Ala Ser Asn Phe Thr Asn Thr Asn
                165                 170                 175

Asn Tyr Phe Thr Ser Val Pro Lys Asn Phe Met Glu Leu Leu Thr Asn
            180                 185                 190

Gln Glu Ala Gln Gln Trp Val Ser Gly Trp Arg Leu Asn Ala Asp Ser
        195                 200                 205

Val Leu Trp Gly Gly His Lys Val Phe Met Ser Lys Pro Glu Glu Pro
    210                 215                 220

Phe Gln Pro Val Lys Glu Ala Thr Gln Leu Met Asn Glu Leu Val Tyr
225                 230                 235                 240

Ser Gln
```

<210> SEQ ID NO 13
<211> LENGTH: 182
<212> TYPE: PRT
<213> ORGANISM: Artificial Sequence
<220> FEATURE:
<223> OTHER INFORMATION: Synthetic Polypeptide

<400> SEQUENCE: 13

```
Ala Pro Ile Thr Ala Tyr Ala Gln Gln Thr Arg Gly Leu Leu Gly Cys
1               5                   10                  15

Ile Ile Thr Ser Leu Thr Gly Arg Asp Lys Asn Gln Val Glu Gly Glu
            20                  25                  30

Val Gln Val Val Ser Thr Ala Thr Gln Ser Phe Leu Ala Ser Cys Val
        35                  40                  45

Asn Gly Val Cys Trp Thr Val Phe His Gly Ala Gly Ser Lys Thr Leu
    50                  55                  60
```

```
Ala Gly Pro Lys Gly Pro Val Thr Gln Met Tyr Thr Asn Val Asp Gln
65                  70                  75                  80

Asp Leu Val Gly Trp Pro Ala Pro Pro Gly Ala Arg Ser Leu Thr Pro
                85                  90                  95

Cys Thr Cys Gly Ser Ser Asp Leu Tyr Leu Val Thr Arg His Ala Asp
            100                 105                 110

Val Ile Pro Val Arg Arg Arg Gly Asp Ser Arg Gly Ala Leu Leu Ser
        115                 120                 125

Pro Arg Pro Val Ser Tyr Leu Lys Gly Ser Ser Gly Gly Pro Leu Leu
    130                 135                 140

Cys Pro Ser Gly His Ala Val Gly Ile Phe Arg Ala Ala Val Cys Thr
145                 150                 155                 160

Arg Gly Val Ala Lys Ala Val Asp Phe Ile Pro Val Glu Ser Met Glu
                165                 170                 175

Thr Thr Met Arg Ser Pro
            180
```

```
<210> SEQ ID NO 14
<211> LENGTH: 182
<212> TYPE: PRT
<213> ORGANISM: Artificial Sequence
<220> FEATURE:
<223> OTHER INFORMATION: Synthetic Polypeptide

<400> SEQUENCE: 14

Gly Pro Asn Thr Glu Phe Ala Leu Ser Leu Leu Arg Lys Asn Ile Met
1               5                   10                  15

Thr Ile Thr Thr Ser Lys Gly Glu Phe Thr Gly Leu Gly Ile His Asp
            20                  25                  30

Arg Val Cys Val Ile Pro Thr His Ala Gln Pro Gly Asp Asp Val Leu
        35                  40                  45

Val Asn Gly Gln Lys Ile Arg Val Lys Asp Lys Tyr Lys Leu Val Asp
    50                  55                  60

Pro Glu Asn Ile Asn Leu Glu Leu Thr Val Leu Thr Leu Asp Arg Asn
65                  70                  75                  80

Glu Lys Phe Arg Asp Ile Arg Gly Phe Ile Ser Glu Asp Leu Glu Gly
                85                  90                  95

Val Asp Ala Thr Leu Val Val His Ser Asn Asn Phe Thr Asn Thr Ile
            100                 105                 110

Leu Glu Val Gly Pro Val Thr Met Ala Gly Leu Ile Asn Leu Ser Ser
        115                 120                 125

Thr Pro Thr Asn Arg Met Ile Arg Tyr Asp Tyr Ala Thr Lys Thr Gly
    130                 135                 140

Gln Cys Gly Gly Val Leu Cys Ala Thr Gly Lys Ile Phe Gly Ile His
145                 150                 155                 160

Val Gly Gly Asn Gly Arg Gln Gly Phe Ser Ala Gln Leu Lys Lys Gln
                165                 170                 175

Tyr Phe Val Glu Lys Gln
            180
```

```
<210> SEQ ID NO 15
<211> LENGTH: 31
<212> TYPE: DNA
<213> ORGANISM: Artificial Sequence
<220> FEATURE:
<223> OTHER INFORMATION: Synthetic Polynucleotide

<400> SEQUENCE: 15
```

tgttttagtg tattctttcg cctctttcgt t 31

<210> SEQ ID NO 16
<211> LENGTH: 35
<212> TYPE: DNA
<213> ORGANISM: Artificial Sequence
<220> FEATURE:
<223> OTHER INFORMATION: Synthetic Polynucleotide

<400> SEQUENCE: 16
cccacaagaa ttgagttaag cccaataata agagc 35

<210> SEQ ID NO 17
<211> LENGTH: 5628
<212> TYPE: DNA
<213> ORGANISM: Artificial Sequence
<220> FEATURE:
<223> OTHER INFORMATION: Synthetic Polynucleotide

<400> SEQUENCE: 17
acggatcgct tcatgtggca ggagaaaaaa gactgcaccg gtgcgtcagc agaatatgtg 60
atacaggata tattccgctt cctcgctcac tgactcgcta cgctcggtcg ttcgactgcg 120
gcgagcggaa atggcttacg aacggggcgg agatttcctg gaagatgcca ggaagatact 180
taacagggaa gtgagagggc cgcggcaaag ccgtttttcc ataggctccg cccccctgac 240
aagcatcacg aaatctgacg ctcaaatcag tggtggcgaa acccgacagg actataaaga 300
taccaggcgt ttccccctgg cggctccctc gtgcgctctc ctgttcctgc ctttcggttt 360
accggtgtca ttccgctgtt atggccgcgt ttgtctcatt ccacgcctga cactcagttc 420
cgggtaggca gttcgctcca agctggactg tatgcacgaa ccccccgttc agtccgaccg 480
ctgcgcctta tccggtaact atcgtcttga gtccaacccg gaaagacatg caaaagcacc 540
actggcagca gccactggta attgatttag aggagttagt cttgaagtca tgcgccggtt 600
aaggctaaac tgaaaggaca agttttggtg actgcgctcc tccaagccag ttacctcggt 660
tcaaagagtt ggtagctcag agaaccttcg aaaaaccgcc ctgcaaggcg gttttttcgt 720
tttcagagca agagattacg cgcagaccaa aacgatctca agaagatcat cttattaagg 780
ggtctgacgc tcagtggaac gaaaactcac gttaagggat tttggtcatg agattatcaa 840
aaaggatctt cacctagatc cttttaaatt aaaaatgaag ttttaaatca atctaaagta 900
tatatgagta aacttggtct gacagttacc aatgcttaat cagtgaggca cctatctcag 960
cgatctgtct atttcgttca tccatagttg cctgactccc cgtcgtgtag ataactacga 1020
tacgggaggg cttaccatct ggccccagtg ctgcaatgat accgcgagac ccacgctcac 1080
cggctccaga tttatcagca ataaaccagc cagccgattc gagctcgccc ggggatcgac 1140
cagttggtga ttttgaactt ttgctttgcc acggaacggt ctgcgttgtc gggaagatgc 1200
gtgatctgat ccttcaactc agcaaaagtt cgatttattc aacaaagccg ccgtcccgtc 1260
aagtcagcgt aatgctctgc cagtgttaca accaattaac caattctgat ttccggtcaa 1320
ataaaacgaa aggctcagtc gaaagactgg gcctttcgtt ttgtttatac ataggcgagt 1380
actctgttat ggttccttcc tcgaaaggaa aaaaaaaatg gctcgtgtac agtttaaaca 1440
acgtgaatct actgacgcaa tctttgttca ctgctcggct accaagccaa gtcagaatgt 1500
tggtgtccgt gagattcgcc agtggcacaa agagcagggt tggctcgatg tgggatacca 1560
ctttatcatc aagcgagacg gtactgtgga ggcaggacga gatgagatgg ctgtaggctc 1620

```
tcacgctaag ggttacaacc acaactctat cggcgtctgc cttgttggtg gtatcgacga   1680
taaaggtaag ttcgacgcta actttacgcc agcccaaatg caatcccttc gctcactgct   1740
tgtcacactg ctggctaagt acgaaggcgc tgtgcttcgc gcccatcatg aggtggcgcc   1800
gaaggcttcc ccttcgttcg accttaagcg ttggtgggag aagaacgaac tggtcacttc   1860
tgaccgtggt agcggcggtg gtgcgagtgg tggcgcgctg gaggtcctgt tccagggccc   1920
gggcggtagc gcaggcagtg gagcgggcgg taacacgatt aacatcgcta agaacgactt   1980
ctctgacatc gaactggctg ctatcccgtt caacactctg gctgaccatt acggtgagcg   2040
tttagctcgc gaacagttgg cccttgagca tgagtcttac gagatgggtg aagcacgctt   2100
ccgcaagatg tttgagcgtc aacttaaagc tggtgaggtt gcggataacg ctgccgccaa   2160
gcctctcatc actaccctac tccctaagat gattgcacgc atcaacgact ggtttgagga   2220
agtgaaagct aagcgcggca agcgcccgac agccttccag ttcctgcaag aaatcaagcc   2280
ggaagccgta gcgtacatca ccattaagac cactctggct tgcctaacca gtgctgacaa   2340
tacaaccgtt caggctgtag caagcgcaat cggtcgggcc attgaggacg aggctcgctt   2400
cggtcgtatc cgtgaccttg aagctaagca cttcaagaaa aacgttgagg aacaactcaa   2460
caagcgcgta gggcacgtct acaagaaagc atttatgcaa gttgtcgagg ctgacatgct   2520
ctctaagggt ctactcggtg gcgaggcgtg gtcttcgtgg cataaggaag actctattca   2580
tgtaggagta cgctgcatcg agatgctcat tgagtcaacc ggaatggtta gcttacaccg   2640
ccaaaatgct ggcgtagtag gtcaagactc tgagactatc gaactcgcac ctgaatacgc   2700
tgaggctatc gcaacccgtg caggtgcgct ggctggcatc tctccgatgt tccaaccttg   2760
cgtagttcct cctaagccgt ggactggcat tactggtggt ggctattggg ctaacggtcg   2820
tcgtcctctg gcgctggtgc gtactcacag taagaaagca ctgatgcgct acgaagacgt   2880
ttacatgcct gaggtgtaca aagcgattaa cattgcgcaa aacaccgcat ggaaaatcaa   2940
caagaaagtc ctagcggtcg ccaacgtaat caccaagtgg aagcattgtc cggtcgagga   3000
catccctgcg attgagcgtg aagaactccc gatgaaaccg gaagacatcg acatgaatcc   3060
tgaggctctc accgcgtgga aacgtgctgc cgctgctgtg taccgcaagg acaaggctcg   3120
caagtctcgc cgtatcagcc ttgagttcat gcttgagcaa gccaataagt ttgctaacca   3180
taaggccatc tggttccctt acaacatgga ctggcgcggt cgtgtttacg ctgtgtcaat   3240
gttcaacccg caaggtaacg atatgaccaa aggactgctt acgctggcga aaggtaaacc   3300
aatcggtaag gaaggttact actggctgaa aatccacggt gcaaactgtg cgggtgtcga   3360
taaggttccg ttccctgagc gcatcaagtt cattgaggaa aaccacgaga acatcatggc   3420
ttgcgctaag tctccactgg agaacacttg gtgggctgag caagattctc cgttctgctt   3480
ccttgcgttc tgctttgagt acgctggggt acagcaccac ggcctgagct ataactgctc   3540
ccttccgctg gcgtttgacg ggtcttgctc tggcatccag cacttctccg cgatgctccg   3600
agatgaggta ggtggtcgcg cggttaactt gcttcctagt gaaaccgttc aggacatcta   3660
cgggattgtt gctaagaaag tcaacgagat tctacaagca gacgcaatca atgggaccga   3720
taacgaagta gttaccgtga ccgatgagaa cactggtgaa atctctgaga aagtcaagct   3780
gggcactaag gcactggctg gtcaatggct ggcttacggt gttactcgca gtgtgactaa   3840
gcgttcagtc atgacgctgg cttacgggtc caaagagttc ggcttccgtc aacaagtgct   3900
ggaagatacc attcagccag ctattgattc cggcaagggt ctgatgttca ctcagccgaa   3960
tcaggctgct ggatacatgg ctaagctgat ttgggaatct gtgagcgtga cggtggtagc   4020
```

```
tgcggttgaa gcaatgaact ggcttaagtc tgctgctaag ctgctggctg ctgaggtcaa   4080

agataagaag actggagaga ttcttcgcaa gcgttgcgct gtgcattggg taactcctga   4140

tggtttccct gtgtggcagg aatacaagaa gcctattcag acgcgcttga acctgatgtt   4200

cctcggtcag ttccgcttac agcctaccat taacaccaac aaagatagcg agattgatgc   4260

acacaaacag gagtctggta tcgctcctaa ctttgtacac agccaagacg gtagccacct   4320

tcgtaagact gtagtgtggg cacacgagaa gtacggaatc gaatcttttg cactgattca   4380

cgactccttc ggtaccattc cggctgacgc tgcgaacctg ttcaaagcag tgcgcgaaac   4440

tatggttgac acatatgagt cttgtgatgt actggctgat ttctacgacc agttcgctga   4500

ccagttgcac gagtctcaat tggacaaaat gccagcactt ccggctaaag gtaacttgaa   4560

cctccgtgac atcttagagt cggacttcgc gttcgcgtaa tggagatttt caacatgctc   4620

cctcaatcgg ttgaatgtcg ccctttttgtc tttggcgctg gtaaaccata tgaattttct   4680

attgattgtg acaaaataaa cttattccgt ggtgtctttg cgtttctttt atatgttgcc   4740

acctttatgt atgtattttc tacgtttgct aacatactgc gtaataagga gtcttaatca   4800

tgccagttct tttgggtatt ccgtagaaaa aggaagagta tgagggaagc ggtgatcgcc   4860

gaagtatcga ctcaactatc agaggtagtt ggcgtcatcg agcgccatct cgaaccgacg   4920

ttgctggccg tacatttgta cggctccgca gtggatggcg gcctgaagcc acacagtgat   4980

attgatttgc tggttacggt gaccgtaagg cttgatgaaa caacgcggcg agctttgatc   5040

aacgaccttt tggaaacttc ggcttcccct ggagagagcg agattctccg cgctgtagaa   5100

gtcaccattg ttgtgcacga cgacatcatt ccgtggcgtt atccagctaa gcgcgaactg   5160

caatttggag aatggcagcg caatgacatt cttgcaggta tcttcgagcc agccacgatc   5220

gacattgatc tggctatctt gctgacaaaa gcaagagaac atagcgttgc cttggtaggt   5280

ccagcggcgg aggaactctt tgatccggtt cctgaacagg atctatttga ggcgctaaat   5340

gaaaccttaa cgctatggaa ctcgccgccc gactgggctg gcgatgagcg aaatgtagtg   5400

cttacgttgt cccgcatttg gtacagcgca gtaaccggca aaatcgcgcc gaaggatgtc   5460

gctgccgact gggcaatgga gcgcctgccg gcccagtatc agcccgtcat acttgaagct   5520

agacaggctt atcttggaca agaagaagat cgcttggcct cgcgcgcaga tcagttggaa   5580

gaatttgtcc actacgtgaa aggcgagatc accaaggtag tcggcaaa               5628
```

<210> SEQ ID NO 18
<211> LENGTH: 4231
<212> TYPE: DNA
<213> ORGANISM: Artificial Sequence
<220> FEATURE:
<223> OTHER INFORMATION: Synthetic Polynucleotide

<400> SEQUENCE: 18

```
tgagatcctt tttttctgcg cgtaatctgc tgcttgcaaa caaaaaaacc accgctacca     60

gcggtggttt gtttgccgga tcaagagcta ccaactcttt ttccgaaggt aactggcttc    120

agcagagcgc agataccaaa tactgtcctt ctagtgtagc cgtagttagg ccaccacttc    180

aagaactctg tagcaccgcc tacatacctc gctctgctaa tcctgttacc agtggctgct    240

gccagtggcg ataagtcgtg tcttaccggg ttggactcaa gacgatagtt accggataag    300

gcgcagcggt cgggctgaac ggggggttcg tgcacacagc ccagcttgga gcgaacgacc    360

tacaccgaac tgagatacct acagcgtgag ctatgagaaa gcgccacgct tcccgaaggg    420
```

```
agaaaggcgg acaggtatcc ggtaagcggc agggtcggaa caggagagcg cacgagggag    480
cttccagggg gaaacgcctg gtatctttat agtcctgtcg ggtttcgcca cctctgactt    540
gagcgtcgat ttttgtgatg ctcgtcaggg gggcggagcc tatggaaaaa cgccagcaac    600
gcggcctttt tacggttcct ggccttttgc tggccttttg ctcacatgtt ctttcctgcg    660
ttatcccctg attctgtgga taaccgtatt accgcctttg agtgagctga taccgctcgc    720
cgcagccgaa cgaccgagcg cagcgagtca gtgagcgagg aagcggaaga gcgcctgatg    780
cggtattttc tccttacgca tctgtgcggt atttcacacc gcatatggtg cactctcagt    840
acaatctgct ctgatgccgc atagttaagc cagtatacac tccgctatcg ctacgtgact    900
gggtcatggc tgcgccccga cacccgccaa cacccgctga cgcgccctga cgggcttgtc    960
tgctcccggc atccgcttac agacaagctg tgaccgtctc cgggagctgc atgtgtcaga   1020
ggttttcacc gtcatcaccg aaacgcgcga ggcagctgcg gtaaagctca tcagcgtggt   1080
cgtgaagcga ttcacagatg tctgcctgtt catccgcgtc cagctcgttg agtttctcca   1140
gaagcgttaa tgtctggctt ctgataaagc gggccatgtt aagggcggtt ttttcctgtt   1200
tggtcactga tgcctccgtg taagggggat ttctgttcat gggggtaatg ataccgatga   1260
aacgagagag gatgctcacg atacgggtta ctgatgatga acaagaggac atccggtcaa   1320
ataaaacgaa aggctcagtc gaaagactgg gcctttcgtt ttagacttag ggacccttta   1380
tgacaacttg acggctacat cattcacttt ttcttcacaa ccggcacgga actcgctcgg   1440
gctggccccg gtgcattttt taaatacccg cgagaaatag agttgatcgt caaaaccaac   1500
attgcgaccg acggtggcga taggcatccg ggtggtgctc aaaagcagct tcgcctggct   1560
gatacgttgg tcctcgcgcc agcttaagac gctaatccct aactgctggc ggaaaagatg   1620
tgacagacgc gacggcgaca agcaaacatg ctgtgcgacg ctggcgatat caaaattgct   1680
gtctgccagg tgatcgctga tgtactgaca agcctcgcgt acccgattat ccatcggtgg   1740
atggagcgac tcgttaatcg cttccatgcg ccgcagtaac aattgctcaa gcagatttat   1800
cgccagcagc tccgaatagc gcccttcccc ttgcccggcg ttaatgattt gcccaaacag   1860
gtcgctgaaa tgcggctggt gcgcttcatc cgggcgaaag aaccccgtat tggcaaatat   1920
tgacggccag ttaagccatt catgccagta ggcgcgcgga cgaaagtaaa cccactggtg   1980
ataccattcg cgagcctccg gatgacgacc gtagtgatga atctctcctg gcgggaacag   2040
caaaatatca cccggtcggc aaacaaattc tcgtccctga tttttcacca ccccctgacc   2100
gcgaatggtg agattgagaa tataaccttt cattcccagc ggtcggtcga taaaaaaatc   2160
gagataaccg ttggcctcaa tcggcgttaa acccgccacc agatgggcat taaacgagta   2220
tcccggcagc aggggatcat tttgcgcttc agccatactt ttcatactcc caccattcag   2280
agaagaaacc aattgtccat attgcatcag acattgccgt cactgcgtct tttactggct   2340
cttctcgcta acccaaccgg taaccccgct tattaaaagc attctgtaac aaagcgggac   2400
caaagccatg acaaaaacgc gtaacaaaag tgtctataat cacggcagaa aagtccacat   2460
tgattatttg cacggcgtca cactttgcta tgccatagca tttttatcca taagattagc   2520
ggatcctacc tgacgctttt tatcgcaact ctctactgtt tctccatacc cgttttttta   2580
cctgcaggtg cagtaaggag gaaaaaaaaa tgcatcatca tcatcatcat ggtgaaaacc   2640
tgtattttca gagtcatatg gctagcatga aaaaaaaagg atccgttgtt atcgtcggcc   2700
gtatcaacct gtccggtgac accgcttacg ctcagcagac tcgaggtgag gagggttgcc   2760
aagaaacctc ccagaccggt cgtgacaaaa accaggttga aggtgaagtt cagatcgttt   2820
```

```
ccaccgctac ccagaccttc ctggctacct ccatcaacgg tgttctgtgg accgtttacc   2880

acggtgctgg tacccgtacc atcgcttccc cgaaaggtcc ggttacccag atgtacacca   2940

acgttgacaa agacctggtt ggttggcagg ctccgcaggg ttcccgttcc ctgaccccgt   3000

gcacctgcgg ttcctccgac ctgtacctgg ttacccgtca cgctgacgtt atcccggttc   3060

gtcgtcgtgg tgactcccgt ggttccctgc tgtccccgcg tccgatctcc tacctgaaag   3120

gttcctccgg tggtccgctg ctgtgcccgg ctggtcacgc tgttggtatc ttcagggctg   3180

ctgtttccac ccgtggtgtt gctaaagctg ttgacttcat cccggttgaa tccctggaaa   3240

ccaccatgcg ttccccgtga cttaattaac ggcactcctc agcaaatata atgaccctct   3300

tgataaccca agagggcatt ttttaatgcc catggcgttt atttgccgac taccttggtg   3360

atctcgcctt tcacgtagtg gacaaattct tccaactgat ctgcgcgcga ggccaagcga   3420

tcttcttctt gtccaagata agcctgtcta gcttcaagta tgacgggctg atactgggcc   3480

ggcaggcgct ccattgccca gtcggcagcg acatccttcg gcgcgatttt gccggttact   3540

gcgctgtacc aaatgcggga caacgtaagc actacatttc gctcatcgcc agcccagtcg   3600

ggcggcgagt tccatagcgt taaggtttca tttagcgcct caaatagatc ctgttcagga   3660

accggatcaa agagttcctc cgccgctgga cctaccaagg caacgctatg ttctcttgct   3720

tttgtcagca agatagccag atcaatgtcg atcgtggctg gctcgaagat acctgcaaga   3780

atgtcattgc gctgccattc tccaaattgc agttcgcgct tagctggata acgccacgga   3840

atgatgtcgt cgtgcacaac aatggtgact tctacagcgc ggagaatctc gctctctcca   3900

ggggaagccg aagtttccaa aaggtcgttg atcaaagctc gccgcgttgt ttcatcaagc   3960

cttacggtca ccgtaaccag caaatcaata tcactgtgtg gcttcaggcc gccatccact   4020

gcggagccgt acaaatgtac ggccagcaac gtcggttcga gatggcgctc gatgacgcca   4080

actacctctg atagttgagt cgatacttcg gcgatcaccg cttccctcat actcttcctt   4140

tttcaatatt attgaagcat ttatcagggt tattgtctca tgagcggata catatttgaa   4200

tgtatttaga aaaataggcc aaataggccg t                                  4231
```

<210> SEQ ID NO 19
<211> LENGTH: 6534
<212> TYPE: DNA
<213> ORGANISM: Artificial Sequence
<220> FEATURE:
<223> OTHER INFORMATION: Synthetic Polynucleotide

<400> SEQUENCE: 19

```
tcagatcctt ccgtatttag ccagtatgtt ctctagtgtg gttcgttgtt tttgcgtgag     60

ccatgagaac gaaccattga gatcatgctt actttgcatg tcactcaaaa attttgcctc    120

aaaactggtg agctgaattt ttgcagttaa agcatcgtgt agtgtttttc ttagtccgtt    180

acgtaggtag gaatctgatg taatggttgt tggtattttg tcaccattca tttttatctg    240

gttgttctca agttcggtta cgagatccat ttgtctatct agttcaactt ggaaaatcaa    300

cgtatcagtc gggcggcctc gcttatcaac caccaatttc atattgctgt aagtgtttaa    360

atctttactt attggtttca aaacccattg gttaagcctt ttaaactcat ggtagttatt    420

ttcaagcatt aacatgaact taaattcatc aaggctaatc tctatatttg ccttgtgagt    480

tttcttttgt gttagttctt ttaataacca ctcataaatc ctcatagagt atttgttttc    540

aaaagactta acatgttcca gattatattt tatgaatttt tttaactgga aaagataagg    600
```

```
caatatctct tcactaaaaa ctaattctaa tttttcgctt gagaacttgg catagtttgt    660
ccactggaaa atctcaaagc ctttaaccaa aggattcctg atttccacag ttctcgtcat    720
cagctctctg gttgctttag ctaatacacc ataagcattt tccctactga tgttcatcat    780
ctgagcgtat tggttataag tgaacgatac cgtccgttct ttccttgtag ggttttcaat    840
cgtggggttg agtagtgcca cacagcataa aattagcttg gtttcatgct ccgttaagtc    900
atagcgacta atcgctagtt catttgcttt gaaaacaact aattcagaca tacatctcaa    960
ttggtctagg tgattttaat cactatacca attgagatgg gctagtcaat gataattact   1020
agtccttttc ctttgagttg tgggtatctg taaattctgc tagacctttg ctggaaaact   1080
tgtaaattct gctagaccct ctgtaaattc cgctagacct ttgtgtgttt tttttgttta   1140
tattcaagtg gttataattt atagaataaa gaaagaataa aaaaagataa aaagaataga   1200
tcccagccct gtgtataact cactacttta gtcagttccg cagtattaca aaaggatgtc   1260
gcaaacgctg tttgctcctc tacaaaacag accttaaaac cctaaaggct taagtagcac   1320
cctcgcaagc tcgggcaaat cgctgaatat tccttttgtc tccgaccatc aggcacctga   1380
gtcgctgtct tttcgtgac attcagttcg ctgcgctcac ggctctggca gtgaatgggg   1440
gtaaatggca ctacaggcgc cttttatgga ttcatgcaag gaaactaccc ataatacaag   1500
aaaagcccgt cacgggcttc tcagggcgtt ttatggcggg tctgctatgt ggtgctatct   1560
gactttttgc tgttcagcag ttcctgccct ctgattttcc agtctgacca cttcggatta   1620
tcccgtgaca ggtcattcag actggctaat gcacccagta aggcagcggt atcatcaaca   1680
ggcttacccg tcttactgtc aagaggacat ccggtcaaat aaaacgaaag gctcagtcga   1740
aagactgggc ctttcgtttt gctgaggaga cttagggacc ctactaatac gactcactat   1800
agggagaaag aaggagcgac attgctccgt gtattcactc gttggaatga atacacagtg   1860
cagtgtttat tctgttattt atgccaaaaa taaaggccac tatcaggcag ctttgttgtt   1920
ctgtttacca agttcaggag gtaactcata agaaagacct gcaggtgcag taaaggaaaa   1980
aaaaaatgaa aaaattatta ttcgcaattc ctttagttgt tcctttctat tctcactccg   2040
ctgaaactgt tgaaagttgt ttagcaaaac cccatacaga aaattcattt actaacgtct   2100
ggaaagacga caaaacttta gatcgttacg ctaactatga gggctgtctg tggaatgcta   2160
caggcgttgt agtttgtact ggtgacgaaa ctcagtgtta cggtacatgg gttcctattg   2220
ggcttgctat ccctgaaaat gagggtggtg gctctgaggg tggcggttct gagggtggcg   2280
gttctgaggg tggcggtact aaacctcctg agtacggtga tacacctatt ccgggctata   2340
cttatatcaa ccctctcgac ggcacttatc cgcctggtac tgagcaaaac cccgctaatc   2400
ctaatccttc tcttgaggag tctcagcctc ttaatacttt catgtttcag aataataggt   2460
tccgaaatag gcagggggca ttaactgttt atacgggcac tgttactcaa ggcactgacc   2520
ccgttaaaac ttattaccag tacactcctg tatcatcaaa agccatgtat gacgcttact   2580
ggaacggtaa attcagagac tgcgctttcc attctggctt taatgaggat ccattcgttt   2640
gtgaatatca aggccaatcg tctgacctgc ctcaacctcc tgtcaatgct ggcggcggct   2700
ctggtggtgg ttctggtggc ggctctgagg gtggtggctc tgagggtggc ggttctgagg   2760
gtggcggctc tgagggaggc ggttccggtg gtggctctgg ttccggtgat tttgattatg   2820
aaaagatggc aaacgctaat aagggggcta tgaccgaaaa tgccgatgaa aacgcgctac   2880
agtctgacgc taaaggcaaa cttgattctg tcgctactga ttacggtgct gctatcgatg   2940
gtttcattgg tgacgtttcc ggccttgcta atggtaatgg tgctactggt gattttgctg   3000
```

```
gctctaattc ccaaatggct caagtcggtg acggtgataa ttcaccttta atgaataatt   3060
tccgtcaata tttaccttcc ctccctcaat cggttgaatg tcgccctttt gtctttggcg   3120
ctggtaaacc ttacgagttc agtatcgact gcgataagat caacctgttc cgcggtgtct   3180
ttgcgtttct tttatatgtt gccaccttta tgtatgtatt ttctacgttt gctaacatac   3240
tgcgtaataa ggagtcttaa tgaaatttgg aaactttttg cttacatacc aacctcccca   3300
attttcccaa acagaggtaa tgaaacgttt ggttaaatta ggtcgcatct ctgaggagtg   3360
tggttttgat accgtatggt tactggagca tcatttcacg gagtttggtt tgcttggtaa   3420
cccttatgtc gctgctgcat atttacttgg cgcgactaaa aaattgaatg taggaactgc   3480
cgctattgtt cttcccacag cccatccagt acgccaactt gaagatgtga atttattgga   3540
tcaaatgtca aaaggacgat ttcggtttgg tatttgccga gggctttaca acaaggactt   3600
tcgcgtattc ggcacagata tgaataacag tcgcgcctta gcggaatgct ggtacgggct   3660
gataaagaat ggcatgacag agggatatat ggaagctgat aatgaacata tcaagttcca   3720
taaggtaaaa gtaaaccccg cggcgtatag cagaggtggc gcaccggttt atgtggtggc   3780
tgaatcagct tcgacgactg agtgggctgc tcaatttggc ctaccgatga tattaagttg   3840
gattataaat actaacgaaa agaaagcaca acttgagctt tataatgaag tggctcaaga   3900
atatgggcac gatattcata atatcgacca ttgcttatca tatataacat ctgtagatca   3960
tgactcaatt aaagcgaaag agatttgccg gaaatttctg gggcattggt atgattctta   4020
tgtgaatgct acgactattt ttgatgattc agaccaaaca agaggttatg atttcaataa   4080
agggcagtgg cgtgactttg tattaaaagg acataaagat actaatcgcc gtattgatta   4140
cagttacgaa atcaatcccg tgggaacgcc gcaggaatgt attgacataa ttcaaaaaga   4200
cattgatgct acaggaatat caaatatttg ttgtggattt gaagctaatg gaacagtaga   4260
cgaaattatt gcttccatga agctcttcca gtctgatgtc atgccatttc ttaaagaaaa   4320
acaacgttcg ctattatatt atggcggtgg cggtagcggc ggtggcggta gcggcggtgg   4380
cggtagcggc ggtggcggta gcaaatttgg attgttcttc cttaacttca tcaattcaac   4440
aactgttcaa gaacagagta tagttcgcat gcaggaaata acggagtatg ttgataagtt   4500
gaattttgaa cagattttag tgtatgaaaa tcatttttca gataatggtg ttgtcggcgc   4560
tcctctgact gtttctggtt ttctgctcgg tttaacagag aaaattaaaa ttggttcatt   4620
aaatcacatc attacaactc atcatcctgt ccgcatagcg gaggaagctt gcttattgga   4680
tcagttaagt gaagggagat ttattttagg gtttagtgat tgcgaaaaaa aagatgaaat   4740
gcattttttt aatcgcccgg ttgaatatca acagcaacta tttgaagagt gttatgaaat   4800
cattaacgat gctttaacaa caggctattg taatccagat aacgattttt atagcttccc   4860
taaaatatct gtaaatcccc atgcttatac gccaggcgga cctcggaaat atgtaacagc   4920
aaccagtcat catattgttg agtgggcggc caaaaaaggt attcctctca tctttaagtg   4980
ggatgattct aatgatgtta gatatgaata tgctgaaaga tataaagccg ttgcggataa   5040
atatgacgtt gacctatcag agatagacca tcagttaatg atattagtta actataacga   5100
agatagtaat aaagctaaac aagagacgcg tgcatttatt agtgattatg ttcttgaaat   5160
gcaccctaat gaaaatttcg aaaataaact tgaagaaata attgcagaaa acgctgtcgg   5220
aaattatacg gagtgtataa ctgcggctaa gttggcaatt gaaaagtgtg gtgcgaaaag   5280
tgtattgctg tcctttgaac caatgaatga tttgatgagc caaaaaaatg taatcaatat   5340
```

```
tgttgatgat aatattaaga agtaccacac ggaatatacc taaacttaat taacggcact   5400

cctcagcaaa tataatgacc ctcttgataa cccaagaggg catttttttaa tgcccatggc   5460

gtttaccaat gcttaatcag tgaggcacct atctcagcga tctgtctatt tcgttcatcc   5520

atagttgcct gactccccgt cgtgtagata actacgatac gggagggctt accatctggc   5580

cccagtgctg caatgatacc gcgagaccca cgctcaccgg ctccagattt atcagcaata   5640

aaccagccag ccggaagggc cgagcgcaga agtggtcctg caactttatc cgcctccatc   5700

cagtctatta attgttgccg ggaagctaga gtaagtagtt cgccagttaa tagtttgcgc   5760

aacgttgttg ccattgctac aggcatcgtg gtgtcacgct cgtcgtttgg tatggcttca   5820

ttcagctccg gttcccaacg atcaaggcga gttacatgat cccccatgtt gtgcaaaaaa   5880

gcggttagct ccttcggtcc tccgatcgtt gtcagaagta agttggccgc agtgttatca   5940

ctcatggtta tggcagcact gcataattct cttactgtca tgccatccgt aagatgcttt   6000

tctgtgactg gtgagtactc aaccaagtca ttctgagaat agtgtatgcg gcgaccgagt   6060

tgctcttgcc cggcgtcaat acgggataat accgcgccac atagcagaac tttaaaagtg   6120

ctcatcattg gaaaacgttc ttcggggcga aaactctcaa ggatcttacc gctgttgaga   6180

tccagttcga tgtaacccac tcgtgcaccc aactgatctt cagcatcttt tactttcacc   6240

agcgtttctg ggtgagcaaa aacaggaagg caaaatgccg caaaaaaggg aataagggcg   6300

acacggaaat gttgaatact catactcttc ctttttcaat attattgaag catttatcag   6360

ggttattgtc tcatgagcgg atacatattt gaatgtattt agaaaaataa acaaataggg   6420

gttccgcgca catttccccg aaaagtgcca cctgacgtct aagaaaccat tattatcatg   6480

acattaacct ataaaaatag gcgtatcacg aggcccttag gccaaatagg ccgt         6534
```

<210> SEQ ID NO 20
<211> LENGTH: 5892
<212> TYPE: DNA
<213> ORGANISM: Artificial Sequence
<220> FEATURE:
<223> OTHER INFORMATION: Synthetic Polynucleotide

<400> SEQUENCE: 20

```
atgattgaca tgctagtttt acgattaccg ttcatcgatt ctcttgtttg ctccagactc     60

tcaggcaatg acctgatagc ctttgtagac ctctcaaaaa tagctaccct ctccggcatg    120

aatttatcag ctagaacggt tgaatatcat gttgatggtg atttgactgt ctccggcctt    180

tctcaccctt ttgaatcttt acctacacat tactcaggca ttgcatttaa aatatatgag    240

ggttctaaaa atttttatcc ttgcgttgaa ataaaggctt ctcccgcaaa agtattacag    300

ggtcataatg tttttggtac aaccgattta gctttatgct ctgaggcttt attgcttaat    360

tttgctaatt ctttgccttg cctgtatgat ttattggatg ttaacgctac tactattagt    420

agaattgatg ccacctttttc agctcgcgcc ccaaatgaaa atatagctaa acaggttatt    480

gaccatttgc gaaatgtatc taatggtcaa actaaatcta ctcgttcgca gaattgggaa    540

tcaactgtta catggaatga aacttccaga caccgtactt tagttgcata tttaaaacat    600

gttgagctac agcaccagat tcagcaatta agctctaagc catccgcaaa aatgacctct    660

tatcaaaagg agcaattaaa ggtactctct aatcctgacc tgttggagtt tgcttccggg    720

ctggttcgct ttgaagctcg aattagaacg cgatatttga agtctttcgg gcttcctctt    780

aatctttttg atgcaatccg ctttgcttct gactataata gtcagggtaa agacctgatt    840

tttgatttat ggtcattctc gttttctgaa ctgtttaaag catttgaggg ggattcaatg    900
```

```
aatatttatg acgattccgc agtattggac gctatccagt ctaaacattt tactattacc    960
ccctctggca aaacttcttt tgcaaaagcc tctcgctatt ttggttttta tcgtcgtctg   1020
gtaaacgagg gttatgatag tgttgctctt actatgcctc gtaattcctt ttggcgttat   1080
gtatctgcat tagttgaatg tggtattcct aaatctcaac tgatgaatct ttctacctgt   1140
aataatgttg ttccgttagt tcgttttatt aacgtagatt tttcttccca acgtcctgac   1200
tggtataatg agccagttct taaaatcgca taaggtaatt cacaatgatt aaagttgaaa   1260
ttaaaccatc tcaagcccaa tttactactc gttctggtgt ttctcgtcag ggcaagcctt   1320
attcactgaa tgagcagctt tgttacgttg atttgggtaa tgaatatccg gttcttgtca   1380
agattactct tgatgaaggt cagccagcct atgcgcctgg tctgtacacc gttcatctgt   1440
cctctttcaa agttggtcag ttcggttccc ttatgattga ccgtctgcgc ctcgttccgg   1500
ctaagtaaca tggagcaggt cgcggatttc gacacaattt atcaggcgat gatacaaatc   1560
tccgttgtac tttgtttcgc gcttggtata atcgctgggg gtcaaagatg agtgttttag   1620
tgtattcttt cgcctctttc gttttaggtt ggtgccttcg tagtggcatt acgtatttta   1680
cccgtttaat ggaaacttcc tcatgaaaaa gtctttagtc ctcaaagcct ctgtagccgt   1740
tgctaccctc gttccgatgc tgtctttcgc tgctgagggt gacgatcccg caaaagcggc   1800
ctttaactcc ctgcaagcct cagcgaccga atatatcggt tatgcgtggg cgatggttgt   1860
tgtcattgtc ggcgcaacta tcggtatcaa gctgtttaag aaattcacct cgaaagcaag   1920
ctgataaacc gatacaatta aaggctcctt ttggagcctt tttttcgcg ccaataagga   1980
ggaaaaaaaa atgggcagca gccatcatca tcatcatcac agcagcggcc tggtgccgcg   2040
cggcagccat atggctagca tgaaaaaaaa aggatccgtt gttatcgtcg gccgtatcaa   2100
cctgtccggt gacaccgctt acgctcagca gactcgaggt gaggagggtt gccaagaaac   2160
ctcccagacc ggtcgtgaca aaaaccaggt tgaaggtgaa gttcagatcg tttccaccgc   2220
tacccagacc ttcctggcta cctccatcaa cggtgttctg tggaccgttt accacggtgc   2280
tggtacccgt accatcgctt ccccgaaagg tccggttacc cagatgtaca ccaacgttga   2340
caaagacctg gttggttggc aggctccgca gggttcccgt tccctgaccc cgtgcacctg   2400
cggttcctcc gacctgtacc tggttacccg tcacgctgac gttatcccgg ttcgtcgtcg   2460
tggtgactcc cgtggttccc tgctgtcccc gcgtccgatc tcctacctga aaggttcctc   2520
cggtggtccg ctgctgtgcc cggctggtca cgctgttggt atcttcaagg ctgctgtttc   2580
cacccgtggt gttgctaaag ctgttgactt catcccggtt gaatccctgg aaaccaccat   2640
gcgttccccg tgatgatgat aataatggag attttcaaca tgggctagct cagccctagg   2700
tattatgcta gcgtggtgtc tgcgtaataa ggagtcttaa tcatgccagt tcttttgggt   2760
attccgttat tattgcgttt cctcggtttc cttctggtaa ctttgttcgg ctatctgctt   2820
acttttctta aaaagggctt cggtaagata gctattgcta tttcattgtt tcttgctctt   2880
attattgggc ttaactcaat tcttgtgggt tatctctctg atattagcgc tcaattaccc   2940
tctgactttg ttcagggtgt tcagttaatt ctcccgtcta atgcgcttcc ctgtttttat   3000
gttattctct ctgtaaaggc tgctattttc atttttgacg ttaaacaaaa aatcgtttct   3060
tatttggatt gggataaata atatggctgt ttattttgta actggcaaat taggctctgg   3120
aaagacgctc gttagcgttg gtaagattca ggataaaatt gtagctgggt gcaaaatagc   3180
aactaatctt gatttaaggc ttcaaaacct cccgcaagtc gggaggttcg ctaaaacgcc   3240
```

```
tcgcgttctt agaataccgg ataagccttc tatatctgat ttgcttgcta ttgggcgcgg   3300
taatgattcc tacgatgaaa ataaaaacgg cttgcttgtt ctcgatgagt gcggtacttg   3360
gtttaatacc cgttcttgga atgataagga aagacagccg attattgatt ggtttctaca   3420
tgctcgtaaa ttaggatggg atattatttt tcttgttcag gacttatcta ttgttgataa   3480
acaggcgcgt tctgcattag ctgaacatgt tgtttattgt cgtcgtctgg acagaattac   3540
tttacctttt gtcggtactt tatattctct tattactggc tcgaaaatgc ctctgcctaa   3600
attacatgtt ggcgttgtta aatatggcga ttctcaatta agccctactg ttgagcgttg   3660
gctttatact ggtaagaatt tgtataacgc atatgatact aaacaggctt tttctagtaa   3720
ttatgattcc ggtgtttatt cttatttaac gccttattta tcacacggtc ggtatttcaa   3780
accattaaat ttaggtcaga agatgaaatt aactaaaata tatttgaaaa agttttctcg   3840
cgttctttgt cttgcgattg gatttgcatc agcatttaca tatagttata taacccaacc   3900
taagccggag gttaaaaagg tagtctctca gacctatgat tttgataaat tcactattga   3960
ctcttctcag cgtcttaatc taagctatcg ctatgttttc aaggattcta agggaaaatt   4020
aattaatagc gacgatttac agaagcaagg ttattcactc acatatattg atttatgtac   4080
tgtttccatt aaaaaaggta attcaaatga aattgttaaa tgtaattaat tttgttttct   4140
tgatgtttgt ttcatcatct tcttttgctc aggtaattga aatgaataat tcgcctctgc   4200
gcgattttgt aacttggtat tcaaagcaat caggcgaatc cgttattgtt tctcccgatg   4260
taaaaggtac tgttactgta tattcatctg acgttaaacc tgaaaatcta cgcaatttct   4320
ttatttctgt tttacgtgca agtaattttg atatggttgg ttctaaccct tccattattc   4380
agaagtataa tccaaacaat caggattata ttgatgaatt gccatcatct gataatcagg   4440
aatatgatga taattccgct ccttctggtg gtttctttgt tccgcaaaat gataatgtta   4500
ctcaaacttt taaaattaat aacgttcggg caaaggattt aatacgagtt gtcgaattgt   4560
ttgtaaagtc taatacttct aaatcctcaa atgtattatc tattgacggc tctaatctat   4620
tagttgttag tgcacctaaa gatattttag ataaccttcc tcaattcctt tctactgttg   4680
atttgccaac tgaccagata ttgattgagg gtttgatatt tgaggttcag caaggtgatg   4740
ctttagattt ttcatttgct gctggctctc agcgtggcac tgttgcaggc ggtgttaata   4800
ctgaccgcct cacctctgtt ttatcttctg ctggtggttc gttcggtatt tttaatggcg   4860
atgttttagg gctatcagtt cgcgcattaa agactaatag ccattcaaaa atattgtctg   4920
tgccacgtat tcttacgctt tcaggtcaga agggttctat ctttgttggc cagaatgtcc   4980
cttttattac tggtcgtgtg actggtgaat ctgccaatgt aaataatcca tttcagacga   5040
ttgagcgtca aaatgtaggt atttccatga gcgtttttcc tgttgcaatg gctggcggta   5100
atattgttct ggatattacc agcaaggccg atagtttgag ttcttctact caggcaagtg   5160
atgttattac taatcaaaga agtactgcta caacggttaa tttgcgtgat ggacagactc   5220
ttttactcgg tggcctcact gattataaaa acacttctca ggattctggc gtaccgttcc   5280
tgtctaaaat ccctttaatc ggcctcctgt ttagctcccg ctctgattct aacgaggaaa   5340
gcacgttata cgtgctcgtc aaagcaacca tagtacgcgc cctgtagcgg cgcattaagc   5400
gcggcgggtg tggtggttac gcgcagcgtg accgctacac ttgccagcgc cctagcgccc   5460
gctcctttcg ctttcttccc ttcctttctc gccacgttcg ccggctttcc ccgtcaagct   5520
ctaaatcggg ggctcccttt agggttccga tttagtgctt tacggcacct cgaccccaaa   5580
aaacttgatt tgggtgatgg ttcacgtagt gggccatcgc cctgatagac ggtttttcgc   5640
```

```
cctttgacgt tggagtccac gttctttaat agtggactct tgttccaaac tggaacaaca   5700

ctcaacccta tctcgggcta ttcttttgat ttataaggga ttttgccgat ttcggcctat   5760

tggttaaaaa atgagctgat ttaacaaaaa tttaacgcga attttaacaa aatattaacg   5820

tttacaattt aaatatttgc ttatacaatc ttcctgtttt tggggctttt cttattatca   5880

accggggtac at                                                       5892
```

<210> SEQ ID NO 21
<211> LENGTH: 5183
<212> TYPE: DNA
<213> ORGANISM: Artificial Sequence
<220> FEATURE:
<223> OTHER INFORMATION: Synthetic Polynucleotide

<400> SEQUENCE: 21

```
cactcggtcg ctacgctccg ggcgtgagac tgcggcgggc gctgcggaca catacaaagt     60

tacccacaga ttccgtggat aagcagggga ctaacatgtg aggcaaaaca gcagggccgc    120

gccggtggcg tttttccata ggctccgccc tcctgccaga gttcacataa acagacgctt    180

ttccggtgca tctgtgggag ccgtgaggct caaccatgaa tctgacagta cgggcgaaac    240

ccgacaggac ttaaagatcc ccaccgtttc cggcgggtcg ctccctcttg cgctctcctg    300

ttccgaccct gccgtttacc ggatacctgt tccgcctttc tcccttacgg gaagtgtggc    360

gctttctcat agctcacaca ctggtatctc ggctcggtgt aggtcgttcg ctccaagctg    420

ggctgtaagc aagaactccc cgttcagccc gactgctgcg ccttatccgg taactgttca    480

cttgagtcca acccggaaaa gcacggtaaa acgccactgg cagcagccat tggtaactgg    540

gagttcgcag aggatttgtt tagctaaaca cgcggttgct cttgaagtgt gcgccaaagt    600

ccggctacac tggaaggaca gatttggttg ctgtgctctg cgaaagccag ttaccacggt    660

taagcagttc cccaactgac ttaaccttcg atcaaaccac ctccccaggt ggtttttttcg   720

tttacagggc aaaagattac gcgcagaaaa aaaggatctc aagaagatcc tttgatcttt    780

tctactgaac cgctctagat ttcagtgcaa tttatctctt caaatgtagc acctgaagtc    840

agcccaggag gaagaggaca tccggtcaaa taaaacgaaa ggctcagtcg aaagactggg    900

cctttcgttt tagacttagg gaccctttat gacaacttga cggctacatc attcactttt    960

tcttcacaac cggcacggaa ctcgctcggg ctggccccgg tgcatttttt aaatacccgc   1020

gagaaataga gttgatcgtc aaaaccaaca ttgcgaccga cggtggcgat aggcatccgg   1080

gtggtgctca aaagcagctt cgcctggctg atacgttggt cctcgcgcca gcttaagacg   1140

ctaatcccta actgctggcg gaaaagatgt gacagacgcg acggcgacaa gcaaacatgc   1200

tgtgcgacgc tggcgatatc aaaattgctg tctgccaggt gatcgctgat gtactgacaa   1260

gcctcgcgta cccgattatc catcggtgga tggagcgact cgttaatcgc ttccatgcgc   1320

cgcagtaaca attgctcaag cagatttatc gccagcagct ccgaatagcg cccttcccct   1380

tgcccggcgt taatgatttg cccaaacagg tcgctgaaat gcggctggtg cgcttcatcc   1440

gggcgaaaga accccgtatt ggcaaatatt gacggccagt taagccattc atgccagtag   1500

gcgcgcggac gaaagtaaac ccactggtga taccattcgc gagcctccgg atgacgaccg   1560

tagtgatgaa tctctcctgg cgggaacagc aaaatatcac ccggtcggca aacaaattct   1620

cgtccctgat tttcaccac cccctgaccg cgaatggtga gattgagaat ataacctttc    1680

attcccagcg gtcggtcgat aaaaaaatcg agataaccgt tggcctcaat cggcgttaaa   1740
```

-continued

```
cccgccacca gatgggcatt aaacgagtat cccggcagca ggggatcatt ttgcgcttca   1800
gccatacttt tcatactccc accattcaga gaagaaacca attgtccata ttgcatcaga   1860
cattgccgtc actgcgtctt ttactggctc ttctcgctaa cccaaccggt aaccccgctt   1920
attaaaagca ttctgtaaca aagcgggacc aaagccatga caaaaacgcg taacaaaagt   1980
gtctataatc acggcagaaa agtccacatt gattatttgc acggcgtcac actttgctat   2040
gccatagcat ttttatccat aagattagcg gatcctacct gacgcttttt atcgcaactc   2100
tctactgttt ctccataccc gtttttttgg acgcgtacaa ctcaagtctg acataaatga   2160
ccgctatgag cactgcaatt acacgccaga tcgttctcgc taccgcaacc accggtatga   2220
accagattgg tgcgcactat gaaggccaca agatcattga gattggtgcc gttgaagtgg   2280
tgaaccgtcg cctgacgggc aataacttcc atgtttatct caaacccgat cggctggtgg   2340
atccggaagc ctttggcgta catggtattg ccgatgaatt tttgctcgat aagcccacgt   2400
ttgccgaagt agccgatgag ttcatggact atattcgcgg cgcggagttg gtgatccata   2460
acgcagcgtt cgatatcggc tttatggact acgagttttc gttgcttaag cgcgatattc   2520
cgaagaccaa tactttctgt aaggtcaccg atagccttgc ggtggcgagg aaaatgtttc   2580
ccggtaagcg caacagcctc gatgcgttat gtgctcgcta cgaaatagat aacagtaaac   2640
gaacgctgca cggggcatta ctcgatgccc agatccttgc ggaagtttat ctggcgatga   2700
ccggtggtca aacgtcgatg gcttttgcga tggaaggaga gacacaacag caacaaggtg   2760
aagcaacaat tcagcgcatt gtacgtcagg caagtaagtt acgcgttgtt tttgcgacag   2820
atgaagagat tgcagctcat gaagcccgtc tcgatctggt gcagaagaaa ggcggaagtt   2880
gcctctggcg agcataattt aatatcagta aaccggacat aacccatgaa gaaaaatcgc   2940
gctttttgga agtgggcagg gggcaagtat cccctgcttg atgatattaa acggcatttg   3000
cccaagggcg aatgtctggt tgagcctttt gtaggtgccg ggtcggtgtt tctcaacacc   3060
gacttttctc gttatatcct tgccgatatc aatagcgacc tgatcagtct ctataacatt   3120
gtgaagatgc gtactgatga gtacgtacag gccgcacgcg agctgtttgt tcccgaaaca   3180
aattgcgccg aggtttacta tcagttccgc gaagagttca acaaaagcca ggatccgttc   3240
cgtcgggcgg tactgttttt atatttgaac cgctacggtt acaacggcct gtgtcgttac   3300
aatctgcgcg gtgagtttaa cgtgccgttc ggccgctaca aaaaacccta tttcccggaa   3360
gcagagttgt atcacttcgc tgaaaaagcg cagaatgcct tttctattg tgagtcttac    3420
gccgatagca tggcgcgcgc agatgatgca tccgtcgtct attgcgatcc gccttatgca   3480
ccgctgtctg cgaccgccaa ctttacggcg tatcacacaa acagttttac gcttgaacaa   3540
caagcgcatc tggcggagat cgccgaaggt ctggttgagc gccatattcc agtgctgatc   3600
tccaatcacg atacgatgtt aacgcgtgag tggtatcagc gcgcaaaatt gcatgtcgtc   3660
aaagttcgac gcagtataag cagcaacggc ggcacacgta aaaaggtgga cgaactgctg   3720
gctttgtaca aaccaggagt cgtttcaccc gcgaaaaaat aattcagcta agacactgca   3780
ctggattaag atgaaaacga ttgaagttga tgatgaactc tacagctata ttgccagcca   3840
cactaagcat atcggcgaga gcgcatccga cattttacgg cgtatgttga aattttccgc   3900
cgcatcacag cctgctgctc cggtgacgaa agaggttcgc gttgcgtcac ctgctatcgt   3960
cgaagcgaag ccggtcaaaa cgattaaaga caaggttcgc gcaatgcgtg aacttctgct   4020
ttcggatgaa tacgcagagc aaaagcgagc ggtcaatcgc tttatgctgc tgttgtctac   4080
actatattct cttgacgccc aggcgtttgc cgaagcaacg gaatcgttgc acggtcgtac   4140
```

```
acgcgtttac tttgcggcag atgaacaaac gctgctgaaa aatggtaatc agaccaagcc   4200

gaaacatgtg ccaggcacgc cgtattgggt gatcaccaac accaacaccg gccgtaaatg   4260

cagcatgatc gaacacatca tgcagtcgat gcaattcccg gcggaattga ttgagaaggt   4320

ttgcggaact atctaaactt aattaacggc actcctcagc caagtcaaaa gcctccgacc   4380

ggaggctttt gactacatgc ccatggcgtt tacgccccgc cctgccactc atcgcagtac   4440

tgttgtaatt cattaagcat tctgccgaca tggaagccat cacaaacggc atgatgaacc   4500

tgaatcgcca gcggcatcag caccttgtcg ccttgcgtat aatatttgcc catagtgaaa   4560

acgggggcga agaagttgtc catattggcc acgtttaaat caaaactggt gaaactcacc   4620

cagggattgg ctgagacgaa aaacatattc tcaataaacc ctttagggaa ataggccagg   4680

ttttcaccgt aacacgccac atcttgcgaa tatatgtgta gaaactgccg gaaatcgtcg   4740

tggtattcac tccagagcga tgaaaacgtt tcagtttgct catggaaaac ggtgtaacaa   4800

gggtgaacac tatcccatat caccagctca ccgtctttca ttgccatacg gaactccgga   4860

tgagcattca tcaggcgggc aagaatgtga ataaaggccg gataaaactt gtgcttattt   4920

ttctttacgg tctttaaaaa ggccgtaata tccagctgaa cggtctggtt ataggtacat   4980

tgagtaactg actgaaatgc ctcaaaatgt tctttacgat gccattggga tatatcaacg   5040

gtggtatatc cagtgatttt tttctccatt ttagcttcct tagctcctga aaatctcgat   5100

aactcaaaaa atacgcccgg tagtgatctt atttcattat ggtgaaagtt ggaacctctt   5160

acgtgccaag ccaaataggc cgt                                           5183
```

```
<210> SEQ ID NO 22
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 22

Leu Glu Val Leu Phe Gln Gly Pro
1               5


<210> SEQ ID NO 23
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 23

Leu Glu Val Leu Phe Gln Tyr Pro
1               5


<210> SEQ ID NO 24
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 24

Glu Asn Leu Tyr Phe Gln Ser Ala
1               5


<210> SEQ ID NO 25
<211> LENGTH: 8
```

<212> TYPE: PRT
<213> ORGANISM: Artificial Sequence
<220> FEATURE:
<223> OTHER INFORMATION: Synthetic Polypeptide

<400> SEQUENCE: 25

Glu Asn Leu Tyr Phe Glu Ser Ala
1               5

<210> SEQ ID NO 26
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 26

Glu Met Leu Tyr Phe Gln Ser Ala
1               5

<210> SEQ ID NO 27
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 27

His Asn Leu Tyr Phe Gln Ser Ala
1               5

<210> SEQ ID NO 28
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 28

Glu Asn Leu Tyr Ala Gln Ser
1               5

<210> SEQ ID NO 29
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 29

Glu Asn Leu Tyr Phe Gln Ser
1               5

<210> SEQ ID NO 30
<211> LENGTH: 5389
<212> TYPE: DNA
<213> ORGANISM: Artificial Sequence
<220> FEATURE:
<223> OTHER INFORMATION: Synthetic Polynucleotide

<400> SEQUENCE: 30
atgattgaca tgctagtttt acgattaccg ttcatcgatt ctcttgtttg ctccagactc     60
tcaggcaatg acctgatagc ctttgtagac ctctcaaaaa tagctaccct ctccggcatg    120
aatttatcag ctagaacggt tgaatatcat gttgatggtg atttgactgt ctccggcctt    180
tctcaccctt ttgaatcttt acctacacat tactcaggca ttgcatttaa aatatatgag    240

```
ggttctaaaa atttttatcc ttgcgttgaa ataaaggctt ctcccgcaaa agtattacag    300
ggtcataatg tttttggtac aaccgattta gctttatgct ctgaggcttt attgcttaat    360
tttgctaatt ctttgccttg cctgtatgat ttattggatg ttaacgctac tactattagt    420
agaattgatg ccaccttttc agctcgcgcc ccaaatgaaa atatagctaa acaggttatt    480
gaccatttgc gaaatgtatc taatggtcaa actaaatcta ctcgttcgca gaattgggaa    540
tcaactgtta catggaatga aacttccaga caccgtactt tagttgcata tttaaaacat    600
gttgagctac agcaccagat tcagcaatta agctctaagc catccgcaaa aatgacctct    660
tatcaaaagg agcaattaaa ggtactctct aatcctgacc tgttggagtt tgcttccggg    720
ctggttcgct ttgaagctcg aattagaacg cgatatttga agtctttcgg gcttcctctt    780
aatctttttg atgcaatccg ctttgcttct gactataata gtcagggtaa agacctgatt    840
tttgatttat ggtcattctc gttttctgaa ctgtttaaag catttgaggg ggattcaatg    900
aatatttatg acgattccgc agtattggac gctatccagt ctaaacattt tactattacc    960
ccctctggca aaacttcttt tgcaaaagcc tctcgctatt ttggttttta tcgtcgtctg   1020
gtaaacgagg gttatgatag tgttgctctt actatgcctc gtaattcctt ttggcgttat   1080
gtatctgcat tagttgaatg tggtattcct aaatctcaac tgatgaatct ttctacctgt   1140
aataatgttg ttccgttagt tcgttttatt aacgtagatt tttcttccca acgtcctgac   1200
tggtataatg agccagttct taaaatcgca taaggtaatt cacaatgatt aaagttgaaa   1260
ttaaaccatc tcaagcccaa tttactactc gttctggtgt ttctcgtcag ggcaagcctt   1320
attcactgaa tgagcagctt tgttacgttg atttgggtaa tgaatatccg gttcttgtca   1380
agattactct tgatgaaggt cagccagcct atgcgcctgg tctgtacacc gttcatctgt   1440
cctctttcaa agttggtcag ttcggttccc ttatgattga ccgtctgcgc ctcgttccgg   1500
ctaagtaaca tggagcaggt cgcggatttc gacacaattt atcaggcgat gatacaaatc   1560
tccgttgtac tttgtttcgc gcttggtata atcgctgggg gtcaaagatg agtgttttag   1620
tgtattcttt cgcctctttc gttttaggtt ggtgccttcg tagtggcatt acgtatttta   1680
cccgtttaat ggaaacttcc tcatgaaaaa gtctttagtc ctcaaagcct ctgtagccgt   1740
tgctaccctc gttccgatgc tgtctttcgc tgctgagggt gacgatcccg caaaagcggc   1800
ctttaactcc ctgcaagcct cagcgaccga atatatcggt tatgcgtggg cgatggttgt   1860
tgtcattgtc ggcgcaacta tcggtatcaa gctgtttaag aaattcacct cgaaagcaag   1920
ctgataaacc gatacaatta aaggctcctt ttggagcctt tttttcgcg ccagaaggag    1980
accaagcttg catgcctgca ggtcgactct agaggatccc cgggtaccga gctcgaattc   2040
tggagatttt caacatgctc cctcaatcgg ttgaatgtcg cccttttgtc tttagcgctg   2100
gtaaaccata tgaattttct attgattgtg acaaaatgaa cttattccgt ggtgtctttg   2160
cgtttctttt atatgttgcc acctttatgt atgtattttc tacgtttgct aacatactgc   2220
gtaataagga gtcttaatca tgccagttct tttgggtatt ccgttattat tgcgtttcct   2280
cggtttcctt ctggtaactt tgttcggcta tctgcttact tttcttaaaa agggcttcgg   2340
taagatagct attgctattt cattgtttct tgctcttatt attgggctta actcaattct   2400
tgtgggttat ctctctgata ttagcgctca attaccctct gactttgttc agggtgttca   2460
gttaattctc ccgtctaatg cgcttccctg tttttatgtt attctctctg taaaggctgc   2520
tattttcatt tttgacgtta aacaaaaaat cgtttcttat ttggattggg ataaataata   2580
```

```
tggctgttta ttttgtaact ggcaaattag gctctggaaa gacgctcgtt agcgttggta   2640
agattcagga taaaattgta gctgggtgca aaatagcaac taatcttgat ttaaggcttc   2700
aaaacctccc gcaagtcggg aggttcgcta aaacgcctcg cgttcttaga ataccggata   2760
agccttctat atctgatttg cttgctattg ggcgcggtaa tgattcctac gatgaaaata   2820
aaaacggctt gcttgttctc gatgagtgcg gtacttggtt taatacccgt tcttggaatg   2880
ataaggaaag acagccgatt attgattggt ttctacatgc tcgtaaatta ggatgggata   2940
ttatttttct tgttcaggac ttatctattg ttgataaaca ggcgcgttct gcattagctg   3000
aacatgttgt ttattgtcgt cgtctggaca gaattacttt accttttgtc ggtactttat   3060
attctcttat tactggctcg aaaatgcctc tgcctaaatt acatgttggc gttgttaaat   3120
atggcgattc tcaattaagc cctactgttg agcgttggct ttatactggt aagaatttgt   3180
ataacgcata tgatactaaa caggcttttt ctagtaatta tgattccggt gtttattctt   3240
atttaacgcc ttatttatca cacggtcggt atttcaaacc attaaattta ggtcagaaga   3300
tgaaattaac taaaatatat ttgaaaaagt tttctcgcgt tctttgtctt gcgattggat   3360
ttgcatcagc atttacatat agttatataa cccaacctaa gccggaggtt aaaaaggtag   3420
tctctcagac ctatgatttt gataaattca ctattgactc ttctcagcgt cttaatctaa   3480
gctatcgcta tgttttcaag gattctaagg gaaaattaat taatagcgac gatttacaga   3540
agcaaggtta ttcactcaca tatattgatt tatgtactgt ttccattaaa aaaggtaatt   3600
caaatgaaat tgttaaatgt aattaatttt gttttcttga tgtttgtttc atcatcttct   3660
tttgctcagg taattgaaat gaataattcg cctctgcgcg attttgtaac ttggtattca   3720
aagcaatcag gcgaatccgt tattgtttct cccgatgtaa aaggtactgt tactgtatat   3780
tcatctgacg ttaaacctga aaatctacgc aatttcttta tttctgtttt acgtgcaagt   3840
aattttgata tggttggttc taacccttcc attattcaga agtataatcc aaacaatcag   3900
gattatattg atgaattgcc atcatctgat aatcaggaat atgatgataa ttccgctcct   3960
tctggtggtt tctttgttcc gcaaaatgat aatgttactc aaacttttaa aattaataac   4020
gttcgggcaa aggatttaat acgagttgtc gaattgtttg taaagtctaa tacttctaaa   4080
tcctcaaatg tattatctat tgacggctct aatctattag ttgttagtgc acctaaagat   4140
attttagata accttcctca attcctttct actgttgatt tgccaactga ccagatattg   4200
attgagggtt tgatatttga ggttcagcaa ggtgatgctt tagatttttc atttgctgct   4260
ggctctcagc gtggcactgt tgcaggcggt gttaatactg accgcctcac ctctgtttta   4320
tcttctgctg gtggttcgtt cggtattttt aatggcgatg ttttagggct atcagttcgc   4380
gcattaaaga ctaatagcca ttcaaaaata ttgtctgtgc cacgtattct tacgctttca   4440
ggtcagaagg gttctatctt tgttggccag aatgtccctt ttattactgg tcgtgtgact   4500
ggtgaatctg ccaatgtaaa taatccattt cagacgattg agcgtcaaaa tgtaggtatt   4560
tccatgagcg tttttcctgt tgcaatggct ggcggtaata ttgttctgga tattaccagc   4620
aaggccgata gtttgagttc ttctactcag gcaagtgatg ttattactaa tcaaagaagt   4680
actgctacaa cggttaattt gcgtgatgga cagactcttt tactcggtgg cctcactgat   4740
tataaaaaca cttctcagga ttctggcgta ccgttcctgt ctaaaatccc tttaatcggc   4800
ctcctgttta gctcccgctc tgattctaac gaggaaagca cgttatacgt gctcgtcaaa   4860
gcaaccatag tacgcgccct gtagcggcgc attaagcgcg gcgggtgtgg tggttacgcg   4920
cagcgtgacc gctacacttg ccagcgccct agcgcccgct cctttcgctt tcttcccttc   4980
```

```
ctttctcgcc acgttcgccg gctttccccg tcaagctcta aatcgggggc tccctttagg   5040

gttccgattt agtgctttac ggcacctcga ccccaaaaaa cttgatttgg gtgatggttc   5100

acgtagtggg ccatcgccct gatagacggt ttttcgccct ttgacgttgg agtccacgtt   5160

ctttaatagt ggactcttgt tccaaactgg aacaacactc aaccctatct cgggctattc   5220

ttttgattta taagggattt tgccgatttc ggcctattgg ttaaaaaatg agctgattta   5280

acaaaaattt aacgcgaatt ttaacaaaat attaacgttt acaatttaaa tatttgctta   5340

tacaatcttc ctgtttttgg ggcttttctt attatcaacc ggggtacat              5389
```

<210> SEQ ID NO 31
<211> LENGTH: 4630
<212> TYPE: DNA
<213> ORGANISM: Artificial Sequence
<220> FEATURE:
<223> OTHER INFORMATION: Synthetic Polynucleotide

<400> SEQUENCE: 31

```
ggctgttttg gcggatgaga gaagattttc agcctgatac agattaaatc agaacgcaga     60

agcggtctga taaaacagaa tttgcctggc ggcagtagcg cggtggtccc acctgacccc    120

atgccgaact cagaagtgaa acgccgtagc gccgatggta gtgtggggtc tccccatgcg    180

agagtaggga actgccaggc atcaaataaa acgaaaggct cagtcgaaag actgggcctt    240

tcgttttatc tgttgtttgt cggtgaacgc tctcctgagt aggacaaatc cgccgggagc    300

ggatttgaac gttgcgaagc aacggcccgg agggtggcgg gcaggacgcc cgccataaac    360

tgccaggcat caaattaagc agaaggccat cctgacggat ggcctttttg cgtttctaca    420

aactctactc tgctagcaag taaggccgac aagcttgcat gcctgcaggt cgactctaga    480

ggatccccgg gtaccgagct cgaattccct ttttttttgg agattttcaa cgtgaaaaaa    540

ttattattcg caattccttt agttgttcct ttctattctc actccgctga aactgttgaa    600

agttgtttag caaaacccca tacagaaaat tcatttacta acgtctggaa agacgacaaa    660

actttagatc gttacgctaa ctatgagggc tgtctgtgga atgctacagg cgttgtagtt    720

tgtactggtg acgaaactca gtgttacggt acatgggttc ctattgggct tgctatccct    780

gaaaatgagg gtggtggctc tgagggtggc ggttctgagg gtggcggttc tgagggtggc    840

ggtactaaac ctcctgagta cggtgataca cctattccgg gctatactta tatcaaccct    900

ctcgacggca cttatccgcc tggtactgag caaaaccccg ctaatcctaa tccttctctt    960

gaggagtctc agcctcttaa tactttcatg tttcagaata ataggttccg aaataggcag   1020

ggggcattaa ctgtttatac gggcactgtt actcaaggca ctgaccccgt taaaacttat   1080

taccagtaca ctcctgtatc atcaaaagcc atgtatgacg cttactggaa cggtaaattc   1140

agagactgcg ctttccattc tggctttaat gaggatccat tcgtttgtga atatcaaggc   1200

caatcgtctg acctgcctca acctcctgtc aatgctggcg gcggctctgg tggtggttct   1260

ggtggcggct ctgagggtgg tggctctgag ggtggcggtt ctgagggtgg cggctctgag   1320

ggaggcggtt ccggtggtgg ctctggttcc ggtgattttg attatgaaaa gatggcaaac   1380

gctaataagg gggctatgac cgaaaatgcc gatgaaaacg cgctacagtc tgacgctaaa   1440

ggcaaacttg attctgtcgc tactgattac ggtgctgcta tcgatggttt cattggtgac   1500

gtttccggcc ttgctaatgg taatggtgct actggtgatt ttgctggctc taattcccaa   1560

atggctcaag tcggtgacgg tgataattca cctttaatga ataatttccg tcaatattta   1620
```

```
ccttccctcc ctcaatcggt tgaatgtcgc ccttttgtct ttggcgctgg taaaccatat   1680

gaattttcta ttgattgtga caaaataaac ttattccgtg gtgtctttgc gtttctttta   1740

tatgttgcca cctttatgta tgtattttct acgtttgcta acatactgcg taataaggag   1800

tcttaatcat gccagttcta gcataacccc ttggggcctc taaacgggtc ttgaggggtt   1860

ttttgccttg tcggccttac ttgctaaata cattcaaata tgtatccgct catgagacaa   1920

taaccctgat aaatgcttca ataatattga aaaaggaaga gtatgagtat tcaacatttc   1980

cgtgtcgccc ttattccctt ttttgcggca ttttgccttc ctgtttttgc tcacccagaa   2040

acgctggtga aagtaaaaga tgctgaagat cagttgggtg cacgagtggg ttacatcgaa   2100

ctggatctca acagcggtaa gatccttgag agttttcgcc ccgaagaacg ttttccaatg   2160

atgagcactt ttaaagttct gctatgtggc gcggtattat cccgtattga cgccgggcaa   2220

gagcaactcg gtcgccgcat acactattct cagaatgact tggttgagta ctcaccagtc   2280

acagaaaagc atcttacgga tggcatgaca gtaagagaat tatgcagtgc tgccataacc   2340

atgagtgata acactgcggc caacttactt ctgacaacga tcggaggacc gaaggagcta   2400

accgcttttt tgcacaacat gggggatcat gtaactcgcc ttgatcgttg ggaaccggag   2460

ctgaatgaag ccataccaaa cgacgagcgt gacaccacga tgcctgtagc aatggcaaca   2520

acgttgcgca aactattaac tggcgaacta cttactctag cttcccggca acaattgata   2580

gactggatgg aggcggataa agttgcagga ccacttctgc gctcggccct tccggctggc   2640

tggtttattg ctgataaatc tggagccggt gagcgtggct ctcgcggtat cattgcagca   2700

ctggggccag atggtaagcc ctcccgtatc gtagttatct acacgacggg gagtcaggca   2760

actatggatg aacgaaatag acagatcgct gagataggtg cctcactgat taagcattgg   2820

taagaacctc agatccttcc gtgatggtaa cttcactagt ttaaaaggat ctaggtgaag   2880

atcctttttg ataatctcat gaccaaaatc ccttaacgtg agttttcgtt ccactgagcg   2940

tcagagaacc tcagatcctt ccgtatttag ccagtatgtt ctctagtgtg gttcgttgtt   3000

tttgcgtgag ccatgagaac gaaccattga gatcatgctt actttgcatg tcactcaaaa   3060

attttgcctc aaaactggtg agctgaattt ttgcagttaa agcatcgtgt agtgtttttc   3120

ttagtccgtt acgtaggtag gaatctgatg taatggttgt tggtattttg tcaccattca   3180

tttttatctg gttgttctca agttcggtta cgagatccat ttgtctatct agttcaactt   3240

ggaaaatcaa cgtatcagtc gggcggcctc gcttatcaac caccaatttc atattgctgt   3300

aagtgtttaa atctttactt attggtttca aaacccattg gttaagcctt ttaaactcat   3360

ggtagttatt ttcaagcatt aacatgaact taaattcatc aaggctaatc tctatatttg   3420

ccttgtgagt tttcttttgt gttagttctt ttaataacca ctcataaatc ctcatagagt   3480

atttgttttc aaaagactta acatgttcca gattatattt tatgaatttt tttaactgga   3540

aaagataagg caatatctct tcactaaaaa ctaattctaa tttttcgctt gagaacttgg   3600

catagtttgt ccactggaaa atctcaaagc ctttaaccaa aggattcctg atttccacag   3660

ttctcgtcat cagctctctg gttgctttag ctaatacacc ataagcattt tccctactga   3720

tgttcatcat ctgagcgtat tggttataag tgaacgatac cgtccgttct ttccttgtag   3780

ggttttcaat cgtggggttg agtagtgcca cacagcataa aattagcttg gtttcatgct   3840

ccgttaagtc atagcgacta atcgctagtt catttgcttt gaaaacaact aattcagaca   3900

tacatctcaa ttggtctagg tgattttaat cactatacca attgagatgg gctagtcaat   3960

gataattact agtccttttc ctttgagttg tgggtatctg taaattctgc tagacctttg   4020
```

```
ctggaaaact tgtaaattct gctagaccct ctgtaaattc cgctagacct ttgtgtgttt   4080

tttttgttta tattcaagtg gttataattt atagaataaa gaaagaataa aaaaagataa   4140

aaagaataga tcccagccct gtgtataact cactacttta gtcagttccg cagtattaca   4200

aaaggatgtc gcaaacgctg tttgctcctc tacaaaacag accttaaaac cctaaaggct   4260

taagtagcac cctcgcaagc tcgggcaaat cgctgaatat tccttttgtc tccgaccatc   4320

aggcacctga gtcgctgtct ttttcgtgac attcagttcg ctgcgctcac ggctctggca   4380

gtgaatgggg gtaaatggca ctacaggcgc cttttatgga ttcatgcaag gaaactaccc   4440

ataatacaag aaaagcccgt cacgggcttc tcagggcgtt ttatggcggg tctgctatgt   4500

ggtgctatct gactttttgc tgttcagcag ttcctgccct ctgattttcc agtctgacca   4560

cttcggatta tcccgtgaca ggtcattcag actggctaat gcacccagta aggcagcggt   4620

atcatcaact                                                          4630
```

<210> SEQ ID NO 32
<211> LENGTH: 4630
<212> TYPE: DNA
<213> ORGANISM: Artificial Sequence
<220> FEATURE:
<223> OTHER INFORMATION: Synthetic Polynucleotide

<400> SEQUENCE: 32

```
ggctgttttg gcggatgaga gaagattttc agcctgatac agattaaatc agaacgcaga     60

agcggtctga taaaacagaa tttgcctggc ggcagtagcg cggtggtccc acctgacccc    120

atgccgaact cagaagtgaa acgccgtagc gccgatggta gtgtggggtc tccccatgcg    180

agagtaggga actgccaggc atcaaataaa acgaaaggct cagtcgaaag actgggcctt    240

tcgttttatc tgttgtttgt cggtgaacgc tctcctgagt aggacaaatc cgccgggagc    300

ggatttgaac gttgcgaagc aacggcccgg agggtggcgg gcaggacgcc cgccataaac    360

tgccaggcat caaattaagc agaaggccat cctgacggat ggcctttttg cgtttctaca    420

aactctactc tgctagcaag taaggccgac aagcttgcat gcctgcaggt cgactctaga    480

ggatccccgg gtaccgagct cgaattccct tttttttgg agattttcaa cgtgaaaaaa    540

ttattattcg caattccttt agttgttcct ttctattctc actccgctga aactgttgaa    600

agttgtttag caaaacccca tacagaaaat tcatttacta acgtctggaa agacgacaaa    660

actttagatc gttacgctaa ctatgagggc tgtctgtgga atgctacagg cgttgtagtt    720

tgtactggtg acgaaactca gtgttacggt acatgggttc ctattgggct tgctatccct    780

gaaaatgagg gtggtggctc tgagggtggc ggttctgagg gtggcggttc tgagggtggc    840

ggtactaaac ctcctgagta cggtgataca cctattccgg gctatactta tatcaaccct    900

ctcgacggca cttatccgcc tggtactgag caaaaccccg ctaatcctaa tccttctctt    960

gaggagtctc agcctcttaa tactttcatg tttcagaata ataggttccg aaataggcag   1020

ggggcattaa ctgtttatac gggcactgtt actcaaggca ctgaccccgt taaaacttat   1080

taccagtaca ctcctgtatc atcaaaagcc atgtatgacg cttactggaa cggtaaattc   1140

agagactgcg ctttccattc tggctttaat gaggatccat tcgtttgtga atatcaaggc   1200

caatcgtctg acctgcctca acctcctgtc aatgctggcg gcggctctgg tggtggttct   1260

ggtggcggct ctgagggtgg tggctctgag ggtggcggtt ctgagggtgg cggctctgag   1320

ggaggcggtt ccggtggtgg ctctggttcc ggtgattttg attatgaaaa gatggcaaac   1380
```

```
gctaataagg gggctatgac cgaaaatgcc gatgaaaacg cgctacagtc tgacgctaaa   1440
ggcaaacttg attctgtcgc tactgattac ggtgctgcta tcgatggttt cattggtgac   1500
gtttccggcc ttgctaatgg taatggtgct actggtgatt ttgctggctc taattcccaa   1560
atggctcaag tcggtgacgg tgataattca cctttaatga ataatttccg tcaatattta   1620
ccttccctcc ctcaatcggt tgaatgtcgc ccttttgtct ttggcgctgg taaaccatat   1680
gaattttcta ttgattgtga caaaataaac ttattccgtg gtgtctttgc gtttctttta   1740
tatgttgcca cctttatgta tgtattttct acgtttgcta acatactgcg taataaggag   1800
tcttaatcat gccagttcta gcataacccc ttggggcctc taaacgggtc ttgaggggtt   1860
ttttgccttg tcggccttac ttgctaaata cattcaaata tgtatccgct catgagacaa   1920
taaccctgat aaatgcttca ataatattga aaaaggaaga gtatgagtat tcaacatttc   1980
cgtgtcgccc ttattccctt ttttgcggca ttttgccttc ctgtttttgc tcacccagaa   2040
acgctggtga aagtaaaaga tgctgaagat cagttgggtg cacgagtggg ttacatcgaa   2100
ctggatctca acagcggtaa gatccttgag agttttcgcc ccgaagaacg ttttccaatg   2160
atgagcactt ttaaagttct gctatgtggc gcggtattat cccgtattga cgccgggcaa   2220
gagcaactcg gtcgccgcat acactattct cagaatgact tggttgagta ctcaccagtc   2280
acagaaaagc atcttacgga tggcatgaca gtaagagaat tatgcagtgc tgccataacc   2340
atgagtgata acactgcggc caacttactt ctgacaacga tcggaggacc gaaggagcta   2400
accgcttttt tgcacaacat gggggatcat gtaactcgcc ttgatcgttg ggaaccggag   2460
ctgaatgaag ccataccaaa cgacgagcgt gacaccacga tgcctgtagc aatggcaaca   2520
acgttgcgca aactattaac tggcgaacta cttactctag cttcccggca acaattgata   2580
gactggatgg aggcggataa agttgcagga ccacttctgc gctcggccct tccggctggc   2640
tggtttattg ctgataaatc tggagccggt gagcgtggct ctcgcggtat cattgcagca   2700
ctggggccag atggtaagcc ctcccgtatc gtagttatct acacgacggg gagtcaggca   2760
actatggatg aacgaaatag acagatcgct gagataggtg cctcactgat taagcattgg   2820
taagaacctc agatccttcc gtgatggtaa cttcactagt ttaaaaggat ctaggtgaag   2880
atcctttttg ataatctcat gaccaaaatc ccttaacgtg agttttcgtt ccactgagcg   2940
tcagagaacc tcagatcctt ccgtatttag ccagtatgtt ctctagtgtg gttcgttgtt   3000
tttgcgtgag ccatgagaac gaaccattga gatcatgctt actttgcatg tcactcaaaa   3060
attttgcctc aaaactggtg agctgaattt ttgcagttaa agcatcgtgt agtgtttttc   3120
ttagtccgtt acgtaggtag gaatctgatg taatggttgt tggtattttg tcaccattca   3180
tttttatctg gttgttctca agttcggtta cgagatccat ttgtctatct agttcaactt   3240
ggaaaatcaa cgtatcagtc gggcggcctc gcttatcaac caccaatttc atattgctgt   3300
aagtgtttaa atctttactt attggtttca aaacccattg gttaagcctt ttaaactcat   3360
ggtagttatt ttcaagcatt aacatgaact taaattcatc aaggctaatc tctatatttg   3420
ccttgtgagt tttcttttgt gttagttctt ttaataacca ctcataaatc ctcatagagt   3480
atttgttttc aaaagactta acatgttcca gattatattt tatgaatttt tttaactgga   3540
aaagataagg caatatctct tcactaaaaa ctaattctaa tttttcgctt gagaacttgg   3600
catagtttgt ccactggaaa atctcaaagc ctttaaccaa aggattcctg atttccacag   3660
ttctcgtcat cagctctctg gttgctttag ctaatacacc ataagcattt tccctactga   3720
tgttcatcat ctgagcgtat tggttataag tgaacgatac cgtccgttct ttccttgtag   3780
```

```
ggttttcaat cgtggggttg agtagtgcca cacagcataa aattagcttg gtttcatgct   3840

ccgttaagtc atagcgacta atcgctagtt catttgcttt gaaaacaact aattcagaca   3900

tacatctcaa ttggtctagg tgattttaat cactatacca attgagatgg gctagtcaat   3960

gataattact agtccttttc ctttgagttg tgggtatctg taaattctgc tagacctttg   4020

ctggaaaact tgtaaattct gctagaccct ctgtaaattc cgctagacct ttgtgtgttt   4080

tttttgttta tattcaagtg gttataattt atagaataaa gaaagaataa aaaaagataa   4140

aaagaataga tcccagccct gtgtataact cactacttta gtcagttccg cagtattaca   4200

aaaggatgtc gcaaacgctg tttgctcctc tacaaaacag accttaaaac cctaaaggct   4260

taagtagcac cctcgcaagc tcgggcaaat cgctgaatat tccttttgtc tccgaccatc   4320

aggcacctga gtcgctgtct ttttcgtgac attcagttcg ctgcgctcac ggctctggca   4380

gtgaatgggg gtaaatggca ctacaggcgc cttttatgga ttcatgcaag gaaactaccc   4440

ataatacaag aaaagcccgt cacgggcttc tcagggcgtt ttatggcggg tctgctatgt   4500

ggtgctatct gactttttgc tgttcagcag ttcctgccct ctgattttcc agtctgacca   4560

cttcggatta tcccgtgaca ggtcattcag actggctaat gcacccagta aggcagcggt   4620

atcatcaact                                                          4630
```

```
<210> SEQ ID NO 33
<211> LENGTH: 189
<212> TYPE: PRT
<213> ORGANISM: Homo sapiens

<400> SEQUENCE: 33

Met Leu Gly Ser Arg Ala Val Met Leu Leu Leu Leu Leu Pro Trp Thr
1               5                   10                  15

Ala Gln Gly Arg Ala Val Pro Gly Gly Ser Ser Pro Ala Trp Thr Gln
            20                  25                  30

Cys Gln Gln Leu Ser Gln Lys Leu Cys Thr Leu Ala Trp Ser Ala His
        35                  40                  45

Pro Leu Val Gly His Met Asp Leu Arg Glu Glu Gly Asp Glu Glu Thr
    50                  55                  60

Thr Asn Asp Val Pro His Ile Gln Cys Gly Asp Gly Cys Asp Pro Gln
65                  70                  75                  80

Gly Leu Arg Asp Asn Ser Gln Phe Cys Leu Gln Arg Ile His Gln Gly
                85                  90                  95

Leu Ile Phe Tyr Glu Lys Leu Leu Gly Ser Asp Ile Phe Thr Gly Glu
            100                 105                 110

Pro Ser Leu Leu Pro Asp Ser Pro Val Gly Gln Leu His Ala Ser Leu
        115                 120                 125

Leu Gly Leu Ser Gln Leu Leu Gln Pro Glu Gly His His Trp Glu Thr
    130                 135                 140

Gln Gln Ile Pro Ser Leu Ser Pro Ser Gln Pro Trp Gln Arg Leu Leu
145                 150                 155                 160

Leu Arg Phe Lys Ile Leu Arg Ser Leu Gln Ala Phe Val Ala Val Ala
                165                 170                 175

Ala Arg Val Phe Ala His Gly Ala Ala Thr Leu Ser Pro
            180                 185


<210> SEQ ID NO 34
<211> LENGTH: 352
<212> TYPE: PRT
```

<213> ORGANISM: Homo sapiens

<400> SEQUENCE: 34

```
Met Asp Tyr Gln Val Ser Ser Pro Ile Tyr Asp Ile Asn Tyr Tyr Thr
1               5                   10                  15

Ser Glu Pro Cys Gln Lys Ile Asn Val Lys Gln Ile Ala Ala Arg Leu
            20                  25                  30

Leu Pro Pro Leu Tyr Ser Leu Val Phe Ile Phe Gly Phe Val Gly Asn
        35                  40                  45

Met Leu Val Ile Leu Ile Leu Ile Asn Cys Lys Arg Leu Lys Ser Met
    50                  55                  60

Thr Asp Ile Tyr Leu Leu Asn Leu Ala Ile Ser Asp Leu Phe Phe Leu
65                  70                  75                  80

Leu Thr Val Pro Phe Trp Ala His Tyr Ala Ala Ala Gln Trp Asp Phe
                85                  90                  95

Gly Asn Thr Met Cys Gln Leu Leu Thr Gly Leu Tyr Phe Ile Gly Phe
            100                 105                 110

Phe Ser Gly Ile Phe Phe Ile Ile Leu Leu Thr Ile Asp Arg Tyr Leu
        115                 120                 125

Ala Val Val His Ala Val Phe Ala Leu Lys Ala Arg Thr Val Thr Phe
    130                 135                 140

Gly Val Val Thr Ser Val Ile Thr Trp Val Val Ala Val Phe Ala Ser
145                 150                 155                 160

Leu Pro Gly Ile Ile Phe Thr Arg Ser Gln Lys Glu Gly Leu His Tyr
                165                 170                 175

Thr Cys Ser Ser His Phe Pro Tyr Ser Gln Tyr Gln Phe Trp Lys Asn
            180                 185                 190

Phe Gln Thr Leu Lys Ile Val Ile Leu Gly Leu Val Leu Pro Leu Leu
        195                 200                 205

Val Met Val Ile Cys Tyr Ser Gly Ile Leu Lys Thr Leu Leu Arg Cys
    210                 215                 220

Arg Asn Glu Lys Lys Arg His Arg Ala Val Arg Leu Ile Phe Thr Ile
225                 230                 235                 240

Met Ile Val Tyr Phe Leu Phe Trp Ala Pro Tyr Asn Ile Val Leu Leu
                245                 250                 255

Leu Asn Thr Phe Gln Glu Phe Phe Gly Leu Asn Asn Cys Ser Ser Ser
            260                 265                 270

Asn Arg Leu Asp Gln Ala Met Gln Val Thr Glu Thr Leu Gly Met Thr
        275                 280                 285

His Cys Cys Ile Asn Pro Ile Ile Tyr Ala Phe Val Gly Glu Lys Phe
    290                 295                 300

Arg Asn Tyr Leu Leu Val Phe Phe Gln Lys His Ile Ala Lys Arg Phe
305                 310                 315                 320

Cys Lys Cys Cys Ser Ile Phe Gln Gln Glu Ala Pro Glu Arg Ala Ser
                325                 330                 335

Ser Val Tyr Thr Arg Ser Thr Gly Glu Gln Glu Ile Ser Val Gly Leu
            340                 345                 350
```

<210> SEQ ID NO 35
<211> LENGTH: 245
<212> TYPE: PRT
<213> ORGANISM: Homo sapiens

<400> SEQUENCE: 35

```
Met Arg Ile Phe Ala Val Phe Ile Phe Met Thr Tyr Trp His Leu Leu
```

1 5 10 15

Asn Ala Phe Thr Val Thr Val Pro Lys Asp Leu Tyr Val Val Glu Tyr
20 25 30

Gly Ser Asn Met Thr Ile Glu Cys Lys Phe Pro Val Glu Lys Gln Leu
35 40 45

Asp Leu Ala Ala Leu Ile Val Tyr Trp Glu Met Glu Asp Lys Asn Ile
50 55 60

Ile Gln Phe Val His Gly Glu Glu Asp Leu Lys Val Gln His Ser Ser
65 70 75 80

Tyr Arg Gln Arg Ala Arg Leu Leu Lys Asp Gln Leu Ser Leu Gly Asn
85 90 95

Ala Ala Leu Gln Ile Thr Asp Val Lys Leu Gln Asp Ala Gly Val Tyr
100 105 110

Arg Cys Met Ile Ser Tyr Gly Gly Ala Asp Tyr Lys Arg Ile Thr Val
115 120 125

Lys Val Asn Ala Pro Tyr Asn Lys Ile Asn Gln Arg Ile Leu Val Val
130 135 140

Asp Pro Val Thr Ser Glu His Glu Leu Thr Cys Gln Ala Glu Gly Tyr
145 150 155 160

Pro Lys Ala Glu Val Ile Trp Thr Ser Ser Asp His Gln Val Leu Ser
165 170 175

Gly Lys Thr Thr Thr Thr Asn Ser Lys Arg Glu Glu Lys Leu Phe Asn
180 185 190

Val Thr Ser Thr Leu Arg Ile Asn Thr Thr Thr Asn Glu Ile Phe Tyr
195 200 205

Cys Thr Phe Arg Arg Leu Asp Pro Glu Glu Asn His Thr Ala Glu Leu
210 215 220

Val Ile Pro Gly Asn Ile Leu Asn Val Ser Ile Lys Ile Cys Leu Thr
225 230 235 240

Leu Ser Pro Ser Thr
245

<210> SEQ ID NO 36
<211> LENGTH: 233
<212> TYPE: PRT
<213> ORGANISM: Homo sapiens

<400> SEQUENCE: 36

Met Ser Thr Glu Ser Met Ile Arg Asp Val Glu Leu Ala Glu Glu Ala
1 5 10 15

Leu Pro Lys Lys Thr Gly Gly Pro Gln Gly Ser Arg Arg Cys Leu Phe
20 25 30

Leu Ser Leu Phe Ser Phe Leu Ile Val Ala Gly Ala Thr Thr Leu Phe
35 40 45

Cys Leu Leu His Phe Gly Val Ile Gly Pro Gln Arg Glu Glu Phe Pro
50 55 60

Arg Asp Leu Ser Leu Ile Ser Pro Leu Ala Gln Ala Val Arg Ser Ser
65 70 75 80

Ser Arg Thr Pro Ser Asp Lys Pro Val Ala His Val Val Ala Asn Pro
85 90 95

Gln Ala Glu Gly Gln Leu Gln Trp Leu Asn Arg Arg Ala Asn Ala Leu
100 105 110

Leu Ala Asn Gly Val Glu Leu Arg Asp Asn Gln Leu Val Val Pro Ser
115 120 125

```
Glu Gly Leu Tyr Leu Ile Tyr Ser Gln Val Leu Phe Lys Gly Gln Gly
    130                 135                 140

Cys Pro Ser Thr His Val Leu Leu Thr His Thr Ile Ser Arg Ile Ala
145                 150                 155                 160

Val Ser Tyr Gln Thr Lys Val Asn Leu Leu Ser Ala Ile Lys Ser Pro
                165                 170                 175

Cys Gln Arg Glu Thr Pro Glu Gly Ala Glu Ala Lys Pro Trp Tyr Glu
            180                 185                 190

Pro Ile Tyr Leu Gly Gly Val Phe Gln Leu Glu Lys Gly Asp Arg Leu
        195                 200                 205

Ser Ala Glu Ile Asn Arg Pro Asp Tyr Leu Asp Phe Ala Glu Ser Gly
    210                 215                 220

Gln Val Tyr Phe Gly Ile Ile Ala Leu
225                 230


<210> SEQ ID NO 37
<211> LENGTH: 1019
<212> TYPE: PRT
<213> ORGANISM: Homo sapiens

<400> SEQUENCE: 37

Met Arg Tyr Arg Leu Ala Trp Leu Leu His Pro Ala Leu Pro Ser Thr
1               5                   10                  15

Phe Arg Ser Val Leu Gly Ala Arg Leu Pro Pro Pro Glu Arg Leu Cys
            20                  25                  30

Gly Phe Gln Lys Lys Thr Tyr Ser Lys Met Asn Asn Pro Ala Ile Lys
        35                  40                  45

Arg Ile Gly Asn His Ile Thr Lys Ser Pro Glu Asp Lys Arg Glu Tyr
    50                  55                  60

Arg Gly Leu Glu Leu Ala Asn Gly Ile Lys Val Leu Leu Ile Ser Asp
65                  70                  75                  80

Pro Thr Thr Asp Lys Ser Ser Ala Ala Leu Asp Val His Ile Gly Ser
                85                  90                  95

Leu Ser Asp Pro Pro Asn Ile Ala Gly Leu Ser His Phe Cys Glu His
            100                 105                 110

Met Leu Phe Leu Gly Thr Lys Lys Tyr Pro Lys Glu Asn Glu Tyr Ser
        115                 120                 125

Gln Phe Leu Ser Glu His Ala Gly Ser Ser Asn Ala Phe Thr Ser Gly
    130                 135                 140

Glu His Thr Asn Tyr Tyr Phe Asp Val Ser His Glu His Leu Glu Gly
145                 150                 155                 160

Ala Leu Asp Arg Phe Ala Gln Phe Phe Leu Cys Pro Leu Phe Asp Glu
                165                 170                 175

Ser Cys Lys Asp Arg Glu Val Asn Ala Val Asp Ser Glu His Glu Lys
            180                 185                 190

Asn Val Met Asn Asp Ala Trp Arg Leu Phe Gln Leu Glu Lys Ala Thr
        195                 200                 205

Gly Asn Pro Lys His Pro Phe Ser Lys Phe Gly Thr Gly Asn Lys Tyr
    210                 215                 220

Thr Leu Glu Thr Arg Pro Asn Gln Glu Gly Ile Asp Val Arg Gln Glu
225                 230                 235                 240

Leu Leu Lys Phe His Ser Ala Tyr Tyr Ser Ser Asn Leu Met Ala Val
                245                 250                 255

Cys Val Leu Gly Arg Glu Ser Leu Asp Asp Leu Thr Asn Leu Val Val
            260                 265                 270
```

```
Lys Leu Phe Ser Glu Val Glu Asn Lys Asn Val Pro Leu Pro Glu Phe
        275                 280                 285

Pro Glu His Pro Phe Gln Glu Glu His Leu Lys Gln Leu Tyr Lys Ile
    290                 295                 300

Val Pro Ile Lys Asp Ile Arg Asn Leu Tyr Val Thr Phe Pro Ile Pro
305                 310                 315                 320

Asp Leu Gln Lys Tyr Tyr Lys Ser Asn Pro Gly His Tyr Leu Gly His
            325                 330                 335

Leu Ile Gly His Glu Gly Pro Gly Ser Leu Leu Ser Glu Leu Lys Ser
            340                 345                 350

Lys Gly Trp Val Asn Thr Leu Val Gly Gly Gln Lys Glu Gly Ala Arg
        355                 360                 365

Gly Phe Met Phe Phe Ile Ile Asn Val Asp Leu Thr Glu Glu Gly Leu
    370                 375                 380

Leu His Val Glu Asp Ile Ile Leu His Met Phe Gln Tyr Ile Gln Lys
385                 390                 395                 400

Leu Arg Ala Glu Gly Pro Gln Glu Trp Val Phe Gln Glu Cys Lys Asp
            405                 410                 415

Leu Asn Ala Val Ala Phe Arg Phe Lys Asp Lys Glu Arg Pro Arg Gly
            420                 425                 430

Tyr Thr Ser Lys Ile Ala Gly Ile Leu His Tyr Tyr Pro Leu Glu Glu
        435                 440                 445

Val Leu Thr Ala Glu Tyr Leu Leu Glu Glu Phe Arg Pro Asp Leu Ile
    450                 455                 460

Glu Met Val Leu Asp Lys Leu Arg Pro Glu Asn Val Arg Val Ala Ile
465                 470                 475                 480

Val Ser Lys Ser Phe Glu Gly Lys Thr Asp Arg Thr Glu Glu Trp Tyr
            485                 490                 495

Gly Thr Gln Tyr Lys Gln Glu Ala Ile Pro Asp Glu Val Ile Lys Lys
            500                 505                 510

Trp Gln Asn Ala Asp Leu Asn Gly Lys Phe Lys Leu Pro Thr Lys Asn
        515                 520                 525

Glu Phe Ile Pro Thr Asn Phe Glu Ile Leu Pro Leu Glu Lys Glu Ala
    530                 535                 540

Thr Pro Tyr Pro Ala Leu Ile Lys Asp Thr Ala Met Ser Lys Leu Trp
545                 550                 555                 560

Phe Lys Gln Asp Asp Lys Phe Phe Leu Pro Lys Ala Cys Leu Asn Phe
            565                 570                 575

Glu Phe Phe Ser Pro Phe Ala Tyr Val Asp Pro Leu His Cys Asn Met
            580                 585                 590

Ala Tyr Leu Tyr Leu Glu Leu Leu Lys Asp Ser Leu Asn Glu Tyr Ala
        595                 600                 605

Tyr Ala Ala Glu Leu Ala Gly Leu Ser Tyr Asp Leu Gln Asn Thr Ile
    610                 615                 620

Tyr Gly Met Tyr Leu Ser Val Lys Gly Tyr Asn Asp Lys Gln Pro Ile
625                 630                 635                 640

Leu Leu Lys Lys Ile Ile Glu Lys Met Ala Thr Phe Glu Ile Asp Glu
            645                 650                 655

Lys Arg Phe Glu Ile Ile Lys Glu Ala Tyr Met Arg Ser Leu Asn Asn
            660                 665                 670

Phe Arg Ala Glu Gln Pro His Gln His Ala Met Tyr Tyr Leu Arg Leu
        675                 680                 685
```

```
Leu Met Thr Glu Val Ala Trp Thr Lys Asp Glu Leu Lys Glu Ala Leu
    690                 695                 700

Asp Asp Val Thr Leu Pro Arg Leu Lys Ala Phe Ile Pro Gln Leu Leu
705                 710                 715                 720

Ser Arg Leu His Ile Glu Ala Leu Leu His Gly Asn Ile Thr Lys Gln
                725                 730                 735

Ala Ala Leu Gly Ile Met Gln Met Val Glu Asp Thr Leu Ile Glu His
            740                 745                 750

Ala His Thr Lys Pro Leu Leu Pro Ser Gln Leu Val Arg Tyr Arg Glu
        755                 760                 765

Val Gln Leu Pro Asp Arg Gly Trp Phe Val Tyr Gln Gln Arg Asn Glu
    770                 775                 780

Val His Asn Asn Cys Gly Ile Glu Ile Tyr Tyr Gln Thr Asp Met Gln
785                 790                 795                 800

Ser Thr Ser Glu Asn Met Phe Leu Glu Leu Phe Cys Gln Ile Ile Ser
                805                 810                 815

Glu Pro Cys Phe Asn Thr Leu Arg Thr Lys Glu Gln Leu Gly Tyr Ile
            820                 825                 830

Val Phe Ser Gly Pro Arg Arg Ala Asn Gly Ile Gln Gly Leu Arg Phe
        835                 840                 845

Ile Ile Gln Ser Glu Lys Pro Pro His Tyr Leu Glu Ser Arg Val Glu
    850                 855                 860

Ala Phe Leu Ile Thr Met Glu Lys Ser Ile Glu Asp Met Thr Glu Glu
865                 870                 875                 880

Ala Phe Gln Lys His Ile Gln Ala Leu Ala Ile Arg Arg Leu Asp Lys
                885                 890                 895

Pro Lys Lys Leu Ser Ala Glu Cys Ala Lys Tyr Trp Gly Glu Ile Ile
            900                 905                 910

Ser Gln Gln Tyr Asn Phe Asp Arg Asp Asn Thr Glu Val Ala Tyr Leu
        915                 920                 925

Lys Thr Leu Thr Lys Glu Asp Ile Ile Lys Phe Tyr Lys Glu Met Leu
    930                 935                 940

Ala Val Asp Ala Pro Arg Arg His Lys Val Ser Val His Val Leu Ala
945                 950                 955                 960

Arg Glu Met Asp Ser Cys Pro Val Val Gly Glu Phe Pro Cys Gln Asn
                965                 970                 975

Asp Ile Asn Leu Ser Gln Ala Pro Ala Leu Pro Gln Pro Glu Val Ile
            980                 985                 990

Gln Asn Met Thr Glu Phe Lys Arg  Gly Leu Pro Leu Phe  Pro Leu Val
        995                 1000                 1005

Lys Pro  His Ile Asn Phe Met  Ala Ala Lys Leu
    1010                 1015


<210> SEQ ID NO 38
<211> LENGTH: 750
<212> TYPE: PRT
<213> ORGANISM: Homo sapiens

<400> SEQUENCE: 38

Met Gly Lys Ser Glu Ser Gln Met Asp Ile Thr Asp Ile Asn Thr Pro
1               5                   10                  15

Lys Pro Lys Lys Lys Gln Arg Trp Thr Pro Leu Glu Ile Ser Leu Ser
            20                  25                  30

Val Leu Val Leu Leu Leu Thr Ile Ile Ala Val Thr Met Ile Ala Leu
        35                  40                  45
```

```
Tyr Ala Thr Tyr Asp Asp Gly Ile Cys Lys Ser Ser Asp Cys Ile Lys
    50                  55                  60

Ser Ala Ala Arg Leu Ile Gln Asn Met Asp Ala Thr Thr Glu Pro Cys
65                  70                  75                  80

Thr Asp Phe Phe Lys Tyr Ala Cys Gly Gly Trp Leu Lys Arg Asn Val
                85                  90                  95

Ile Pro Glu Thr Ser Ser Arg Tyr Gly Asn Phe Asp Ile Leu Arg Asp
            100                 105                 110

Glu Leu Glu Val Val Leu Lys Asp Val Leu Gln Glu Pro Lys Thr Glu
        115                 120                 125

Asp Ile Val Ala Val Gln Lys Ala Lys Ala Leu Tyr Arg Ser Cys Ile
    130                 135                 140

Asn Glu Ser Ala Ile Asp Ser Arg Gly Gly Glu Pro Leu Leu Lys Leu
145                 150                 155                 160

Leu Pro Asp Ile Tyr Gly Trp Pro Val Ala Thr Glu Asn Trp Glu Gln
                165                 170                 175

Lys Tyr Gly Ala Ser Trp Thr Ala Glu Lys Ala Ile Ala Gln Leu Asn
            180                 185                 190

Ser Lys Tyr Gly Lys Lys Val Leu Ile Asn Leu Phe Val Gly Thr Asp
        195                 200                 205

Asp Lys Asn Ser Val Asn His Val Ile His Ile Asp Gln Pro Arg Leu
    210                 215                 220

Gly Leu Pro Ser Arg Asp Tyr Tyr Glu Cys Thr Gly Ile Tyr Lys Glu
225                 230                 235                 240

Ala Cys Thr Ala Tyr Val Asp Phe Met Ile Ser Val Ala Arg Leu Ile
                245                 250                 255

Arg Gln Glu Glu Arg Leu Pro Ile Asp Glu Asn Gln Leu Ala Leu Glu
            260                 265                 270

Met Asn Lys Val Met Glu Leu Glu Lys Glu Ile Ala Asn Ala Thr Ala
        275                 280                 285

Lys Pro Glu Asp Arg Asn Asp Pro Met Leu Leu Tyr Asn Lys Met Thr
    290                 295                 300

Leu Ala Gln Ile Gln Asn Asn Phe Ser Leu Glu Ile Asn Gly Lys Pro
305                 310                 315                 320

Phe Ser Trp Leu Asn Phe Thr Asn Glu Ile Met Ser Thr Val Asn Ile
                325                 330                 335

Ser Ile Thr Asn Glu Glu Asp Val Val Val Tyr Ala Pro Glu Tyr Leu
            340                 345                 350

Thr Lys Leu Lys Pro Ile Leu Thr Lys Tyr Ser Ala Arg Asp Leu Gln
        355                 360                 365

Asn Leu Met Ser Trp Arg Phe Ile Met Asp Leu Val Ser Ser Leu Ser
    370                 375                 380

Arg Thr Tyr Lys Glu Ser Arg Asn Ala Phe Arg Lys Ala Leu Tyr Gly
385                 390                 395                 400

Thr Thr Ser Glu Thr Ala Thr Trp Arg Arg Cys Ala Asn Tyr Val Asn
                405                 410                 415

Gly Asn Met Glu Asn Ala Val Gly Arg Leu Tyr Val Glu Ala Ala Phe
            420                 425                 430

Ala Gly Glu Ser Lys His Val Val Glu Asp Leu Ile Ala Gln Ile Arg
        435                 440                 445

Glu Val Phe Ile Gln Thr Leu Asp Asp Leu Thr Trp Met Asp Ala Glu
    450                 455                 460
```

```
Thr Lys Lys Arg Ala Glu Glu Lys Ala Leu Ala Ile Lys Glu Arg Ile
465                 470                 475                 480

Gly Tyr Pro Asp Asp Ile Val Ser Asn Asp Asn Lys Leu Asn Asn Glu
                485                 490                 495

Tyr Leu Glu Leu Asn Tyr Lys Glu Asp Glu Tyr Phe Glu Asn Ile Ile
            500                 505                 510

Gln Asn Leu Lys Phe Ser Gln Ser Lys Gln Leu Lys Lys Leu Arg Glu
        515                 520                 525

Lys Val Asp Lys Asp Glu Trp Ile Ser Gly Ala Ala Val Val Asn Ala
    530                 535                 540

Phe Tyr Ser Ser Gly Arg Asn Gln Ile Val Phe Pro Ala Gly Ile Leu
545                 550                 555                 560

Gln Pro Pro Phe Phe Ser Ala Gln Gln Ser Asn Ser Leu Asn Tyr Gly
                565                 570                 575

Gly Ile Gly Met Val Ile Gly His Glu Ile Thr His Gly Phe Asp Asp
            580                 585                 590

Asn Gly Arg Asn Phe Asn Lys Asp Gly Asp Leu Val Asp Trp Trp Thr
        595                 600                 605

Gln Gln Ser Ala Ser Asn Phe Lys Glu Gln Ser Gln Cys Met Val Tyr
    610                 615                 620

Gln Tyr Gly Asn Phe Ser Trp Asp Leu Ala Gly Gly Gln His Leu Asn
625                 630                 635                 640

Gly Ile Asn Thr Leu Gly Glu Asn Ile Ala Asp Asn Gly Gly Leu Gly
                645                 650                 655

Gln Ala Tyr Arg Ala Tyr Gln Asn Tyr Ile Lys Lys Asn Gly Glu Glu
            660                 665                 670

Lys Leu Leu Pro Gly Leu Asp Leu Asn His Lys Gln Leu Phe Phe Leu
        675                 680                 685

Asn Phe Ala Gln Val Trp Cys Gly Thr Tyr Arg Pro Glu Tyr Ala Val
    690                 695                 700

Asn Ser Ile Lys Thr Asp Val His Ser Pro Gly Asn Phe Arg Ile Ile
705                 710                 715                 720

Gly Thr Leu Gln Asn Ser Ala Glu Phe Ser Glu Ala Phe His Cys Arg
                725                 730                 735

Lys Asn Ser Tyr Met Asn Pro Glu Lys Lys Cys Arg Val Trp
            740                 745                 750


<210> SEQ ID NO 39
<211> LENGTH: 45
<212> TYPE: PRT
<213> ORGANISM: Artificial Sequence
<220> FEATURE:
<223> OTHER INFORMATION: Synthetic Polypeptide

<400> SEQUENCE: 39

Asn Glu Leu Val Thr Ser Asp Arg Gly Ser Gly Gly Gly Ala Ser Gly
1               5                   10                  15

Gly Ala Gly Glu Asn Leu Tyr Phe Gln Ser Ala Gly Gly Ser Ala Gly
            20                  25                  30

Ser Gly Ala Gly Gly Asn Thr Ile Asn Ile Ala Lys Asn
        35                  40                  45


<210> SEQ ID NO 40
<211> LENGTH: 46
<212> TYPE: PRT
<213> ORGANISM: Artificial Sequence
<220> FEATURE:
```

<223> OTHER INFORMATION: Synthetic Polypeptide

<400> SEQUENCE: 40

```
Asn Glu Leu Val Thr Ser Asp Arg Gly Ser Gly Gly Gly Ala Ser Gly
1               5                   10                  15

Gly Thr Glu Asp Val Val Cys Cys Ser Met Ser Tyr Gly Gly Ser Ala
            20                  25                  30

Gly Ser Gly Ala Gly Gly Asn Thr Ile Asn Ile Ala Lys Asn
        35                  40                  45
```

<210> SEQ ID NO 41
<211> LENGTH: 44
<212> TYPE: PRT
<213> ORGANISM: Artificial Sequence
<220> FEATURE:
<223> OTHER INFORMATION: Synthetic Polypeptide

<400> SEQUENCE: 41

```
Asn Glu Leu Val Thr Ser Asp Arg Gly Ser Gly Gly Gly Ala Ser Gly
1               5                   10                  15

Gly Ala Leu Glu Val Leu Phe Gln Gly Pro Gly Gly Ser Ala Gly Ser
            20                  25                  30

Gly Ala Gly Gly Asn Thr Ile Asn Ile Ala Lys Asn
        35                  40
```

<210> SEQ ID NO 42
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 42

```
Gly Glu Asn Leu Tyr Phe Gln Ser Ala
1               5
```

<210> SEQ ID NO 43
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 43

```
Gly Glu Asn Leu Tyr Phe Glu Ser Ala
1               5
```

<210> SEQ ID NO 44
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 44

```
His Asn Leu Tyr Phe Gln Ser
1               5
```

<210> SEQ ID NO 45
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 45

Asn Leu Tyr Phe Gln Ser
1 5

<210> SEQ ID NO 46
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 46

Glu Asn Leu Tyr Gly Gln Ser
1 5

<210> SEQ ID NO 47
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 47

His Asn Leu Tyr Phe His Ser
1 5

<210> SEQ ID NO 48
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 48

Glu Asn Leu Tyr Phe Glu Ser
1 5

<210> SEQ ID NO 49
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 49

Glu Asn Leu Tyr Phe His Ser
1 5

<210> SEQ ID NO 50
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 50

His Asn Leu Tyr Gly Gln Ser
1 5

<210> SEQ ID NO 51
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 51

His Asn Leu Tyr Gly His Ser
1               5

<210> SEQ ID NO 52
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 52

His Asn Leu Val Gly Gln Ser
1               5

<210> SEQ ID NO 53
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 53

His Pro Leu Val Gly His Met
1               5

<210> SEQ ID NO 54
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 54

Glu Asn Leu Val Phe Gln Ser
1               5

<210> SEQ ID NO 55
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 55

His Asn Leu Val Gly His Ser
1               5

<210> SEQ ID NO 56
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 56

Thr Glu Asp Val Gly Cys Cys Ser Met Ser Tyr
1               5                   10

<210> SEQ ID NO 57
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 57

```
Thr Glu Asp Val Val Cys Cys Ser Met Ser Tyr
1               5                   10


<210> SEQ ID NO 58
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 58

Thr Glu Asp Val Ala Cys Cys Ser Met Ser Tyr
1               5                   10


<210> SEQ ID NO 59
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 59

Gln Glu Arg Glu Val Pro Cys His Arg Pro Ser
1               5                   10


<210> SEQ ID NO 60
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 60

Gln Glu Arg Glu Ala Pro Cys His Arg Pro Ser
1               5                   10


<210> SEQ ID NO 61
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 61

Gln Glu Arg Glu Gly Pro Cys His Arg Pro Ser
1               5                   10


<210> SEQ ID NO 62
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 62

Thr Glu Asp Val Val Cys Val Ser Met Ser Tyr
1               5                   10


<210> SEQ ID NO 63
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 63

Thr Glu Asp Val Val Gln Val Ser Met Ser Tyr
```

1 5 10

<210> SEQ ID NO 64
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 64

Thr Glu Asp Tyr Val Cys Val Ser Met Ser Tyr
1 5 10

<210> SEQ ID NO 65
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 65

Thr Glu Asp Tyr Ile Gln Val Ser Met Ser Tyr
1 5 10

<210> SEQ ID NO 66
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 66

Glu Glu Asp Tyr Ile Gln Val Ser Thr Trp Ala
1 5 10

<210> SEQ ID NO 67
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 67

Thr Glu Asp Val Ile Gln Val Ser Met Ser Tyr
1 5 10

<210> SEQ ID NO 68
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 68

Thr Glu Asp Val Val Gln Val Ser Met Trp Tyr
1 5 10

<210> SEQ ID NO 69
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 69

Leu Glu Val Leu Phe Gln
1 5

<210> SEQ ID NO 70
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 70

```
Glu Asn Leu Tyr Phe Gln
1               5
```

<210> SEQ ID NO 71
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 71

```
Glu Asn Leu Tyr Phe Glu
1               5
```

<210> SEQ ID NO 72
<211> LENGTH: 46
<212> TYPE: PRT
<213> ORGANISM: Artificial Sequence
<220> FEATURE:
<223> OTHER INFORMATION: Synthetic polypeptide

<400> SEQUENCE: 72

```
Asn Glu Leu Val Thr Ser Asp Arg Gly Ser Gly Gly Gly Ala Ser Gly
1               5                   10                  15

Gly Ala Gly Glu Asn Leu Tyr Phe Gln Ser Ala Gly Gly Ser Ala Gly
            20                  25                  30

Ser Gly Ala Gly Gly Asn Thr Ile Asn Ile Ala Asn Lys Asn
        35                  40                  45
```

<210> SEQ ID NO 73
<211> LENGTH: 46
<212> TYPE: PRT
<213> ORGANISM: Artificial Sequence
<220> FEATURE:
<223> OTHER INFORMATION: Synthetic polypeptide

<400> SEQUENCE: 73

```
Asn Glu Leu Val Thr Ser Asp Arg Gly Ser Gly Gly Gly Ala Ser Gly
1               5                   10                  15

Gly Thr Glu Asp Val Val Cys Cys Ser Met Ser Tyr Gly Gly Ser Ala
            20                  25                  30

Gly Ser Gly Ala Gly Gly Asn Thr Ile Asn Ile Ala Lys Asn
        35                  40                  45
```

<210> SEQ ID NO 74
<211> LENGTH: 44
<212> TYPE: PRT
<213> ORGANISM: Artificial Sequence
<220> FEATURE:
<223> OTHER INFORMATION: Synthetic polypeptide

<400> SEQUENCE: 74

```
Asn Glu Leu Val Thr Ser Asp Arg Gly Ser Gly Gly Gly Ala Ser Gly
1               5                   10                  15

Gly Ala Leu Glu Val Leu Phe Gln Gly Pro Gly Gly Ser Ala Gly Ser
```

```
            20                  25                  30

Gly Ala Gly Gly Asn Thr Ile Asn Ile Ala Lys Asn
        35                  40


<210> SEQ ID NO 75
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 75

Thr Glu Asp Val Val Gln Val Ser Met Ser Tyr
1               5                   10


<210> SEQ ID NO 76
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 76

Thr Glu Asp Tyr Ile Gln Val Ser Met Ser Tyr
1               5                   10


<210> SEQ ID NO 77
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 77

Glu Glu Asp Tyr Ile Gln Val Ser Thr Trp Ala
1               5                   10


<210> SEQ ID NO 78
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 78

Thr Glu Asp Val Val Cys Val Ser Met Ser Tyr
1               5                   10


<210> SEQ ID NO 79
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 79

Thr Glu Asp Tyr Ile Gln Val Ser Met Ser Tyr
1               5                   10


<210> SEQ ID NO 80
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 80
```

Glu Glu Asp Tyr Ile Gln Val Ser Thr Trp Ala
1 5 10

<210> SEQ ID NO 81
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 81

Thr Glu Asp Tyr Val Cys Val Ser Met Ser Tyr
1 5 10

<210> SEQ ID NO 82
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 82

Thr Glu Asp Val Val Cys Cys Ser Met Ser Tyr
1 5 10

<210> SEQ ID NO 83
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 83

Thr Glu Asp Tyr Ile Gln Val Ser Met Ser Tyr
1 5 10

<210> SEQ ID NO 84
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 84

Glu Glu Asp Tyr Ile Gln Val Ser Thr Trp Ala
1 5 10

<210> SEQ ID NO 85
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 85

Thr Glu Asp Val Val Cys Cys Ser Met Ser Tyr
1 5 10

<210> SEQ ID NO 86
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 86

```
Thr Glu Asp Val Val Cys Val Ser Met Ser Tyr
1               5                   10


<210> SEQ ID NO 87
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 87

Thr Glu Asp Val Val Gln Val Ser Met Ser Tyr
1               5                   10


<210> SEQ ID NO 88
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 88

Thr Glu Asp Tyr Val Cys Val Ser Met Ser Tyr
1               5                   10


<210> SEQ ID NO 89
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 89

Thr Glu Asp Val Val Cys Cys Ser Met Ser Tyr
1               5                   10


<210> SEQ ID NO 90
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 90

Thr Glu Asp Val Val Cys Val Ser Met Ser Tyr
1               5                   10


<210> SEQ ID NO 91
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 91

Thr Glu Asp Val Val Gln Ser Met Ser Tyr
1               5                   10


<210> SEQ ID NO 92
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 92

Thr Glu Asp Tyr Val Cys Val Ser Met Ser Tyr
```

1 5 10

<210> SEQ ID NO 93
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 93

Thr Glu Asp Val Ile Gln Val Ser Met Ser Tyr
1 5 10

<210> SEQ ID NO 94
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 94

Thr Glu Asp Tyr Ile Gln Val Ser Met Ser Tyr
1 5 10

<210> SEQ ID NO 95
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 95

Thr Glu Asp Val Val Gln Val Ser Met Trp Tyr
1 5 10

<210> SEQ ID NO 96
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 96

Glu Glu Asp Tyr Ile Gln Val Ser Thr Trp Ala
1 5 10

<210> SEQ ID NO 97
<211> LENGTH: 1134
<212> TYPE: DNA
<213> ORGANISM: Escherichia coli

<400> SEQUENCE: 97
ggatcctttt tttctgcgcg taatctgctg cttgcaaaca aaaaaaccac cgctaccagc 60
ggtggtttgt ttgccggatc tgaagtaatc aaggttatct cccgcaatgg tttatcgttg 120
cgggagttgc ctgaagcgct ggatgctgtc ggagctttct ccacagccgg agaaggtgta 180
attagttagt cagcatgaag aaaaatcgcg ctttttttgaa gtgggcaggg ggcaagtatc 240
ccctgcttga tgatattaaa cggcatttgc ccaagggcga atgtctggtt gagccttttg 300
taggtgccgg gtcggtgttt ctcaacaccg acttttctcg ttacatcctt gccgatatca 360
atagcgacct gatcagtctc tataacattg tgaagatgcg tactgatgag tacgtacagg 420
ccgcacgcga gctgtttgtt cccgaaacaa attgcgccga ggtttactat cagttccgcg 480
aagagttcaa caaaagccag gatccgttcc gtcgggcggt actgttttta tatttgaacc 540

```
gctacggtta caacggcctg tgtcgttaca atctgcgcgg tgagtttaac gtgccgttcg    600
gccgctacaa aaaaccctat ttcccggaag cagagttgta tcacttcgct gaaaaagcgc    660
agaatgcctt tttctattgt gagtcttacg ccgatagcat ggcgcgcgca gatgatgcat    720
ccgtcgtcta ttgcgatccg ccttatgcac cgctgtctgc gaccgccaac tttacggcgt    780
atcacacaaa cagttttacg cttgaacaac aagcgcatct ggcggagatc gccgaaggtc    840
tggttgagcg ccatattcca gtgctgatct ccaatcacga tacgatgtta acgcgtgagt    900
ggtatcagcg cgcaaaattg catgtcgtca aagttcgacg cagtataagc agcaacggcg    960
gcacacgtaa aaaggtggac gaactgctgg ctttgtacaa accaggagtc gtttcacccg   1020
cgaaaaaata attctcaagg agaagcggat caaacagtat tttgattgcc ccctcaattc   1080
tgtcggctga ttttgcccgc ctgggtgaag ataccgcaaa agccctggca gctg         1134
```

<210> SEQ ID NO 98
<211> LENGTH: 2280
<212> TYPE: DNA
<213> ORGANISM: Escherichia coli

<400> SEQUENCE: 98

```
aagcttccag atcttctttg ctgctttttg caatgtcatg gacatcggca acgtctttac     60
caagctgttt ttgaatcatt tttgcgatat tttcggtatt accggtgtcg ctgccgaaaa    120
agatgccagt gatagccatg agtgaaataa cctcttgaaa cttattgaaa tgggggtgga    180
aaattgccca cggataaagg caatcatagc agaacaggca gtcttgcgga atcagcaaac    240
gagcaggact gcacactgtg ctacatgaaa gtggaaattt aaacgatgcc ctgactacgc    300
agcgccgcca gttgctgcat taacatctct tcgatcagtt cgctacggct catattgcgc    360
gactccgcca gctcgttcag cgcctcgaca gcttccgcgt tcagcttcag ttcgacacgc    420
ttaaggccac gtactttgtc gcgttttagc tggttgcgtt tattaatacg cagctgttca    480
tcgcgcgaaa gcggattagt tttcggtcgt cccggtcgac gctcgtgcgc gaacagatct    540
aatgtcgtac ggtccgtttg ttctttggcc atgatcttgg tgacttcggg ggaaacaatc    600
agccaggcct ctgcccggat ggatagcgcg ccataataca tcagcgcgat gagtcacgcc    660
aacgcccacg cgcggaaagc gacgcggacg ctgggttttt aatcagttgc gttaatcatt    720
gagatagcga cggatagcgc gtaataccgc atccggtttt tcagcatgga cccagtgacc    780
cgcgcctgca atcacatgcg cccgtgcctg tggaaattga gccagtaaat catcacggta    840
ctgctcgcta acatacggag aattgccgcc agggataaac agggcagggt gatcccatgc    900
cgggattttc tcccaaccta caatatgcgg atactgatcc cacaataccg gcacgttaaa    960
gcgccactcc ccgtcaacaa aagatttcag cagaaactga atcacccctt cttcattaag   1020
atgctggcgc attattgctg ctgcttgctg gcgagtttgt gcgtccgatt cactgaccgc   1080
gttgatagcc gcaaaaatct catcatgacg gcgtacgtga tagtcgaccg gcgcgatatc   1140
gatcgccacc agtttatcga tgcgatcgga ggctagtgca gtaagtgcca ttaccgcttt   1200
accgcccatg gagtgaccga taaatgttgc tttgtcgatc tgctgtgcat ccagagtatc   1260
aacaagatcc tgcgccatcg ccgggtaatt cattaccgga tctctcggtg aaagaccgtg   1320
gttacgcata tcaacctgga tgatattgtg atcgtttacc agatcgcgag ccagtacgcc   1380
aaggttgtcg aggctgccaa acagaccgtg gacaagaacg atgggagaat tattgtgctg   1440
gttttgtgca gtttgcgcgc ggatattcaa tttcatggca aagttctttt tttcgcgttg   1500
```

-continued

```
tcgggttagg gtattatgtt gaccattgtg ccacagggct gcaacaaata aggtttattc   1560

cgagtttttc tgcaagccag gcttgacgct atccgctgcc gggatttatt catatactcc   1620

tggcgacttg tattcagcta agacactgca ctggattaag atgaaaacga ttgaagttga   1680

tgatgaactc tacagctata ttgccagcca cactaagcat atcggcgaga gcgcatccga   1740

cattttacgg cgtatgttga aattttccgc cgcatcacag cctgctgctc cggtgacgaa   1800

agaggttcgc gttgcgtcac ctgctatcgt cgaagcgaag ccggtcaaaa cgattaaaga   1860

caaggttcgc gcaatgcgtg aacttctgct ttcggatgaa tacgcagagc aaaagcgagc   1920

ggtcaatcgc tttatgctgc tgttgtctac actatattct cttgacgccc aggcgtttgc   1980

cgaagcaacg gaatcgttgc acggtcgtac acgcgtttac tttgcggcag atgaacaaac   2040

gctgctgaaa aatggtaatc agaccaagcc gaaacatgtg ccaggcacgc cgtattgggt   2100

gatcaccaac accaacaccg gccgtaaatg cagcatgatc gaacacatca tgcagtcgat   2160

gcaattcccg gcggaattga ttgagaaggt ttgcggaact atctaaaacg ttgcagacaa   2220

aggacaaagc aatggcaatc cacaatcgtg caggccaacc tgcacaacag agtgatttga   2280
```